United States Patent
Querbes et al.

(10) Patent No.: US 10,570,393 B2
(45) Date of Patent: Feb. 25, 2020

(54) ANGIOPOIETIN-LIKE 3 (ANGPTL3) IRNA COMPOSITIONS AND METHODS OF USE THEREOF

(71) Applicant: Alnylam Pharmaceuticals, Inc., Cambridge, MA (US)

(72) Inventors: William Querbes, Boston, MA (US); Kevin Fitzgerald, Brookline, MA (US); James Butler, Lynnfield, MA (US); Stephanie Williams, Littleton, MA (US); Gregory Hinkle, Cambridge, MA (US); Martin Maier, Belmont, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/782,091

(22) Filed: Oct. 12, 2017

(65) Prior Publication Data

US 2018/0087054 A1 Mar. 29, 2018

Related U.S. Application Data

(63) Continuation of application No. PCT/US2016/027271, filed on Apr. 13, 2016.

(60) Provisional application No. 62/261,361, filed on Dec. 1, 2015, provisional application No. 62/146,604, filed on Apr. 13, 2015.

(51) Int. Cl.
*C12N 15/113* (2010.01)
*A61K 47/54* (2017.01)
*A61K 31/713* (2006.01)

(52) U.S. Cl.
CPC ........ *C12N 15/1136* (2013.01); *A61K 31/713* (2013.01); *A61K 47/549* (2017.08); *C12N 2310/14* (2013.01); *C12N 2310/315* (2013.01); *C12N 2310/34* (2013.01); *C12N 2310/344* (2013.01); *C12N 2310/346* (2013.01); *C12N 2310/351* (2013.01); *C12N 2310/3515* (2013.01); *C12N 2320/32* (2013.01); *C12N 2320/35* (2013.01); *C12N 2320/51* (2013.01)

(58) Field of Classification Search
CPC ............ A01K 2207/05; C12N 15/1136; C12N 2310/14; C12N 2310/31; C12N 2310/32; C12N 2310/33; A61K 47/549
See application file for complete search history.

(56) References Cited

U.S. PATENT DOCUMENTS

| | | | |
|---|---|---|---|
| 7,935,796 B2 | 5/2011 | Lee et al. | |
| 9,322,018 B2 | 4/2016 | Bettencourt et al. | |
| 9,708,607 B2 | 7/2017 | Rajeev et al. | |
| 9,771,591 B2 | 9/2017 | Bettencourt et al. | |
| 9,796,974 B2 | 10/2017 | Rajeev et al. | |
| 2004/0259247 A1 | 12/2004 | Tuschl et al. | |
| 2005/0246794 A1 | 11/2005 | Khvorova et al. | |
| 2005/0255487 A1 | 11/2005 | Khvorova et al. | |
| 2010/0010066 A1 | 1/2010 | Fitzgerald et al. | |
| 2013/0023579 A1 | 1/2013 | Crooke et al. | |
| 2014/0179768 A1 | 6/2014 | Bettencourt et al. | |
| 2014/0288158 A1* | 9/2014 | Rajeev ................. | C12N 15/113 514/44 A |
| 2015/0315594 A1* | 11/2015 | Prakash ................. | C07H 19/20 536/24.5 |
| 2016/0186180 A1* | 6/2016 | Bettencourt ....... | C12N 15/1136 514/44 A |
| 2017/0275626 A1 | 9/2017 | Maier et al. | |
| 2017/0355994 A1* | 12/2017 | Bettencourt ....... | C12N 15/1136 |
| 2018/0008724 A1 | 1/2018 | Rajeev et al. | |

FOREIGN PATENT DOCUMENTS

| | | |
|---|---|---|
| WO | WO-2008/073300 A2 | 6/2008 |
| WO | WO-2010/148013 A2 | 12/2010 |
| WO | WO-2012/177784 A2 † | 12/2012 |
| WO | WO-2013/074974 A2 † | 5/2013 |
| WO | WO-2013/165816 A2 | 11/2013 |
| WO | WO-2014/182661 A2 | 11/2014 |
| WO | WO-2016/028649 A1 | 2/2016 |
| WO | WO-2016/168286 A1 | 10/2016 |

OTHER PUBLICATIONS

International Search Report from PCT/US2016/027271, dated Sep. 8, 2016.
GaLNAc-siRNA with Enhanced Stabilization chemistry:ESC-GaLNAc-siRNA, Muthiah Manoharan TIDES, (Mar. 14, 2014). Retrieved from the Internet: URL: http://www.alnylam.com/web/assets/ALNY-ESC-GalNAc-siRNA-TIDES-May2014-Capella.pdf.
International Search Report from PCT/US2012/043378, dated Dec. 17, 2012.
International Preliminary Report on Patentability from PCT/US2012/043378, dated Jul. 29, 2013.
Gao et al., "Angiopoietin-like protein 3 regulates the motility and permeability of podocytes by alterning nephrin expression in vitro", Biochemical and Biophysical Research Communications, 2010, pp. 31-36, vol. 399:1.
English translation of a Chinese Office Action and Chinese Search Report issued by the Chinese Intellectual Property Office dated Feb. 16, 2015.

(Continued)

*Primary Examiner* — Brian Whiteman

(74) *Attorney, Agent, or Firm* — McCarter & English, LLP; Maria Laccotripe Zacharakis; Deborah L. Nagle

(57) ABSTRACT

The invention relates to double-stranded ribonucleic acid (dsRNA) compositions targeting the ANGPTL3 gene, as well as methods of inhibiting expression of ANGPTL3 and methods of treating subjects having a disorder of lipid metabolism, such as hyperlipidemia or hypertriglyceridemia, using such dsRNA compositions.

46 Claims, 22 Drawing Sheets

Specification includes a Sequence Listing.

(56) References Cited

OTHER PUBLICATIONS

Watts et al., "Silencing disease genes in the laboratory and the clinic", J Pathol 2012; 226: 365-379.
International Search Report and Written Opinion from PCT/US2012/043378, dated Dec. 17, 2012.
Reynolds et al., "Rational siRNA design for RNA interference," Nature Biotechnology, vol. 22, pp. 326-330, 2004.
Ando et al, "A decreased expression of angiopoietin-like 3 is protective against atherosclerosis in apoE-deficient mice," J. Lipid Res., vol. 44, pp. 1216-1223 (2003).

* cited by examiner
† cited by third party

| Vector | Vector Dose (GC/mouse) | Cross reactivity | Angptl3-GalNAc3 | siRNA Dose (mg/kg) | N= |
|---|---|---|---|---|---|
| AAV8-TBG-ANGPTL3 | 1.00E+11 | - | PBS | 0 | 3 |
| | | m/r/cy/h | AD-65695, 6PS low FI lead | 3 | 3 |
| | | m/r/cy/h | AD-65695, 6PS low FI lead | 1 | 3 |
| | | m/r/cy/h | AD-65695, 6PS low FI lead | 0.3 | 3 |
| | | cy/h | AD-62865, 6PS toffee | 3 | 3 |
| | | cy/h | AD-62865, 6PS toffee | 1 | 3 |
| | | cy/h | AD-62866, 6PS toffee | 0.3 | 3 |

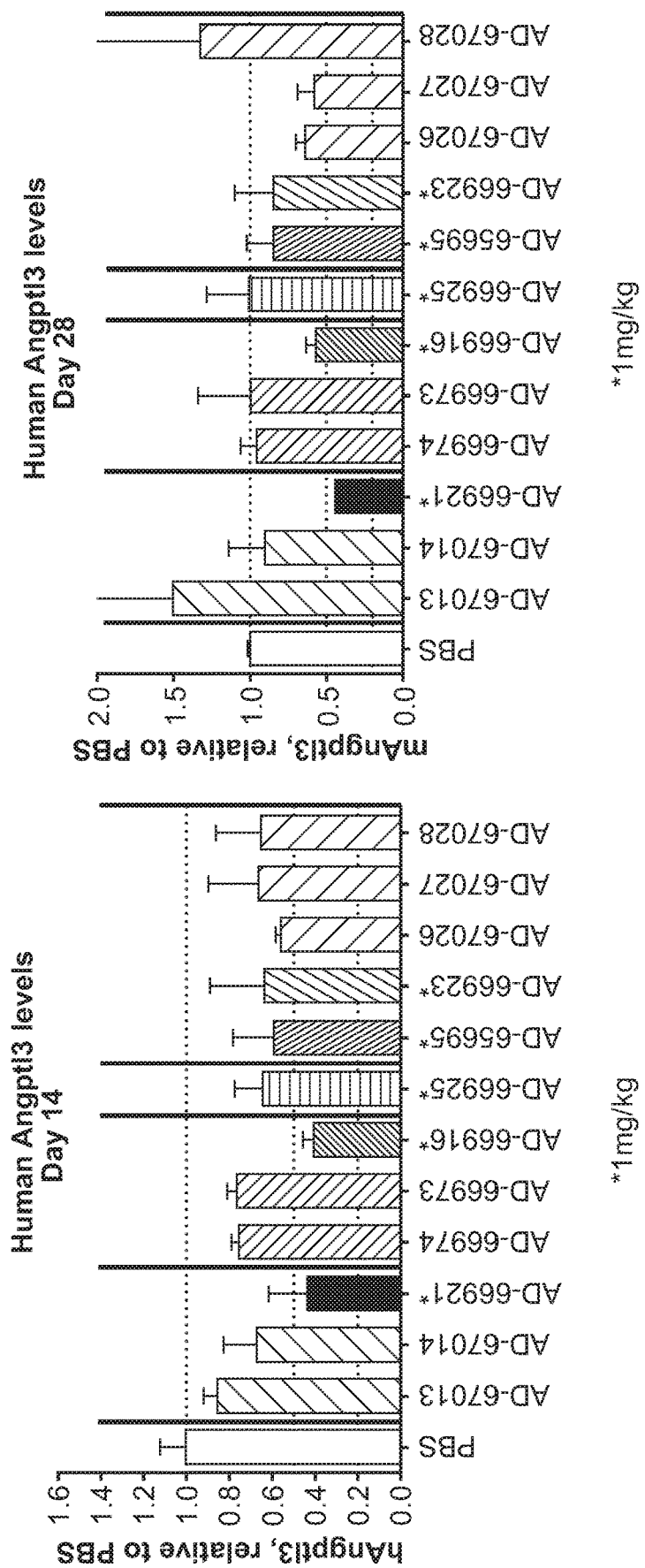

SEQUENCE LISTING

<160> NUMBER OF SEQ ID NOS: 670

<210> SEQ ID NO 1
<211> LENGTH: 2951
<212> TYPE: DNA
<213> ORGANISM: Homo sapiens

<400> SEQUENCE: 1

```
atatatagag ttaagaagtc taggtctgct tccagaagaa aacagttcca cgttgcttga    60
aattgaaaat caagataaaa atgttcacaa ttaagctcct tcttttttatt gttcctctag   120 ttatttcctc cagaattgat caagacaatt catcatttga ttctctatct ccagagccaa   180
aatcaagatt tgctatgtta gacgatgtaa aaattttagc caatggcctc cttcagttgg   240
gacatggtct taaagacttt gtccataaga cgaagggcca aattaatgac atatttcaaa   300
aactcaacat atttgatcag tcttttttatg atctatcgct gcaaaccagt gaaatcaaag   360
aagaagaaaa ggaactgaga agaactacat ataaactaca agtcaaaaat gaagaggtaa   420
agaatatgtc acttgaactc aactcaaaac ttgaaagcct cctagaagaa aaaattctac   480
ttcaacaaaa agtgaaatat ttagaagagc aactaactaa cttaattcaa aatcaacctg   540
aaactccaga cacccagaa gtaacttcac ttaaaacttt tgtagaaaaa caagataata   600
gcatcaaaga ccttctccag accgtggaag accaatataa acaattaaac caacagcata   660
gtcaaataaa agaaatagaa aatcagctca gaaggactag tattcaagaa cccacagaaa   720
tttctctatc ttccaagcca agagcaccaa gaactactcc ctttcttcag ttgaatgaaa   780
taagaaatgt aaaacatgat ggcattcctg ctgaatgtac caccatttat aacagaggtg   840
aacatacaag tggcatgtat gccatcagac ccagcaactc tcaagttttt catgtctact   900
gtgatgttat atcaggtagt ccatggacat taattcaaca tcgaatagat ggatcacaaa   960
acttcaatga aacgtgggag aactacaaat atggttttgg gaggcttgat ggagaatttt  1020
ggttgggcct agagaagata tactccatag tgaagcaatc taattatgtt ttacgaattg  1080
agttggaaga ctggaaagac aacaaacatt atattgaata ttcttttttac ttgggaaatc  1140 acgaaaccaa ctatacgcta catctagttg cgattactgg caatgtcccc aatgcaatcc  1200
cggaaaacaa agatttggtg ttttctactt gggatcacaa agcaaaagga cacttcaact  1260
```

```
gtccagaggg ttattcagga ggctggtggt ggcatgatga gtgtggagaa acaacctaa     1320 atggtaaata taacaaacca agagcaaaat ctaagccaga gaggagaaga ggattatctt    1380
ggaagtctca aaatggaagg ttatactcta taaaatcaac caaaatgttg atccatccaa    1440
cagattcaga aagctttgaa tgaactgagg caaatttaaa aggcaataat ttaaacatta    1500
acctcattcc aagttaatgt ggtctaataa tctggtatta aatccttaag agaaagcttg    1560
agaaatagat ttttttatc ttaaagtcac tgtctattta agattaaaca tacaatcaca     1620
taaccttaaa gaataccgtt tacatttctc aatcaaaatt cttataatac tatttgtttt    1680
aaattttgtg atgtgggaat caattttaga tggtcacaat ctagattata atcaataggt    1740
gaacttatta ataacttttt ctaaataaaa aatttagaga cttttatttt aaaaggcatc    1800
atatgagcta atatcacaac tttcccagtt taaaaaacta gtactcttgt taaaactcta    1860
aacttgacta aatacagagg actggtaatt gtacagttct taaatgttgt agtattaatt    1920
tcaaaactaa aaatcgtcag cacagagtat gtgtaaaaat ctgtaataca aattttttaaa    1980 ctgatgcttc attttgctac aaaataattt ggagtaaatg tttgatatga tttatttatg    2040
aaacctaatg aagcagaatt aaatactgta ttaaaataag ttcgctgtct ttaaacaaat    2100
ggagatgact actaagtcac attgacttta acatgaggta tcactatacc ttatttgtta    2160
aaatatatac tgtatacatt ttatatattt taacacttaa tactatgaaa acaataatt     2220 gtaaggaat cttgtcagat tacagtaaga atgaacatat ttgtggcatc gagttaaagt     2280
ttatatttcc cctaaatatg ctgtgattct aatacattcg tgtaggtttt caagtagaaa    2340
taaacctcgt aacaagttac tgaacgttta acagcctga caagcatgta tatatgttta     2400
aaattcaata acaaagacc cagtccctaa attatagaaa tttaaattat tcttgcatgt     2460
ttatcgacat cacaacagat ccctaaatcc ctaaatccct aaagattaga tacaaatttt    2520
ttaccacagt atcacttgtc agaatttatt tttaaatatg atttttttaaa actgccagta    2580 agaaattta aattaaaccc atttgttaaa ggatatagtg cccaagttat atggtgacct     2640 accttgtca atacttagca ttatgtattt caaattatcc aatatacatg tcatatatat      2700
ttttatatgt cacatatata aaagatatgt atgatctatg tgaatcctaa gtaaatattt    2760
tgttccagaa aagtacaaaa taataaggt aaaaataatc tataattttc aggaccacag     2820
actaagctgt cgaaattaac gctgattttt ttagggccag aataccaaaa tggctcctct    2880
cttcccccaa aattggacaa tttcaaatgc aaaataattc attatttaat atatgagttg    2940
cttcctctat t                                                         2951

<210> SEQ ID NO 2
<211> LENGTH: 2149
<212> TYPE: DNA
<213> ORGANISM: Macaca mulatta

<400> SEQUENCE: 2
atatatagag ttaagaagtc taggtctgct tccagaagaa cacagttcca cgttgcttga     60
aattgaaaat caggataaaa atgttcacaa ttaagctcct tcttttttatt gttcctctag    120 ttatttcctc cagaattgac caagacaatt catcatttga ttctgtatct ccagagccaa     180
aatcaagatt tgctatgtta gacgatgtaa aaatttttagc caatggcctc cttcagttgg    240
gacatggtct taaagacttt gtccataaga ctaagggcca aattaatgac atatttcaaa    300
aactcaacat atttgatcag tcttttttatg atctatcact gcaaaccagt gaaatcaaag    360
aagaagaaaa ggaactgaga agaactacat ataaactaca agtcaaaaat gaagaggtaa    420
```

```
agaatatgtc acttgaactc aactcaaaac ttgaaagcct cctagaagaa aaaattctac        480
ttcaacaaaa agtgaaatat ttagaagagc aactaactaa cttaattcaa aatcaacctg        540
aaactccaga acatccagaa gtaacttcac ttaaaagttt tgtagaaaaa caagataata        600
gcatcaaaga ccttctccag actgtggaag aacaatataa gcaattaaac caacagcaca        660
gtcaaataaa agaaatagaa aatcagctca gaatgactaa tattcaagaa cccacagaaa        720
tttctctatc ttccaagcca agagcaccaa gaactactcc ctttcttcag ctgaatgaaa        780
taagaaatgt aaaacatgat ggcattcctg ctgattgtac caccatttac aatagaggtg        840
aacatataag tggcatgtat gccatcagac ccagcaactc tcaagttttt catgtctact        900
gtgatgttgt atcaggtaaa acctgtctaa ggagaataga tggatcacaa aacttcaatg        960
aaacgtggga gaactacaaa tatggtttcg ggaggcttga tggagaattc tggttgggcc       1020
tagagaagat atactccata gtgaagcaat ctaattacgt tttacgaatt gagttggaag       1080
actggaaaga caacaaacat tatattgaat attctttta cttgggaaat cacgaaacca       1140
actatacgct acatgtagtt aagattactg gcaatgtccc caatgcaatc ccggaaaaca       1200
aagatttggt gttttctact tgggatcaca aagcaaaagg acacttcagc tgtccagaga       1260
gttattcagg aggctggtgg tggcatgatg agtgtggaga aaacaaccta aatggtaaat       1320
ataacaaacc aagaacaaaa tctaagccag agcggagaag aggattatcc tggaagtctc       1380
aaaatggaag gttatactct ataaaatcaa ccaaaatgtt gatccatcca acagattcag       1440
aaagctttga atgaactgag gcaaatttaa aaggcaataa attaaacatt aaactcattc       1500
caagttaatg tggtttaata atctggtatt aaatccttaa gagaaggctt gagaaataga       1560 ttttttatc ttaaagtcac tgtcaattta agattaaaca tacaatcaca taaccttaaa       1620
gaataccatt tacatttctc aatcaaaatt cctacaacac tatttgtttt atattttgtg       1680
atgtgggaat caattttaga tggtcgcaat ctaaattata atcaacaggt gaacttacta       1740
aataactttt ctaaataaaa aacttagaga ctttaatttt aaaagtcatc atatgagcta       1800
atatcacaat tttcccagtt taaaaaacta gttttcttgt taaaactcta aacttgacta       1860
aataaagagg actgataatt atacagttct taaatttgtt gtaatattaa tttcaaaact       1920
aaaaattgtc agcacagagt atgtgtaaaa atctgtaata taaattttta aactgatgcc       1980
tcattttgct acaaaataat ctggagtaaa ttttgatag gatttattta tgaaacctaa       2040
tgaagcagga ttaaatactg tattaaaata ggttcgctgt cttttaaaca aatggagatg       2100
atgattacta agtcacattg actttaatat gaggtatcac tataacctta                  2149

<210> SEQ ID NO 3
<211> LENGTH: 1598
<212> TYPE: DNA
<213> ORGANISM: Mus musculus

<400> SEQUENCE: 3
caggagggag aagttccaaa ttgcttaaaa ttgaataatt gagacaaaaa atgcacacaa         60
ttaaattatt ccttttttgtt gttccttag taattgcatc cagagtggat ccagaccttt        120
catcatttga ttctgcacct tcagagccaa aatcaagatt tgctatgttg gatgatgtca        180
aaattttagc gaatggcctc ctgcagctgg gtcatggact taaagatttt gtccataaga        240
ctaagggaca aattaacgac atatttcaga agctcaacat atttgatcag tcttttttatg       300 acctatcact tcgaaccaat gaaatcaaag aagaggaaaa ggagctaaga agaactacat        360
```

|  |  |
|---|---|
| ctacactaca agttaaaaac gaggaggtga agaacatgtc agtagaactg aactcaaagc | 420 |
| ttgagagtct gctggaagag aagacagccc ttcaacacaa ggtcagggct ttggaggagc | 480 |
| agctaaccaa cttaattcta agcccagctg gggctcagga gcacccagaa gtaacatcac | 540 |
| tcaaaagttt tgtagaacag caagacaaca gcataagaga actcctccag agtgtggaag | 600 |
| aacagtataa acaattaagt caacagcaca tgcagataaa agaaatagaa aagcagctca | 660 |
| gaaagactgg tattcaagaa ccctcagaaa attctctttc ttctaaatca agagcaccaa | 720 |
| gaactactcc ccctcttcaa ctgaacgaaa cagaaaatac agaacaagat gaccttcctg | 780 |
| ccgactgctc tgccgtttat aacagaggcg aacatacaag tggcgtgtac actattaaac | 840 |
| caagaaactc ccaagggttt aatgtctact gtgatacccca atcaggcagt ccatggacat | 900 |
| taattcaaca ccggaaagat ggctcacagg acttcaacga acatgggaa actacgaaa | 960 |
| agggctttgg gaggctcgat ggagaatttt ggttgggcct agagaagatc tatgctatag | 1020 |
| tccaacagtc taactacatt ttacgactcg agctacaaga ctggaaagac agcaagcact | 1080 |
| acgttgaata ctcctttcac ctgggcagtc acgaaaccaa ctacacgcta catgtggctg | 1140 |
| agattgctgg caatatccct ggggccctcc cagagcacac agacctgatg ttttctacat | 1200 |
| ggaatcacag agcaaaggga cagctctact gtccagaaaa ttactcaggt ggctggtggt | 1260 |
| ggaatgacat atgtggagaa acaacctaa atggaaaata caacaaaccc agaaccaaat | 1320 |
| ccagaccaga gaagaagaa gggatctact ggagacctca gagcagaaag ctctatgcta | 1380 |
| tcaaatcatc caaaatgatg ctccagccca ccacctaaga agcttcaact gaactgagac | 1440 |
| aaaataaaag atcaataaat taatattaa agtcctcccg atcactgtag taatctggta | 1500 |
| ttaaaatttt aatggaaagc ttgagaattg aatttcaatt aggtttaaac tcattgttaa | 1560 |
| gatcagatat caccgaatca acgtaaacaa aatttatc | 1598 |

<210> SEQ ID NO 4
<211> LENGTH: 1785
<212> TYPE: DNA
<213> ORGANISM: Rattus norvegicus

<400> SEQUENCE: 4

|  |  |
|---|---|
| gacgttccaa attgcttgaa attgaataat tgaaacaaaa atgcacacaa ttaagctgct | 60 |
| cctttttgtt gttcctctag taatttcgtc cagagttgat ccagaccttt cgccatttga | 120 |
| ttctgtaccg tcagagccaa aatcaagatt tgctatgttg gatgatgtca aaattttagc | 180 |
| caatggcctc ctgcagctgg gtcatggtct taaagatttt gtccataaga caaagggaca | 240 |
| aattaatgac atatttcaga agctcaacat atttgatcag tgtttttatg acctatcact | 300 |
| tcaaaccaat gaaatcaaag aagaggaaaa ggagctaaga agaaccacat ctaaactaca | 360 |
| agttaaaaac gaagaggtga agaatatgtc acttgaactg aactcaaagc ttgaaagtct | 420 |
| actggaggag aagatggcgc tccaacacag agtcagggct ttggaggaac agctgaccag | 480 |
| cttggttcag aacccgcctg gggctcggga gcacccagag gtaacgtcac ttaaaagttt | 540 |
| tgtagaacag caagataaca gcataagaga actcctccag agtgtggaag aacaatataa | 600 |
| acaactaagt caacagcaca ttcagataaa agaaatagaa aatcagctca gaaagactgg | 660 |
| cattcaagaa cccactgaaa attctcttta ttctaaacca agagcaccaa gaactactcc | 720 |
| ccctcttcat ctgaaggaag caaaaaatat agaacaagat gatctgcctg ctgactgctc | 780 |
| tgccattat aacagaggtg aacatacaag tggcgtgtat actattagac caagcagctc | 840 |
| tcaagtgttt aatgtctact gtgacaccca atcaggcact ccacggacat taattcaaca | 900 |

-continued

```
ccggaaagat ggctctcaaa acttcaacca aacgtgggaa aactacgaaa agggttttgg      960
gaggcttgat ggtaaagtga tttccttgca tcactcactt atctgttgat ttaatagtat     1020
tagttgggtg tgttgacaca ggcctgagac catagcgctt ttgggcaagg ggggaggagg     1080
agcagcaggt gaattgaaag ttcaagacca gtctgggcca cacattgata ctccttctcg     1140
acattaagaa ttataaatta agcagcaatt ataaaatggg ctgtggaaat gtaacaataa     1200
gcaaaagcag accccagtct tcataaaact gattggtaaa tattatccat gatagcaact     1260
gcaatgatct cattgtactt atcactactg catgcctgca gtatgcttgt tgaaacttaa     1320
ttctatagtt catggttatc ataagtctta ttaaggaaca tagtatacgc cattggctct     1380
agtgaggggc catgctacaa atgagctgca aagatagcag tatagagctc tttcagtgat     1440
atcctaagca caacgtaaca caggtgaaat gggctggagg cacagttgtg gtggaacacg     1500
cggccagcag gacactggga ctgatcccca gcagcacaaa gaaagtgata ggaacacaga     1560
gcgagagtta gaagggacag ggtcaccgtc agagatacgg tgtctaactc ctgcaaccct     1620
acctgtaatt attccatatt ataaacatat actatataac tgtgggtctc tgcatgttct     1680
agaatatgaa ttctatttga ttgtaaaaca aaactataaa aataagtaaa aaaataaaaa     1740
ataaacagat acttaaaatc aaaaaaaaaa aaaaaaaaaa aaaaa                     1785

<210> SEQ ID NO 5
<211> LENGTH: 2951
<212> TYPE: DNA
<213> ORGANISM: Homo sapiens

<400> SEQUENCE: 5
aatagaggaa gcaactcata tattaaataa tgaattattt tgcatttgaa attgtccaat       60
tttgggggaa gagaggagcc attttggtat tctggcccta aaaaaatcag cgttaatttc      120
gacagcttag tctgtggtcc tgaaaattat agattatttt tacctttatt attttgtact      180
tttctggaac aaaatatttta cttaggattc acatagatca tacatatctt ttatatatgt      240
gacatataaa aatatatatg acatgtatat tggataattt gaaatacata atgctaagta      300
ttgacaaagg taggtcacca tataacttgg gcactatatc ctttaacaaa tgggtttaat      360
ttaaaatttc ttactggcag ttttaaaaaa tcatatttaa aaataaattc tgacaagtga      420
tactgtggta aaaaatttgt atctaatctt tagggattta gggatttagg gatctgttgt      480
gatgtcgata aacatgcaag aataatttaa atttctataa tttagggact gggtctttgt      540
ttattgaatt ttaaacatat atacatgctt gtcaggctgt ttaaacgttc agtaacttgt      600
tacgaggttt atttctactt gaaaacctac acgaatgtat tagaatcaca gcatatttag      660
gggaaatata aactttaact cgatgccaca atatgttca ttcttactgt aatctgacaa      720
gattccttta caattatttg ttttcatagt attaagtgtt aaaatatata aaatgtatac      780
agtatatatt ttaacaaata aggtatagtg atacctcatg ttaaagtcaa tgtgacttag      840
tagtcatctc catttgttta aagacagcga acttatttta atacagtatt taattctgct      900
tcattaggtt tcataaataa atcatatcaa acatttactc caaattattt tgtagcaaaa      960
tgaagcatca gttaaaaaat ttgtattaca gattttttaca catactctgt gctgacgatt     1020
tttagttttg aaattaatac tacaacattt aagaactgta caattaccag tcctctgtat     1080
ttagtcaagt ttagagtttt aacaagagta ctagtttttt aaactgggaa agttgtgata     1140
ttagctcata tgatgccttt taaaataaaa gtctctaaat tttttatttta gaaaagttat     1200
```

```
ttaataagtt cacctattga ttataatcta gattgtgacc atctaaaatt gattcccaca      1260
tcacaaaatt taaaacaaat agtattataa gaattttgat tgagaaatgt aaacggtatt      1320
ctttaaggtt atgtgattgt atgtttaatc ttaaatagac agtgacttta agataaaaaa      1380
aatctatttc tcaagctttc tcttaaggat ttaataccag attattagac cacattaact      1440
tggaatgagg ttaatgttta aattattgcc ttttaaattt gcctcagttc attcaaagct      1500
ttctgaatct gttggatgga tcaacatttt ggttgatttt atagagtata accttccatt      1560
ttgagacttc caagataatc ctcttctcct ctctggctta gattttgctc ttggtttgtt      1620
atatttacca tttaggttgt tttctccaca ctcatcatgc caccaccagc ctcctgaata      1680
accctctgga cagttgaagt gtccttttgc tttgtgatcc caagtagaaa acaccaaatc      1740
tttgttttcc gggattgcat tgggacatt  gccagtaatc gcaactagat gtagcgtata      1800
gttggtttcg tgatttccca agtaaaaaga atattcaata taatgtttgt tgtctttcca      1860
gtcttccaac tcaattcgta aaacataatt agattgcttc actatggagt atatcttctc      1920
taggcccaac caaaattctc catcaagcct cccaaaacca tatttgtagt tctcccacgt      1980
ttcattgaag ttttgtgatc catctattcg atgttgaatt aatgtccatg gactacctga      2040
tataacatca cagtagacat gaaaaacttg agagttgctg ggtctgatgg catacatgcc      2100
acttgtatgt tcacctctgt tataaatggt ggtacattca gcaggaatgc catcatgttt      2160
tacatttctt atttcattca actgaagaaa gggagtagtt cttggtgctc ttggcttgga      2220
agatagagaa atttctgtgg gttcttgaat actagtcctt ctgagctgat tttctatttc      2280
ttttatttga ctatgctgtt ggtttaattg tttatattgg tcttccacgg tctggagaag      2340
gtctttgatg ctattatctt gttttttctac aaaagtttta agtgaagtta cttctgggtg      2400
ttctggagtt tcaggttgat tttgaattaa gttagtagt  tgctcttcta aatatttcac      2460
tttttgttga agtagaattt tttcttctag gaggctttca agttttgagt tgagttcaag      2520
tgacatattc tttacctctt catttttgac ttgtagttta tatgtagttc ttctcagttc      2580
cttttcttct tctttgattt cactggtttg cagcgataga tcataaaaag actgatcaaa      2640
tatgttgagt ttttgaaata tgtcattaat ttggcccttc gtcttatgga caaagtcttt      2700
aagaccatgt cccaactgaa ggaggccatt ggctaaaatt tttacatcgt ctaacatagc      2760
aaatcttgat tttggctctg gagatagaga atcaaatgat gaattgtctt gatcaattct      2820
ggaggaaata actagaggaa caataaaaag aaggagctta attgtgaaca ttttttatctt     2880 gattttcaat ttcaagcaac gtggaactgt tttcttctgg aagcagacct agacttctta      2940
actctatata t                                                          2951

<210> SEQ ID NO 6
<211> LENGTH: 2149
<212> TYPE: DNA
<213> ORGANISM: Macaca mulatta

<400> SEQUENCE: 6
taaggtatag tgatacctca tattaaagtc aatgtgactt agtaatcatc atctccattt        60
gtttaaaaga cagcgaacct atttaatac  agtatttaat cctgcttcat taggtttcat       120
aaataaatcc tatcaaaaat ttactccaga ttattttgta gcaaaatgag gcatcagttt       180
aaaaatttat attacagatt tttacacata ctctgtgctg acaattttta gttttgaaat       240
taatattaca acaaatttaa gaactgtata attatcagtc ctctttattt agtcaagttt       300
agagttttaa caagaaaact agttttttaa actgggaaaa ttgtgatatt agctcatatg       360
```

```
atgactttta aaattaaagt ctctaagttt tttatttaga aaagttattt agtaagttca    420
cctgttgatt ataatttaga ttgcgaccat ctaaaattga ttcccacatc acaaaatata    480
aaacaaatag tgttgtagga attttgattg agaaatgtaa atggtattct ttaaggttat    540
gtgattgtat gtttaatctt aaattgacag tgactttaag ataaaaaaat ctatttctca    600
agccttctct taaggattta ataccagatt attaaaccac attaacttgg aatgagttta    660
atgtttaatt tattgccttt taaatttgcc tcagttcatt caaagctttc tgaatctgtt    720
ggatggatca acattttggt tgattttata gagtataacc ttccattttg agacttccag    780
gataatcctc ttctccgctc tggcttagat tttgttcttg gtttgttata tttaccattt    840
aggttgtttt ctccacactc atcatgccac caccagcctc ctgaataact ctctggacag    900
ctgaagtgtc cttttgcttt gtgatcccaa gtagaaaaca ccaaatcttt gttttccggg    960
attgcattgg ggacattgcc agtaatctta actacatgta gcgtatagtt ggtttcgtga   1020
tttcccaagt aaaagaata ttcaatataa tgtttgttgt cttccagtc ttccaactca   1080 attcgtaaaa cgtaattaga ttgcttcact atggagtata tcttctctag gcccaaccag   1140
aattctccat caagcctccc gaaaccatat ttgtagttct cccacgtttc attgaagttt   1200
tgtgatccat ctattctcct tagacaggtt ttacctgata caacatcaca gtagacatga   1260
aaaacttgag agttgctggg tctgatggca tacatgccac ttatatgttc acctctattg   1320
taaatggtgg tacaatcagc aggaatgcca tcatgtttta catttcttat ttcattcagc   1380
tgaagaaagg gagtagttct tggtgctctt ggcttggaag atagagaaat ttctgtgggt   1440
tcttgaatat tagtcattct gagctgattt tctatttctt ttatttgact gtgctgttgg   1500
tttaattgct tatattgttc ttccacagtc tggagaaggt ctttgatgct attatcttgt   1560
ttttctacaa aactttttaag tgaagttact tctggatgtt ctggagtttc aggttgatttt  1620 tgaattaagt tagttagttg ctcttctaaa tatttcactt tttgttgaag tagaattttt   1680
tcttctagga ggctttcaag ttttgagttg agttcaagtg acatattctt tacctcttca   1740
tttttgactt gtagtttata tgtagttctt ctcagttcct tttcttcttc tttgatttca   1800
ctggtttgca gtgatagatc ataaaaagac tgatcaaata tgttgagttt ttgaaatatg   1860
tcattaattt ggcccttagt cttatggaca aagtctttaa gaccatgtcc caactgaagg   1920
aggccattgg ctaaaatttt tacatcgtct aacatagcaa atcttgattt tggctctgga   1980
gatacagaat caaatgatga attgtcttgg tcaattctgg aggaaataac tagaggaaca   2040
ataaaaagaa ggagcttaat tgtgaacatt tttatcctga ttttcaattt caagcaacgt   2100
ggaactgtgt tcttctggaa gcagacctag acttcttaac tctatatat               2149
```

<210> SEQ ID NO 7
<211> LENGTH: 1598
<212> TYPE: DNA
<213> ORGANISM: Mus musculus

<400> SEQUENCE: 7

```
caggagggag aagttccaaa ttgcttaaaa ttgaataatt gagacaaaaa atgcacacaa     60
ttaaattatt cctttttgtt gttcctttag taattgcatc cagagtggat ccagaccttt    120
catcatttga ttctgcacct tcagagccaa atcaagatt tgctatgttg gatgatgtca    180
aaattttagc gaatggcctc ctgcagctgg gtcatggact taaagatttt gtccataaga    240
ctaagggaca aattaacgac atatttcaga agctcaacat atttgatcag tcttttatg    300
```

```
acctatcact tcgaaccaat gaaatcaaag aagaggaaaa ggagctaaga agaactacat      360
ctacactaca agttaaaaac gaggaggtga agaacatgtc agtagaactg aactcaaagc      420
ttgagagtct gctggaagag aagacagccc ttcaacacaa ggtcagggct tggaggagc       480 agctaaccaa cttaattcta agcccagctg gggctcagga gcacccagaa gtaacatcac      540
tcaaaagttt tgtagaacag caagacaaca gcataagaga actcctccag agtgtggaag      600
aacagtataa acaattaagt caacagcaca tgcagataaa agaaatagaa aagcagctca      660
gaaagactgg tattcaagaa ccctcagaaa attctctttc ttctaaatca agagcaccaa      720
gaactactcc ccctcttcaa ctgaacgaaa cagaaaatac agaacaagat gaccttcctg      780
ccgactgctc tgccgtttat aacagaggcg aacatacaag tggcgtgtac actattaaac      840
caagaaactc ccaagggttt aatgtctact gtgataccca atcaggcagt ccatggacat      900
taattcaaca ccggaaagat ggctcacagg acttcaacga acatgggaa aactacgaaa      960 agggctttgg gaggctcgat ggagaatttt ggttgggcct agagaagatc tatgctatag     1020
tccaacagtc taactacatt ttacgactcg agctacaaga ctggaaagac agcaagcact     1080
acgttgaata ctcctttcac ctgggcagtc acgaaaccaa ctacacgcta catgtggctg     1140
agattgctgg caatatccct ggggcctcc cagagcacac agacctgatg ttttctacat      1200
ggaatcacag agcaaaggga cagctctact gtccagaaag ttactcaggt ggctggtggt     1260
ggaatgacat atgtgtagaa aacaacctaa atggaaaata caacaaaccc agaaccaaat     1320
ccagaccaga gagaagaaga gggatctact ggagacctca gagcagaaag ctctatgcta     1380
tcaaatcatc caaaatgatg ctccagccca ccacctaaga agcttcaact gaactgagac     1440
aaaataaaag atcaataaat taaatattaa agtcctcccg atcactgtag taatctggta     1500
ttaaaatttt aatggaaagc ttgagaattg aatttcaatt aggtttaaac tcattgttaa     1560
gatcagatat caccgaatca acgtaaacaa aatttatc                            1598
```

<210> SEQ ID NO 8
<211> LENGTH: 1785
<212> TYPE: DNA
<213> ORGANISM: Rattus norvegicus

<400> SEQUENCE: 8

```
tttttttttt tttttttttt tttttgattt taagtatctg tttattttt atttttttac       60 ttatttttat agttttgttt tacaatcaaa tagaattcat attctagaac atgcagagac      120
ccacagttat atagtatatg tttataatat ggaataatta caggtagggt tgcaggagtt      180
agacaccgta tctctgacgg tgaccctgtc ccttctaact ctcgctctgt gttcctatca      240
ctttctttgt gctgctgggg atcagtccca gtgtcctgct ggccgcgtgt tccaccacaa      300
ctgtgcctcc agcccatttc acctgtgtta cgttgtgctt aggatatcac tgaaagagct      360
ctatactgct atctttgcag ctcatttgta gcatggcccc tcactagagc caatggcgta      420
tactatgttc cttaataaga cttatgataa ccatgaacta tagaattaag tttcaacaag      480
catactgcag gcatgcagta gtgataagta caatgagatc attgcagttg ctatcatgga      540
taatatttac caatcagttt tatgaagact ggggtctgct tttgcttatt gttacatttc      600
cacagcccat tttataattg ctgcttaatt tataattctt aatgtcgaga aggagtatca      660
atgtgtggcc cagactggtc ttgaactttc aattcacctg ctgctcctcc tcccccttg      720 cccaaaagcg ctatggtctc aggcctgtgt caacacaccc aactaatact attaaatcaa      780
cagataagtg agtgatgcaa ggaaatcact ttaccatcaa gcctcccaaa acccttttcg      840
```

```
tagttttccc acgtttggtt gaagttttga gagccatctt tccggtgttg aattaatgtc    900
cgtggagtgc ctgattgggt gtcacagtag acattaaaca cttgagagct gcttggtcta    960
atagtataca cgccacttgt atgttcacct ctgttataaa tggcagagca gtcagcaggc   1020
agatcatctt gttctatatt ttttgcttcc ttcagatgaa gaggggagt agttcttggt    1080 gctcttggtt tagaataaag agaattttca gtgggttctt gaatgccagt ctttctgagc   1140
tgattttcta tttcttttat ctgaatgtgc tgttgactta gttgtttata ttgttcttcc   1200
acactctgga ggagttctct tatgctgtta tcttgctgtt ctacaaaact tttaagtgac   1260
gttacctctg ggtgctcccg agccccaggc gggttctgaa ccaagctggt cagctgttcc   1320
tccaaagccc tgactctgtg ttggagcgcc atcttctcct ccagtagact tcaagctttt   1380
gagttcagtt caagtgacat attcttcacc tcttcgtttt taacttgtag tttagatgtg   1440
gttcttctta gctccttttc ctcttctttg atttcattgg tttgaagtga taggtcataa   1500
aaacactgat caaatatgtt gagcttctga aatatgtcat taatttgtcc ctttgtctta   1560
tggacaaaat ctttaagacc atgacccagc tgcaggaggc cattggctaa aattttgaca   1620
tcatccaaca tagcaaatct tgattttggc tctgacggta cagaatcaaa tggcgaaagg   1680
tctggatcaa ctctggacga aattactaga ggaacaacaa aaaggagcag cttaattgtg   1740 tgcattttg tttcaattat tcaatttcaa gcaatttgga acgtc              1785

<210> SEQ ID NO 9
<211> LENGTH: 2201
<212> TYPE: DNA
<213> ORGANISM: Macaca fascicularis

<400> SEQUENCE: 9
gggtagtata tagagttaag aagtctaggt ctgcttccag aagaacacag ttccacgctg     60
cttgaaattg aaaatcagga taaaatgtt cacaattaag ctccttcttt ttattgttcc    120
tctagttatt tcctccagaa ttgaccaaga caattcatca tttgattctg tatctccaga    180
gccaaaatca agatttgcta tgttagacga tgtaaaaatt ttagccaatg gcctccttca    240
gttgggacat ggtcttaaag actttgtcca taagactaag ggccaaatta atgacatatt    300
tcaaaaactc aacatatttg atcagtcttt ttatgatcta tcactgcaaa ccagtgaaat    360
caaagaagaa gaaaaggaac tgagaagaac tacatataaa ctacaagtca aaatgaaga    420 ggtaaagaat atgtcacttg aactcaactc aaaacttgaa agcctcctag aagaaaaat    480 tctacttcaa caaaaagtga aatatttaga agagcaacta actaacttaa ttcaaaatca    540
acctgcaact ccagaacatc agaagtaac ttcacttaaa agttttgtag aaaaacaaga    600
taatagcatc aaagaccttc tccagactgt ggaagaacaa tataagcaat taaaccaaca    660
gcatagtcaa ataaagaaa tagaaaatca gctcagaatg actaatattc aagaacccac    720
agaaatttct ctatcttcca gccaagagc accaagaact actcccttc ttcagctgaa    780 tgaaataaga aatgtaaaac atgatggcat tcctgctgat tgtaccacca tttacaatag    840
aggtgaacat ataagtggca cgtatgccat cagacccagc aactctcaag tttttcatgt    900
ctactgtgat gttgtatcag gtagtccatg gacattaatt caacatcgaa tagatggatc    960
acaaaacttc aatgaaacgt gggagaacta caaatatggt ttcggaggc ttgatggaga   1020 attctggttg ggcctagaga agatatactc catagtgaag caatctaatt acgttttacg   1080
aattgagttg gaagactgga aagacaacaa acattatatt gaatattctt tttacttggg   1140
```

-continued

```
aaatcacgaa accaactata cgctacatgt agttaagatt actggcaatg tccccaatgc      1200
aatcccggaa acaaagatt tggtgttttc tacttgggat cacaaagcaa aaggacactt       1260
cagctgtcca gagagttatt caggaggctg gtggtggcat gatgagtgtg gagaaaacaa      1320
cctaaatggt aaatataaca aaccaagaac aaaatctaag ccagagcgga gaagaggatt      1380
atcctggaag tctcaaaatg gaaggttata ctctataaaa tcaaccaaaa tgttgatcca      1440
tccaacagat tcagaaagct ttgaatgaac tgaggcaaat ttaaaaggca ataaattaaa      1500
cattaaactc attccaagtt aatgtggttt aataatctgg tattaaatcc ttaagagaag      1560
gcttgagaaa tagatttttt tatcttaaag tcactgtcaa tttagatta aacatacaat       1620 cacataaccct taaagaatac catttacatt tctcaatcaa aattcttaca acactatttg     1680
ttttatattt tgtgatgtgg gaatcaattt tagatggtcg caatctaaat tataatcaac      1740
aggtgaactt actaaataac ttttctaaat aaaaaactta gagactttaa ttttaaaagt      1800
catcatatga gctaatgtca caattttccc agtttaaaaa actagttttc ttgttaaaac      1860
tctaaacttg actaaataaa gaggactgat aattatacag ttcttaaatt tgttgtaata     1920
ttaatttcaa aactaaaaat tgtcagcaca gagtatgtgt aaaaatctgt aatataaatt      1980
tttaaactga tgcctcattt tgctacaaaa taatctggag taaattttg ataggattta       2040 tttatgaaac ctaatgaagc aggattaaat actgtattaa aataggttcg ctgtcttta       2100 aacaaatgga gatgatgatt actaagtcac attgactta atatgaggta tcactatacc       2160
ttaacatatt tgttaaaacg tatactgtat acattttgtg t                          2201
```

<210> SEQ ID NO 10
<211> LENGTH: 11
<212> TYPE: PRT
<213> ORGANISM: Unknown
<220> FEATURE:
<221> NAME/KEY: source
<223> OTHER INFORMATION: /note="Description of Unknown:
    RFGF analogue sequence"

<400> SEQUENCE: 10

Ala Ala Leu Leu Pro Val Leu Leu Ala Ala Pro
1               5                   10

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Pro Pro Gln
1               5                   10

<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 16
<212> TYPE: PRT
<213> ORGANISM: Unknown
<220> FEATURE:

```
<221> NAME/KEY: source
<223> OTHER INFORMATION: /note="Description of Unknown:
      RFGF sequence"

<400> SEQUENCE: 13

Ala Ala Val Ala Leu Leu Pro Ala Val Leu Leu Ala Leu Leu Ala Pro
1               5                  10                  15

<210> SEQ ID NO 14
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gaauauguca cuugaacuca a                                              21

<210> SEQ ID NO 15
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
utgaguucaa gtgacauauu cuu                                            23

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
gaauatguga cuugaacuca a                                              21

<210> SEQ ID NO 17
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
uugaguucaa gugacauauu cuu                                            23

<210> SEQ ID NO 18
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 18
auuaagcugc uucuuutuau u                                              21

<210> SEQ ID NO 19
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
aauaaaaaga aggagcuuaa uug                                            23

<210> SEQ ID NO 20
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
acauauuuga ucagucuuuu u                                              21

<210> SEQ ID NO 21
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
aaaaagacug aucaaauaug uug                                            23

<210> SEQ ID NO 22
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
ugucacuuga acucaacuca a                                              21

<210> SEQ ID NO 23
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
```
uugaguugag uucaagugac aua                                             23

<210> SEQ ID NO 24
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
aacuaacuaa cuuaauucaa a                                               21

<210> SEQ ID NO 25
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
uuugaauuaa guuaguuagu ugc                                             23

<210> SEQ ID NO 26
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ucacaauuaa gcuccuucuu u                                               21

<210> SEQ ID NO 27
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
aaagaaggag cuuaauugug aac                                             23

<210> SEQ ID NO 28
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gagcaacuaa cuaacuuaau u                                               21

<210> SEQ ID NO 29
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 29
aauuaaguua guuaguugcu cuu                                              23

<210> SEQ ID NO 30
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
uuauuguucc ucuaguuauu u                                                21

<210> SEQ ID NO 31
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
aaauaacuag aggaacaaua aaa                                              23

<210> SEQ ID NO 32
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
auuaagcucc uucuuuuuau u                                                21

<210> SEQ ID NO 33
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
aauaaaaaga aggagcuuaa uug                                              23

<210> SEQ ID NO 34
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gaauauguca cuugaacuca a                                                21
```

```
<210> SEQ ID NO 35
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
uugaguucaa gugacauauu cuu                                              23

<210> SEQ ID NO 36
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
caacauauuu gaucagucuu u                                                21

<210> SEQ ID NO 37
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
aaagacugau caaauauguu gag                                              23

<210> SEQ ID NO 38
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
cuccauagug aagcaaucua a                                                21

<210> SEQ ID NO 39
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
uuagauugcu ucacuaugga gua                                              23

<210> SEQ ID NO 40
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 40
acauauuuga ucagucuuuu u                                              21

<210> SEQ ID NO 41
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
aaaaagacug aucaaauaug uug                                            23

<210> SEQ ID NO 42
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ugucacuuga acucaacuca a                                              21

<210> SEQ ID NO 43
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
uugaguugag uucaagugac aua                                            23

<210> SEQ ID NO 44
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
gaauauguca cuugaacuca a                                              21

<210> SEQ ID NO 45
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 45
utgaguucaa gtgacauauu cuu                                            23
```

```
<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 46
gaauatguga cuugaacuca a                                              21

<210> SEQ ID NO 47
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
uugaguucaa gugacauauu cuu                                            23

<210> SEQ ID NO 48
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 48
auuaagcugc uucuuutuau u                                              21

<210> SEQ ID NO 49
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
aauaaaaaga aggagcuuaa uug                                            23

<210> SEQ ID NO 50
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
acauauuuga ucagucuuuu u                                              21

<210> SEQ ID NO 51
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
aaaaagacug aucaaauaug uug                                              23

<210> SEQ ID NO 52
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ugucacuuga acucaacuca a                                                21

<210> SEQ ID NO 53
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
uugaguugag uucaagugac aua                                              23

<210> SEQ ID NO 54
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
aacuaacuaa cuuaauucaa a                                                21

<210> SEQ ID NO 55
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
uuugaauuaa guuaguuagu ugc                                              23

<210> SEQ ID NO 56
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
```
ucacaauuaa gcuccuucuu u                                      21

<210> SEQ ID NO 57
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
aaagaaggag cuuaauugug aac                                    23

<210> SEQ ID NO 58
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gagcaacuaa cuaacuuaau u                                      21

<210> SEQ ID NO 59
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
aauuaaguua guuaguugcu cuu                                    23

<210> SEQ ID NO 60
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
uuauuguucc ucuaguuauu u                                      21

<210> SEQ ID NO 61
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
aaauaacuag aggaacaaua aaa                                    23

<210> SEQ ID NO 62
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 62
auuaagcucc uucuuuuuau u                                              21

<210> SEQ ID NO 63
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
aauaaaaaga aggagcuuaa uug                                            23

<210> SEQ ID NO 64
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gaauauguca cuugaacuca a                                              21

<210> SEQ ID NO 65
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
uugaguucaa gugacauauu cuu                                            23

<210> SEQ ID NO 66
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
caacauauuu gaucagucuu u                                              21

<210> SEQ ID NO 67
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
aaagacugau caaauauguu gag                                            23
```

```
<210> SEQ ID NO 68
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
cuccauagug aagcaaucua a                                          21

<210> SEQ ID NO 69
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
uuagauugcu ucacuaugga gua                                        23

<210> SEQ ID NO 70
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
acauauuuga ucagucuuuu u                                          21

<210> SEQ ID NO 71
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
aaaaagacug aucaaauaug uug                                        23

<210> SEQ ID NO 72
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
acauauuuga ucagucuuuu u                                          21

<210> SEQ ID NO 73
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 73
aaaaagacug aucaaauaug uug                                                    23

<210> SEQ ID NO 74
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
acauauuuga ucagucuuuu u                                                      21

<210> SEQ ID NO 75
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
acauauuuga ucagucuuuu u                                                      21

<210> SEQ ID NO 76
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 76
acauauuuga tcagucuuuu u                                                      21

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
acauauuuga ucagucuuuu u                                                      21

<210> SEQ ID NO 78
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
acauauuuga ucagucuuuu u                                                      21
```

```
<210> SEQ ID NO 79
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Inverted abasic DNA (2-hydroxymethyl-
      tetrahydrofurane-5-phosphate)

<400> SEQUENCE: 79
nacauauuug aucagucuuu uu                                                  22

<210> SEQ ID NO 80
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 80
acauauuuga ucagucuutu u                                                   21

<210> SEQ ID NO 81
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 81
acauauuuga tcagucuuuu u                                                   21

<210> SEQ ID NO 82
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
acauauuuga ucagucuuuu u                                                   21

<210> SEQ ID NO 83
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
```
acauauuuga ucagucuuuu u     21

<210> SEQ ID NO 84
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
acauauuuga ucagucuuuu u     21

<210> SEQ ID NO 85
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 85
acauauuuga ucaguctuuu u     21

<210> SEQ ID NO 86
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 86
acauauuuga tcaguctuuu u     21

<210> SEQ ID NO 87
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
acauauuuga ucagucuuuu u     21

<210> SEQ ID NO 88
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA

```
         Molecule: Synthetic oligonucleotide"

<400> SEQUENCE: 88
acauauuuga ucagucuutu u                                          21

<210> SEQ ID NO 89
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(1)
<223> OTHER INFORMATION: Inverted abasic DNA (2-hydroxymethyl-
      tetrahydrofurane-5-phosphate)

<400> SEQUENCE: 89
nacauauuug aucagucuuu uu                                         22

<210> SEQ ID NO 90
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 90
acauauuuga tcagucuuuu u                                          21

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
acauauuuga ucagucuuuu u                                          21

<210> SEQ ID NO 92
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
acauauuuga ucagucuuuu u                                          21

<210> SEQ ID NO 93
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 93
acauauuuga ucaguctuuu u                                                   21

<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
auauuugauc agucuuuuu                                                      19

<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
acauauuuga ucagucuuuu u                                                   21

<210> SEQ ID NO 96
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 96
acauauuuga ucagucuutu u                                                   21

<210> SEQ ID NO 97
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
acauauuuga ucagucuuuu u                                                   21

<210> SEQ ID NO 98
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 98
acauauuuga ucagucuuuu u                                              21

<210> SEQ ID NO 99
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 99
acauauuuga tcagucuuuu u                                              21

<210> SEQ ID NO 100
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
acauauuuga ucagucuuuu u                                              21

<210> SEQ ID NO 101
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 101
acauauuuga ucaguctuuu u                                              21

<210> SEQ ID NO 102
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
acauauuuga ucagucuuuu u                                              21

<210> SEQ ID NO 103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 103
acauauuuga ucagucuuuu u                                              21

<210> SEQ ID NO 104
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 104
acauauuuga ucagucuutu u                                              21

<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
acauauuuga ucagucuuuu u                                              21

<210> SEQ ID NO 106
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 106
acauauuuga ucagucuuuu u                                              21

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
acauauuuga ucagucuuuu u                                              21

<210> SEQ ID NO 108
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
```
acauauuuga ucagucuuuu u                                    21

<210> SEQ ID NO 109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 109
acauauuuga ucaguctuuu u                                    21

<210> SEQ ID NO 110
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
acauauuuga ucagucuuuu u                                    21

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
acauauuuga ucagucuuuu u                                    21

<210> SEQ ID NO 112
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 112
acauauuuga ucagucuuuu u                                    21

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
acauauuuga ucagucuuuu u					21

<210> SEQ ID NO 114
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
acauauuuga ucagucuuuu u					21

<210> SEQ ID NO 115
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 115
acauauuuga ucagucuuuu u					21

<210> SEQ ID NO 116
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
acauauuuga ucagucuuuu u					21

<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
acauauuuga ucagucuuuu u					21

<210> SEQ ID NO 118
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
acauauuuga ucagucuuuu u					21

<210> SEQ ID NO 119
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
acauauuuga ucagucuuuu u                                             21

<210> SEQ ID NO 120
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
acauauuuga ucagucuuuu u                                             21

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
acauauuuga ucagucuuuu u                                             21

<210> SEQ ID NO 122
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
acauauuuga ucagucuuuu u                                             21

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
acauauuuga ucagucuuuu u                                             21

<210> SEQ ID NO 124
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
```
acauauuuga ucagucuuuu u                                        21

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
acauauuuga ucagucuuuu u                                        21

<210> SEQ ID NO 126
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
acauauuuga ucagucuuuu u                                        21

<210> SEQ ID NO 127
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 127
acauauuuga tcaguctuuu u                                        21

<210> SEQ ID NO 128
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
acauauuuga ucagucuuuu u                                        21

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
acauauuuga ucagucuuuu u                                        21

<210> SEQ ID NO 130
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
acauauuuga ucagucuuuu u                                              21

<210> SEQ ID NO 131
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 131
acauauuuga tcagucauuu u                                              21

<210> SEQ ID NO 132
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
acauauuuga ucagucuuuu u                                              21

<210> SEQ ID NO 133
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 133
acauauuuga tcaguctuuu u                                              21

<210> SEQ ID NO 134
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
acauauuuga ucagucuuuu u                                              21

<210> SEQ ID NO 135
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
acauauuuga ucagucuuuu u                                              21

<210> SEQ ID NO 136
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 136
acauauuuga tcagucauuu u                                              21

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
acauauuuga ucagucuuuu u                                              21

<210> SEQ ID NO 138
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 138
acauauuuga tcaguccuuu u                                              21

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
acauauuuga ucagucuuuu u                                              21

<210> SEQ ID NO 140
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 140
acauauuuga ucagucuuuu u                                                  21

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
acauauuuga ucagucuuuu u                                                  21

<210> SEQ ID NO 142
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 142
acauauuuga tcagucauuu u                                                  21

<210> SEQ ID NO 143
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 143
acauauuuua tcagucuuuu u                                                  21

<210> SEQ ID NO 144
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 144
acauauuuga tcagucguuu u                                                  21

<210> SEQ ID NO 145
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
acauauuuga ucagucuuuu u                                              21

<210> SEQ ID NO 146
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
acauauuuga ucagucuuuu u                                              21

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
acauauuuga ucagucuuuu u                                              21

<210> SEQ ID NO 148
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 148
acauauuuga ucaguctuuu u                                              21

<210> SEQ ID NO 149
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 149
acauauuuga tcagucuuuu u                                              21

<210> SEQ ID NO 150
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 150
acauauuuga tcaguccuuu u                                              21

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
acauauuuga ucagucuuuu u                                              21

<210> SEQ ID NO 152
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
acauauuuga ucagucuuuu u                                              21

<210> SEQ ID NO 153
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 153
acauauuuga tcaguctuuu u                                              21

<210> SEQ ID NO 154
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 154
acauauuuga ucaguctuuu u                                              21
```

<210> SEQ ID NO 155
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 155
acauauuuga tcagucauuu u                                              21

<210> SEQ ID NO 156
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
acauauuuga ucagucuuuu u                                              21

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
acauauuuga ucagucuuuu u                                              21

<210> SEQ ID NO 158
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 158
acauauuuga tcaguctuuu u                                              21

<210> SEQ ID NO 159
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 159
acauauuuga ucaguctuuu u                                          21

<210> SEQ ID NO 160
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 160
acauauuuga tcagucutuu u                                          21

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
acauauuuga ucagucuuuu u                                          21

<210> SEQ ID NO 162
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
acauauuuga ucagucuuuu u                                          21

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
acauauuuga ucagucuuuu u                                          21

<210> SEQ ID NO 164
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 164
acauauuuga tcaguctuuu u                                          21

<210> SEQ ID NO 165
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 165
acauauuuga ucaguctuuu u                                          21

<210> SEQ ID NO 166
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
acauauuuga ucagucuuuu u                                          21

<210> SEQ ID NO 167
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
acauauuuga ucagucuuuu u                                          21

<210> SEQ ID NO 168
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
acauauuuga ucagucuuuu u                                          21

<210> SEQ ID NO 169
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 169
acauauuuga tcaguctuuu u                                          21

```
<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
aaaaagacug aucaaauaug uug                                           23

<210> SEQ ID NO 171
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
aaaaagacug aucaaauaug uug                                           23

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
aaaaagacug aucaaauaug uug                                           23

<210> SEQ ID NO 173
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
aaaaagacug aucaaauaug uug                                           23

<210> SEQ ID NO 174
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
aaaaagacug aucaaauaug uug                                           23

<210> SEQ ID NO 175
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 175
aaaaagacug aucaaauaug uug                                              23

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
aaaaagacug aucaaauaug uug                                              23

<210> SEQ ID NO 177
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
aaaaagacug aucaaauaug uug                                              23

<210> SEQ ID NO 178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
aaaaagacug aucaaauaug uug                                              23

<210> SEQ ID NO 179
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
aaaaagacug aucaaauaug uug                                              23

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
aaaaagacug aucaaauaug uug                                              23

<210> SEQ ID NO 181
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
aaaaagacug aucaaauaug uug                                              23

<210> SEQ ID NO 182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
aaaaagacug aucaaauaug uug                                              23

<210> SEQ ID NO 183
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
aaaaagacug aucaaauaug uug                                              23

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
aaaaagacug aucaaauaug uug                                              23

<210> SEQ ID NO 185
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
aaaaagacug aucaaauaug uug                                              23

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
```
aaaaagacug aucaaauaug uug 23

<210> SEQ ID NO 187
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
aaaaagacug aucaaauaug uug 23

<210> SEQ ID NO 188
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
aaaaagacug aucaaauaug uug 23

<210> SEQ ID NO 189
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aaaaagacug aucaaauaug uug 23

<210> SEQ ID NO 190
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
aaaaagacug aucaaauaug u 21

<210> SEQ ID NO 191
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
aaaaagacug aucaaauaug uug 23

<210> SEQ ID NO 192
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 192
aaaaagacug aucaaauaug uug                                                23

<210> SEQ ID NO 193
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
aaaaagacug aucaaauaug uug                                                23

<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
aaaaagacug aucaaauaug uug                                                23

<210> SEQ ID NO 195
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
aaaaagacug aucaaauaug uug                                                23

<210> SEQ ID NO 196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
aaaaagacug aucaaauaug uug                                                23

<210> SEQ ID NO 197
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
aaaaagacug aucaaauaug uug                                                23

<210> SEQ ID NO 198
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
aaaaagacug aucaaauaug uug                                              23

<210> SEQ ID NO 199
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
aaaaagacug aucaaauaug uug                                              23

<210> SEQ ID NO 200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
aaaaagacug aucaaauaug uug                                              23

<210> SEQ ID NO 201
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
aaaaagacug aucaaauaug uug                                              23

<210> SEQ ID NO 202
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
aaaaagacug aucaaauaug uug                                              23

<210> SEQ ID NO 203
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
```
aaaaagacug aucaaauaug uug                                        23

<210> SEQ ID NO 204
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
aaaaagacug aucaaauaug uug                                        23

<210> SEQ ID NO 205
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
aaaaagacug aucaaauaug uug                                        23

<210> SEQ ID NO 206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
aaaaagacug aucaaauaug uug                                        23

<210> SEQ ID NO 207
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
aaaaagacug aucaaauaug uug                                        23

<210> SEQ ID NO 208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
aaaaagacug aucaaauaug uug                                        23

<210> SEQ ID NO 209
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 209
aaaaagacug aucaaauaug uug                                              23

<210> SEQ ID NO 210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
aaaaagacug aucaaauaug uug                                              23

<210> SEQ ID NO 211
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
aaaaagacug aucaaauaug uug                                              23

<210> SEQ ID NO 212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
aaaaagacug aucaaauaug uug                                              23

<210> SEQ ID NO 213
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
aaaaagacug aucaaauaug uug                                              23

<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
aaaaagacug aucaaauaug uug                                              23
```

```
<210> SEQ ID NO 215
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
aaaaagacug aucaaauaug uug                                              23

<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
aaaaagacug aucaaauaug uug                                              23

<210> SEQ ID NO 217
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
aaaaagacug aucaaauaug uug                                              23

<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
aaaaagacug aucaaauaug uug                                              23

<210> SEQ ID NO 219
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
aaaaagacug aucaaauaug uug                                              23

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 220
aaaaagacug aucaaauaug uug                                      23

<210> SEQ ID NO 221
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
aaaaagacug aucaaauaug uug                                      23

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
aaaaagacug aucaaauaug uug                                      23

<210> SEQ ID NO 223
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
aaaaagacug aucaaauaug uug                                      23

<210> SEQ ID NO 224
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
aaaaagacug aucaaauaug uug                                      23

<210> SEQ ID NO 225
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 225
aaaaagacug aucaaauaug uug                                      23
```

```
<210> SEQ ID NO 226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
aaaaagacug aucaaauaug uug                                              23

<210> SEQ ID NO 227
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 227
aaaaagacug aucaaauaug uug                                              23

<210> SEQ ID NO 228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
aaaaagacug aucaaauaug uug                                              23

<210> SEQ ID NO 229
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
aaaaagacug aucaaauaug uug                                              23

<210> SEQ ID NO 230
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 230
aaaaagacug aucaaauaug uug                                              23

<210> SEQ ID NO 231
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
aaaaagacug aucaaauaug uug                                                23

<210> SEQ ID NO 232
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 232
aaaaagacug aucaaauaug uug                                                23

<210> SEQ ID NO 233
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
aaaaagacug aucaaauaug uug                                                23

<210> SEQ ID NO 234
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
aaaaagacug aucaaauaug uug                                                23

<210> SEQ ID NO 235
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
aaaaagacug aucaaauaug uug                                                23

<210> SEQ ID NO 236
<211> LENGTH: 23
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 236
aaaaagacug aucaaauaug uug                                            23

<210> SEQ ID NO 237
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
aaaaagacug aucaaauaug uug                                            23

<210> SEQ ID NO 238
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 238
aaaaagacug aucaaauaug uug                                            23

<210> SEQ ID NO 239
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
aaaaagacug aucaaauaug uug                                            23

<210> SEQ ID NO 240
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
aaaaagacug aucaaauaug uug                                            23

<210> SEQ ID NO 241
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

```
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 241
aaaaagacug aucaaauaug uug                                              23

<210> SEQ ID NO 242
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 242
aaaaagacug aucaaauaug uug                                              23

<210> SEQ ID NO 243
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 243
aaaaagacug aucaaauaug uug                                              23

<210> SEQ ID NO 244
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
        Synthetic oligonucleotide"
<220> FEATURE:
<221> NAME/KEY: source
<223> OTHER INFORMATION: /note="Description of Combined DNA/RNA
        Molecule: Synthetic oligonucleotide"

<400> SEQUENCE: 244
aaaaagacug aucaaauaug uug                                              23

<210> SEQ ID NO 245
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 245
aaaaagacug aucaaauaug uug                                              23

<210> SEQ ID NO 246
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 246
aaaaagacug aucaaauaug uug                                          23

<210> SEQ ID NO 247
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 247
aaaaagacug aucaaauaug uug                                          23

<210> SEQ ID NO 248
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 248
aaaaagacug aucaaauaug uug                                          23

<210> SEQ ID NO 249
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 249
aaaaagacug aucaaauaug uug                                          23

<210> SEQ ID NO 250
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 250
```

```
aaaaagacug aucaaauaug uug                                              23
```

<210> SEQ ID NO 251
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251

```
aaaaagacug aucaaauaug uug                                              23
```

<210> SEQ ID NO 252
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 252

```
aaaaagacug aucaaauaug uug                                              23
```

<210> SEQ ID NO 253
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 253

```
aaaaagacug aucaaauaug uug                                              23
```

<210> SEQ ID NO 254
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 254

```
aaaaagacug aucaaauaug uug                                              23
```

<210> SEQ ID NO 255
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<220> FEATURE:
<221> NAME/KEY: source
<223> OTHER INFORMATION: /note="Description of Combined DNA/RNA
      Molecule: Synthetic oligonucleotide"

<400> SEQUENCE: 255
aaaaagacug aucaaauaug uug                                              23

<210> SEQ ID NO 256
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
aaaaagacug aucaaauaug uug                                              23

<210> SEQ ID NO 257
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
aaaaagacug aucaaauaug uug                                              23

<210> SEQ ID NO 258
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 258
aaaaagacug aucaaauaug uug                                              23

<210> SEQ ID NO 259
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 259
aaaaagacug aucaaauaug uug                                              23

<210> SEQ ID NO 260
<211> LENGTH: 23
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 260
aaaaagacug aucaaauaug uug                                               23

<210> SEQ ID NO 261
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
aaaaagacug aucaaauaug uug                                               23

<210> SEQ ID NO 262
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
aaaaagacug aucaaauaug uug                                               23

<210> SEQ ID NO 263
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 263
aaaaagacug aucaaauaug uug                                               23

<210> SEQ ID NO 264
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 264
aaaaagacug aucaaauaug uug                                               23

<210> SEQ ID NO 265
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 265
aaaaagacug aucaaauaug uug                                            23

<210> SEQ ID NO 266
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
ugucacuuga acucaacuca a                                              21

<210> SEQ ID NO 267
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
aacuaacuaa cuuaauucaa a                                              21

<210> SEQ ID NO 268
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
ucacaauuaa gcuccuucuu u                                              21

<210> SEQ ID NO 269
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
gagcaacuaa cuaacuuaau u                                              21

<210> SEQ ID NO 270
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 270
uuauuguucc ucaguuauu u                                      21

<210> SEQ ID NO 271
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
auuaagcucc uucuuuuau u                                      21

<210> SEQ ID NO 272
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
ugucacuuga acucaacuca a                                     21

<210> SEQ ID NO 273
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
gaauauguca cuugaacuca a                                     21

<210> SEQ ID NO 274
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
acauauuuga ucagucuuuu u                                     21

<210> SEQ ID NO 275
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
caacauauuu gaucagucuu u                                     21

<210> SEQ ID NO 276
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
cuccauagug aagcaaucua a                                            21

<210> SEQ ID NO 277
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
acauauuuga ucagucuuuu u                                            21

<210> SEQ ID NO 278
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
uugaguugag uucaagugac aua                                          23

<210> SEQ ID NO 279
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
uuugaauuaa guuaguuagu ugc                                          23

<210> SEQ ID NO 280
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
aaagaaggag cuuaauugug aac                                          23

<210> SEQ ID NO 281
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
```
aauuaaguua guuaguugcu cuu                                                23

<210> SEQ ID NO 282
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
aaauaacuag aggaacaaua aaa                                                23

<210> SEQ ID NO 283
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
aauaaaaaga aggagcuuaa uug                                                23

<210> SEQ ID NO 284
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
uugaguugag uucaagugac aua                                                23

<210> SEQ ID NO 285
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
uugaguucaa gugacauauu cuu                                                23

<210> SEQ ID NO 286
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
aaaaagacug aucaaauaug uug                                                23

<210> SEQ ID NO 287
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 287
aaagacugau caaauauguu gag                                          23

<210> SEQ ID NO 288
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
uuagauugcu ucacuaugga gua                                          23

<210> SEQ ID NO 289
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
aaaaagacug aucaaauaug uug                                          23

<210> SEQ ID NO 290
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
ugucacuuga acucaacuca a                                            21

<210> SEQ ID NO 291
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
aacuaacuaa cuuaauucaa a                                            21

<210> SEQ ID NO 292
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
ucacaauuaa gcuccuucuu u                                            21

<210> SEQ ID NO 293
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
gagcaacuaa cuaacuuaau u                                              21

<210> SEQ ID NO 294
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
uuauuguucc ucuaguuauu u                                              21

<210> SEQ ID NO 295
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
auuaagcucc uucuuuuau u                                               21

<210> SEQ ID NO 296
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296 ugcacuuga acucaacuca a                                               21

<210> SEQ ID NO 297
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
gaauauguca cuugaacuca a                                              21

<210> SEQ ID NO 298
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
```

```
acauauuuga ucagucuuuu u                                              21

<210> SEQ ID NO 299
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
caacauauuu gaucagucuu u                                              21

<210> SEQ ID NO 300
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
cuccauagug aagcaaucua a                                              21

<210> SEQ ID NO 301
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
acauauuuga ucagucuuuu u                                              21

<210> SEQ ID NO 302
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
uugaguugag uucaagugac aua                                            23

<210> SEQ ID NO 303
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
uuugaauuaa guuaguuagu ugc                                            23

<210> SEQ ID NO 304
<211> LENGTH: 23
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 304
aaagaaggag cuuaauugug aac                                        23

<210> SEQ ID NO 305
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
aauuaaguua guuaguugcu cuu                                        23

<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
aaauaacuag aggaacaaua aaa                                        23

<210> SEQ ID NO 307
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
aauaaaaaga aggagcuuaa uug                                        23

<210> SEQ ID NO 308
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
uugaguugag uucaagugac aua                                        23

<210> SEQ ID NO 309
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
uugaguucaa gugacauauu cuu                                        23
```

```
<210> SEQ ID NO 310
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
aaaaagacug aucaaauaug uug                                              23

<210> SEQ ID NO 311
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
aaagacugau caaauauguu gag                                              23

<210> SEQ ID NO 312
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
uuagauugcu ucacuaugga gua                                              23

<210> SEQ ID NO 313
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
aaaaagacug aucaaauaug uug                                              23

<210> SEQ ID NO 314
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 314
gaauatguga cuugaacuca a                                                21

<210> SEQ ID NO 315
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 315
gaauatguga cuugaacuca a                                              21

<210> SEQ ID NO 316
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
gaauauguca cuugaacuca a                                              21

<210> SEQ ID NO 317
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 317
gaauatguga cuugaacuca a                                              21

<210> SEQ ID NO 318
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gaauauguca cuugaacuca a                                              21

<210> SEQ ID NO 319
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 319
auuaagcugc uucuuutuau u                                              21

<210> SEQ ID NO 320
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 320
auuaagcugc uucuuutuau u                                              21

<210> SEQ ID NO 321
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
auuaagcucc uucuuuuuau u                                              21

<210> SEQ ID NO 322
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
auuaagcucc uucuuuuuau u                                              21

<210> SEQ ID NO 323
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 323
acauatuuca ucaguctuuu u                                              21

<210> SEQ ID NO 324
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 324
ugucacuuca acucaacuca a                                              21
```

```
<210> SEQ ID NO 325
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 325
ugucacuuca acucaacuca a                                              21

<210> SEQ ID NO 326
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
ugucacuuga acucaacuca a                                              21

<210> SEQ ID NO 327
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 327
aacuaacuua cuuaautcaa a                                              21

<210> SEQ ID NO 328
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 328
aacuaacuua cuuaautcaa a                                              21

<210> SEQ ID NO 329
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
```
aacuaacuaa cuuaauucaa a                                              21

<210> SEQ ID NO 330
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
cuccauagug aagcaaucua a                                              21

<210> SEQ ID NO 331
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 331
cuccatagag aagcaatcua a                                              21

<210> SEQ ID NO 332
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
acauauuuga ucagucuuuu u                                              21

<210> SEQ ID NO 333
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
acauauuuga ucagucuuuu u                                              21

<210> SEQ ID NO 334
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 334
acauauuuca ucagucuuuu u                               21

<210> SEQ ID NO 335
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 335
utgaguucaa gtgacauauu cuu                             23

<210> SEQ ID NO 336
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 336
uugaguucaa gtgacauauu cuu                             23

<210> SEQ ID NO 337
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 337
utgaguucaa gtgacauauu cuu                             23

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
uugaguucaa gugacauauu cuu                             23

<210> SEQ ID NO 339
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 339
uugaguucaa gugacauauu cuu                                          23

<210> SEQ ID NO 340
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 340
aauaaaaaga aggagcuuaa uug                                          23

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
aauaaaaaga aggagcuuaa uug                                          23

<210> SEQ ID NO 342
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 342
aauaaaaaga aggagcuuaa uug                                          23

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
aauaaaaaga aggagcuuaa uug                                          23

<210> SEQ ID NO 344
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<220> FEATURE:
<221> NAME/KEY: source
<223> OTHER INFORMATION: /note="Description of Combined DNA/RNA
      Molecule: Synthetic oligonucleotide"

<400> SEQUENCE: 344
aaaaagacug atcaaauaug uug                                          23

<210> SEQ ID NO 345
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 345
utgaguugag utcaagugac aua                                          23

<210> SEQ ID NO 346
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 346
uugaguugag utcaagugac aua                                          23

<210> SEQ ID NO 347
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
uugaguugag uucaagugac aua                                          23

<210> SEQ ID NO 348
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 348
utugaauuaa gtuaguuagu ugc                                          23

<210> SEQ ID NO 349
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 349
utugaauuaa gtaaguuagu ugc                                              23

<210> SEQ ID NO 350
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
uuugaauuaa guuaguuagu ugc                                              23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
uuagauugcu ucacuaugga gua                                              23

<210> SEQ ID NO 352
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 352
utagauugcu ucacuaugga gua                                              23

<210> SEQ ID NO 353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
aaaaagacug aucaaauaug uug                                              23

<210> SEQ ID NO 354
<211> LENGTH: 23
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 354
aaaaagacug atcaaauaug uug                                          23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
aaaaagacug aucaaauaug uug                                          23

<210> SEQ ID NO 356
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 356
gaauatguga cuugaacuca a                                            21

<210> SEQ ID NO 357
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 357
gaauatguga cuugaacuca a                                            21

<210> SEQ ID NO 358
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
gaauauguca cuugaacuca a                                            21
```

```
<210> SEQ ID NO 359
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 359
gaauatguga cuugaacuca a                                              21

<210> SEQ ID NO 360
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
gaauauguca cuugaacuca a                                              21

<210> SEQ ID NO 361
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 361
auuaagcugc uucuuutuau u                                              21

<210> SEQ ID NO 362
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 362
auuaagcugc uucuuutuau u                                              21

<210> SEQ ID NO 363
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
```
auuaagcucc uucuuuuuau u                                               21

<210> SEQ ID NO 364
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
auuaagcucc uucuuuuuau u                                               21

<210> SEQ ID NO 365
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 365
acauauuuca ucagucuuuu u                                               21

<210> SEQ ID NO 366
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
ugucacuuca acucaacuca a                                               21

<210> SEQ ID NO 367
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
ugucacuuca acucaacuca a                                               21

<210> SEQ ID NO 368
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
ugucacuuga acucaacuca a                                               21

<210> SEQ ID NO 369
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 369
aacuaacuua cuuaautcaa a                                            21

<210> SEQ ID NO 370
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 370
aacuaacuua cuuaautcaa a                                            21

<210> SEQ ID NO 371
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
aacuaacuaa cuuaauucaa a                                            21

<210> SEQ ID NO 372
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
cuccauagug aagcaaucua a                                            21

<210> SEQ ID NO 373
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 373
cuccatagag aagcaatcua a                                            21
```

```
<210> SEQ ID NO 374
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
acauauuuga ucagucuuuu u                                              21

<210> SEQ ID NO 375
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
acauauuuga ucagucuuuu u                                              21

<210> SEQ ID NO 376
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 376
acauatuuca ucaguctuuu u                                              21

<210> SEQ ID NO 377
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 377
utgaguucaa gtgacauauu cuu                                            23

<210> SEQ ID NO 378
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 378
```

```
uugaguucaa gtgacauauu cuu                                          23
```

<210> SEQ ID NO 379
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 379

```
utgaguucaa gtgacauauu cuu                                          23
```

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380

```
uugaguucaa gugacauauu cuu                                          23
```

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381

```
uugaguucaa gugacauauu cuu                                          23
```

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382

```
aauaaaaaga aggagcuuaa uug                                          23
```

<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383

```
aauaaaaaga aggagcuuaa uug                                          23
```

<210> SEQ ID NO 384

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
aauaaaaaga aggagcuuaa uug                                             23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
aauaaaaaga aggagcuuaa uug                                             23

<210> SEQ ID NO 386
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 386
aaaaagacug atcaaauaug uug                                             23

<210> SEQ ID NO 387
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 387
utgaguugag utcaagugac aua                                             23

<210> SEQ ID NO 388
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 388
uugaguugag utcaagugac aua                                             23
```

<210> SEQ ID NO 389
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
uugaguugag uucaagugac aua                                              23

<210> SEQ ID NO 390
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 390
utugaauuaa gtaguuagu ugc                                               23

<210> SEQ ID NO 391
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 391
utugaauuaa gtaguuagu ugc                                               23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
uuugaauuaa guaguuagu ugc                                               23

<210> SEQ ID NO 393
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
uuagauugcu ucacuaugga gua                                              23

<210> SEQ ID NO 394
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 394
utagauugcu ucacuaugga gua                                        23

<210> SEQ ID NO 395
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 395
aaaaagacug aucaaauaug uug                                        23

<210> SEQ ID NO 396
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 396
aaaaagacug atcaaauaug uug                                        23

<210> SEQ ID NO 397
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 397
aaaaagacug aucaaauaug uug                                        23

<210> SEQ ID NO 398
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 398
gaauauguga cuugaacuca a 21

<210> SEQ ID NO 399
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 399
gaauatguga cuugaacuca a 21

<210> SEQ ID NO 400
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
gaauauguca cuugaacuca a 21

<210> SEQ ID NO 401
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 401
gaauatguga cuugaacuca a 21

<210> SEQ ID NO 402
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
gaauauguca cuugaacuca a 21

<210> SEQ ID NO 403
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 403
auuaagcugc uucuuutuau u                                              21

<210> SEQ ID NO 404
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 404
auuaagcugc uucuuutuau u                                              21

<210> SEQ ID NO 405
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
auuaagcucc uucuuuuuau u                                              21

<210> SEQ ID NO 406
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
auuaagcucc uucuuuuuau u                                              21

<210> SEQ ID NO 407
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 407
acauauuuca ucaguctuuu u                                              21

<210> SEQ ID NO 408
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 408
utgaguucaa gtgacauauu cuu                                          23

<210> SEQ ID NO 409
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 409
uugaguucaa gtgacauauu cuu                                          23

<210> SEQ ID NO 410
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 410
utgaguucaa gtgacauauu cuu                                          23

<210> SEQ ID NO 411
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
uugaguucaa gugacauauu cuu                                          23

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
uugaguucaa gugacauauu cuu                                          23

<210> SEQ ID NO 413
<211> LENGTH: 23
<212> TYPE: DNA
<213> ORGANISM: Artificial Sequence
<220> FEATURE:
```

-continued

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 413
aauaaaaaga aggagcuuaa uug                                           23

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
aauaaaaaga aggagcuuaa uug                                           23

<210> SEQ ID NO 415
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 415
aauaaaaaga aggagcuuaa uug                                           23

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
aauaaaaaga aggagcuuaa uug                                           23

<210> SEQ ID NO 417
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 417
aaaaagacug atcaaauaug uug                                           23

<210> SEQ ID NO 418
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 418 ugcacuuca acucaacuca a                                             21

<210> SEQ ID NO 419
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 419
ugucacuuca acucaacuca a                                            21

<210> SEQ ID NO 420
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
ugucacuuga acucaacuca a                                            21

<210> SEQ ID NO 421
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 421
aacuaacuua cuuaautcaa a                                            21

<210> SEQ ID NO 422
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 422
aacuaacuua cuuaautcaa a                                              21

<210> SEQ ID NO 423
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
aacuaacuaa cuuaauucaa a                                              21

<210> SEQ ID NO 424
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
cuccauagug aagcaaucua a                                              21

<210> SEQ ID NO 425
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 425
cuccatagag aagcaatcua a                                              21

<210> SEQ ID NO 426
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
acauauuuga ucagucuuuu u                                              21

<210> SEQ ID NO 427
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
acauauuuga ucagucuuuu u                                              21
```

```
<210> SEQ ID NO 428
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 428
acauatuuca ucaguctuuu u                                              21

<210> SEQ ID NO 429
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 429
acauatuuca ucaguctuuu u                                              21

<210> SEQ ID NO 430
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 430
utgaguugag utcaagugac aua                                            23

<210> SEQ ID NO 431
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 431
uugaguugag utcaagugac aua                                            23

<210> SEQ ID NO 432
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 432
uugaguugag uucaagugac aua                                             23

<210> SEQ ID NO 433
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 433
utugaauuaa gtaguuagu ugc                                              23

<210> SEQ ID NO 434
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 434
utugaauuaa gtaguuagu ugc                                              23

<210> SEQ ID NO 435
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
uuugaauuaa guaguuagu ugc                                              23

<210> SEQ ID NO 436
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
uuagauugcu ucacuaugga gua                                             23

<210> SEQ ID NO 437
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 437
utagauugcu ucacuaugga gua                                          23

<210> SEQ ID NO 438
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
aaaaagacug aucaaauaug uug                                          23

<210> SEQ ID NO 439
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 439
aaaaagacug atcaaauaug uug                                          23

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
aaaaagacug aucaaauaug uug                                          23

<210> SEQ ID NO 441
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 441
aaaaagacug atcaaauaug uug                                          23

<210> SEQ ID NO 442
<211> LENGTH: 21
<212> TYPE: RNA
<213> ORGANISM: Artificial Sequence
<220> FEATURE:
```

-continued

<221> NAME/KEY: source
<223> OTHER INFORMATION: /note="Description of Artificial Sequence:
      Synthetic oligonucleotide"

<400> SEQUENCE: 442
auuaagcucc uucuuuuuau u                                                 21

<210> SEQ ID NO 443
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
auuaagcucc uucuuuuuau a                                                 21

<210> SEQ ID NO 444
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
auuaagcucc uucuuuuuau u                                                 21

<210> SEQ ID NO 445
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
auuaagcucc uucuuuuuau u                                                 21

<210> SEQ ID NO 446
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 446
auuaagcucc uucuuutuau u                                                 21

<210> SEQ ID NO 447
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447

-continued auuaagcucc uucuauauau u                                          21

<210> SEQ ID NO 448
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
acauauuuga ucagucuuuu u                                          21

<210> SEQ ID NO 449
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
acauauuuga ucagucuuuu a                                          21

<210> SEQ ID NO 450
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
acauauuuga ucagucuuuu u                                          21

<210> SEQ ID NO 451
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
acauauuuga ucagucuuuu u                                          21

<210> SEQ ID NO 452
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 452
acauauuuga ucaguctuuu u                                          21

<210> SEQ ID NO 453

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
acauauuuga ucagacauuu u                                              21

<210> SEQ ID NO 454
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
aauaaaaaga aggagcuuaa uug                                            23

<210> SEQ ID NO 455
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 455
tauaaaaaga aggagcuuaa uug                                            23

<210> SEQ ID NO 456
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
aauaaaaaga aggagcuuaa uug                                            23

<210> SEQ ID NO 457
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 457
aauaaaaaga aggagcuuaa uug                                            23

<210> SEQ ID NO 458
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
aauaaaaaga aggagcuuaa uug                                              23

<210> SEQ ID NO 459
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
aauaaaaaga aggagcuuaa uug                                              23

<210> SEQ ID NO 460
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
aaaaagacug aucaaauaug uug                                              23

<210> SEQ ID NO 461
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 461
taaaagacug aucaaauaug uug                                              23

<210> SEQ ID NO 462
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
aaaaagacug aucaaauaug uug                                              23

<210> SEQ ID NO 463
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

```
                              Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 463
aaaaagacug atcaaauaug uug                                              23

<210> SEQ ID NO 464
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
aaaaagacug aucaaauaug uug                                              23

<210> SEQ ID NO 465
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
aaaaagacug aucaaauaug uug                                              23

<210> SEQ ID NO 466
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
aacuaacuaa cuuaauucaa a                                                21

<210> SEQ ID NO 467
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
gaauauguca cuugaacuca a                                                21

<210> SEQ ID NO 468
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
aaacucuaaa cuugacuaaa u                                                21
```

<210> SEQ ID NO 469
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 469
aacuaacuua auucaaaauc a                                              21

<210> SEQ ID NO 470
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 470
ccagaaguaa cuucacuuaa a                                              21

<210> SEQ ID NO 471
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 471
gaacucaacu caaaacuuga a                                              21

<210> SEQ ID NO 472
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 472
caacucaaaa cuugaaagcc u                                              21

<210> SEQ ID NO 473
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 473
uuccacguug cuugaaauug a                                              21

<210> SEQ ID NO 474
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 474
guugcuugaa auugaaaauc a                                           21

<210> SEQ ID NO 475
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 475
gaucacaaaa cuucaaugaa a                                           21

<210> SEQ ID NO 476
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 476
ucaagauuug cuauguuaga a                                           21

<210> SEQ ID NO 477
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 477
caaaaucaag auuugcuaug u                                           21

<210> SEQ ID NO 478
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 478
gaacuacucc cuuucuucag u                                           21

<210> SEQ ID NO 479
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 479
agaaauuucu cuaucuucca a                                           21

<210> SEQ ID NO 480
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
ugaacugagg caaauuuaaa a                                          21

<210> SEQ ID NO 481
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
cauccaacag auucagaaag a                                          21

<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
aaaaucaaga uuugcuaugu u                                          21

<210> SEQ ID NO 483
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
agagcaaaau cuaagccaga a                                          21

<210> SEQ ID NO 484
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
aucauaugag cuaauaucac a                                          21

<210> SEQ ID NO 485
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
```
aauaaaccuc guaacaaguu a                          21

<210> SEQ ID NO 486
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
caacagcaua gucaaauaaa a                          21

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
aaaacaaccu aaauguaaa u                           21

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
cacuuaaaac uuuuguagaa a                          21

<210> SEQ ID NO 489
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
auuaaaauaa guucgcuguc u                          21

<210> SEQ ID NO 490
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
caaaacuuca augaaacgug a                          21

<210> SEQ ID NO 491
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 491
agauggauca caaaacuuca a                                              21

<210> SEQ ID NO 492
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
cacuuaauac uaugaaaaca a                                              21

<210> SEQ ID NO 493
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
acuaagucac auugacuuua a                                              21

<210> SEQ ID NO 494
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
uauuaaauaa cuuuucuaaa u                                              21

<210> SEQ ID NO 495
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
acacuuaaua cuaugaaaac a                                              21

<210> SEQ ID NO 496
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
uuuaugaaac cuaaugaagc a                                              21

<210> SEQ ID NO 497
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
caaacauuau auugaauauu a                                              21

<210> SEQ ID NO 498
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
aaaccaguga aaucaaagaa a                                              21

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
gaguuaaagu uuauauuucc a                                              21

<210> SEQ ID NO 500
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
ccaauauaaa caauuaaacc a                                              21

<210> SEQ ID NO 501
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
guggagaaaa caaccuaaau a                                              21

<210> SEQ ID NO 502
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
```

```
aacucaacuc aaaacuugaa a                                              21
```

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503

```
aauguucaca auuaagcucc u                                              21
```

<210> SEQ ID NO 504
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504

```
gcagaauuaa auacuguauu a                                              21
```

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505

```
ugaaugaaau aagaaaugua a                                              21
```

<210> SEQ ID NO 506
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506

```
uacauauaaa cuacaaguca a                                              21
```

<210> SEQ ID NO 507
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507

```
uuugaauuaa guuaguuagu ugc                                            23
```

<210> SEQ ID NO 508
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 508
uugaguucaa gugacauauu cuu                                          23

<210> SEQ ID NO 509
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
auuuagucaa guuuagaguu uua                                          23

<210> SEQ ID NO 510
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
ugauuuugaa uuaaguuagu uag                                          23

<210> SEQ ID NO 511
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
uuuaagugaa guuacuucug ggu                                          23

<210> SEQ ID NO 512
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
uucaaguuuu gaguugaguu caa                                          23

<210> SEQ ID NO 513
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
aggcuuucaa guuugaguu gag                                           23
```

```
<210> SEQ ID NO 514
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
ucaauuucaa gcaacgugga acu                                             23

<210> SEQ ID NO 515
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
ugauuuucaa uuucaagcaa cgu                                             23

<210> SEQ ID NO 516
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
uuucauugaa guuugugau cca                                              23

<210> SEQ ID NO 517
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
uucuaacaua gcaaaucuug auu                                             23

<210> SEQ ID NO 518
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
acauagcaaa ucuugauuuu ggc                                             23

<210> SEQ ID NO 519
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 519
acugaagaaa gggaguaguu cuu                                              23

<210> SEQ ID NO 520
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
uuggaagaua gagaaauuuc ugu                                              23

<210> SEQ ID NO 521
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
uuuuaaauuu gccucaguuc auu                                              23

<210> SEQ ID NO 522
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
ucuuucugaa ucuguuggau gga                                              23

<210> SEQ ID NO 523
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
aacauagcaa aucuugauuu ugg                                              23

<210> SEQ ID NO 524
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
uucuggcuua gauuuugcuc uug                                              23

<210> SEQ ID NO 525
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 525
ugugauauua gcucauauga ugc                                           23

<210> SEQ ID NO 526
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
uaacuuguua cgagguuuau uuc                                           23

<210> SEQ ID NO 527
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
uuuuauuuga cuaugcuguu ggu                                           23

<210> SEQ ID NO 528
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
auuuaccauu uagguuguuu ucu                                           23

<210> SEQ ID NO 529
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
uuucuacaaa aguuuuaagu gaa                                           23

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
agacagcgaa cuuauuuuaa uac                                           23
```

```
<210> SEQ ID NO 531
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
ucacguuuca uugaaguuuu gug                                                23

<210> SEQ ID NO 532
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
uugaaguuuu gugauccauc uau                                                23

<210> SEQ ID NO 533
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
uuguuuucau aguauuaagu guu                                                23

<210> SEQ ID NO 534
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
uuaaagucaa ugugacuuag uag                                                23

<210> SEQ ID NO 535
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
auuuagaaaa guuauuuaau aag                                                23

<210> SEQ ID NO 536
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 536 uguuucaua guauuaagug uua                                              23

<210> SEQ ID NO 537
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
ugcuucauua gguuucauaa aua                                             23

<210> SEQ ID NO 538
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
uaauauucaa uauaauguuu guu                                             23

<210> SEQ ID NO 539
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
uuucuuugau uucacugguu ugc                                             23

<210> SEQ ID NO 540
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
uggaaauaua aacuuuaacu cga                                             23

<210> SEQ ID NO 541
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
ugguuuaauu guuuauauug guc                                             23

<210> SEQ ID NO 542
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
uauuuagguu guuucucca cac                                              23

<210> SEQ ID NO 543
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
uuucaaguuu ugaguugagu uca                                             23

<210> SEQ ID NO 544
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
aggagcuuaa uugugaacau uuu                                             23

<210> SEQ ID NO 545
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
uaauacagua uuuaauucug cuu                                             23

<210> SEQ ID NO 546
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
uuacauuucu uauuucauuc aac                                             23

<210> SEQ ID NO 547
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
uugacuugua guuuauaugu agu                                             23
```

```
<210> SEQ ID NO 548
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
aacuaacuaa cuuaauucaa a                                              21

<210> SEQ ID NO 549
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
gaauauguca cuugaacuca a                                              21

<210> SEQ ID NO 550
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
aaacucuaaa cuugacuaaa u                                              21

<210> SEQ ID NO 551
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
aacuaacuua auucaaaauc a                                              21

<210> SEQ ID NO 552
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
ccagaaguaa cuucacuuaa a                                              21

<210> SEQ ID NO 553
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 553
gaacucaacu caaaacuuga a                                         21

<210> SEQ ID NO 554
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 554
caacucaaaa cuugaaagcc u                                         21

<210> SEQ ID NO 555
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 555
uuccacguug cuugaaauug a                                         21

<210> SEQ ID NO 556
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 556
guugcuugaa auugaaaauc a                                         21

<210> SEQ ID NO 557
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 557
gaucacaaaa cuucaaugaa a                                         21

<210> SEQ ID NO 558
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 558
ucaagauuug cuauguuaga a                                         21

<210> SEQ ID NO 559
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
caaaaucaag auuugcuaug u                                              21

<210> SEQ ID NO 560
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
gaacuacucc cuuucuucag u                                              21

<210> SEQ ID NO 561
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
agaaauuucu cuaucuucca a                                              21

<210> SEQ ID NO 562
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
ugaacugagg caaauuuaaa a                                              21

<210> SEQ ID NO 563
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
cauccaacag auucagaaag a                                              21

<210> SEQ ID NO 564
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
```
aaaaucaaga uuugcuaugu u                                               21

<210> SEQ ID NO 565
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
agagcaaaau cuaagccaga a                                               21

<210> SEQ ID NO 566
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
aucauaugag cuaauaucac a                                               21

<210> SEQ ID NO 567
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
aauaaaccuc guaacaaguu a                                               21

<210> SEQ ID NO 568
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
caacagcaua gucaaauaaa a                                               21

<210> SEQ ID NO 569
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
aaaacaaccu aaaugguaaa u                                               21

<210> SEQ ID NO 570
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 570
cacuuaaaac uuuuguagaa a                                              21

<210> SEQ ID NO 571
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
auuaaaauaa guucgcuguc u                                              21

<210> SEQ ID NO 572
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
caaaacuuca augaaacgug a                                              21

<210> SEQ ID NO 573
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
agauggauca caaaacuuca a                                              21

<210> SEQ ID NO 574
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
cacuuaauac uaugaaaaca a                                              21

<210> SEQ ID NO 575
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
acuaagucac auugacuuua a                                              21

<210> SEQ ID NO 576
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
uauuaaauaa cuuuucuaaa u                                            21

<210> SEQ ID NO 577
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
acacuuaaua cuaugaaaac a                                            21

<210> SEQ ID NO 578
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
uuuaugaaac cuaaugaagc a                                            21

<210> SEQ ID NO 579
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
caaacauuau auugaauauu a                                            21

<210> SEQ ID NO 580
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
aaaccaguga aaucaaagaa a                                            21

<210> SEQ ID NO 581
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
```

-continued gaguuaaagu uuauauuucc a                                              21

<210> SEQ ID NO 582
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
ccaauauaaa caauuaaacc a                                              21

<210> SEQ ID NO 583
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
guggagaaaa caaccuaaau a                                              21

<210> SEQ ID NO 584
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
aacucaacuc aaaacuugaa a                                              21

<210> SEQ ID NO 585
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
aauguucaca auuaagcucc u                                              21

<210> SEQ ID NO 586
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
gcagaauuaa auacuguauu a                                              21

<210> SEQ ID NO 587
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 587
ugaaugaaau aagaaaugua a                                             21

<210> SEQ ID NO 588
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
uacauauaaa cuacaaguca a                                             21

<210> SEQ ID NO 589
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
uuugaauuaa guuaguuagu ugc                                           23

<210> SEQ ID NO 590
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
uugaguucaa gugacauauu cuu                                           23

<210> SEQ ID NO 591
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
auuuagucaa guuuagaguu uua                                           23

<210> SEQ ID NO 592
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
ugauuuugaa uuaaguuagu uag                                           23
```

```
<210> SEQ ID NO 593
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
uuuaagugaa guuacuucug ggu                                            23

<210> SEQ ID NO 594
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
uucaaguuuu gaguugaguu caa                                            23

<210> SEQ ID NO 595
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
aggcuuucaa guuuugaguu gag                                            23

<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
ucaauuucaa gcaacgugga acu                                            23

<210> SEQ ID NO 597
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
ugauuuucaa uuucaagcaa cgu                                            23

<210> SEQ ID NO 598
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 598
uuucauugaa guuugugau cca                                              23

<210> SEQ ID NO 599
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
uucuaacaua gcaaucuug auu                                              23

<210> SEQ ID NO 600
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
acauagcaaa ucuugauuuu ggc                                             23

<210> SEQ ID NO 601
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
acugaagaaa gggaguaguu cuu                                             23

<210> SEQ ID NO 602
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
uuggaagaua gagaaauuuc ugu                                             23

<210> SEQ ID NO 603
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
uuuuaaauuu gccucaguuc auu                                             23

<210> SEQ ID NO 604
<211> LENGTH: 23
<212> TYPE: RNA
<213> ORGANISM: Artificial Sequence
```

```
-continued

<220> FEATURE:
<221> NAME/KEY: source
<223> OTHER INFORMATION: /note="Description of Artificial Sequence:
      Synthetic oligonucleotide"

<400> SEQUENCE: 604
ucuuucugaa ucuguuggau gga                                              23

<210> SEQ ID NO 605
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
aacauagcaa aucuugauuu ugg                                              23

<210> SEQ ID NO 606
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
uucuggcuua gauuuugcuc uug                                              23

<210> SEQ ID NO 607
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
ugugauauua gcucauauga ugc                                              23

<210> SEQ ID NO 608
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
uaacuuguua cgagguuuau uuc                                              23

<210> SEQ ID NO 609
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
uuuuauuuga cuaugcuguu ggu                                              23
```

```
<210> SEQ ID NO 610
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
auuuaccauu uagguuguuu ucu                                         23

<210> SEQ ID NO 611
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
uuucuacaaa aguuuuaagu gaa                                         23

<210> SEQ ID NO 612
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
agacagcgaa cuuauuuuaa uac                                         23

<210> SEQ ID NO 613
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
ucacguuuca uugaaguuuu gug                                         23

<210> SEQ ID NO 614
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
uugaaguuuu gugauccauc uau                                         23

<210> SEQ ID NO 615
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 615
uuguuuucau aguauuaagu guu                                                 23

<210> SEQ ID NO 616
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
uuaaagucaa ugugacuuag uag                                                 23

<210> SEQ ID NO 617
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
auuuagaaaa guuauuuaau aag                                                 23

<210> SEQ ID NO 618
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
uguuuucaua guauuaagug uua                                                 23

<210> SEQ ID NO 619
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
ugcuucauua gguuucauaa aua                                                 23

<210> SEQ ID NO 620
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
uaauauucaa uauaauguuu guu                                                 23

<210> SEQ ID NO 621
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
uuucuuugau uucacugguu ugc                                          23

<210> SEQ ID NO 622
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
uggaaauaua aacuuuaacu cga                                          23

<210> SEQ ID NO 623
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
ugguuuaauu guuuauauug guc                                          23

<210> SEQ ID NO 624
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
uauuuagguu guuucucca cac                                           23

<210> SEQ ID NO 625
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
uuucaaguuu ugaguugagu uca                                          23

<210> SEQ ID NO 626
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
aggagcuuaa uugugaacau uuu                                          23
```

<210> SEQ ID NO 627
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
uaauacagua uuuaauucug cuu                                              23

<210> SEQ ID NO 628
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
uuacauuucu uauuucauuc aac                                              23

<210> SEQ ID NO 629
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
uugacuugua guuuauaugu agu                                              23

<210> SEQ ID NO 630
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
gcaacuaacu aacuuaauuc aaa                                              23

<210> SEQ ID NO 631
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
aagaauaugu cacuugaacu caa                                              23

<210> SEQ ID NO 632
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 632
uaaaacucua aacuugacua aau                                              23

<210> SEQ ID NO 633
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
cuaacuaacu uaauucaaaa uca                                              23

<210> SEQ ID NO 634
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
acccagaagu aacuucacuu aaa                                              23

<210> SEQ ID NO 635
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
uugaacucaa cucaaaacuu gaa                                              23

<210> SEQ ID NO 636
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
cucaacucaa aacuugaaag ccu                                              23

<210> SEQ ID NO 637
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
aguuccacgu ugcuugaaau uga                                              23

<210> SEQ ID NO 638
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
acguugcuug aaauugaaaa uca                                           23

<210> SEQ ID NO 639
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
uggaucacaa aacuucaaug aaa                                           23

<210> SEQ ID NO 640
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
aaucaagauu ugcuauguua gac                                           23

<210> SEQ ID NO 641
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
gccaaaauca agauuugcua ugu                                           23

<210> SEQ ID NO 642
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
aagaacuacu cccuuucuuc agu                                           23

<210> SEQ ID NO 643
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
```

-continued

```
acagaaauuu cucuaucuuc caa                                             23

<210> SEQ ID NO 644
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
aaugaacuga ggcaaauuua aaa                                             23

<210> SEQ ID NO 645
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
uccauccaac agauucagaa agc                                             23

<210> SEQ ID NO 646
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
ccaaaaucaa gauuugcuau guu                                             23

<210> SEQ ID NO 647
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
caagagcaaa aucuaagcca gag                                             23

<210> SEQ ID NO 648
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
gcaucauaug agcuaauauc aca                                             23

<210> SEQ ID NO 649
<211> LENGTH: 23
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 649
gaaauaaacc ucguaacaag uua                                           23

<210> SEQ ID NO 650
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
accaacagca uagucaaaua aaa                                           23

<210> SEQ ID NO 651
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
agaaaacaac cuaaauggua aau                                           23

<210> SEQ ID NO 652
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
uucacuuaaa acuuuuguag aaa                                           23

<210> SEQ ID NO 653
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
guauuaaaau aaguucgcug ucu                                           23

<210> SEQ ID NO 654
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
cacaaaacuu caaugaaacg ugg                                           23

<210> SEQ ID NO 655
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
auagauggau cacaaaacuu caa                                           23

<210> SEQ ID NO 656
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
aacacuuaau acuaugaaaa caa                                           23

<210> SEQ ID NO 657
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
cuacuaaguc acauugacuu uaa                                           23

<210> SEQ ID NO 658
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
cuuauuaaau aacuuuucua aau                                           23

<210> SEQ ID NO 659
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
uaacacuuaa uacuaugaaa aca                                           23

<210> SEQ ID NO 660
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
```

```
uauuuaugaa accuaaugaa gca                                              23

<210> SEQ ID NO 661
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
aacaaacauu auauugaaua uuc                                              23

<210> SEQ ID NO 662
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
gcaaaccagu gaaucaaag aag                                               23

<210> SEQ ID NO 663
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
ucgaguuaaa guuuauauuu ccc                                              23

<210> SEQ ID NO 664
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
gaccaauaua aacaauuaaa cca                                              23

<210> SEQ ID NO 665
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
guguggagaa aacaaccuaa aug                                              23

<210> SEQ ID NO 666
<211> LENGTH: 23
<212> TYPE: RNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 666
ugaacucaac ucaaaacuug aaa                                                    23

<210> SEQ ID NO 667
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
aaaauguuca caauuaagcu ccu                                                    23

<210> SEQ ID NO 668
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
aagcagaauu aaauacugua uua                                                    23

<210> SEQ ID NO 669
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
guugaaugaa auaagaaaug uaa                                                    23

<210> SEQ ID NO 670
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
acuacauaua aacucaagu caa                                                     23

ANGIOPOIETIN-LIKE 3 (ANGPTL3) IRNA COMPOSITIONS AND METHODS OF USE THEREOF

RELATED APPLICATIONS

This application is a 35 § U.S.C. 111(a) continuation application which claims the benefit of priority to PCT/US2016/027271, filed on Apr. 13, 2016, which in turn claims priority to U.S. Provisional Application No. 62/146,604, filed on Apr. 13, 2015, and U.S. Provisional Application No. 62/261,361, filed on Dec. 1, 2015. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. Said ASCII copy, created on Oct. 5, 2017, is named 121301_03303_SL.txt and is 213,290 bytes in size.

BACKGROUND OF THE INVENTION

Angiopoietin-like 3 (ANGPTL3) is a member of the angiopoietin-like family of secreted factors that regulates lipid metabolism and that is predominantly expressed in the liver (Koishi, R. et al., (2002) *Nat. Genet.* 30(2):151-157). ANGPTL3 dually inhibits the catalytic activities of lipoprotein lipase (LPL), which catalyzes the hydrolysis of triglycerides, and of endothelial lipase (EL), which hydrolyzes high density lipoprotein (HDL) phospholipids. In hypolipidemic, yet obese, KK/Snk mice, a reduction in ANGPTL3 expression has a protective effect against hyperlipidemia and artherosclerosis by promoting the clearance of triglycerides (Ando et al., (2003) *J. Lipid Res.*, 44:1216-1223). Human ANGPTL3 plasma concentrations positively correlate with plasma HDL cholesterol and HDL phospholipid levels (Shimamura et al., (2007) *Arterioscler. Thromb. Vasc. Biol.*, 27:366-372).

Disorders of lipid metabolism can lead to elevated levels of serum lipids, such as triglycerides and/or cholesterol. Elevated serum lipids are strongly associated with high blood pressure, cardiovascular disease, diabetes and other pathologic conditions. Hypertriglyceridemia is an example of a lipid metabolism disorder that is characterized by high blood levels of triglycerides. It has been associated with atherosclerosis, even in the absence of high cholesterol levels (hypercholesterolemia). When triglyceride concentrations are excessive (i.e., greater than 1000 mg/dl or 12 mmol/l), hypertriglyceridemia can also lead to pancreatitis. Hyperlipidemia is another example of a lipid metabolism disorder that is characterized by elevated levels of any one or all lipids and/or lipoproteins in the blood. Current treatments for disorders of lipid metabolism, including dieting, exercise and treatment with statins and other drugs, are not always effective. Accordingly, there is a need in the art for alternative treatments for subjects having disorders of lipid metabolism.

SUMMARY OF THE INVENTION

The present invention provides iRNA compositions which effect the RNA-induced silencing complex (RISC)-mediated cleavage of RNA transcripts of an ANGPL3 gene. The ANGPL3 gene may be within a cell, e.g., a cell within a subject, such as a human. The present invention also provides methods of using the iRNA compositions of the invention for inhibiting the expression of an ANGPL3 gene and/or for treating a subject who would benefit from inhibiting or reducing the expression of an ANGPL3 gene, e.g., a subject suffering or prone to suffering from a disorder of lipid metabolism, such as a subject suffering or prone to suffering from hyperlipidemia or hypertriglyceridemia.

Accordingly, in one aspect, the present invention provides double-stranded ribonucleic acids (dsRNAs) for inhibiting expression of ANGPTL3. The dsRNAs include a sense strand and an antisense strand, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:5. In certain embodiments, the dsRNAs include a sense strand and an antisense strand, wherein the sense strand comprises at least 15 contiguous nucleotides differing by no more than 3 nucleotides from any one of the antisense sequences listed in any one of Tables 2A, 2B, 4A, 4B, 5, 7A, 7B, 7C, 8A, 8B, 10A, 10B, 13A, 13B, 14, 15A, and 15B.

In another aspect, the invention provides double-stranded ribonucleic acids (dsRNAs) for inhibiting expression of ANGPTL3. The dsRNAs include a sense strand and an antisense strand, the antisense strand comprising a region of complementarity which comprises at least 15 contiguous nucleotides differing no more than 3 nucleotides from any one of the nucleotide sequences selected from the group consisting of

```
                                    (SEQ ID NO: 14)
     5'-GAAUAUGUCACUUGAACUCAA-3'

(SEQ ID NO: 15)
     5'-UTGAGUUCAAGTGACAUAUUCUU-3', (SEQ ID NO: 16)
     5'-GAAUATGUGACUUGAACUCAA-3'

(SEQ ID NO: 17)
     5'-UUGAGUUCAAGUGACAUAUUCUU-3', (SEQ ID NO: 18)
     5'-AUUAAGCUGCUUCUUUTUAUU-3'

(SEQ ID NO: 19)
     5'-AAUAAAAGAAGGAGCUUAAUUG-3', (SEQ ID NO: 20)
     5'-ACAUAUUUGAUCAGUCUUUUU-3'

(SEQ ID NO: 21)
     5'-AAAAAGACUGAUCAAAUAUGUUG-3';

(SEQ ID NO: 22)
     5'-UGUCACUUGAACUCAACUCAA-3'

(SEQ ID NO: 23)
     5'-UUGAGUUGAGUUCAAGUGACAUA-3';

(SEQ ID NO: 24)
     5'-AACUAACUAACUUAAUUCAAA-3'

(SEQ ID NO: 25)
     5'-UUUGAAUUAAGUUAGUUAGUUGC-3';

(SEQ ID NO: 26)
     5'-UCACAAUUAAGCUCCUUCUUU-3'

(SEQ ID NO: 27)
     5'-AAAGAAGGAGCUUAAUUGUGAAC-3';
```

```
                                              (SEQ ID NO: 28)
5'-GAGCAACUAACUAACUUAAUU-3'

(SEQ ID NO: 29)
5'-AAUUAAGUUAGUUAGUUGCUCUU-3';

(SEQ ID NO: 30)
5'-UUAUUGUUCCUCUAGUUAUUU-3'

(SEQ ID NO: 31)
5'-AAAUAACUAGAGGAACAAUAAAA-3';

(SEQ ID NO: 32)
5'-AUUAAGCUCCUUCUUUUUAUU-3'

(SEQ ID NO: 33)
5'-AAUAAAAGAAGGAGCUUAAUUG-3';

(SEQ ID NO: 34)
5'-GAAUAUGUCACUUGAACUCAA-3'

(SEQ ID NO: 35)
5'-UUGAGUUCAAGUGACAUAUUCUU-3';

(SEQ ID NO: 36)
5'-CAACAUAUUUGAUCAGUCUUU-3'

(SEQ ID NO: 37)
5'-AAAGACUGAUCAAAUAUGUUGAG-3';
and (SEQ ID NO: 38)
5'-CUCCAUAGUGAAGCAAUCUAA-3'

(SEQ ID NO: 39)
5'-UUAGAUUGCUUCACUAUGGAGUA-3'.
```

In certain embodiments, the sense and antisense strands comprise nucleotide sequences selected from the group consisting of

```
                                              (SEQ ID NO: 14)
5'-GAAUAUGUCACUUGAACUCAA-3'

(SEQ ID NO: 15)
5'-UTGAGUUCAAGTGACAUAUUCUU-3', (SEQ ID NO: 16)
5'-GAAUATGUGACUUGAACUCAA-3'

(SEQ ID NO: 17)
5'-UUGAGUUCAAGUGACAUAUUCUU-3', (SEQ ID NO: 18)
5'-AUUAAGCUGCUUCUUUUAUU-3'

(SEQ ID NO: 19)
5'-AAUAAAAAGAAGGAGCUUAAUUG-3', (SEQ ID NO: 20)
5'-ACAUAUUUGAUCAGUCUUUUU-3'

(SEQ ID NO: 21)
5'-AAAAAGACUGAUCAAAUAUGUUG-3';

(SEQ ID NO: 22)
5'-UGUCACUUGAACUCAACUCAA-3'

(SEQ ID NO: 23)
5'-UUGAGUUGAGUUCAAGUGACAUA-3';

(SEQ ID NO: 24)
5'-AACUAACUAACUUAAUUCAAA-3'

(SEQ ID NO: 25)
5'-UUUGAAUUAAGUUAGUUAGUUGC-3'

(SEQ ID NO: 26)
5'-UCACAAUUAAGCUCCUUCUUU-3'

(SEQ ID NO: 27)
5'-AAAGAAGGAGCUUAAUUGUGAAC-3';

(SEQ ID NO: 28)
5'-GAGCAACUAACUAACUUAAUU-3'

(SEQ ID NO: 29)
5'-AAUUAAGUUAGUUAGUUGCUCUU-3';

(SEQ ID NO: 30)
5'-UUAUUGUUCCUCUAGUUAUUU-3'

(SEQ ID NO: 31)
5'-AAAUAACUAGAGGAACAAUAAAA-3';

(SEQ ID NO: 32)
5'-AUUAAGCUCCUUCUUUUUAUU-3'

(SEQ ID NO: 33)
5'-AAUAAAAGAAGGAGCUUAAUUG-3';

(SEQ ID NO: 34)
5'-GAAUAUGUCACUUGAACUCAA-3'

(SEQ ID NO: 35)
5'-UUGAGUUCAAGUGACAUAUUCUU-3';

(SEQ ID NO: 36)
5'-CAACAUAUUUGAUCAGUCUUU-3'

(SEQ ID NO: 37)
5'-AAAGACUGAUCAAAUAUGUUGAG-3';
and (SEQ ID NO: 38)
5'-CUCCAUAGUGAAGCAAUCUAA-3'

(SEQ ID NO: 39)
5'-UUAGAUUGCUUCACUAUGGAGUA-3'.
```

In certain embodiments, the dsRNA comprises at least one modified nucleotide. In certain embodiments, the dsRNA comprises no more than 4 (i.e., 4, 3, 2, 1, or 0) unmodified nucleotides in the sense strand. In certain embodiments, the dsRNA comprises no more than 4 (i.e., 4, 3, 2, 1, or 0) unmodified nucleotides in the antisense strand. In certain embodiments, the dsRNA comprises no more than 4 (i.e., 4, 3, 2, 1, or 0) unmodified nucleotides in both the sense strand and the antisense strand. In certain embodiments, all of the nucleotides in the sense strand of the dsRNA are modified nucleotides. In certain embodiments, all of the nucleotides in the antisense strand of the dsRNA are modified nucleotides. In certain embodiments, all of the nucleotides in the sense strand of the dsRNA and all of the nucleotides of the antisense strand are modified nucleotides.

In certain embodiments, the modified nucleotides is/are independently selected from the group consisting of a 2'-O-methyl modified nucleotide, a nucleotide comprising a 5'-phosphorothioate group, and a terminal nucleotide linked to a cholesteryl derivative or a dodecanoic acid bisdecylamide group. In certain embodiments, the modified nucleotide is selected from the group consisting of a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, and a non-natural base comprising nucleotide.

In certain embodiments, the dsRNA comprises a region of complementarity at least 17 nucleotides in length. In certain embodiments, the dsRNA comprises a region of complementarity 19 and 23 nucleotides in length. In certain embodiments, the dsRNA comprises a region of complementarity is 19 nucleotides in length.

In certain embodiments, each strand of the dsRNA is no more than 30 nucleotides in length. In certain embodiments, the dsRNA is at least 15 nucleotides in length.

In other embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of an INSR gene. In some embodiments, the sense and antisense strands form a duplex of 18-30 contiguous nucleotides.

In one embodiment, at least one strand of the RNAi agent comprises a 3' overhang of at least 1 nucleotide. In certain embodiments, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In certain embodiments, the double stranded RNAi agent further comprises a ligand. In certain embodiments, the ligand is an N-acetylgalactosamine (GalNAc). The ligand may be one or more GalNAc attached to the RNAi agent through a monovalent, a bivalent, or a trivalent branched linker. The ligand may be conjugated to the 3' end of the sense strand of the double stranded RNAi agent, the 5' end of the sense strand of the double stranded RNAi agent, the 3' end of the antisense strand of the double stranded RNAi agent, or the 5' end of the antisense strand of the double stranded RNAi agent.

In some embodiments, the double stranded RNAi agents of the invention comprise a plurality, e.g., 2, 3, 4, 5, or 6, of GalNAc, each independently attached to a plurality of nucleotides of the double stranded RNAi agent through a plurality of monovalent linkers.

In certain embodiments, the ligand is

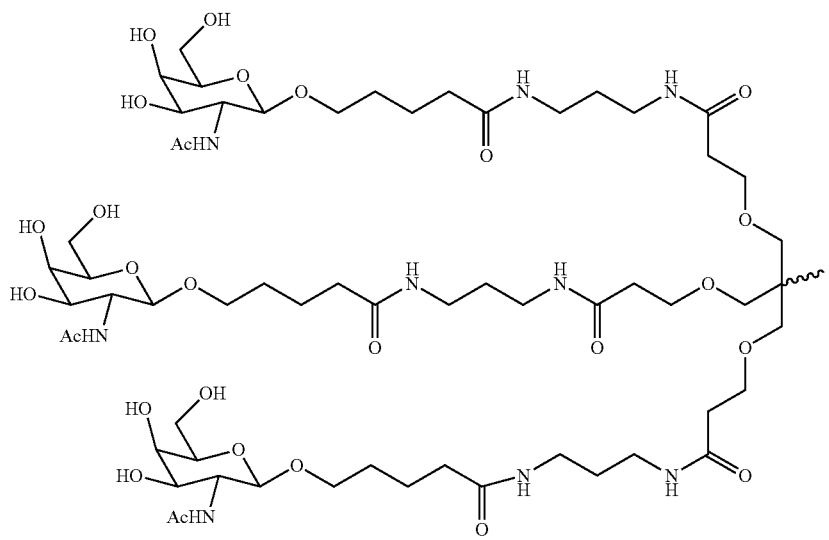

In certain embodiments, the double stranded RNAi agent is conjugated to the ligand as shown in the following schematic

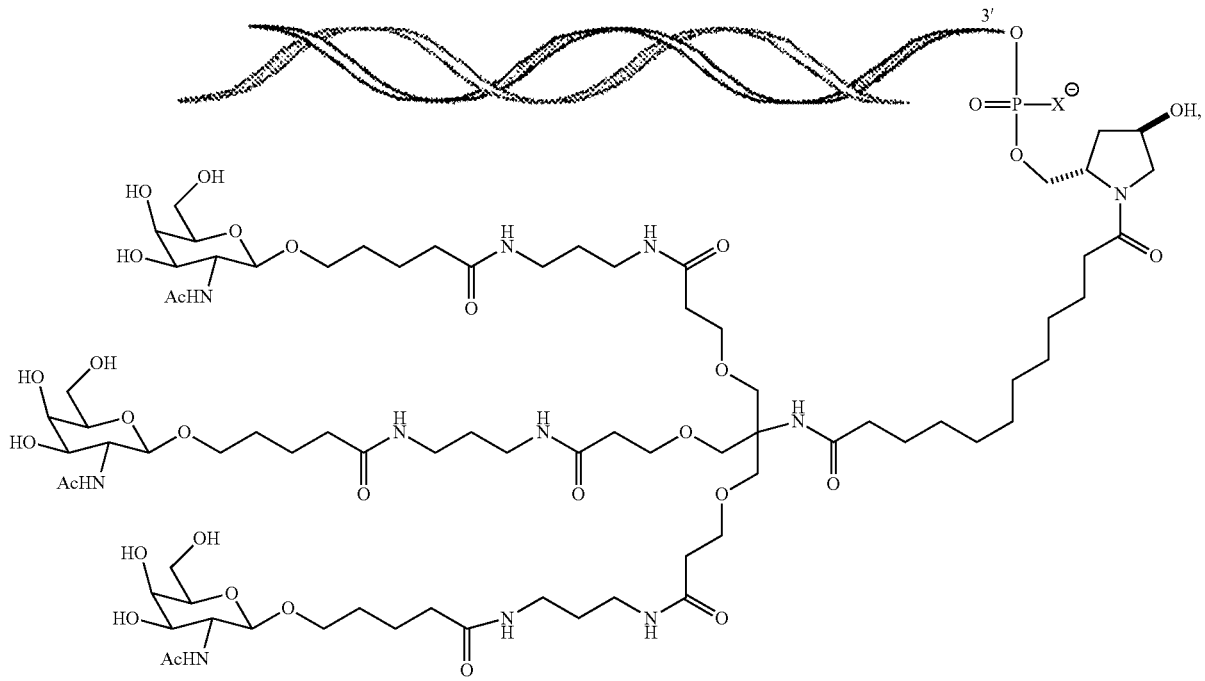

and, wherein X is O or S. In one embodiment, the X is O.

In certain embodiments, the dsRNA comprises a duplex selected from the group consisting of AD-57927.6, AD-63133.1, AD-63136.1, AD-63137.1, AD-63139.1, AD-63142.1, AD-63143.1, AD-63144.1, AD-63145.1, AD-63148.1, AD-63149.1, AD-63150.1, AD-63151.1, AD-63153.1, AD-63154.1, AD-63156.1, AD-63157.1, AD-63160.1, AD-63162.1, AD-63163.1, AD-63167.1, AD-63168.1, AD-63170.1, AD-63173.1, AD-63174.1, AD-63175.1, AD-63176.1, AD-63177.1, AD-63179.1, AD-63181.1, AD-66916, AD-66920, AD-66921, AD-66923, AD-66922, AD-66917, AD-66918, AD-66919, AD-66924, AD66925 and AD-63185.1. In certain embodiments, the dsRNA comprises a duplex selected from the group consisting of AD-57927.6, AD-63136.1, AD-63137.1, AD-63142.1, D-63148.1, AD-63151.1, AD-63156.1, AD-63157.1, AD-63160.1, AD-63163.1, AD-63167.1, AD-63170.1, AD-63173.1, AD-63174.1, AD-63176.1, AD-66916, AD-66920, AD-66921, AD-66923, AD-66922, AD-66917, AD-66918, AD-66919, AD-66924, AD66925, AD-67173, AD-67174, AD-67007, and AD-63179.1. In one embodiment, the sense and antisense strands of the dsRNA comprise nucleotide sequences selected from the group consisting of

```
                                  (SEQ ID NO: 40)
5'-ascsauauUfuGfAfUfcagucuuuuu--3'

(SEQ ID NO: 41)
5'-asAfsaaaGfacugaucAfaAfuaugususg--3';

(SEQ ID NO: 42)
5'-usgsucacUfuGfAfAfcucaacucaaL96--3'
```

-continued
```
                                  (SEQ ID NO: 43)
5'-usUfsgagUfuGfAfguucAfaGfugacasusa--3';

(SEQ ID NO: 44)
5'-gsasauauGfuCfAfCfuugaacucaa-3'

(SEQ ID NO: 45)
5'-usdTsgaguucaagdTgdAcauauucsusu--3';

(SEQ ID NO: 46)
5'-gsasauadTgudGacuugaa(Cgn)ucaa--3'

(SEQ ID NO: 47)
5'-usUfsgagUfuCfAfagugAfcAfuauucsusu--3';

(SEQ ID NO: 48)
5'-asusuaadGcudGcuucuuu(Tgn)uauu--3'

(SEQ ID NO: 49)
5'-asAfsuaaAfaagaaggAfgCfuuaaususg--3';

(SEQ ID NO: 50)
5'-AfscsAfuAfuUfuGfAfUfcAfgUfcUfuUfuUf-3'

(SEQ ID NO: 51)
5'-asAfsaAfaGfaCfuGfaucAfaAfuAfuGfususg-3';

(SEQ ID NO: 52)
5'-UfsgsUfcAfcUfuGfAfAfcUfcAfaCfuCfaAf-3'

(SEQ ID NO: 53)
5'-usUfsgAfgUfuGfaGfuucAfaGfuGfaCfasusa-3';

(SEQ ID NO: 54)
5'-asascuaaCfuAfAfCfuuaauucaaa-3', (SEQ ID NO: 55)
5'-usUfsugaAfuUfAfaguuAfgUfuaguusgsc-3';
```

-continued

```
                                        (SEQ ID NO: 56)
5'-uscsacaaUfuAfAfGfcuccuucuuu-3'

(SEQ ID NO: 57)
5'-asAfsagaAfgGfAfgcuuAfaUfugugasasc-3';

(SEQ ID NO: 58)
5'-gsasgcaaCfuAfAfCfuaacuuaauu-3'

(SEQ ID NO: 59)
5'-asAfsuuaAfgUfUfaguuaGfuUfgcucsusu-3';

(SEQ ID NO: 60)
5'-ususauugUfuCfCfUfcuaguuauuu-3'

(SEQ ID NO: 61)
5'-asAfsauaAfcUfAfgaggAfaCfaauaasasa-3';

(SEQ ID NO: 62)
5'-asusuaagCfuCfCfUfucuuuuuauu-3'

(SEQ ID NO: 63)
5'-asAfsuaaAfaAfGfaaggAfgCfuuaaususg-3';

(SEQ ID NO: 64)
5'-gsasauauGfuCfAfCfuugaacucaa-3'

(SEQ ID NO: 65)
5'-usUfsgagUfuCfAfagugAfcAfuauucsusu-3';

(SEQ ID NO: 66)
5'-csasacauAfuUfUfGfaucagucuuu-3'

(SEQ ID NO: 67)
5'-asAfsagaCfuGfAfucaaAfuAfuguugsasg-3';
and (SEQ ID NO: 68)
5'-csusccauAfgUfGfAfagcaaucuaa-3'

(SEQ ID NO: 69)
5'-usUfsagaUfuGfCfuucaCfuAfuggagsusa-3'.
```

In another aspect, the invention provides cells containing the dsRNAs provided herein.

In yet another aspect, the invention provides pharmaceutical compositions for inhibiting expression of an ANGPTL3 gene. The compositions include the dsRNA agents provided herein. In certain embodiments, the pharmaceutical compositions further comprise a lipid formulation.

The invention also provides methods of inhibiting ANGPTL3 expression in a cell. The methods include contacting the cell with the dsRNA as described herein; and maintaining the cell for a time sufficient to obtain degradation of the mRNA transcript of an ANGPTL3 gene, thereby inhibiting expression of the ANGPTL3 gene in the cell.

In certain embodiments, the cell is within a subject. In certain embodiments, the subject is a human. In certain embodiments, the human subject suffers from a disorder of lipid metabolism. In certain embodiments, the disorder of lipid metabolism is hyperlipidemia or hypertriglyceridemia. In certain embodiments, the ANGPTL3 expression is inhibited by at least about 30%.

In another aspect, the invention provides methods of treating a subject having a disorder that would benefit from reduction in ANGPTL3 expression. The methods include administering to the subject a therapeutically effective amount of any of the dsRNAs provided herein, thereby treating the subject. In certain embodiments, the disorder is a disorder of lipid metabolism. In certain embodiments, the disorder of lipid metabolism is hyperlipidemia or hypertriglyceridemia. In certain embodiments, administration of the dsRNA to the subject causes a decrease in one or more serum lipid and/or a decrease in ANGPTL3 protein accumulation.

In a further aspect, the present invention also provides methods of inhibiting the expression of ANGPTL3 in a subject. The methods include administering to the subject a therapeutically effective amount of any of the dsRNAs provided herein, thereby inhibiting the expression of ANGPTL3 in the subject.

In yet another aspect, the invention provides kits for performing the methods of the invention. In one embodiment, the invention provides a kit for performing a method of inhibiting expression of ANGPTL3 gene in a cell by contacting a cell with a double stranded RNAi agent of the invention in an amount effective to inhibit expression of the ANGPTL3 in the cell. The kit comprises an RNAi agent and instructions for use and, optionally, means for administering the RNAi agent to a subject.

BRIEF DESCRIPTION OF THE DRAWINGS

FIG. 18A is a graph depicting the amount of human ANGPTL3 protein remaining in the serum of AAV8-TBG-ANGPTL3 infected mice after a single 1 mg/kg or 3 mg/kg subcutaneous dose of the indicated iRNA agents at day 14 post-dose. The amount of human ANGPTL3 protein presented is relative to the amount of human ANGPTL3 protein present in a serum sample prior to administration (pre-dose).

FIG. 18B is a graph depicting the amount of human ANGPTL3 protein remaining in the serum of AAV8-TBG-ANGPTL3 infected mice after a single 1 mg/kg or 3 mg/kg subcutaneous dose of the indicated iRNA agents at day 28 post-dose. The amount of human ANGPTL3 protein presented is relative to the amount of human ANGPTL3 protein present in a serum sample prior to administration (pre-dose).

DETAILED DESCRIPTION OF THE INVENTION

Figure 1:
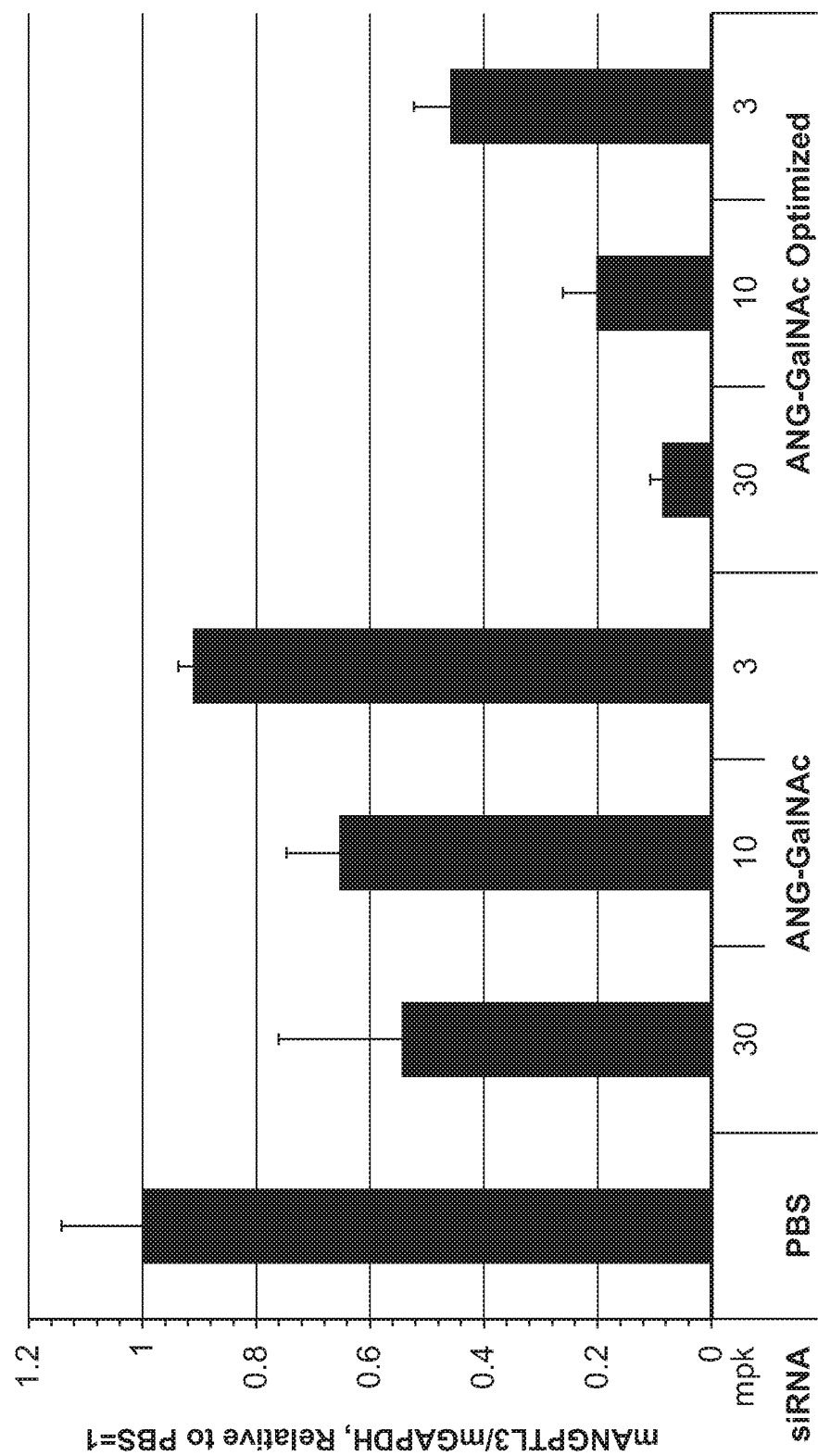
FIG. 1 is a graph showing the amount of ANGPTL3 mRNA remaining at day 3 in the serum of ob/ob female mice after a single 30 mg/kg, 10 mg/kg, or 3 mg/kg subcutaneous dose of the indicated iRNA agents. The amount of ANGPTL3 mRNA is presented as a ratio of the amount of ANGPTL3 mRNA to the amount GAPDH mRNA in a sample relative to the ratio of the amount of ANGPTL3 mRNA to the amount GAPDH mRNA in a control sample (PBS).

The present invention provides iRNA compositions, which effect the RNA-induced silencing complex (RISC)-mediated cleavage of RNA transcripts of an ANGPTL3 gene. The ANGPTL3 gene may be within a cell, e.g., a cell within a subject, such as a human. The present invention also provides methods of using the iRNA compositions of the invention for inhibiting the expression of an ANGPTL3 gene and/or for treating a subject having a disorder that would benefit from inhibiting or reducing the expression of an ANGPTL3 gene, e.g., a disorder of lipid metabolism, such as hyperlipidemia or hypertriglyceridemia.

The iRNAs of the invention may include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an ANGPTL3 gene.

In other embodiments, one or both of the strands of the double stranded RNAi agents of the invention is up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of an ANGPTL3 gene. In some embodiments, the sense and antisense strands form a duplex of 18-30 contiguous nucleotides.

The use of these iRNA agents described herein enables the targeted degradation of mRNAs of an ANGPTL3 gene in mammals. Very low dosages of ANGPTL3 iRNAs, in particular, can specifically and efficiently mediate RNA interference (RNAi), resulting in significant inhibition of expression of an ANGPTL3 gene. Using cell-based and in vivo assays, the present inventors have demonstrated that iRNAs targeting ANGPTL3 can mediate RNAi, resulting in significant inhibition of expression of an ANGPTL3 gene. Thus, methods and compositions including these iRNAs are useful for treating a subject who would benefit by a reduction in the levels and/or activity of an ANGPTL3 protein, such as a subject having a disorder of lipid metabolism, such as hyperlipidemia or hypertriglyceridemia.

In some embodiments, the iRNA agents of the invention include an RNA strand (the antisense strand) which can be up to 66 nucleotides in length, e.g., 36-66, 26-36, 25-36, 31-60, 22-43, 27-53 nucleotides in length, with a region of at least 19 contiguous nucleotides that is substantially complementary to at least a part of an mRNA transcript of an ANGPTL3 gene. In some embodiments, such iRNA agents having longer length antisense strands may include a second RNA strand (the sense strand) of 20-60 nucleotides in length wherein the sense and antisense strands form a duplex of 18-30 contiguous nucleotides.

The following detailed description discloses how to make and use compositions containing iRNAs to inhibit the expression of an ANGPTL3 gene, as well as compositions and methods for treating subjects having diseases and disorders that would benefit from inhibition and/or reduction of the expression of this gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to". The term "or" is used herein to mean, and is used interchangeably with, the term "and/or," unless context clearly indicates otherwise.

The term "ANGPTL3" refers to an angiopoietin like protein 3 having an amino acid sequence from any vertebrate or mammalian source, including, but not limited to, human, bovine, chicken, rodent, mouse, rat, porcine, ovine, primate, monkey, and guinea pig, unless specified otherwise. The term also refers to fragments and variants of native ANGPTL3 that maintain at least one in vivo or in vitro activity of a native ANGPTL3. The term encompasses full-length unprocessed precursor forms of ANGPTL3 as well as mature forms resulting from post-translational cleavage of the signal peptide and forms resulting from proteolytic processing of the fibrinogen-like domain. The sequence of a human ANGPTL3 mRNA transcript can be found at, for example, GenBank Accession No. GI: 452408443 (NM_014495.3; SEQ ID NO:1). The predicted sequence of rhesus ANGPTL3 mRNA can be found at, for example, GenBank Accession No. GI: 297278846 (XM_001086114.2; SEQ ID NO:2). The sequence of mouse ANGPTL3 mRNA can be found at, for example, GenBank Accession No. GI: 142388354 (NM_013913.3; SEQ ID NO:3). The sequence of rat ANGPTL3 mRNA can be found at, for example, GenBank Accession No. GI: 68163568 (NM_001025065.1; SEQ ID NO:4). Additional examples of ANGPTL3 mRNA sequences are readily available using publicly available databases, e.g., GenBank, UniProt, and OMIM.

The term "ANGPTL3" as used herein also refers to a particular polypeptide expressed in a cell by naturally occurring DNA sequence variations of the ANGPTL3 gene, such as a single nucleotide polymorphism in the ANGPTL3 gene. Numerous SNPs within the ANGPTL3 gene have been identified and may be found at, for example, NCBI dbSNP (see, e.g., www.ncbi.nlm.nih.gov/snp). Non-limiting examples of SNPs within the ANGPTL3 gene may be found at, NCBI dbSNP Accession Nos. rs193064039; rs192778191; rs192764027; rs192528948; rs191931953; rs191293319; rs191171206; rs191145608; rs191086880; rs191012841; or rs190255403.

As used herein, "target sequence" refers to a contiguous portion of the nucleotide sequence of an mRNA molecule formed during the transcription of an ANGPTL3gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of an ANGPTL3gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 1). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of ANGPTL3 in a cell, e.g., a cell within a subject, such as a mammalian subject.

In one embodiment, an RNAi agent of the invention includes a single stranded RNA that interacts with a target RNA sequence, e.g., a ANGPTL3 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (sssiRNA) generated within a cell and which promotes the formation of a RISC complex to effect silencing of the target gene, i.e., a ANGPTL3 gene. Accordingly, the term "siRNA" is also used herein to refer to an RNAi as described above.

In another embodiment, the RNAi agent may be a single-stranded RNAi agent that is introduced into a cell or organism to inhibit a target mRNA. Single-stranded RNAi agents (ssRNAi) bind to the RISC endonuclease, Argonaute 2, which then cleaves the target mRNA. The single-stranded siRNAs are generally 15-30 nucleotides and are chemically modified. The design and testing of single-stranded RNAi agents are described in U.S. Pat. No. 8,101,348 and in Lima et al., (2012) Cell 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150:883-894.

In another embodiment, an "iRNA" for use in the compositions and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an ANGPTL3 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/ or a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, and/or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one embodiment, an RNAi agent of the invention is a dsRNA, each strand of which comprises 19-23 nucleotides, that interacts with a target RNA sequence, e.g., an ANGPTL3 target mRNA sequence, to direct the cleavage of the target RNA. Without wishing to be bound by theory, long double stranded RNA introduced into cells is broken down into siRNA by a Type III endonuclease known as Dicer (Sharp et al. (2001) Genes Dev. 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188).

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

In certain embodiments, the overhang on the sense strand or the antisense strand, or both, can include extended lengths longer than 10 nucleotides, e.g., 10-30 nucleotides, 10-25 nucleotides, 10-20 nucleotides or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the extended overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence, e.g., an ANGPTL3 mRNA. As used herein, the term "region of complementarity" refers to the region on the antisense strand that is substantially complementary to a sequence, for example a target sequence, e.g., an ANGPTL3 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand" or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding ANGPTL3). For example, a polynucleotide is complementary to at least a part of an ANGPTL3 mRNA if the sequence is substantially complementary to a non-interrupted portion of an mRNA encoding ANGPTL3.

Accordingly, in some embodiments, the antisense strand polynucleotides disclosed herein are fully complementary to the target ANGPTL3 sequence. In other embodiments, the antisense strand polynucleotides disclosed herein are substantially complementary to the target ANGPTL3 sequence and comprise a contiguous nucleotide sequence which is at least about 80% complementary over its entire length to the equivalent region of the nucleotide sequence of SEQ ID NO:1, or a fragment of SEQ ID NO:1, such as about 85%, about 86%, about 87%, about 88%, about 89%, about 90%, about % 91%, about 92%, about 93%, about 94%, about 95%, about 96%, about 97%, about 98%, or about 99% complementary.

In one embodiment, an RNAi agent of the invention includes a sense strand that is substantially complementary to an antisense polynucleotide which, in turn, is complementary to a target ANGPTL3 sequence, and wherein the sense strand polynucleotide comprises a contiguous nucleotide sequence which is at least about 80% complementary over its entire length to the equivalent region of the nucleotide sequence of SEQ ID NO:5, or a fragment of any one of SEQ ID NO:5, such as about 85%, about 86%, about 87%, about 88%, about 89%, about 90%, about % 91%, about 92%, about 93%, about 94%, about 95%, about 96%, about 97%, about 98%, or about 99% complementary. The term "inhibiting," as used herein, is used interchangeably with "reducing," "silencing," "downregulating," "suppressing" and other similar terms, and includes any level of inhibition.

The phrase "inhibiting expression of an ANGPTL3," as used herein, includes inhibition of expression of any ANGPTL3 gene (such as, e.g., a mouse ANGPTL3 gene, a rat ANGPTL3 gene, a monkey ANGPTL3 gene, or a human ANGPTL3 gene) as well as variants or mutants of an ANGPTL3 gene that encode an ANGPTL3 protein.

"Inhibiting expression of an ANGPTL3 gene" includes any level of inhibition of an ANGPTL3 gene, e.g., at least partial suppression of the expression of an ANGPTL3 gene, such as an inhibition by at least about 20%. In certain embodiments, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an ANGPTL3 gene may be assessed based on the level of any variable associated with ANGPTL3 gene expression, e.g., ANGPTL3 mRNA level or ANGPTL3 protein level. The expression of an ANGPTL3 may also be assessed indirectly based on the levels of a serum lipid, a triglyceride, cholesterol (including LDL-C, HDL-C, VLDL-C, IDL-C and total cholesterol), or free fatty acids. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In one embodiment, at least partial suppression of the expression of an ANGPTL3 gene, is assessed by a reduction of the amount of ANGPTL3 mRNA which can be isolated from or detected in a first cell or group of cells in which an ANGPTL3 gene is transcribed and which has or have been treated such that the expression of an ANGPTL3 gene is inhibited, as compared to a second cell or group of cells substantially identical to the first cell or group of cells but which has or have not been so treated (control cells). The degree of inhibition may be expressed in terms of:

$$\frac{(mRNA \text{ in control cells}) - (mRNA \text{ in treated cells})}{(mRNA \text{ in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one embodiment, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in ANGPTL3 expression; a human at risk for a disease, disorder or condition that would benefit from reduction in ANGPTL3 expression; a human having a disease, disorder or condition that would benefit from reduction in ANGPTL3 expression; and/or human being treated for a disease, disorder or condition that would benefit from reduction in ANGPTL3 expression as described herein.

As used herein, the terms "treating" or "treatment" refer to a beneficial or desired result including, such as lowering levels of triglycerides in a subject. The terms "treating" or "treatment" also include, but are not limited to, alleviation or amelioration of one or more symptoms of a disorder of lipid metabolism, such as, e.g., a decrease in the size of eruptive xanthomas. "Treatment" can also mean prolonging survival as compared to expected survival in the absence of treatment.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, "prevention" or "preventing," when used in reference to a disease, disorder or condition thereof, that would benefit from a reduction in expression of an ANGPTL3 gene, refers to a reduction in the likelihood that a subject will develop a symptom associated with such disease, disorder, or condition, e.g., high triglyceride levels or eruptive xanthoma. The likelihood of developing a high triglyceride levels or eruptive xanthoma is reduced, for example, when an individual having one or more risk factors for a high triglyceride levels or eruptive xanthoma either fails to develop high triglyceride levels or eruptive xanthoma or develops high triglyceride levels or eruptive xanthoma with less severity relative to a population having the same risk factors and not receiving treatment as described herein. The failure to develop a disease, disorder or condition, or the reduction in the development of a symptom associated with such a disease, disorder or condition i (e.g., by at least about 10% on a clinically accepted scale for that disease or disorder), or the exhibition of delayed symptoms delayed (e.g., by days, weeks, months or years) is considered effective prevention.

As used herein, the term "serum lipid" refers to any major lipid present in the blood. Serum lipids may be present in the blood either in free form or as a part of a protein complex, e.g., a lipoprotein complex. Non-limiting examples of serum lipids may include triglycerides and cholesterol, such as total cholesterol (TG), low density lipoprotein cholesterol (LDL-C), high-density lipoprotein cholesterol (HDL-C), very low density lipoprotein cholesterol (VLDL-C) and intermediate-density lipoprotein cholesterol (IDL-C).

As used herein, a "disorder of lipid metabolism" refers to any disorder associated with or caused by a disturbance in lipid metabolism. For example, this term includes any disorder, disease or condition that can lead to hyperlipidemia, or condition characterized by abnormal elevation of levels of any or all lipids and/or lipoproteins in the blood. This term refers to an inherited disorder, such as familial hypertriglyceridemia, familial partial lipodystrophy type 1 (FPLD1), or an induced or acquired disorder, such as a disorder induced or acquired as a result of a disease, disorder or condition (e.g., renal failure), a diet, or intake of certain drugs (e.g., as a result of highly active antiretroviral therapy (HAART) used for treating, e.g., AIDS or HIV). Exemplary disorders of lipid metabolism include, but are not limited to, atherosclerosis, dyslipidemia, hypertriglyceridemia (including drug-induced hypertriglyceridemia, diuretic-induced hypertriglyceridemia, alcohol-induced hypertriglyceridemia, β-adrenergic blocking agent-induced hypertriglyceridemia, estrogen-induced hypertriglyceridemia, glucocorticoid-induced hypertriglyceridemia, retinoid-induced hypertriglyceridemia, cimetidine-induced hypertriglyceridemia, and familial hypertriglyceridemia), acute pancreatitis associated with hypertriglyceridemia, chylomicron syndrom, familial chylomicronemia, Apo-E deficiency or resistance, LPL deficiency or hypoactivity, hyperlipidemia (including familial combined hyperlipidemia), hypercholesterolemia, gout associated with hypercholesterolemia, xanthomatosis (subcutaneous cholesterol deposits), hyperlipidemia with heterogeneous LPL deficiency, and hyperlipidemia with high LDL and heterogeneous LPL deficiency.

Cardiovascular diseases associated with disorders of lipid metabolism are also considered "disorders of lipid metabolism", as defined herein. These diseases may include coronary artery disease (also called ischemic heart disease), inflammation associated with coronary artery disease, restenosis, peripheral vascular diseases, and stroke.

Disorders related to body weight are also considered "disorders of lipid metabolism", as defined herein. Such disorders may include obesity, metabolic syndrome including independent components of metabolic syndrome (e.g., central obesity, FBG/pre-diabetes/diabetes, hypercholesterolemia, hypertriglyceridemia, and hypertension), hypothyroidism, uremia, and other conditions associated with weight gain (including rapid weight gain), weight loss, maintenance of weight loss, or risk of weight regain following weight loss.

Blood sugar disorders are further considered "disorders of lipid metabolism", as defined herein. Such disorders may include diabetes, hypertension, and polycystic ovarian syndrome related to insulin resistance. Other exemplary disorders of lipid metabolism may also include renal transplantation, nephrotic syndrome, Cushing's syndrome, acromegaly, systemic lupus erythematosus, dysglobulinemia, lipodystrophy, glycogenosis type I, and Addison's disease.

"Therapeutically effective amount," as used herein, is intended to include the amount of an RNAi agent that, when administered to a subject having a disorder of lipid metabolism, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA that, when administered to a subject having a disorder of lipid metabolism, is sufficient to prevent or ameliorate the disease or one or more symptoms of the disease. Ameliorating the disease includes slowing the course of the disease or reducing the severity of later-developing disease. The "prophylactically effective amount" may vary depending on the iRNA, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to blood or plasma drawn from the subject.

II. iRNAs of the Invention

Described herein are iRNAs which inhibit the expression of an ANGPTL3 gene. In one embodiment, the iRNA agent includes double-stranded ribonucleic acid (dsRNA) molecules for inhibiting the expression of an ANGPTL3 gene in a cell, such as a cell within a subject, e.g., a mammal, such as a human having a disorder of lipid metabolism, e.g., familial hyperlipidemia. The dsRNA includes an antisense strand having a region of complementarity which is complementary to at least a part of an mRNA formed in the expression of an ANGPTL3 gene, The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the ANGPTL3 gene, the iRNA inhibits the expression of the ANGPTL3 gene (e.g., a human, a primate, a non-primate, or a bird ANGPTL3 gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an ANGPTL3gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is between about 15 and about 23 nucleotides in length, or between about 25 and about 30 nucleotides in length. In general, the dsRNA is long enough to serve as a substrate for the Dicer enzyme. For example, it is well known in the art that dsRNAs longer than about 21-23 nucleotides can serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target ANGPTL3 expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand sequence is selected from the group of sequences provided in any one of Tables 2A, 2B, 4A, 4B, 5, 7A, 7B, 7C, 8A, 8B, 10A, 10B, 13A, 13B, 14, 15A, and 15B and the corresponding nucleotide sequence of the antisense strand of the sense strand is selected from the group of sequences of any one of Tables 2A, 2B, 4A, 4B, 5, 7A, 7B, 7C, 8A, 8B, 10A, 10B, 13A, 13B, 14, 15A, and 15B. In this aspect, one of the two sequences is complementary to the other of the two sequences, with one of the sequences being substantially complementary to a sequence of an mRNA generated in the expression of an ANGPTL3 gene. As such, in this aspect, a dsRNA will include two oligonucleotides, where one oligonucleotide is described as the sense strand (passenger strand) in any one of Tables 2A, 2B, 4A, 4B, 5, 7A, 7B, 7C, 8A, 8B, 10A, 10B, 13A, 13B, 14, 15A, and 15B and the second oligonucleotide is described as the corresponding antisense strand (guide strand) of the sense strand in any one of Tables 2A, 2B, 4A, 4B, 5, 7A, 7B, 7C, 8A, 8B, 10A, 10B, 13A, 13B, 14, 15A, and 15B. In one embodiment, the substantially complementary sequences of the dsRNA are contained on separate oligonucleotides. In another embodiment, the substantially complementary sequences of the dsRNA are contained on a single oligonucleotide.

It will be understood that, although the sequences in Tables 2A, 2B, 4A, 4B, 5, 7A, 7B, 7C, 8A, 8B, 10A, 10B, 13A, 13B, 14, 15A, and 15B are described as modified, unmodified, unconjugated. and/or conjugated sequences, the RNA of the iRNA of the invention e.g., a dsRNA of the invention, may comprise any one of the sequences set forth in any one of Tables 2A, 2B, 4A, 4B, 5, 7A, 7B, 7C, 8A, 8B, 10A, 10B, 13A, 13B, 14, 15A, and 15B that is un-modified, un-conjugated, and/or modified and/or conjugated differently than described therein.

In another aspect, a double-stranded ribonucleic acid (dsRNA) of the invention for inhibiting expression of ANGPTL3 comprises, consists essentially of, or consists of a sense strand and an antisense strand, wherein the sense strand comprises the nucleotide sequence 5'-usgsucacUfuGfAfAfcucaacucaaL96-3', and the antisense strand comprises the nucleotide sequence 5'-as usUfsgagUfuGfAfguucAfaGfugacasusa-3'; or the sense strand comprises the nucleotide sequence 5'-gsasauauGfuCfAfCfuugaacucaaL96-3', and the antisense strand comprises the nucleotide sequence usUfsgagUfuCfAfagugAfcAfuauucsusu.

The skilled person is well aware that dsRNAs having a duplex structure of between about 20 and 23 base pairs, e.g., 21, base pairs have been hailed as particularly effective in inducing RNA interference (Elbashir et al., (2001) *EMBO J.*, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided herein, dsRNAs described herein can include at least one strand of a length of minimally 21 nucleotides. It can be reasonably expected that shorter duplexes minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences provided herein, and differing in their ability to inhibit the expression of an ANGPTL3gene by not more than about 5, 10, 15, 20, 25, or 30% inhibition from a dsRNA comprising the full sequence, are contemplated to be within the scope of the present invention.

In addition, the RNAs described herein identify a site(s) in an ANGPTL3 transcript that is susceptible to RISC-mediated cleavage. As such, the present invention further features iRNAs that target within this site(s). As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided herein coupled to additional nucleotide sequences taken from the region contiguous to the selected sequence in an ANGPTL3gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified herein represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified herein, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA agent as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of an ANGPTL3 gene, generally does not contain any mismatch within the central 13 nucleotides. The methods described herein or methods known in the art can be used to determine whether an iRNA containing a mismatch to a target sequence is effective in inhibiting the expression of an ANGPTL3 gene. Consideration of the efficacy of iRNAs with mismatches in inhibiting expression of an ANGPTL3 gene is important, especially if the particular region of complementarity in an ANGPTL3 gene is known to have polymorphic sequence variation within the population.

III. Modified iRNAs of the Invention

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,316; 5,550,111; 5,563,253; 5,571, 799; 5,587,361; 5,625,050; 6,028,188; 6,124,445; 6,160, 109; 6,169,170; 6,172,209; 6,239,265; 6,277,603; 6,326, 199; 6,346,614; 6,444,423; 6,531,590; 6,534,639; 6,608, 035; 6,683,167; 6,858,715; 6,867,294; 6,878,805; 7,015, 315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O—, S—, or N-alkyl; O—, S—, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$).$_n$O$H_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2$$CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2$$CH_2$O$CH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-O$CH_3$), 2'-aminopropoxy (2'-O$CH_2$$CH_2$$CH_2$$NH_2$) and 2'-fluoro (2'-F) Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA of the invention can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) Angewandte Chemie, International Edition, 30:613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

An iRNA of the invention can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) $Nucleic$ $Acids$ $Research$ 33(1):439-447; Mook, O R. et al., (2007) $Mol$ $Canc$ $Ther$ 6(3):833-843; Grunweller, A. et al., (2003) $Nucleic$ $Acids$ $Research$ 31(12):3185-3193).

An iRNA of the invention can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) $Nucleic$ $Acids$ $Research$ 33(1):439-447; Mook, O R. et al., (2007) $Mol$ $Canc$ $Ther$ 6(3):833-843; Grunweller, A. et al., (2003) $Nucleic$ $Acids$ $Research$ 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., $J.$ $Org.$ $Chem.,$ 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

An iRNA of the invention can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and C-5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the CT and C3' carbons) of the sugar has been removed (see $Nuc.$ $Acids$ $Symp.$ $Series,$ 52, 133-134 (2008) and Fluiter et al., $Mol.$ $Biosyst.,$ 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511, the entire contents of which are incorporated herein by reference.

IV. iRNAs Conjugated to Ligands

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., (1989) *Proc. Natl. Acid. Sci. USA*, 86: 6553-6556), cholic acid (Manoharan et al., (1994) *Biorg. Med. Chem. Let.*, 4:1053-1060), a thioether, e.g., beryl-S-tritylthiol (Manoharan et al., (1992) *Ann. N.Y. Acad. Sci.*, 660:306-309; Manoharan et al., (1993) *Biorg. Med. Chem. Let.*, 3:2765-2770), a thiocholesterol (Oberhauser et al., (1992) *Nucl. Acids Res.*, 20:533-538), an aliphatic chain, e.g., dodecandiol or undecyl residues (Saison-Behmoaras et al., (1991) *EMBO J*, 10:1111-1118; Kabanov et al., (1990) *FEBS Lett.*, 259:327-330; Svinarchuk et al., (1993) *Biochimie*, 75:49-54), a phospholipid, e.g., di-hexadecyl-rac-glycerol or triethyl-ammonium 1,2-di-O-hexadecyl-rac-glycero-3-phosphonate (Manoharan et al., (1995) *Tetrahedron Lett.*, 36:3651-3654; Shea et al., (1990) *Nucl. Acids Res.*, 18:3777-3783), a polyamine or a polyethylene glycol chain (Manoharan et al., (1995) *Nucleosides & Nucleotides*, 14:969-973), or adamantane acetic acid (Manoharan et al., (1995) *Tetrahedron Lett.*, 36:3651-3654), a palmityl moiety (Mishra et al., (1995) *Biochim. Biophys. Acta*, 1264:229-237), or an octadecylamine or hexylaminocarbonyloxycholesterol moiety (Crooke et al., (1996) *J. Pharmacol. Exp. Ther.*, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 13). An RFGF analogue (e.g., amino acid sequence AALLPV-LLAAP (SEQ ID NO: 10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11) and the Drosophila Antennapedia protein (RQIKIWFQNRRMK-WKK (SEQ ID NO: 12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glyciosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In one embodiment, the monosaccharide is an N-acetylgalactosamine, such as

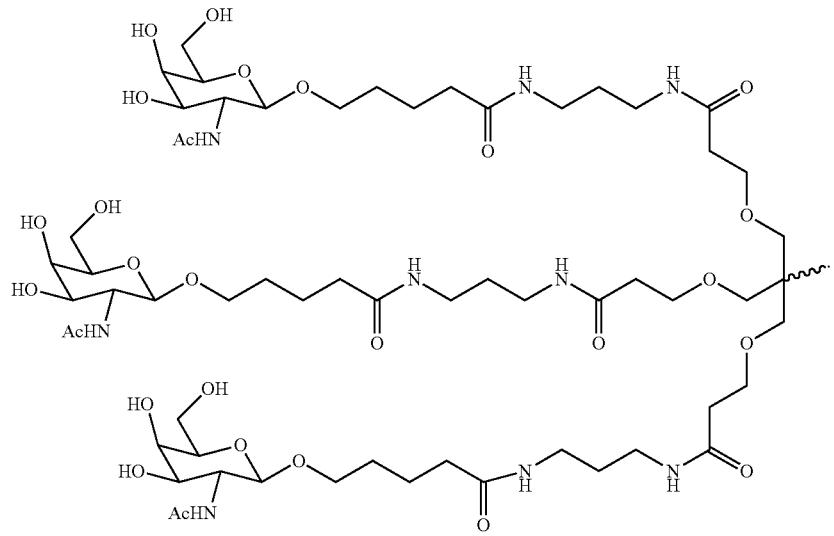 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

Formula II

In another embodiment, a carbohydrate conjugate for use in the compositions and methods of the invention is selected from the group consisting of:
Formula II
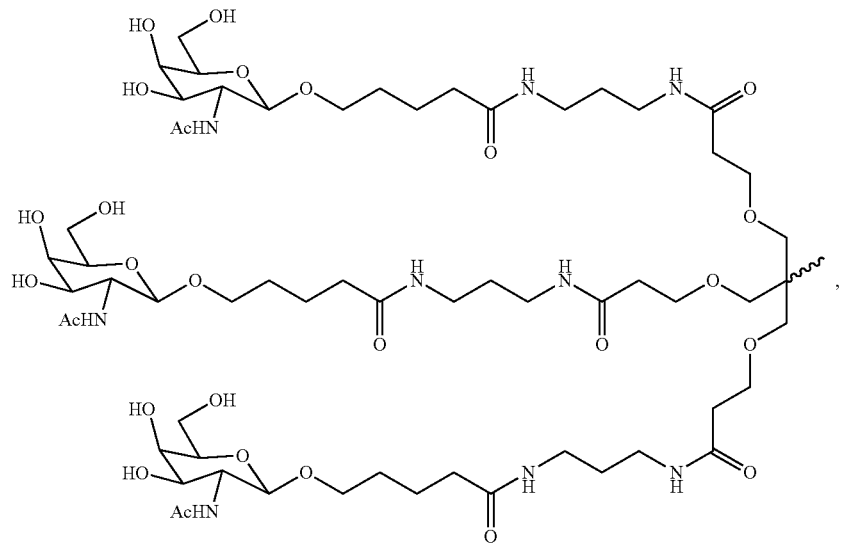
Formula III
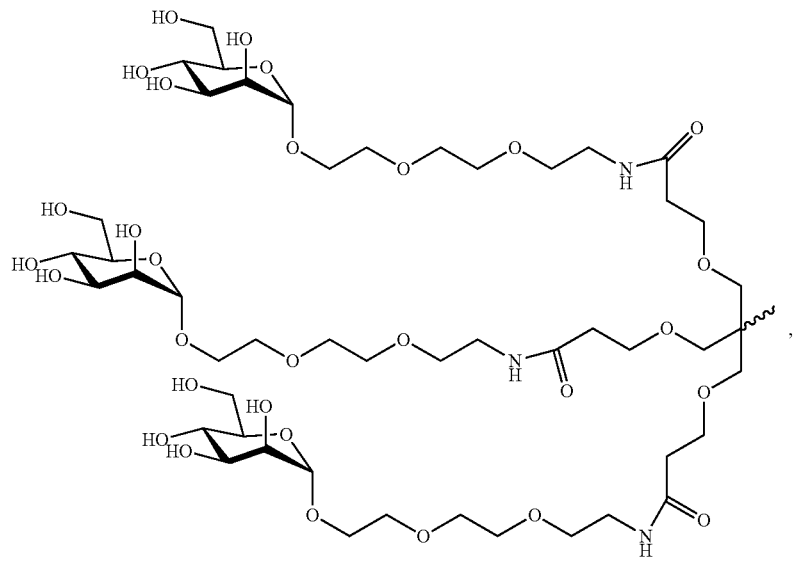
Formula IV
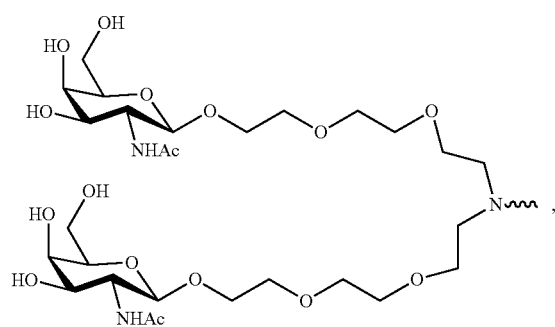
Formula V
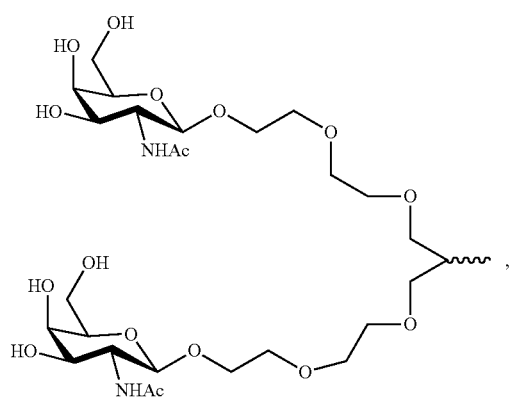

Formula VI
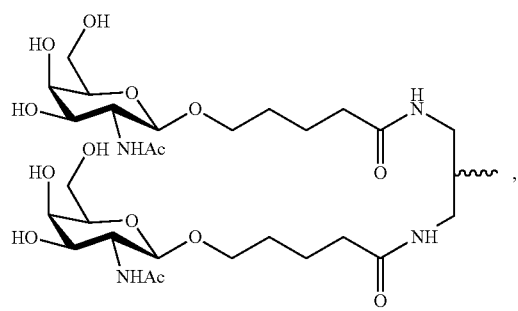
Formula VII
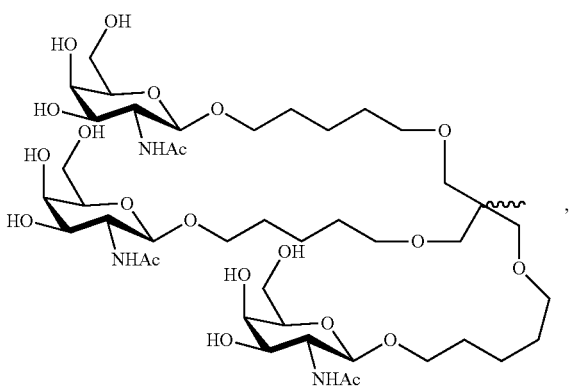
Formula VIII
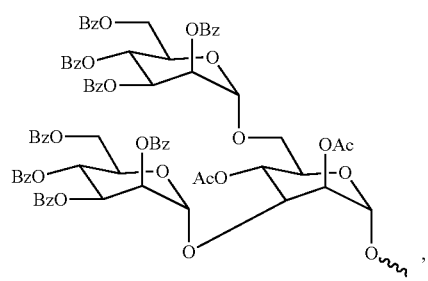
Formula IX
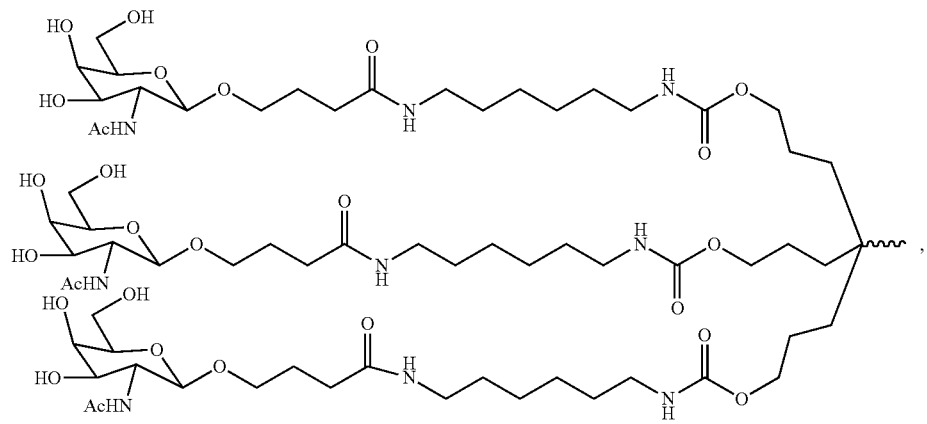
Formula X
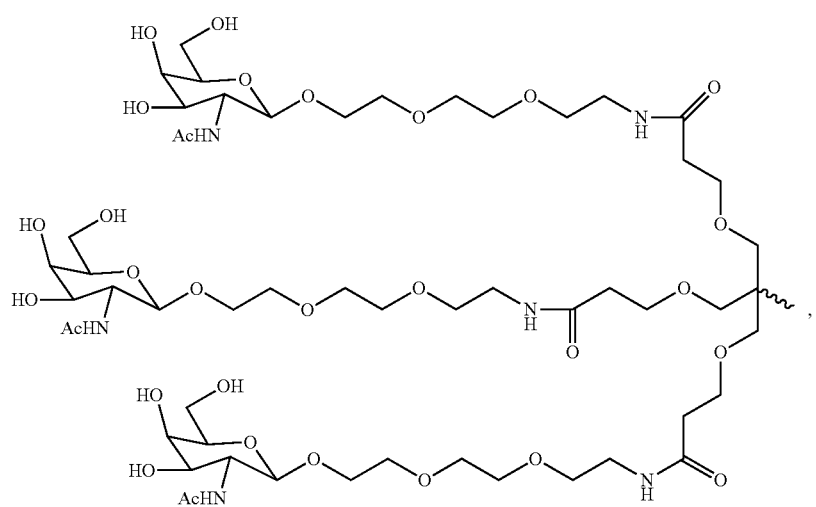

Formula XI
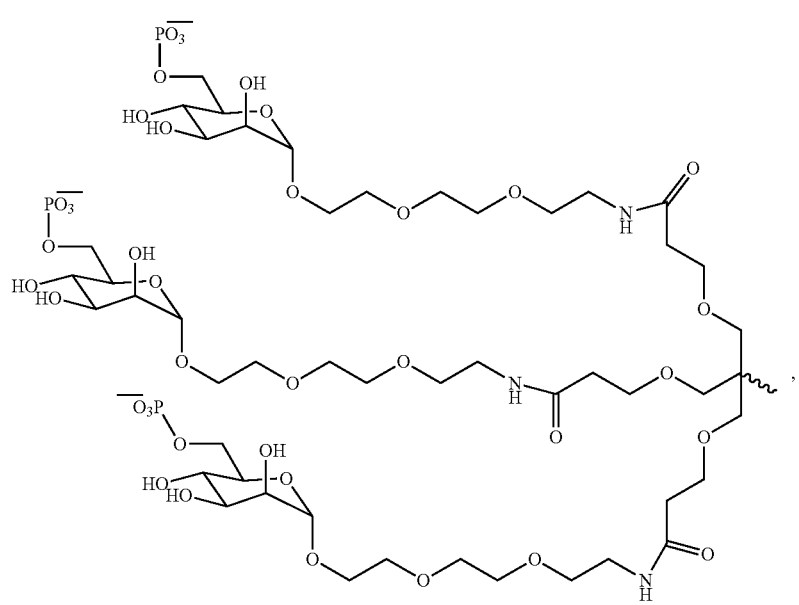
Formula XII
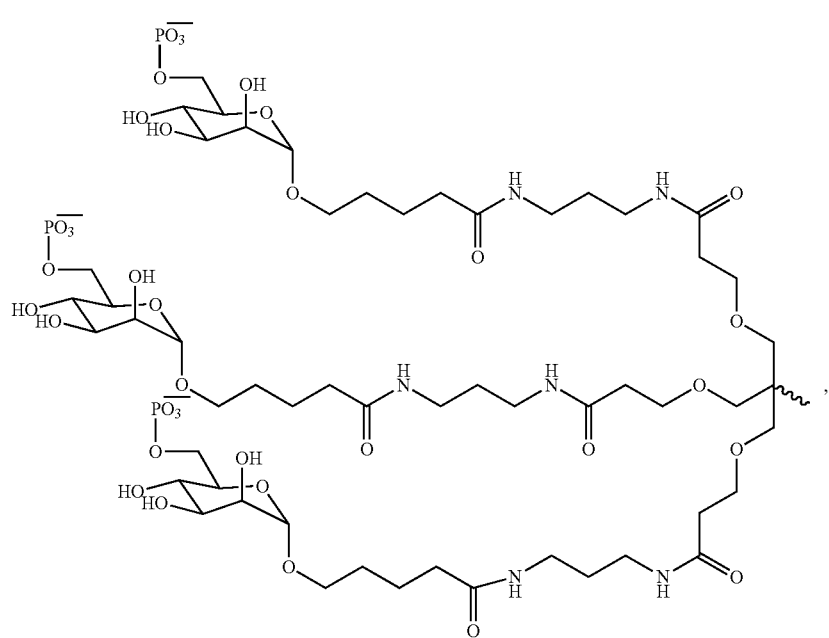
Formula XIII
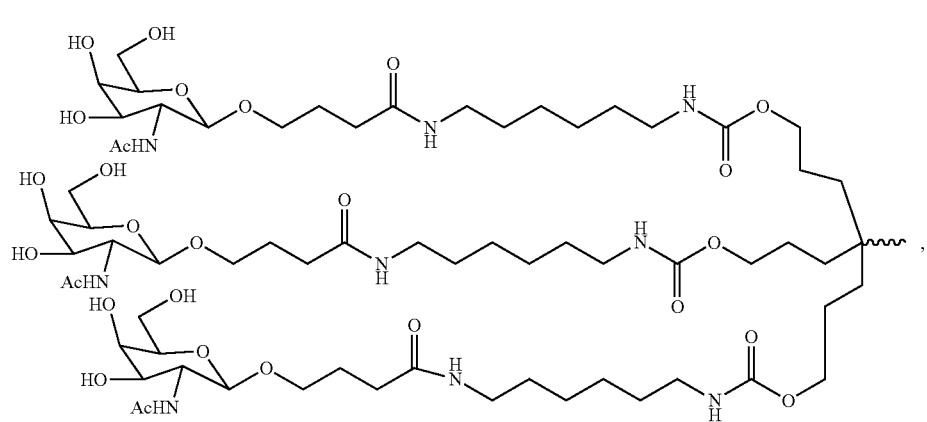

Formula XIV
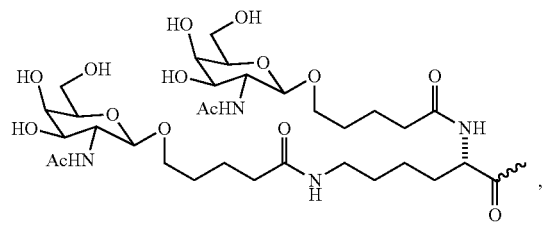
Formula XV
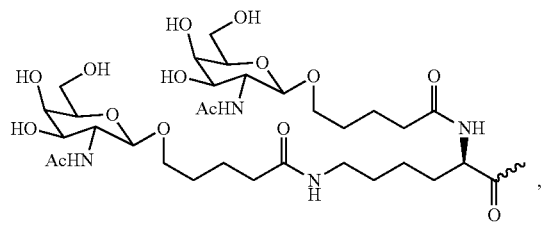
Formula XVI
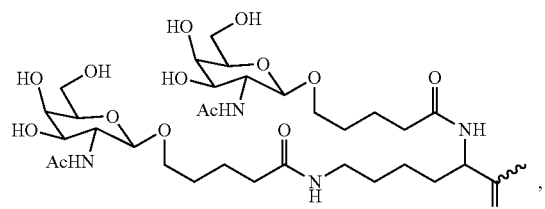
Formula XVII
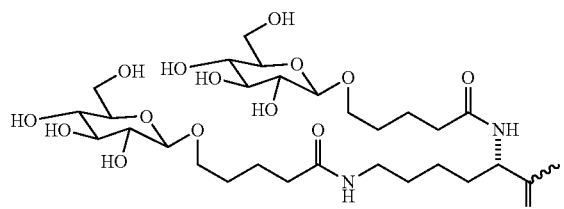
Formula XVIII
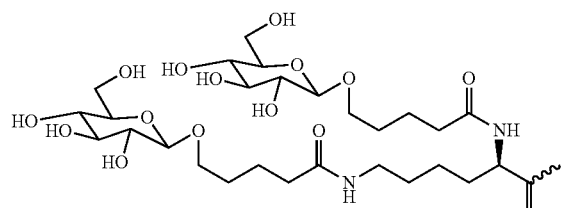
Formula XIX
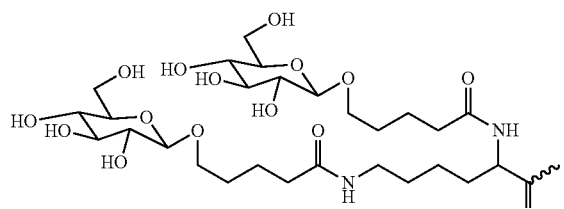
Formula XX
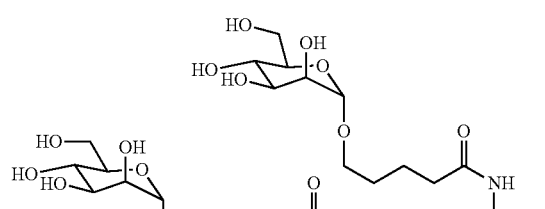
Formula XXI
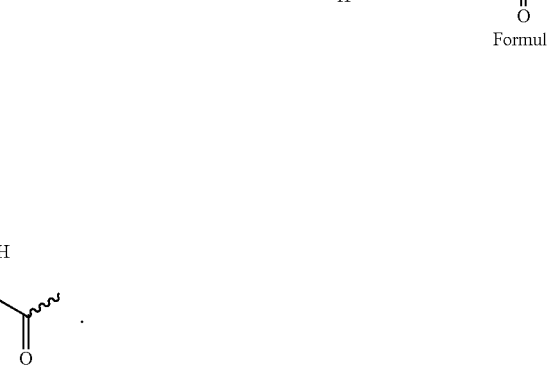
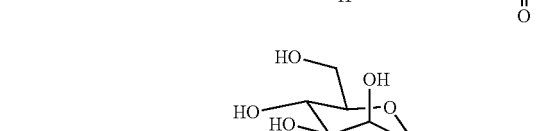
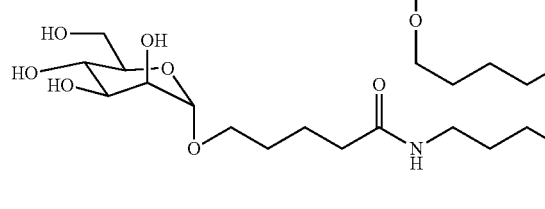
Formula XXII
Another representative carbohydrate conjugate for use in the embodiments described herein includes, but is not limited to, (Formula XXIII)
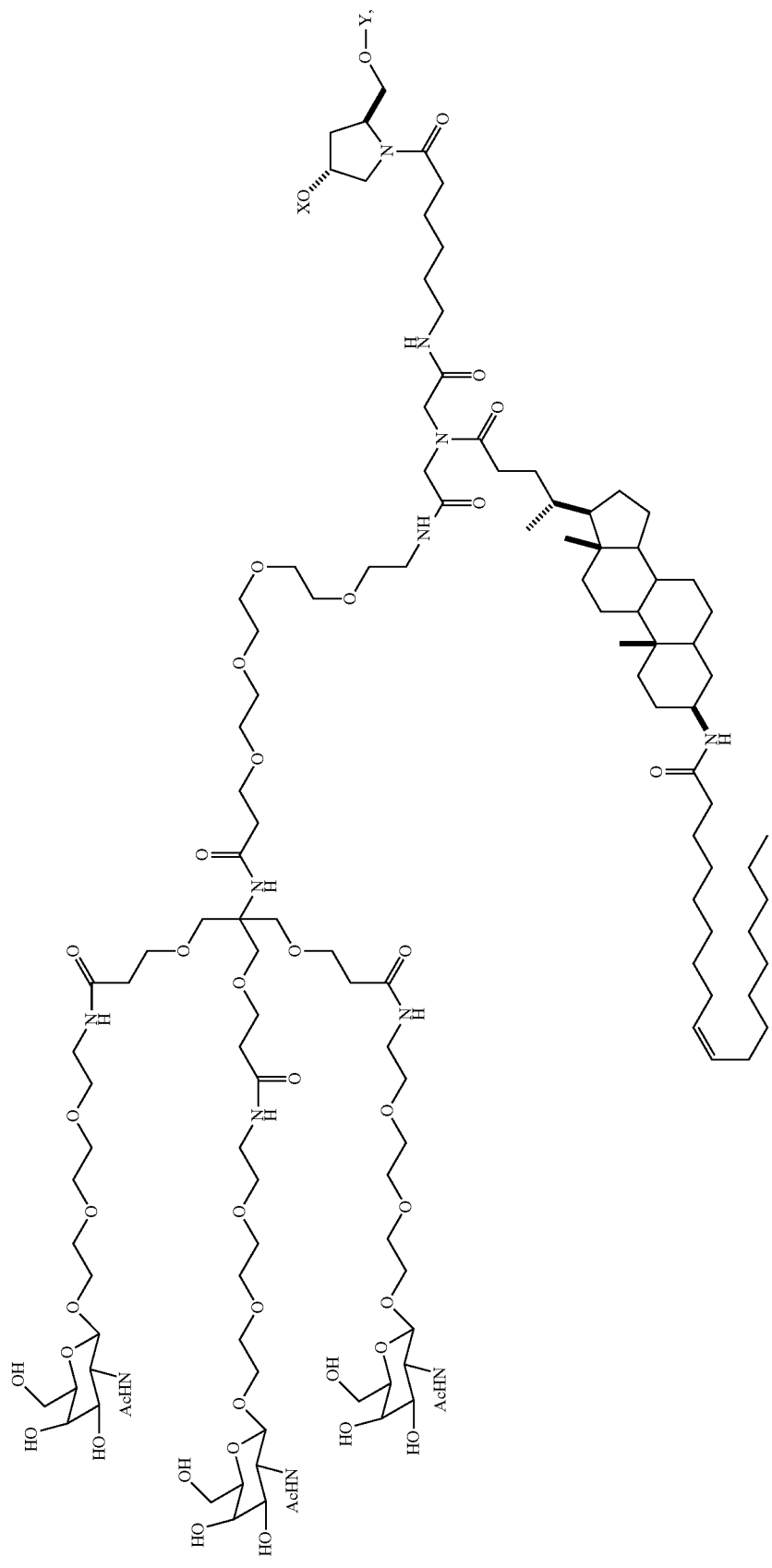

when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the iRNA agent. In another embodiment, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator and/or a cell permeation peptide.

Additional carbohydrate conjugates (and linkers) suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylaryl, alkenylaryl, alkynylaryl, alkylheteroaryl, alkenylheteroaryl, alkynylhereroaryl, which one or more methylenes can be interrupted or terminated by O, S, S(O), SO$_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to,

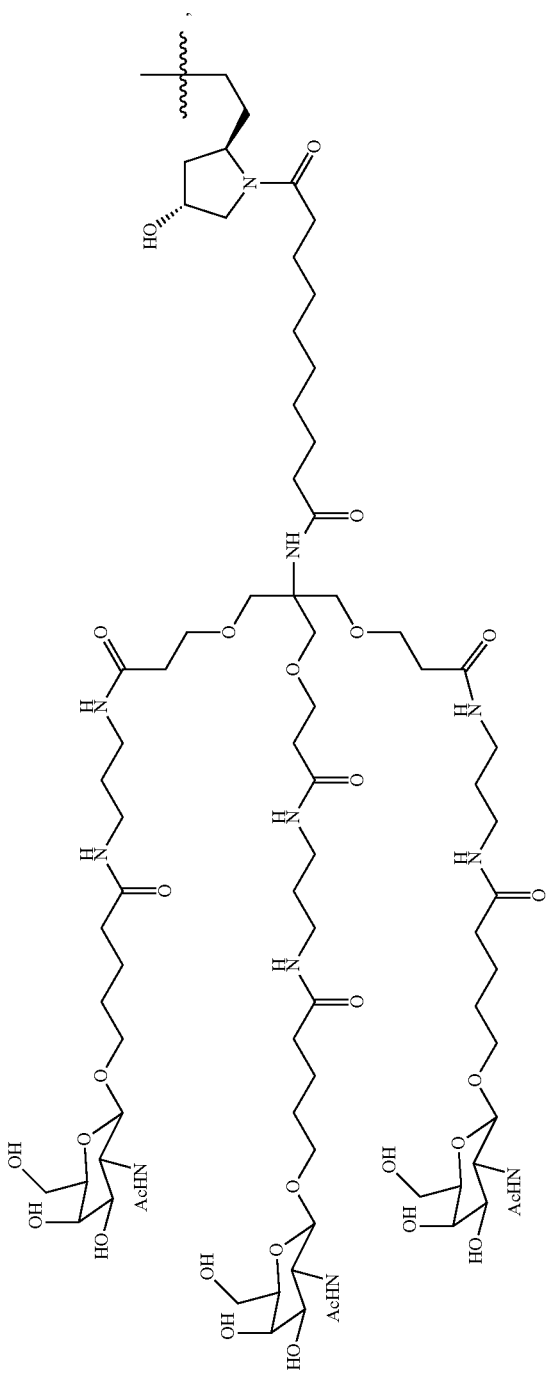
(Formula XXIV)

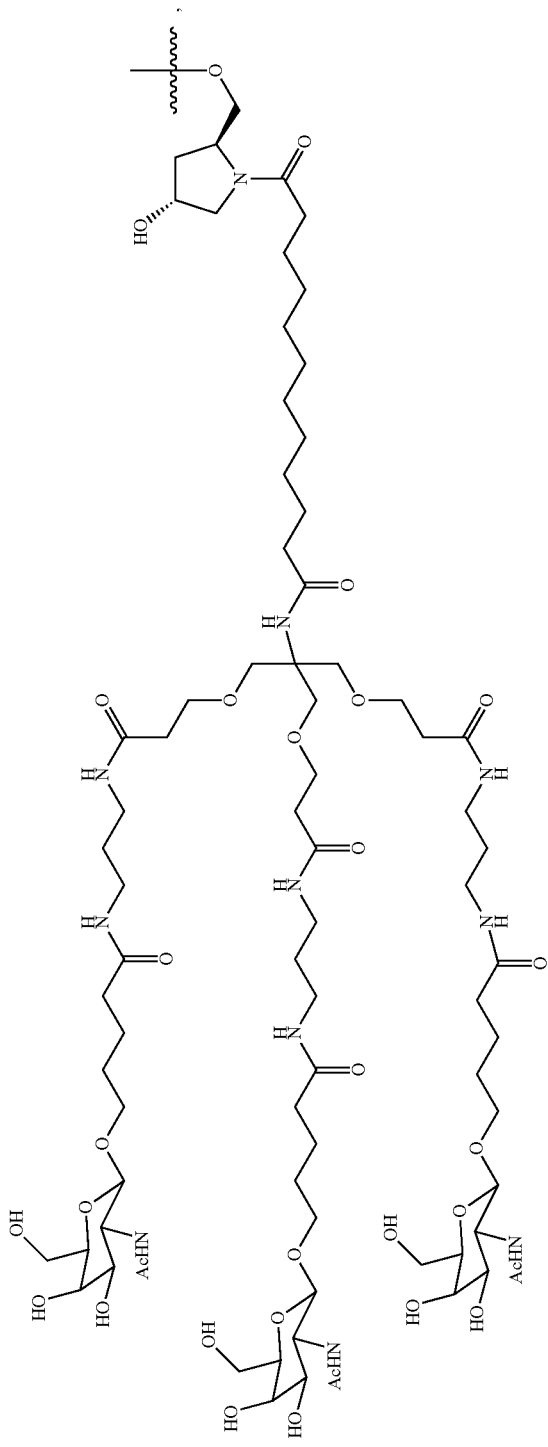
(Formula XXV)
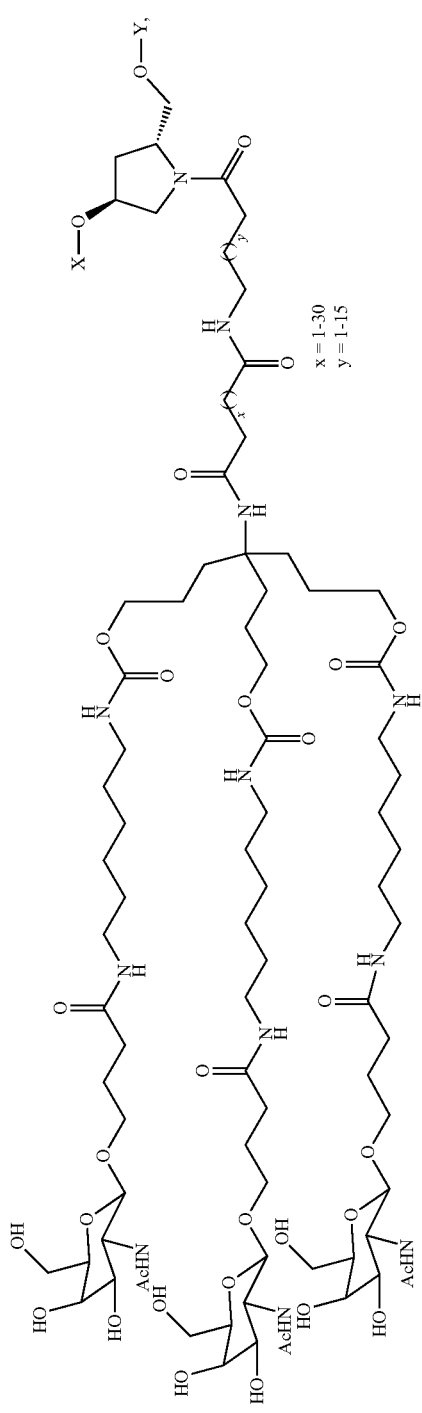
x = 1-30
y = 1-15
(Formula XXVI)

-continued
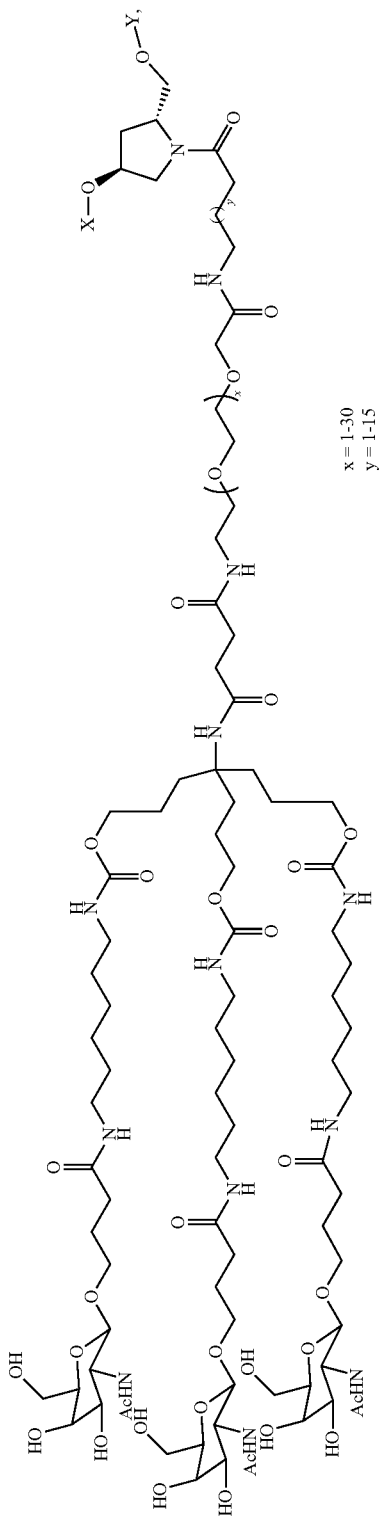
(Formula XXVII)
x = 1-30
y = 1-15
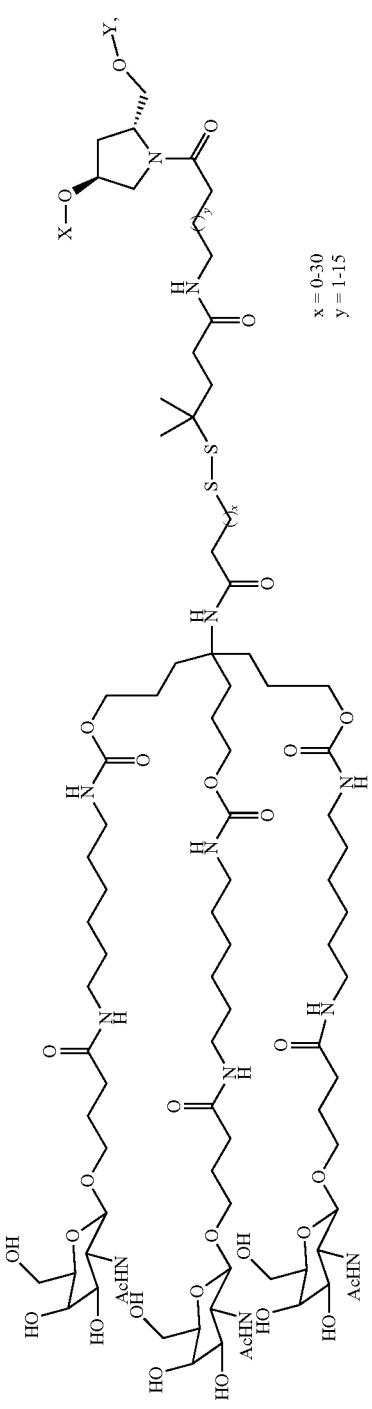
(Formula XXVIII)
x = 0-30
y = 1-15

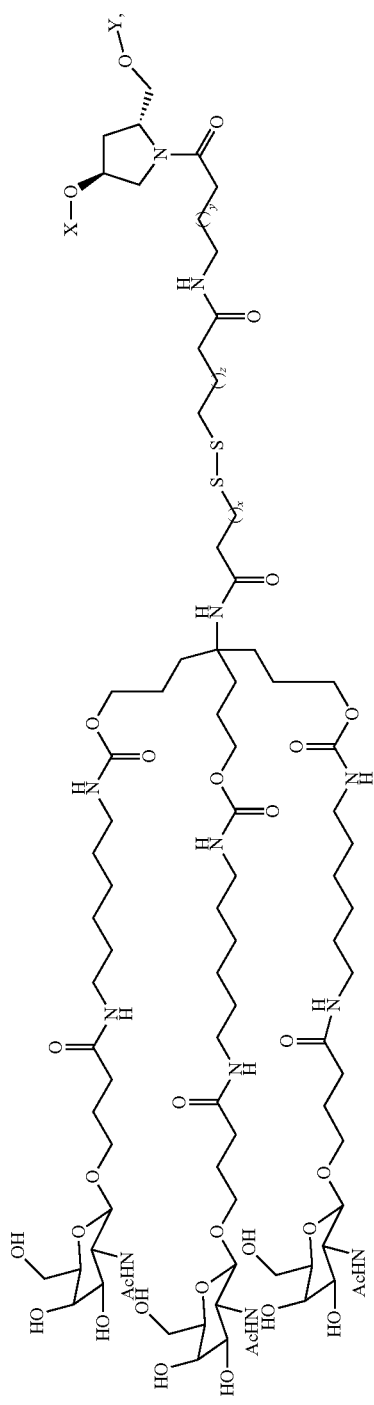
(Formula XXVIX)
x = 0-30
y = 1-15
z = 1-20
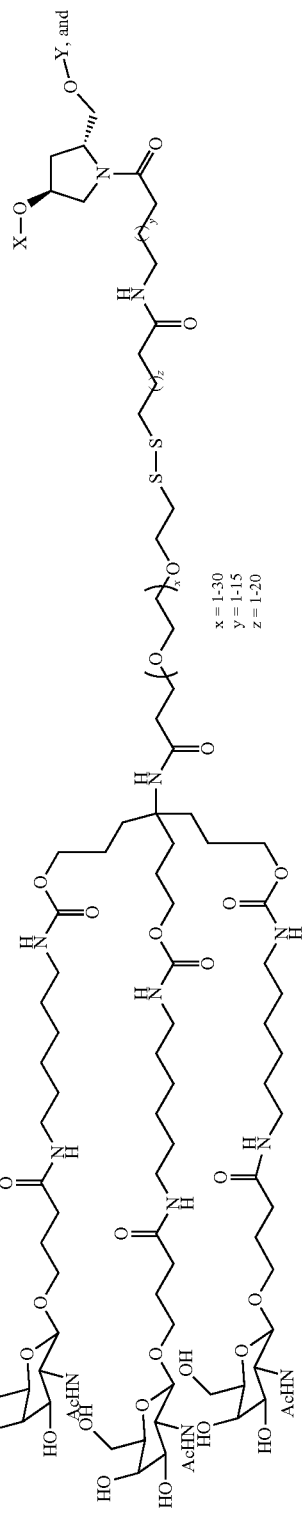
(Formula XXX)
x = 1-30
y = 1-15
z = 1-20
-Y, and

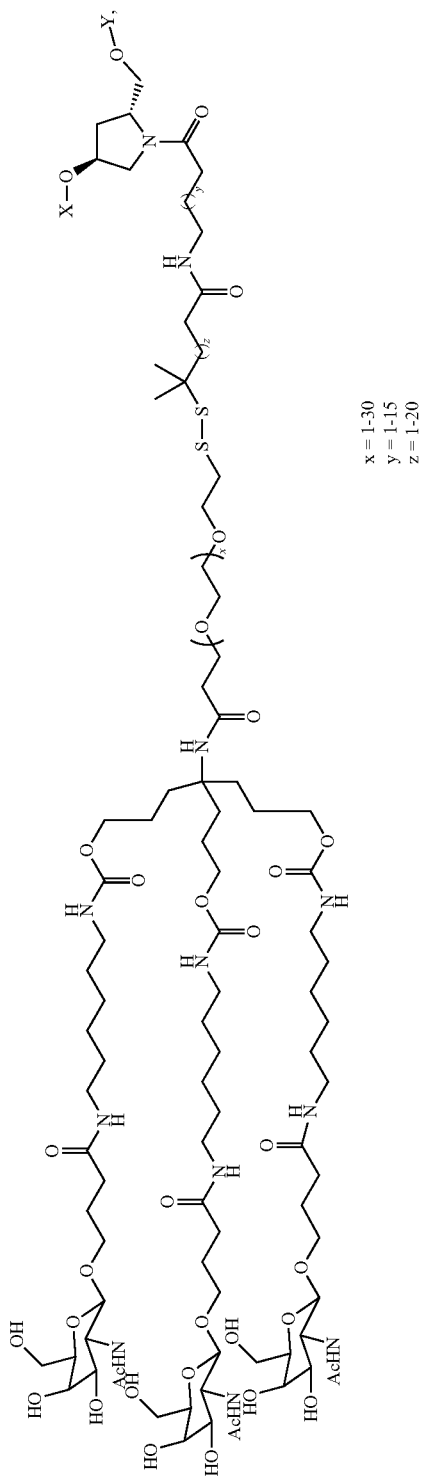
(Formula XXXI)
x = 1-30
y = 1-15
z = 1-20 when one of X or Y is an oligonucleotide, the other is a hydrogen.

In certain embodiments of the compositions and methods of the invention, a ligand is one or more GalNAc (N-acetyl-galactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

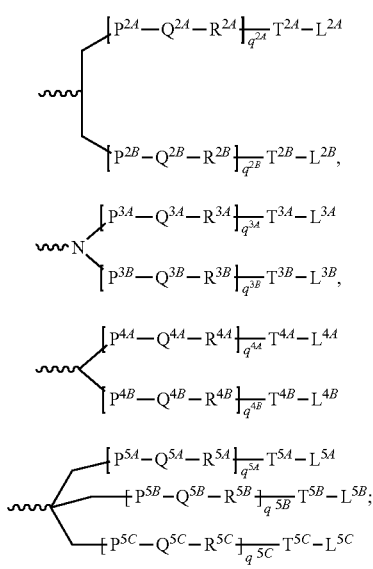

Formula XXXII

Formula XXXIII

Formula XXXIV

Formula XXXV wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), CC or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO,

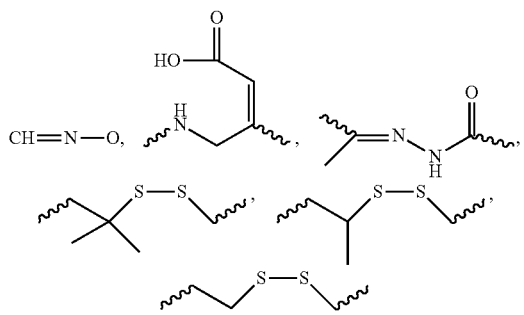

or heterocyclyl;
$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXVI):

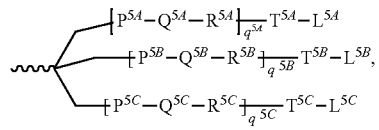

Formula XXXVI wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII Representative U.S. patents that teach the preparation of RNA conjugates include, but are not limited to, U.S. Pat. Nos. 4,828,979; 4,948,882; 5,218,105; 5,525,465; 5,541, 313; 5,545,730; 5,552,538; 5,578,717; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762,779; 4,789,737; 4,824,941; 4,835, 263; 4,876,335; 4,904,582; 4,958,013; 5,082,830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241, 5,391,723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599,928 and 5,688,941; 6,294,664; 6,320, 017; 6,576,752; 6,783,931; 6,900,297; 7,037,646; 8,106, 022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region.

Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject having a disorder of lipid metabolism) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L., (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J. et al., (2004) *Retina* 24:132-138) and subretinal injections in mice (Reich, S J. et al. (2003) *Mol. Vis.* 9:210-216) were both shown to prevent neovascularization in an experimental model of age-related macular degeneration. In addition, direct intratumoral injection of a dsRNA in mice reduces tumor volume (Pille, J. et al. (2005) *Mol. Ther.* 11:267-274) and can prolong survival of tumor-bearing mice (Kim, W J. et al., (2006) *Mol. Ther.* 14:343-350; Li, S. et al., (2007) *Mol. Ther.* 15:515-523). RNA interference has also shown success with local delivery to the CNS by direct injection (Dorn, G. et al., (2004) *Nucleic Acids* 32:e49; Tan, P H. et al. (2005) *Gene Ther.* 12:59-66; Makimura, H. et al (2002) *BMC Neurosci.* 3:18; Shishkina, G T., et al. (2004) *Neuroscience* 129:521-528; Thakker, E R., et al. (2004) *Proc. Natl. Acad. Sci. U.S.A.* 101:17270-17275; Akaneya, Y., et al. (2005) *J. Neurophysiol.* 93:594-602) and to the lungs by intranasal administration (Howard, K A. et al., (2006) *Mol. Ther.* 14:476-484; Zhang, X. et al., (2004) *J. Biol. Chem.* 279:10677-10684; Bitko, V. et al., (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J. et al., (2004) *Nature* 432:173-178). Conjugation of an iRNA to an aptamer has been shown to inhibit tumor growth and mediate tumor regression in a mouse model of prostate cancer (McNamara, J O. et al., (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H. et al., (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al. (2003) *J. Mol. Biol* 327: 761-766; Verma, U N. et al., (2003) *Clin. Cancer Res.* 9:1291-1300; Arnold, A S et al., (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N. et al., (2003), supra), Oligofectamine, "solid nucleic acid lipid particles" (Zimmermann, T S. et al., (2006) *Nature* 441:111-114), cardiolipin (Chien, P Y. et al., (2005) *Cancer Gene Ther.* 12:321-328; Pal, A. et al., (2005) *Int J. Oncol.* 26:1087-1091), polyethyleneimine (Bonnet M E. et al., (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A. et al., (2007) *Biochem. Soc. Trans.* 35:61-67; Yoo, H. et al., (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the ANGPTL3 gene can be expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., (1995) *Proc. Natl. Acad. Sci. USA* 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of an ANGPTL3 gene, e.g., a disorder of lipid metabolism, e.g., an inherited disorder, such as such familial hypertriglyceridemia, familial partial lipodystrophy type 1 (FPLD1), or an induced or acquired disorder, such as a disorder induced or acquired as a result of a disease, disorder or condition (e.g., renal failure), a diet, or intake of certain drugs (e.g., as a result of highly active antiretroviral therapy (HAART) used for treating, e.g., AIDS or HIV).

Such pharmaceutical compositions are formulated based on the mode of delivery. One example is compositions that are formulated for systemic administration via parenteral delivery, e.g., by intravenous (IV) or for subcutaneous delivery. Another example is compositions that are formulated for direct delivery into the liver, e.g., by infusion into the liver, such as by continuous pump infusion.

The pharmaceutical compositions of the invention may be administered in dosages sufficient to inhibit expression of an ANGPTL3 gene. In general, a suitable dose of an iRNA of the invention will be in the range of about 0.001 to about 200.0 milligrams per kilogram body weight of the recipient per day, generally in the range of about 1 to 50 mg per kilogram body weight per day. Typically, a suitable dose of an iRNA of the invention will be in the range of about 0.1 mg/kg to about 5.0 mg/kg, preferably about 0.3 mg/kg and about 3.0 mg/kg.

A repeat-dose regimen may include administration of a therapeutic amount of iRNA on a regular basis, such as every other day to once a year. In certain embodiments, the iRNA is administered about once per month to about once per quarter (i.e., about once every three months).

After an initial treatment regimen, the treatments can be administered on a less frequent basis.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as disorders of lipid metabolism that would benefit from reduction in the expression of ANGPTL3. Such models can be used for in vivo testing of iRNA, as well as for determining a therapeutically effective dose. Suitable mouse models are known in the art and include, for example, an obese (ob/ob) mouse containing a mutation in the obese (ob) gene (Wiegman et al., (2003) *Diabetes,* 52:1081-1089); a mouse containing homozygous knock-out of an LDL receptor (LDLR −/− mouse; Ishibashi et al., (1993) *J Clin Invest* 92(2):883-893); diet-induced artherosclerosis mouse model (Ishida et al., (1991) *J. Lipid. Res.,* 32:559-568); and heterozygous lipoprotein lipase knockout mouse model (Weistock et al., (1995) J. Clin. Invest. 96(6):2555-2568).

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

A. Additional Formulations i. Emulsions

The compositions of the present invention can be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles an RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a disorder of lipid metabolism. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the $ED_{50}$ with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by ANGPTL3 expression. In any event, the administering physician can adjust the amount and timing of iRNA administration on the basis of results observed using standard measures of efficacy known in the art or described herein.

VI. Methods of the Invention

The present invention also provides methods of using an iRNA of the invention and/or a composition containing an iRNA of the invention to reduce and/or inhibit ANGPTL3 expression in a cell. The methods include contacting the cell with a dsRNA of the invention and maintaining the cell for a time sufficient to obtain degradation of the mRNA transcript of an ANGPTL3gene, thereby inhibiting expression of the ANGPTL3 gene in the cell. Reduction in gene expression can be assessed by any methods known in the art. For example, a reduction in the expression of ANGPTL3 may be determined by determining the mRNA expression level of ANGPTL3 using methods routine to one of ordinary skill in the art, e.g., Northern blotting, qRT-PCR; by determining the protein level of ANGPTL3 using methods routine to one of ordinary skill in the art, such as Western blotting, immunological techniques. A reduction in the expression of ANGPTL3 may also be assessed indirectly by measuring a decrease in biological activity of ANGPTL3, e.g., a decrease in the level of serum lipid, triglycerides, cholesterol and/or free fatty acids.

In the methods of the invention the cell may be contacted in vitro or in vivo, i.e., the cell may be within a subject.

A cell suitable for treatment using the methods of the invention may be any cell that expresses an ANGPTL3gene. A cell suitable for use in the methods of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

ANGPTL3 expression is inhibited in the cell by at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100%. In preferred embodiments, ANGPTL3 expression is inhibited by at least 20%.

The in vivo methods of the invention may include administering to a subject a composition containing an iRNA, where the iRNA includes a nucleotide sequence that is complementary to at least a part of an RNA transcript of the ANGPTL3 gene of the mammal to be treated. When the organism to be treated is a mammal such as a human, the composition can be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection.

In some embodiments, the administration is via a depot injection. A depot injection may release the iRNA in a consistent way over a prolonged time period. Thus, a depot injection may reduce the frequency of dosing needed to obtain a desired effect, e.g., a desired inhibition of ANGPTL3, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the iRNA to the liver.

The mode of administration may be chosen based upon whether local or systemic treatment is desired and based upon the area to be treated. The route and site of administration may be chosen to enhance targeting.

In one aspect, the present invention also provides methods for inhibiting the expression of an ANGPTL3 gene in a mammal. The methods include administering to the mammal a composition comprising a dsRNA that targets an ANGPTL3 gene in a cell of the mammal and maintaining the mammal for a time sufficient to obtain degradation of the mRNA transcript of the ANGPTL3 gene, thereby inhibiting expression of the ANGPTL3 gene in the cell. Reduction in gene expression can be assessed by any methods known it the art and by methods, e.g. qRT-PCR, described herein. Reduction in protein production can be assessed by any methods known it the art and by methods, e.g. ELISA, described herein. In one embodiment, a puncture liver biopsy sample serves as the tissue material for monitoring the reduction in ANGPTL3 gene and/or protein expression.

The present invention further provides methods of treatment of a subject in need thereof. The treatment methods of the invention include administering an iRNA of the invention to a subject, e.g., a subject that would benefit from a reduction and/or inhibition of ANGPTL3 expression, in a therapeutically effective amount of an iRNA targeting an ANGPTL3 gene or a pharmaceutical composition comprising an iRNA targeting an ANGPTL3 gene.

An iRNA of the invention may be administered as a "free iRNA." A free iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of ANGPTL3 gene expression are those having a disorder of lipid metabolism, e.g., an inherited disorder of lipid metabolism or an acquired disorder of lipid metabolism. In one embodiment, a subject having disorder of lipid metabolism has hyperlipidemia. In another embodiment, a subject having a disorder of lipid metabolism has hypertriglyceridemia. Treatment of a subject that would benefit from a reduction and/or inhibition of ANGPTL3 gene expression includes therapeutic treatment (e.g., a subject is having eruptive xanthomas) and prophylactic treatment (e.g., the subject is not having eruptive xanthomas or a subject may be at risk of developing eruptive xanthomas).

The invention further provides methods for the use of an iRNA or a pharmaceutical composition thereof, e.g., for treating a subject that would benefit from reduction and/or inhibition of ANGPTL3 expression, e.g., a subject having a disorder of lipid metabolism, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting ANGPTL3 is administered in combination with, e.g., an agent useful in treating a disorder of lipid metabolism as described elsewhere herein. For example, additional agents suitable for treating a subject that would benefit from reduction in ANGPTL3 expression, e.g., a subject having a disorder of lipid metabolism, may include agents that lower one or more serum lipids. Non-limiting examples of such agents may include cholesterol synthesis inhibitors, such as HMG-CoA reductase inhibitors, e.g., statins. Statins may include atorvastatin (Lipitor), fluvastatin (Lescol), lovastatin (Mevacor), lovastatin extended-release (Altoprev), pitavastatin (Livalo), pravastatin (Pravachol), rosuvastatin (Crestor), and simvastatin (Zocor). Other agents useful in treating a disorder of lipid metabolism may include bile sequestering agents, such as cholestyramine and other resins; VLDL secretion inhibitors, such as niacin; lipophilic antioxidants, such as Probucol; acyl-CoA cholesterol acyl transferase inhibitors; farnesoid X receptor antagonists; sterol regulatory binding protein cleavage activating protein (SCAP) activators; microsomal triglyceride transfer protein (MTP) inhibitors; ApoE-related peptide; and therapeutic antibodies against ANGPTL3. The additional therapeutic agents may also include agents that raise high density lipoprotein (HDL), such as cholesteryl ester transfer protein (CETP) inhibitors. Furthermore, the additional therapeutic agents may also include dietary supplements, e.g., fish oil. The iRNA and additional therapeutic agents may be administered at the same time and/or in the same combination, e.g., parenterally, or the additional therapeutic agent can be administered as part of a separate composition or at separate times and/or by another method known in the art or described herein.

In one embodiment, the method includes administering a composition featured herein such that expression of the target ANGPTL3 gene is decreased, such as for about 1, 2, 3, 4, 5, 6, 7, 8, 12, 16, 18, 24 hours, 28, 32, or about 36 hours. In one embodiment, expression of the target ANGPTL3 gene is decreased for an extended duration, e.g., at least about two, three, four days or more, e.g., about one week, two weeks, three weeks, or four weeks or longer.

Preferably, the iRNAs useful for the methods and compositions featured herein specifically target RNAs (primary or processed) of the target ANGPTL3gene. Compositions and methods for inhibiting the expression of these genes using iRNAs can be prepared and performed as described herein.

Administration of the dsRNA according to the methods of the invention may result in a reduction of the severity, signs, symptoms, and/or markers of such diseases or disorders in a patient with a disorder of lipid metabolism. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a disorder of lipid metabolism may be assessed, for example, by periodic monitoring of one or more serum lipid levels. Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting ANGPTL3 or pharmaceutical composition thereof, "effective against" a disorder of lipid metabolism indicates that administration in a clinically appropriate manner results in a beneficial effect for at least a statistically significant fraction of patients, such as a improvement of symptoms, a cure, a reduction in disease, extension of life, improvement in quality of life, or other effect generally recognized as positive by medical doctors familiar with treating disorder of lipid metabolisms and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). Any positive change resulting in e.g., lessening of severity of disease measured using the appropriate scale, represents adequate treatment using an iRNA or iRNA formulation as described herein.

Subjects can be administered a therapeutic amount of dsRNA, such as about 0.01 mg/kg to about 50 mg/kg. Typically, a suitable dose of an iRNA of the invention will be in the range of about 0.1 mg/kg to about 5.0 mg/kg, preferably about 0.3 mg/kg and about 3.0 mg/kg.

The iRNA can be administered by intravenous infusion over a period of time, on a regular basis. In certain embodiments, after an initial treatment regimen, the treatments can be administered on a less frequent basis. Administration of the iRNA can reduce ANGPTL3 levels, e.g., in a cell, tissue, blood, urine or other compartment of the patient by at least about 5%, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 39, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or at least about 99% or more. In a preferred embodiment, administration of the iRNA can reduce ANGPTL3 levels, e.g., in a cell, tissue, blood, urine or other compartment of the patient by at least 20%.

Before administration of a full dose of the iRNA, patients can be administered a smaller dose, such as a 5% infusion reaction, and monitored for adverse effects, such as an allergic reaction. In another example, the patient can be monitored for unwanted immunostimulatory effects, such as increased cytokine (e.g., TNF-alpha or INF-alpha) levels.

Alternatively, the iRNA can be administered subcutaneously, i.e., by subcutaneous injection. One or more injections may be used to deliver the desired daily dose of iRNA to a subject. The injections may be repeated over a period of time. The administration may be repeated on a regular basis. In certain embodiments, after an initial treatment regimen, the treatments can be administered on a less frequent basis. A repeat-dose regimen may include administration of a therapeutic amount of iRNA on a regular basis, such as every other day or to once a year. In certain embodiments, the iRNA is administered about once per month to about once per quarter (i.e., about once every three months).

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. iRNA Design, Synthesis, Selection, and In Vitro Evaluation

This Example describes methods for the design, synthesis, selection, and in vitro evaluation of ANGPTL3 iRNA agents (also see, PCT publication, WO 2012/177784, the entire contents of which is incorporated herein by reference).

Source of Reagents

Where the source of a reagent is not specifically given herein, such reagent can be obtained from any supplier of reagents for molecular biology at a quality/purity standard for application in molecular biology.

A set of siRNAs targeting the human ANGPTL3, "angiopoietin-like 3" (human: NCBI refseqID NM_014995; NCBI GeneID: 27329), as well as toxicology-species ANGPTL3 orthologs (cynomolgus monkey: XM_005543185; mouse: NM_013913; rat, NM_001025065) were designed using custom R and Python scripts. The human ANGPTL3 REFSEQ mRNA has a length of 2951 bases. The rationale and method for the set of siRNA designs is as follows: the predicted efficacy for every potential 19mer siRNA from position 81 through position 2951 (the coding region and 3' UTR) was determined with a linear model derived the direct measure of mRNA knockdown from more than 20,000 distinct siRNA designs targeting a large number of vertebrate genes. Subsets of the ANGPTL3 siRNAs were designed with perfect or near-perfect matches between human, cynomolgus and rhesus monkey. A further subset was designed with perfect or near-perfect matches to mouse and rat ANGPTL3 orthologs. For each strand of the siRNA, a custom Python script was used in a brute force search to measure the number and positions of mismatches between the siRNA and all potential alignments in the target species transcriptome. Extra weight was given to mismatches in the seed region, defined here as positions 2-9 of the antisense oligonucleotide, as well the cleavage site of the siRNA, defined here as positions 10-11 of the antisense oligonucleotide. The relative weight of the mismatches was 2.8; 1.2:1 for seed mismatches, cleavage site, and other positions up through antisense position 19. Mismatches in the first position were ignored. A specificity score was calculated for each strand by summing the value of each weighted mismatch. Preference was given to siRNAs whose antisense score in human and cynomolgus monkey was >=3.0 and predicted efficacy was >=70% knockdown of the ANPTL3 transcript.

Synthesis of ANGPTL3 Sequences

Synthesis of ANGPTL3 Single Strands and Duplexes

ANGPTL3 siRNA sequences were synthesized at 1 umol scale on Mermade 192 synthesizer (BioAutomation) using the solid support mediated phosphoramidite chemistry. The solid support was controlled pore glass (500° A) loaded with custom GalNAc ligand or universal solid support (AM biochemical). Ancillary synthesis reagents, 2'-F and 2'-O-Methyl RNA and deoxy phosphoramidites were obtained from Thermo-Fisher (Milwaukee, Wis.) and Hongene (China). 2'F, 2'-O-Methyl, RNA, DNA and other modified nucleosides were introduced in the sequences using the corresponding phosphoramidites. Synthesis of 3' GalNAc conjugated single strands was performed on a GalNAc modified CPG support. Custom CPG universal solid support was used for the synthesis of antisense single strands. Coupling time for all phosphoramidites (100 mM in acetonitrile) was 5 min employing 5-Ethylthio-1H-tetrazole (ETT) as activator (0.6 M in acetonitrile). Phosphorothioate linkages were generated using a 50 mM solution of 3-((Dimethylamino-methylidene) amino)-3H-1, 2, 4-dithiazole-3-thione (DDTT, obtained from Chemgenes (Wilmington, Mass., USA) in anhydrous acetonitrile/pyridine (1:1 v/v). Oxidation time was 3 minutes. All sequences were synthesized with final removal of the DMT group ("DMT off").

Upon completion of the solid phase synthesis, single strands were cleaved from the solid support and deprotected in sealed 96 deep well plates using 200 μL Aqueous Methylamine reagent at 60° C. for 20 minutes. For sequences containing 2' ribo residues (2'-OH) that are protected with tert-butyl dimethyl silyl (TBDMS) group, a second step deprotection was performed using TEA.3HF (triethylamine trihydro fluoride) reagent. To the methylamine deprotection solution, 200 uL of dimethyl sulfoxide (DMSO) and 300 ul TEA.3HF reagent was added and the solution was incubated for additional 20 min at 60° C. At the end of cleavage and deprotection step, the synthesis plate was allowed to come to room temperature and was precipitated by addition of 1 mL of acetonitrile:ethanol mixture (9:1). The plates were cooled at −80° C. for 2 hrs and the supernatant decanted carefully with the aid of a multi-channel pipette. The oligonucleotide pellet was re-suspended in 20 mM NaOAc buffer and were desalted using a 5 mL HiTrap size exclusion column (GE Healthcare) on an AKTA Purifier System equipped with an A905 autosampler and a Frac 950 fraction collector. Desalted samples were collected in 96 well plates. Samples from each sequence were analyzed by LC-MS to confirm the identity, UV (260 nm) for quantification and a selected set of samples by IEX chromatography to determine purity.

Annealing of ANGPTL3 single strands was performed on a Tecan liquid handling robot. Equimolar mixture of sense and antisense single strands were combined and annealed in 96 well plates. After combining the complementary single strands, the 96 well plate was sealed tightly and heated in an oven at 100° C. for 10 minutes and allowed to come slowly to room temperature over a period 2-3 hours. The concentration of each duplex was normalized to 10 uM in 1×PBS and then submitted for in vitro screening assays.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| dT | 2'-deoxythymidine-3'-phosphate |
| dC | 2'-deoxycytidine-3'-phosphate |
| Y44 | inverted abasic DNA (2-hydroxymethyl-tetrahydrofurane-5-phosphate) |
| (Tgn) | Thymidine-glycol nucleic acid (GNA) S-Isomer |
| P | Phosphate |
| VP | Vinyl-phosphate |
| (Aam) | 2'-O-(N-methylacetamide)adenosine-3'-phosphate |
| (Aams) | 2'-O-(N-methylacetamide)adenosine-3'-phosphorothioate |
| (Cgn) | Cytidine-glycol nucleic acid (GNA) |

Example 2. Lead Selection and Evaluation

Based on the results of various in vitro and in vivo analyses (see, PCT publication, WO 2012/177784, the entire contents of which are incorporated herein by reference), the parent sequences of AD-52981 (sense sequence: ACAUAUUUGAUCAGUCUUUUU (SEQ ID NO: 20); antisense sequence: AAAAAGACUGAUCAAAUAU-GUUG) (SEQ ID NO: 21) were selected for modification and further evaluation in vivo.

Therefore, using the parent sequences of AD-52981, AD-57927 (sense sequence: AfscsAfuAfuUfuGfAfUfcAf-gUfaUfuUfuUfL96 (SEQ ID NO: 70); antisense sequence: asAfsaAfaGfaCfuGfaucAfaAfuAfuGfususg) (SEQ ID NO: 71) was synthesized as described above.

The effect of AD-57927 in vivo was evaluated by subcutaneously administering C57BL/6 female mice with a single 30, 10, or 3 mg/kg dose of AD-52981 (sense sequence: AfcAfuAfuUfuGfAfUfcAfgUfaUfuUfuUfL96 (SEQ ID NO: 72); antisense sequence: aAfaAfaGfaCfuGfaucAfaAfuAfuGfusUfsg) (SEQ ID NO: 73), AD-57927, or PBS control. At 72 hours post dose, animals were sacrificed and liver ANGPTL3 mRNA levels were determined. Surprisingly, and as shown in FIG. 1, AD-57927 ("ANG-GalNAc Optimized") decreased ANGPTL3 mRNA levels by about 10-fold more than the parent iRNA agent, AD-52981 ("ANG-GalNAc").

Figure 2:
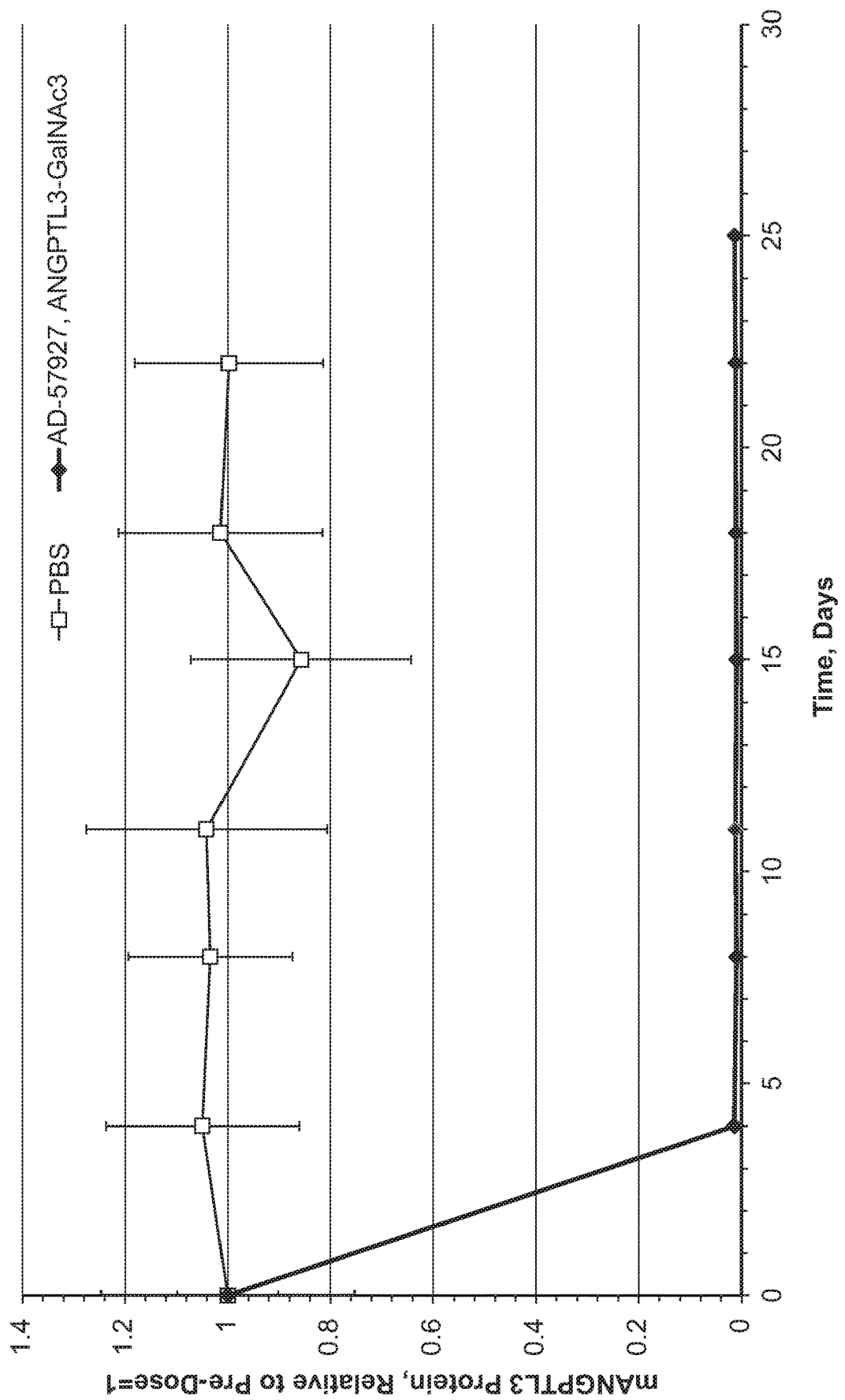
FIG. 2 is a graph showing the effects of a multi-dose administration (3 mg/kg every day for 5 days during week 1, followed by 3 mg/kg two times per week on weeks 2-4 (3.0 mg/kg qd×5; qw×6)) of AD-57927 on serum ANGPTL3 protein levels in ob/ob female mice. The amount of ANGPTL3 protein presented is relative to the amount ANGPTL3 protein present in a serum sample prior to administration of AD-57927.
Figure 3:
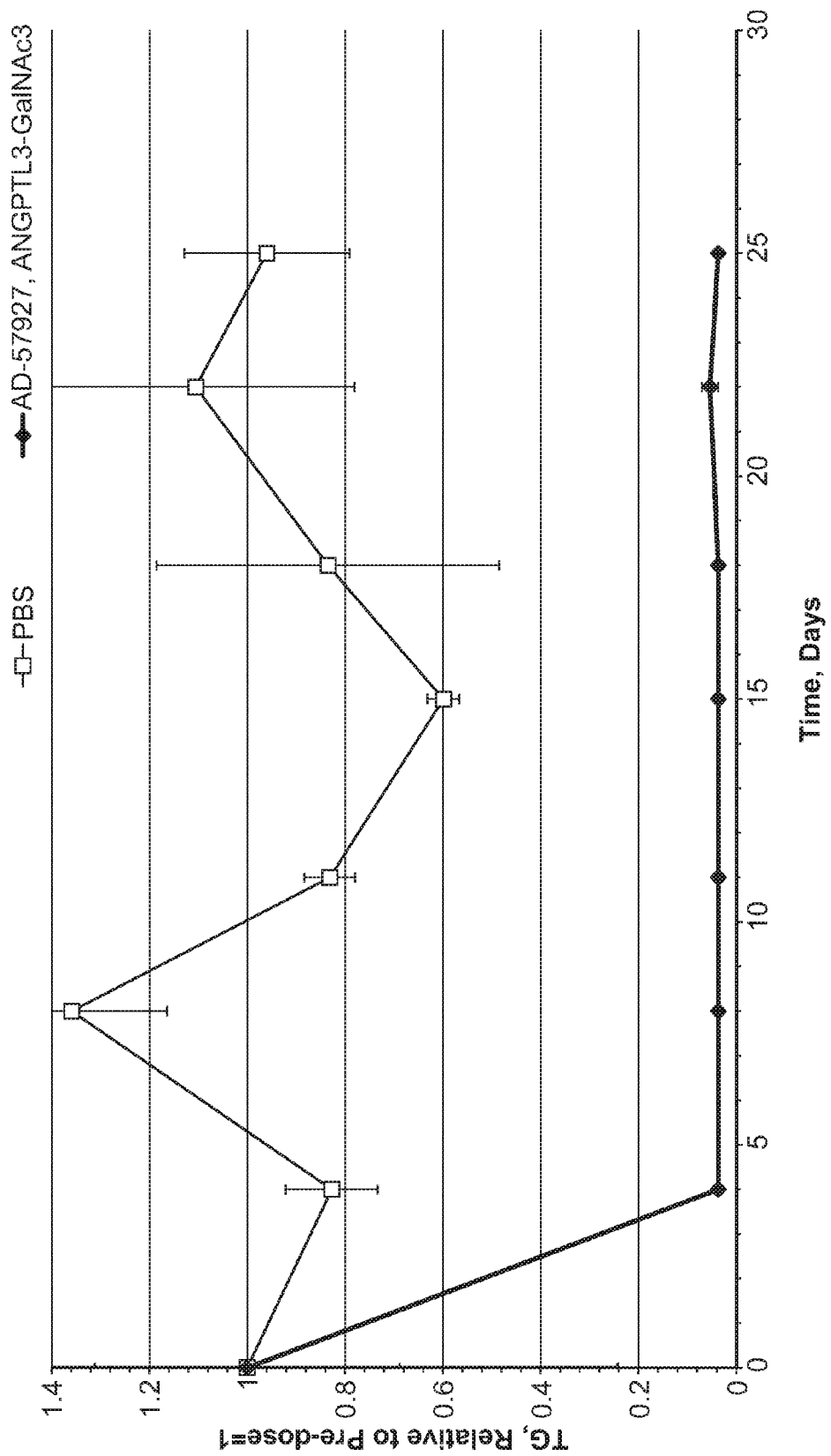
FIG. 3 is a graph showing the effects of a multi-dose administration (3 mg/kg every day for 5 days during week 1, followed by 3 mg/kg two times per week on weeks 2-4 (3.0 mg/kg qd×5; qw×6)) of AD-57927 on triglyceride (TG) levels in ob/ob female mice. The amount of TG presented is relative to the amount TG present in a serum sample prior to administration of AD-57927.
Figure 4:
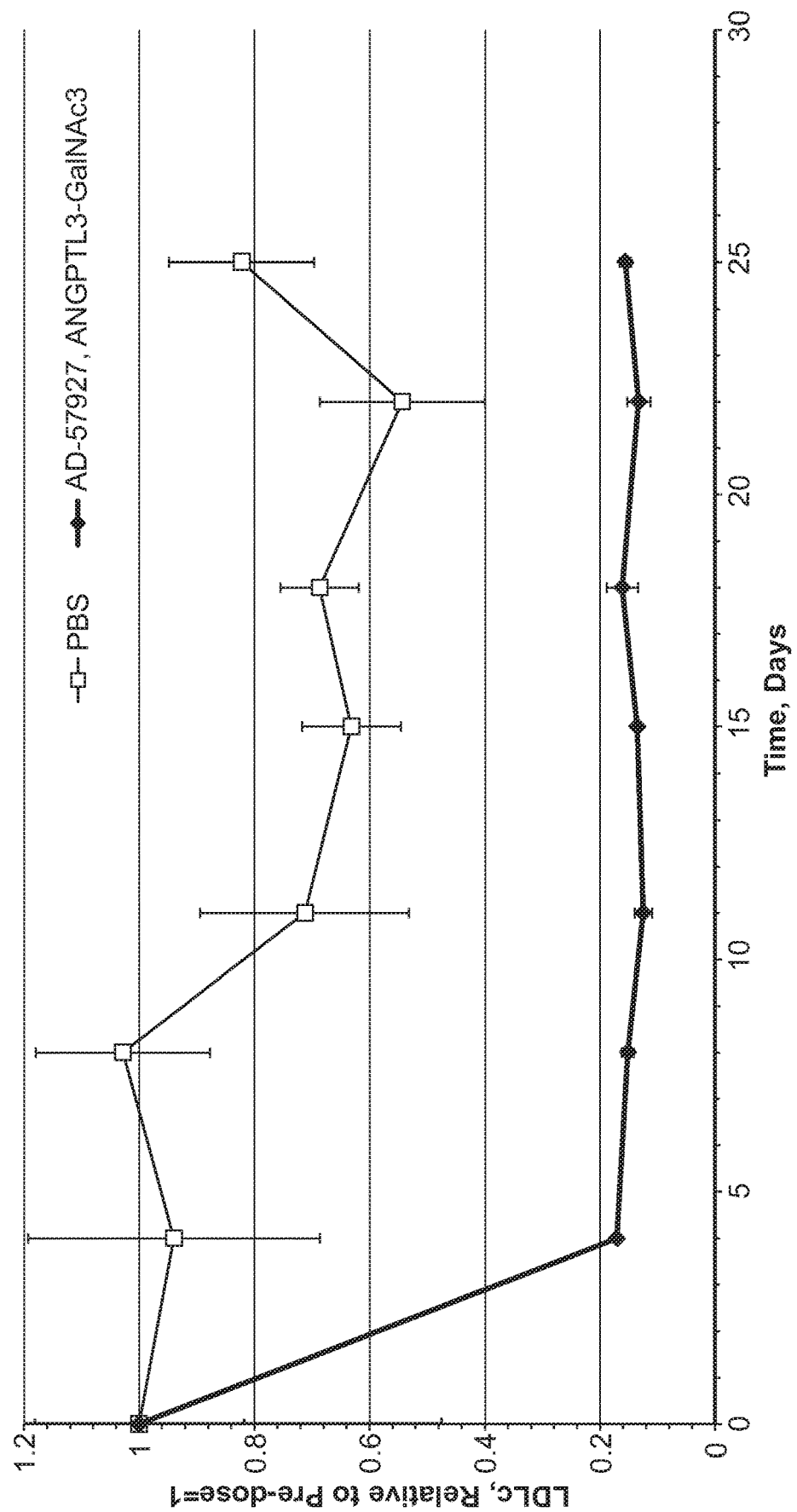
FIG. 4 is a graph showing the effects of a multi-dose administration (3 mg/kg every day for 5 days during week 1, followed by 3 mg/kg two times per week on weeks 2-4 (3.0 mg/kg qd×5; qw×6)) of AD-57927 on LDL cholesterol (LDLc) levels in ob/ob female mice. The amount of LDLc presented is relative to the amount LDLc present in a serum sample prior to administration of AD-57927.
Figure 5:
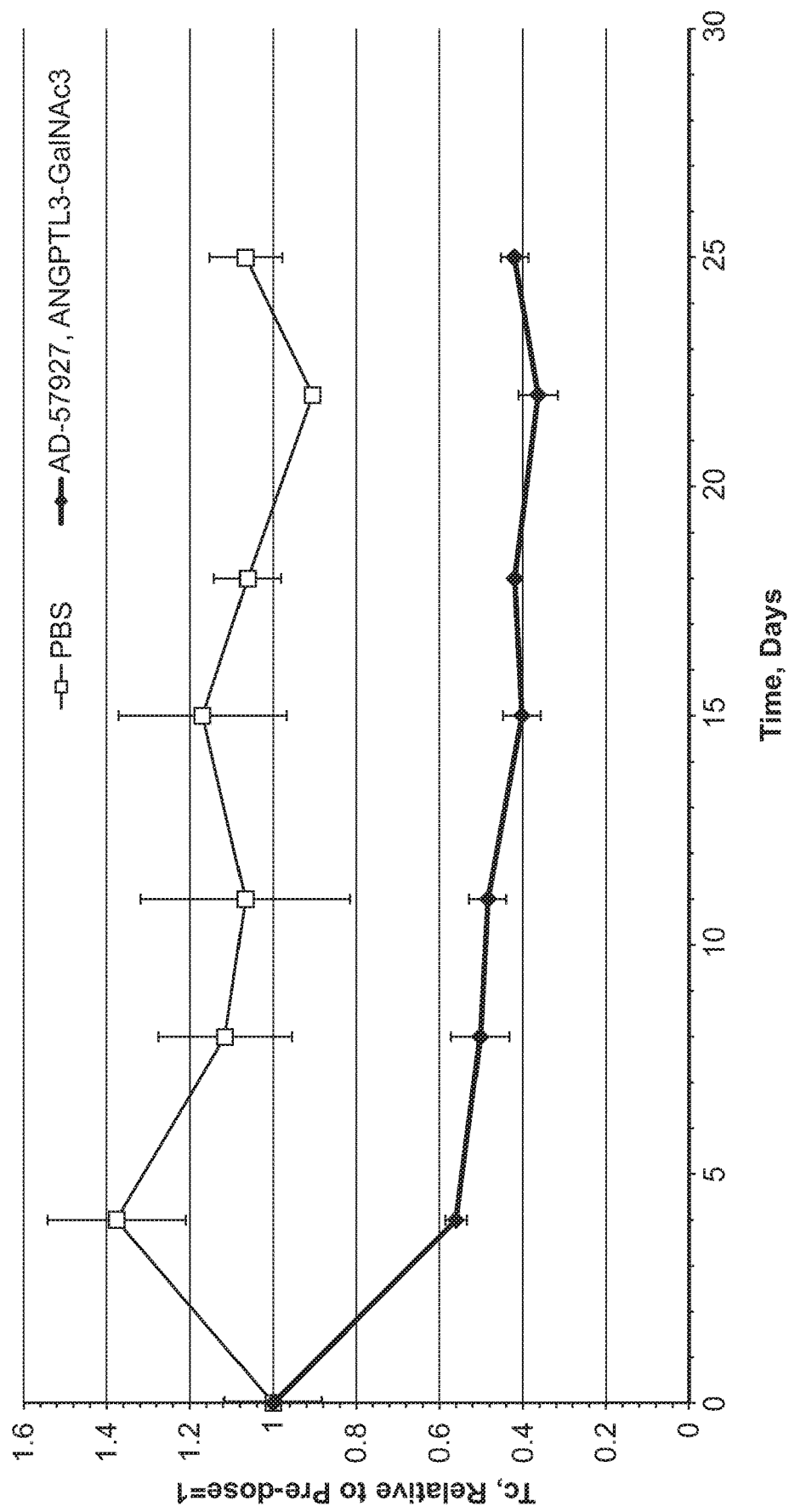
FIG. 5 is a graph showing the effects of a multi-dose administration (3 mg/kg every day for 5 days during week 1, followed by 3 mg/kg two times per week on weeks 2-4 (3.0 mg/kg qd×5; qw×6)) of AD-57927 on total cholesterol (Tc) levels in ob/ob female mice. The amount of Tc presented is relative to the amount Tc present in a serum sample prior to administration of AD-57927.

The ability of AD-57927 to suppress expression of ANGPTL3 protein and to decrease the levels of triglycerides, LDL cholesterol, and total cholesterol in vivo was also assessed using a multi-dose regimen. ob/ob female mice were subcutaneously administered AD-57927 at 3 mg/kg every day for 5 days on week 1 followed by a dose of 3 mg/kg two times per week on weeks 2-4 (qd×5; qw×6). Animals were bled on days 0, 4, 8, 11, 15, 18, 22, and 25, and sacrificed on day 29. ANPTL3 protein levels were measured by ELISA. Triglycerides, LDL cholesterol, and total cholesterol were measured using an Olympus serum analyzer. As shown in FIG. 2, the maximal knockdown of ANGPTL3 protein by AD-57927 was 99%. The maximal levels of triglyceride lowering by AD-57927 was 98% (FIG. 3), the maximal LDL lowering by AD-57927 was 88% (FIG. 4), and the maximal total cholesterol lowering by AD-57927 was 64% (FIG. 5). All of the data presented in FIGS. 2-5 is relative to predose levels.

In summary, AD-57927 was demonstrated to reduce ANGPTL3 mRNA levels about 10-fold more that the parent sequence. AD-57927 was also demonstrated to reduce ANGPTL3 in a dose responsive manner (see FIG. 1) and the efficacy of AD-57927 was further improved upon multi-dose administration resulting in greater than 95% reduction of serum ANPTL3 protein in the ob/ob mouse model of mixed hyperlipidemia. Furthermore, multi-dose administration of AD-57927 at 3 mg/kg eliminated circulating serum ANG-PLT3 protein as measured by ANGPTL3 specific ELISA assay, which resulted in a >95% reduction in TGs, a >85% reduction in LDL cholesterol, and a >60% reduction in total cholesterol in the ob/ob mouse model of hyperlipidemia.

Example 3. iRNA Design, Synthesis, Selection, and In Vitro Evaluation

This Example describes methods for the design, synthesis, selection, and in vitro evaluation of additional ANGPTL3 iRNA agents.

In Vitro Screening:
Cell Culture and Transfections:
Hep3b cells (ATCC, Manassas, Va.) were grown to near confluence at 37° C. in an atmosphere of 5% $CO_2$ in Eagle's Minimum Essential Medium (Gibco) supplemented with 10% FBS (ATCC) before being released from the plate by trypsinization. Transfection was carried out by adding 4.9 µl of Opti-MEM plus 0.1 µl of Lipofectamine RNAiMax per well (Invitrogen, Carlsbad Calif. cat #13778-150) to 5 µl of each siRNA duplex to an individual well in a 384-well plate. The mixture was then incubated at room temperature for 20 minutes. 40 µl of complete growth media containing 5,000 Hep3b cells were then added to the siRNA mixture. Cells were incubated for 24 hrs prior to RNA purification. Single dose experiments were performed at 10 nM and 0.1 nM final duplex concentration.

Total RNA Isolation Using DYNABEADS mRNA Isolation Kit (Invitrogen, Part #: 610-12):
Cells were lysed in 7511 of Lysis/Binding Buffer containing 3 µL of beads per well and mixed for 10 minutes on an electrostatic shaker. The washing steps were automated on a Biotek EL406, using a magnetic plate support. Beads were washed (90 µL) once in Buffer A, once in Buffer B, and twice in Buffer E, with aspiration steps in between. Following a final aspiration, complete 10 µL RT mixture was added to each well, as described below.

cDNA Synthesis Using ABI High Capacity cDNA Reverse Transcription Kit (Applied Biosystems, Foster City, Calif., Cat #4368813):
A master mix of 1 µl 10× Buffer, 0.4 µl 25×dNTPs, 1 µl Random primers, 0.5 µl Reverse Transcriptase, 0.5 µl RNase inhibitor and 6.6 µl of H2O per reaction were added per well. Plates were sealed, agitated for 10 minutes on an electrostatic shaker, and then incubated at 37 degrees C. for 2 hours. Following this, the plates were agitated at 80 degrees C. for 8 minutes.

Real Time PCR:
2 µl of cDNA were added to a master mix containing 0.5 µl of human GAPDH TaqMan Probe (4326317E), 0.5 µl human AngPTL3 (Hs00205581_m1), 2 µl nuclease-free water and 5 µl Lightcycler 480 probe master mix (Roche Cat #04887301001) per well in a 384 well plates (Roche cat #04887301001). Real time PCR was done in a LightCycler480 Real Time PCR system (Roche) using the ΔΔCt(RQ) assay. Each duplex was tested in at least two independent transfections, unless otherwise noted in the summary tables.

To calculate relative fold change, real time data were analyzed using the ΔΔCt method and normalized to assays performed with cells transfected with 10 nM nonspecific siRNA, or mock transfected cells.

A series of ANGPLT3 iRNAs containing various chemical modifications based on the sense sequence 5'-ACAUAUUUGAUCAGUCUUUUU-3' (SEQ ID NO: 20) and the antisense sequence 5'-AAAAAGACUGAUCAAAUAUGUUG-3' (SEQ ID NO: 21) were tested. The chemical modifications of the sequences are shown in Tables 2A and 2B. The results from the assays are shown in Table 3.

Additional iRNA agents targeting the ANGPTL3 gene were synthesized as described above. A detailed list of the additional modified ANGPTL3 sense and antisense strand sequences is shown in Tables 4A, 4B, 7A, and 7B and a detailed list of the unmodified ANGPTL3 sense and antisense strand sequences is shown in Tables 5 and 7C.

TABLE 2A

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-57927 | AfscsAfuAfuUfuGfAfUfcAfgUfcUfuUfuUfL96 | 74 | asAfsaAfaGfaCfuGfaucAfaAfuAfuGfususg | 170 |
| AD-63131 | ascsauauuugaUfCfagucuuuuuL96 | 75 | asAfsaAfaGfaCfuGfaucAfaAfuAfuGfususg | 171 |

TABLE 2A-continued

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-63132 | ascsauauuugadTdCagucuuuuuL96 | 76 | asAfsaAfaGfaCfuGfaucAfaAfuAfuGfususg | 172 |
| AD-63133 | AfscsAfuAfuUfuGfAfUfcAfgUfcUfuUfuUfL96 | 77 | asAfsaAfagaCfuGfaucAfaAfuAfugususg | 173 |
| AD-63134 | ascsauaUfuGfaUfCfagUfCfuuuuuL96 | 78 | asAfsaaaGfacUfgaucAfaAfuaugususg | 174 |
| AD-63136 | Y44AfscsAfuAfuUfuGfAfUfcAfgUfcUfuUfuUfL96 | 79 | asAfsaAfaGfaCfuGfaucAfaAfuAfuGfususg | 175 |
| AD-63137 | ascsauaUfuGfAfUfcagucCfuudTuuL96 | 80 | asAfsaAfaGfaCfuGfaucAfaAfuAfuGfususg | 176 |
| AD-63138 | ascsauauuugadTcagucuuuuuL96 | 81 | asAfsaAfaGfaCfuGfaucAfaAfuAfuGfususg | 177 |
| AD-63139 | AfscsAfuAfuUfuGfAfUfcAfgUfcUfuUfuUfL96 | 82 | asAfsaAfagaCfugaucAfaAfuAfugususg | 178 |
| AD-63140 | ascsauaUfuugaUfcagucuuuuuL96 | 83 | asAfsaaaGfacUfgaucAfaAfuaugususg | 179 |
| AD-63142 | AfscsAfuAfuUfuGfAfUfcAfgUfcUfuUfuUfL96 | 84 | PasAfsaAfaGfaCfuGfaucAfaAfuAfuGfususg | 180 |
| AD-63143 | ascsauauUfuGfAfUfcaguCfdTuuuuL96 | 85 | asAfsaAfaGfaCfuGfaucAfaAfuAfuGfususg | 181 |
| AD-63144 | ascsauauuugadTcaguc(Tgn)uuuuL96 | 86 | asAfsaAfaGfaCfuGfaucAfaAfuAfuGfususg | 182 |
| AD-63145 | AfscsAfuAfuUfuGfAfUfcAfgUfcUfuUfuUfL96 | 87 | asAfsaAfagacuGfaucAfaAfuAfugususg | 183 |
| AD-63146 | ascsauaUfuuGfaUfCfagUfCfuudTuuL96 | 88 | asAfsaaaGfacUfgaucAfaAfuaugususg | 184 |
| AD-63148 | Y44AfscsAfuAfuUfuGfAfUfcAfgUfcUfuUfuUfL96 | 89 | PasAfsaAfaGfaCfuGfaucAfaAfuAfuGfususg | 185 |
| AD-63149 | ascsauaUfuGfAfdTcaguCfuuuuuL96 | 90 | asAfsaAfaGfaCfuGfaucAfaAfuAfuGfususg | 186 |
| AD-63150 | AfscsAfuAfuUfuGfAfUfcAfgUfcUfuUfuUfL96 | 91 | asAfsaAfaGfacuGfaucAfaAfuAfuGfususg | 187 |
| AD-63151 | AfscsAfuAfuUfuGfAfUfcAfgUfcUfuUfuUfL96 | 92 | asAfsaaaGfacUfgaucAfaAfuaugususg | 188 |
| AD-63152 | ascsauaUfuuGfaUfCfagUfCfdTuuuuL96 | 93 | asAfsaaaGfacUfgaucAfaAfuaugususg | 189 |
| AD-63153 | asusAfuUfuGfAfUfcAfgUfcUfuUfuUfL96 | 94 | PasAfsaAfaGfaCfuGfaucAfaAfuAfusgsu | 190 |
| AD-63154 | ascsauaUfuugAfUfcAfguCfuuuuuL96 | 95 | asAfsaAfaGfaCfuGfaucAfaAfuAfuGfususg | 191 |
| AD-63155 | ascsauaUfuugaUfcagucuudTuuL96 | 96 | asAfsaAfaGfaCfuGfaucAfaAfuAfuGfususg | 192 |
| AD-63156 | AfscsAfuAfuUfuGfAfUfcAfgUfcUfuUfuUfL96 | 97 | asAfsaaaGfaCfuGfaucAfaAfuauGfususg | 193 |
| AD-63157 | AfscsAfuAfuUfuGfAfUfcAfgUfcUfuUfuUfL96 | 98 | asAfsaaaGfacugaucAfaAfuaugususg | 194 |
| AD-63158 | ascsauaUfuuGfadTCfagUfCfuuuuuL96 | 99 | asAfsaaaGfacUfgaucAfaAfuaugususg | 195 |
| AD-63160 | ascsauauUfuGfAfUfcaguCfuuuuuL96 | 100 | asAfsaAfaGfaCfuGfaucAfaAfuAfuGfususg | 196 |
| AD-63161 | ascsauaUfuugaUfcagucdTuuuuL96 | 101 | asAfsaAfaGfaCfuGfaucAfaAfuAfuGfususg | 197 |
| AD-63162 | AfscsAfuAfuUfuGfAfUfcAfgUfcUfuUfuUfL96 | 102 | asAfsaAfaGfaCfuGfaucAfaAfuAfugususg | 198 |
| AD-63163 | AfscsAfuAfuUfuGfAfUfcAfgUfcUfuUfuUfL96 | 103 | asAfsaaaGfaCfUfgaucAfaAfuaugususg | 199 |
| AD-63164 | ascsauaUfuugaUfcagucuudTuuL96 | 104 | asAfsaaaGfacUfgaucAfaAfuaugususg | 200 |
| AD-63165 | ascsauaUfuuGfaUfCfagUfCfuuuuuL96 | 105 | asAfsaAfaGfaCfuGfaucAfaAfuAfuGfususg | 201 |
| AD-63166 | ascsauaUfuugaUfdCagucuuuuuL96 | 106 | asAfsaAfaGfaCfuGfaucAfaAfuAfuGfususg | 202 |
| AD-63167 | AfscsAfuAfuUfuGfAfUfcAfgUfcUfuUfuUfL96 | 107 | asAfsaaaGfacuGfaucAfaAfuauGfususg | 203 |
| AD-63168 | ascsauaUfuugAfUfcAfguCfuuuuuL96 | 108 | asAfsaaaGfacUfgaucAfaAfuaugususg | 204 |
| AD-63169 | ascsauaUfuugaUfcagucdTuuuuL96 | 109 | asAfsaaaGfacUfgaucAfaAfuaugususg | 205 |
| AD-63170 | ascsAfuAfuuuGfAfUfcAfguCfUfuuuuL96 | 110 | asAfsAfaaGfaCfuGfaucAfAfAfuAfuGfususg | 206 |
| AD-63171 | ascsauaUfuugaUfcagucuuuuuL96 | 111 | asAfsaAfaGfaCfuGfaucAfaAfuAfuGfususg | 207 |
| AD-63172 | ascsauauuugaUfdCagucuuuuuL96 | 112 | asAfsaAfaGfaCfuGfaucAfaAfuAfuGfususg | 208 |

TABLE 2A-continued

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-63173 | AfscsAfuAfuUfuGfAfUfcAfgUfcUfuUfuUfL96 | 113 | asAfsaaaGfaCfuGfaucAfaAfuaugususg | 209 |
| AD-63174 | ascsauauUfuGfAfUfcaguCfuuuuuL96 | 114 | asAfsaaaGfacUfgaucAfaAfuaugususg | 210 |
| AD-63175 | ascsauaUfuugaUfdCagucuuuuuL96 | 115 | asAfsaaaGfacUfgaucAfaAfuaugususg | 211 |
| AD-63176 | ascsAfuAfuuuGfAfUfcAfguCfUfuuuuL96 | 116 | asAfsAfAfaGfaCfuGfaucAfAfAfuAfuGfususg | 212 |
| AD-63177 | AfscsAfuAfuUfuGfAfUfcAfgUfcUfuUfuUfL96 | 117 | asAfsa(Aam)aGfaCfuGfaucAfaAfuAfuGfususg | 213 |
| AD-63179 | ascsAfuAfuuuGfAfUfcAfguCfUfuuuuL96 | 118 | asAfsAfAfaaGfaCfuGfaucAfAfAfuAfugususg | 214 |
| AD-63180 | AfscsAfuAfuUfuGfAfUfcAfgUfcUfuUfuUfL96 | 119 | as(Aams)aAfaGfaCfuGfaucAfaAfu(Aam)uGfususg | 215 |
| AD-63181 | ascsAfuAfuuuGfAfUfcAfguCfUfuuuuL96 | 120 | asAfsAfAfaGfaCfuGfaucAfAfAfuAfugususg | 216 |
| AD-63182 | AfscsAfuAfuUfuGfAfUfcAfgUfcUfuUfuUfL96 | 121 | asAfsa(Aam)aGfaCfuGfaucAfaAfu(Aam)uGfususg | 217 |
| AD-63183 | AfscsAfuAfuUfuGfAfUfcAfgUfcUfuUfuUfL96 | 122 | asasaAfaGfaCfuGfaucAfaAfuAfuGfususg | 218 |
| AD-63185 | AfscsAfuAfuUfuGfAfUfcAfgUfcUfuUfuUfL96 | 123 | asAfsaAfagaCfuGfaucAfaAfuAfuGfususg | 219 |
| AD-63186 | AfscsAfuAfuUfuGfAfUfcAfgUfcUfuUfuUfL96 | 124 | asAfsaAfaGfaCfuGfaucaaAfuAfuGfususg | 220 |
| AD-63187 | AfscsAfuAfuUfuGfAfucAfgUfcUfuUfuUfL96 | 125 | asAfsaAfaGfaCfuGfaucAfaAfuAfuGfususg | 221 |
| AD-63188 | AfscsAfuAfuUfuGfAfUfcAfgUfcUfuUfuUfL96 | 126 | as(Aams)aAfaGfaCfuGfaucAfaAfuAfuGfususg | 222 |
| AD-64744 | ascsauauuugadTcagucdTuuuuL96 | 127 | asAfsaAfaGfaCfuGfaucAfaAfuAfuGfususg | 223 |
| AD-64745 | AfscsAfuAfuUfuGfAfUfcAfgUfcUfuUfuUfL96 | 128 | asAfsaaaGfacuGfaucAfaauaugususg | 224 |
| AD-64746 | AfscsAfuAfuUfuGfAfUfcAfgUfcUfuUfuUfL96 | 129 | asdAsaaagacugaucdAadAuaugususg | 225 |
| AD-64747 | ascsauauuuGfaUfcagUfcuuUfuuL96 | 130 | asAfsaaaGfacuGfaucAfaAfuaugususg | 226 |
| AD-64748 | ascsauauuuugadTcagucdAuuuuL96 | 131 | asdAsaaagacudGaucdAaauaugususg | 227 |
| AD-64749 | ascsauauuuGfaUfcagUfcuuUfuuL96 | 132 | asAfsaAfaGfaCfuGfaucAfaAfuAfuGfususg | 228 |
| AD-64750 | ascsauauuugadTdCagucdTuuuuL96 | 133 | asAfsaAfaGfaCfuGfaucAfaAfuAfuGfususg | 229 |
| AD-64751 | AfscsAfuAfuUfuGfAfUfcAfgUfcUfuUfuUfL96 | 134 | asdAsaaadGacudGaucdAaauaugususg | 230 |
| AD-64752 | ascsauauuuGfaUfcagUfcuuuuL96 | 135 | asAfsaaaGfacuGfaucAfaAfuaugususg | 231 |
| AD-64753 | ascsauauuugadTcagucdAuuuuL96 | 136 | asdAsaaadGacugaucdAaauaugususg | 232 |
| AD-64754 | ascsauauuuGfaUfcagUfcuuuuL96 | 137 | asAfsaAfaGfaCfuGfaucAfaAfuAfuGfususg | 233 |
| AD-64755 | ascsauauuugadTdCagucdCuuuuL96 | 138 | asAfsaAfaGfaCfuGfaucAfaAfuAfuGfususg | 234 |
| AD-64756 | AfscsAfuAfuUfuGfAfUfcAfgUfcUfuUfuUfL96 | 139 | asAfsaaagacugaucAfaauaugususg | 235 |
| AD-64757 | AfscsAfuAfuUfuGfAfUfcAfgUfcUfuUfuUfL96 | 140 | asAsaaagacudGaucdAaauaugususg | 236 |
| AD-64758 | ascsauauuGfaUfcagUfcuuUfuuL96 | 141 | asAfsaaaGfacUfGfaucAfaAfuaugususg | 237 |
| AD-64759 | ascsauauuugadTcagucdAuuuuL96 | 142 | asdAsaaadGacudGaucdAaauaugususg | 238 |
| AD-64760 | ascsauauuuadTcagucuuuuuL96 | 143 | asAfsaAfaGfaCfuGfaucAfaAfuAfuGfususg | 239 |
| AD-64761 | ascsauauuugadTcagucdGuuuuL96 | 144 | asAfsaAfaGfaCfuGfaucAfaAfuAfuGfususg | 240 |
| AD-64762 | AfscsAfuAfuUfuGfAfUfcAfgUfcUfuUfuUfL96 | 145 | asdAsaaagacugaucdAaauaugususg | 241 |
| AD-64763 | AfscsAfuAfuUfuGfAfUfcAfgUfcUfuUfuUfL96 | 146 | asdAsaaagacudGaucAaauaugususg | 242 |
| AD-64764 | ascsauauuGfaUfcagUfcuuuuuL96 | 147 | asAfsaaaGfacUfGfaucAfaAfuaugususg | 243 |
| AD-64765 | ascsauauuugaUcaguc(Tgn)uuuuL96 | 148 | asdAsaaagacudGaucdAaauaugususg | 244 |
| AD-64766 | ascsauauuugadTcagu(Cgn)uuuuL96 | 149 | asAfsaAfaGfaCfuGfaucAfaAfuAfuGfususg | 245 |

TABLE 2A-continued

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-64767 | ascsauauuugadTcagucdCuuuuL96 | 150 | asAfsaAfaGfaCfuGfaucAfaAfuAfuGfususg | 246 |
| AD-64768 | AfscsAfuAfuUfuGfAfUfcAfgUfcUfuUfuUfL96 | 151 | asasaaagacudGaucdAaauaugususg | 247 |
| AD-64769 | AfscsAfuAfuUfuGfAfUfcAfgUfcUfuUfuUfL96 | 152 | asAsaaagacudGaucAaauaugususg | 248 |
| AD-64770 | ascsauauuugadTcaguc(Tgn)uuuuL96 | 153 | asdAsaaagacudGaucAaauaugususg | 249 |
| AD-64771 | ascsauauuugaUcaguc(Tgn)uuuuL96 | 154 | asdAsaaaDGacugaucdAaauaugususg | 250 |
| AD-64772 | ascsauauuugadTcagucdAuuuuL96 | 155 | asAfsaAfaGfaCfuGfaucAfaAfuAfuGfususg | 251 |
| AD-64773 | AfscsAfuAfuUfuGfAfUfcAfgUfcUfuUfuUfL96 | 156 | asasaaaDGacugaucdAaauaugususg | 252 |
| AD-64774 | AfscsAfuAfuUfuGfAfUfcAfgUfcUfuUfuUfL96 | 157 | asAsaaaDGacugaucAaauaugususg | 253 |
| AD-64775 | ascsauauuugadTcaguc(Tgn)uuuuL96 | 158 | asdAsaaaDGacugaucdAaauaugususg | 254 |
| AD-64776 | ascsauauuugaUcaguc(Tgn)uuuuL96 | 159 | asdAsaaaDGacudGaucdAaauaugususg | 255 |
| AD-64777 | ascsauauuugadTcagucu(Tgn)uuuuL96 | 160 | asAfsaAfaGfaCfuGfaucAfaAfuAfuGfususg | 256 |
| AD-64778 | AfscsAfuAfuUfuGfAfUfcAfgUfcUfuUfuUfL96 | 161 | asAfsaaaGfacuGfaucAfaAfuaugususg | 257 |
| AD-64779 | AfscsAfuAfuUfuGfAfUfcAfgUfcUfuUfuUfL96 | 162 | asdAsaaagacudGaucdAaauaugususg | 258 |
| AD-64780 | AfscsAfuAfuUfuGfAfUfcAfgUfcUfuUfuUfL96 | 163 | PasdAsaaagacudGaucdAaauaugususg | 259 |
| AD-64781 | ascsauauuugadTcaguc(Tgn)uuuuL96 | 164 | asdAsaaagacudGaucdAaauaugususg | 260 |
| AD-64782 | ascsauauuugaUcaguc(Tgn)uuuuL96 | 165 | asAfsaAfaGfaCfuGfaucAfaAfuAfuGfususg | 261 |
| AD-64783 | AfscsAfuAfuUfuGfAfUfcAfgUfcUfuUfuUfL96 | 166 | asAfsaaaGfacUfGfaucAfaAfuaugususg | 262 |
| AD-64784 | AfscsAfuAfuUfuGfAfUfcAfgUfcUfuUfuUfL96 | 167 | asdAsaaaDGacugaucdAaauaugususg | 263 |
| AD-64785 | AfscsAfuAfuUfuGfAfUfcAfgUfcUfuUfuUfL96 | 168 | PasasaaagacudGaucdAaauaugususg | 264 |
| AD-64786 | ascsauauuugadTcaguc(Tgn)uuuuL96 | 169 | PasdAsaaagacudGaucdAaauaugususg | 265 |

TABLE 2B

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-57927 | AfscsAfuAfuUfuGfAfUfcAfgUfcUfuUfuUf | 74 | asAfsaAfaGfaCfuGfaucAfaAfuAfuGfususg | 170 |
| AD-63131 | ascsauauuugaUfCfagucuuuuu | 75 | asAfsaAfaGfaCfuGfaucAfaAfuAfuGfususg | 171 |
| AD-63132 | ascsauauuugadTdCagucuuuuu | 76 | asAfsaAfaGfaCfuGfaucAfaAfuAfuGfususg | 172 |
| AD-63133 | AfscsAfuAfuUfuGfAfUfcAfgUfcUfuUfuUf | 77 | asAfsaAfagaCfuGfaucAfaAfuAfugususg | 173 |
| AD-63134 | ascsauaUfuuGfaUfCfagUfCfuuuuu | 78 | asAfsaaaGfacUfgaucAfaAfuaugususg | 174 |
| AD-63136 | Y44AfscsAfuAfuUfuGfAfUfcAfgUfcUfuUfuUf | 79 | asAfsaAfaGfaCfuGfaucAfaAfuAfuGfususg | 175 |
| AD-63137 | ascsauauUfuGfAfUfcaguCfuudTuu | 80 | asAfsaAfaGfaCfuGfaucAfaAfuAfuGfususg | 176 |
| AD-63138 | ascsauauuugadTcagucuuuuu | 81 | asAfsaAfaGfaCfuGfaucAfaAfuAfuGfususg | 177 |
| AD-63139 | AfscsAfuAfuUfuGfAfUfcAfgUfcUfuUfuUf | 82 | asAfsaAfagaCfugaucAfaAfuAfugususg | 178 |
| AD-63140 | ascsauaUfuugaUfcagucuuuuu | 83 | asAfsaaaGfacUfgaucAfaAfuaugususg | 179 |
| AD-63142 | AfscsAfuAfuUfuGfAfUfcAfgUfcUfuUfuUf | 84 | PasAfsaAfaGfaCfuGfaucAfaAfuAfuGfususg | 180 |
| AD-63143 | ascsauauUfuGfAfUfcaguCfdTuuuu | 85 | asAfsaAfaGfaCfuGfaucAfaAfuAfuGfususg | 181 |

TABLE 2B-continued

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-63144 | ascsauauuugadTcaguc(Tgn)uuuu | 86 | asAfsaAfaGfaCfuGfaucAfaAfuAfuGfususg | 182 |
| AD-63145 | AfscsAfuAfuUfuGfAfUfcAfgUfcUfuUfuUf | 87 | asAfsaAfagacuGfaucAfaAfuAfugususg | 183 |
| AD-63146 | ascsauaUfuuGfaUfCfagUfCfuudTuu | 88 | asAfsaaaGfacUfgaucAfaAfuaugususg | 184 |
| AD-63148 | Y44AfscsAfuAfuUfuGfAfUfcAfgUfcUfuUfuUf | 89 | PasAfsaAfaGfaCfuGfaucAfaAfuAfuGfususg | 185 |
| AD-63149 | ascsauauUfuGfAfdTcaguCfuuuuu | 90 | asAfsaAfaGfaCfuGfaucAfaAfuAfuGfususg | 186 |
| AD-63150 | AfscsAfuAfuUfuGfAfUfcAfgUfcUfuUfuUf | 91 | asAfsaAfaGfacuGfaucAfaAfuAfuGfususg | 187 |
| AD-63151 | AfscsAfuAfuUfuGfAfUfcAfgUfcUfuUfuUf | 92 | asAfsaaaGfacUfgaucAfaAfuaugususg | 188 |
| AD-63152 | ascsauaUfuuGfaUfCfagUfCfdTuuuu | 93 | asAfsaaaGfacUfgaucAfaAfuaugususg | 189 |
| AD-63153 | asusAfuUfuGfAfUfcAfgUfcUfuUfuUf | 94 | PasAfsaAfaGfaCfuGfaucAfaAfuAfusgsu | 190 |
| AD-63154 | ascsauaUfuugAfUfcAfguCfuuuuu | 95 | asAfsaAfaGfaCfuGfaucAfaAfuAfuGfususg | 191 |
| AD-63155 | ascsauaUfuugaUfcagucuudTuu | 96 | asAfsaAfaGfaCfuGfaucAfaAfuAfuGfususg | 192 |
| AD-63156 | AfscsAfuAfuUfuGfAfUfcAfgUfcUfuUfuUf | 97 | asAfsaaaGfaCfuGfaucAfaAfuauGfususg | 193 |
| AD-63157 | AfscsAfuAfuUfuGfAfUfcAfgUfcUfuUfuUf | 98 | asAfsaaaGfacugaucAfaAfuaugususg | 194 |
| AD-63158 | ascsauaUfuuGfadTCfagUfCfuuuuu | 99 | asAfsaaaGfacUfgaucAfaAfuaugususg | 195 |
| AD-63160 | ascsauauUfuGfAfUfcaguCfuuuuu | 100 | asAfsaAfaGfaCfuGfaucAfaAfuAfuGfususg | 196 |
| AD-63161 | ascsauaUfuugaUfcagucdTuuuu | 101 | asAfsaAfaGfaCfuGfaucAfaAfuAfuGfususg | 197 |
| AD-63162 | AfscsAfuAfuUfuGfAfUfcAfgUfcUfuUfuUf | 102 | asAfsaAfaGfaCfuGfaucAfaAfuaugususg | 198 |
| AD-63163 | AfscsAfuAfuUfuGfAfUfcAfgUfcUfuUfuUf | 103 | asAfsaaaGfaCfUfgaucAfaAfuaugususg | 199 |
| AD-63164 | ascsauaUfuugaUfcagucuudTuu | 104 | asAfsaaaGfacUfgaucAfaAfuaugususg | 200 |
| AD-63165 | ascsauaUfuuGfaUfCfagUfCfuuuuu | 105 | asAfsaAfaGfaCfuGfaucAfaAfuAfuGfususg | 201 |
| AD-63166 | ascsauaUfuugaUfdCagucuuuuu | 106 | asAfsaAfaGfaCfuGfaucAfaAfuAfuGfususg | 202 |
| AD-63167 | AfscsAfuAfuUfuGfAfUfcAfgUfcUfuUfuUf | 107 | asAfsaaaGfacuGfaucAfaAfuauGfususg | 203 |
| AD-63168 | ascsauaUfuugAfUfcAfguCfuuuuu | 108 | asAfsaaaGfacUfgaucAfaAfuaugususg | 204 |
| AD-63169 | ascsauaUfuugaUfcagucdTuuuu | 109 | asAfsaaaGfacUfgaucAfaAfuaugususg | 205 |
| AD-63170 | ascsAfuAfuuuGfAfUfcAfguCfUfuuuu | 110 | asAfsAfaaGfaCfuGfaucAfAfAfuAfuGfususg | 206 |
| AD-63171 | ascsauaUfuugaUfcagucuuuuu | 111 | asAfsaAfaGfaCfuGfaucAfaAfuAfuGfususg | 207 |
| AD-63172 | ascsauauuugaUfdCagucuuuuu | 112 | asAfsaAfaGfaCfuGfaucAfaAfuAfuGfususg | 208 |
| AD-63173 | AfscsAfuAfuUfuGfAfUfcAfgUfcUfuUfuUf | 113 | asAfsaaaGfaCfuGfaucAfaAfuaugususg | 209 |
| AD-63174 | ascsauaUfuGfAfUfcagucfuuuuu | 114 | asAfsaaaGfacUfgaucAfaAfuaugususg | 210 |
| AD-63175 | ascsauaUfuugaUfdCagucuuuuu | 115 | asAfsaaaGfacUfgaucAfaAfuaugususg | 211 |
| AD-63176 | ascsAfuAfuuuGfAfUfcAfguCfUfuuuu | 116 | asAfsAfAfaGfaCfuGfaucAfAfAfuAfuGfususg | 212 |
| AD-63177 | AfscsAfuAfuUfuGfAfUfcAfgUfcUfuUfuUf | 117 | asAfsa(Aam)aGfaCfuGfaucAfaAfuAfuGfususg | 213 |
| AD-63179 | ascsAfuAfuuuGfAfUfcAfguCfUfuuuu | 118 | asAfsAfaaGfaCfuGfaucAfAfAfuAfugususg | 214 |
| AD-63180 | AfscsAfuAfuUfuGfAfUfcAfgUfcUfuUfuUf | 119 | as(Aams)aAfaGfaCfuGfaucAfaAfu(Aam)uGfususg | 215 |
| AD-63181 | ascsAfuAfuuuGfAfUfcAfguCfUfuuuu | 120 | asAfsAfAfaGfaCfuGfaucAfAfAfuAfugususg | 216 |
| AD-63182 | AfscsAfuAfuUfuGfAfUfcAfgUfcUfuUfuUf | 121 | asAfsa(Aam)aGfaCfuGfaucAfaAfu(Aam)uGfususg | 217 |
| AD-63183 | AfscsAfuAfuUfuGfAfUfcAfgUfcUfuUfuUf | 122 | asasaAfaGfaCfuGfaucAfaAfuAfuGfususg | 218 |

TABLE 2B-continued

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-63185 | AfscsAfuAfuUfuGfAfUfcAfgUfcUfuUfuUf | 123 | asAfsaAfagaCfuGfaucAfaAfuAfuGfususg | 219 |
| AD-63186 | AfscsAfuAfuUfuGfAfUfcAfgUfcUfuUfuUf | 124 | asAfsaAfaGfaCfuGfaucaaAfuAfuGfususg | 220 |
| AD-63187 | AfscsAfuAfuUfuGfAfucAfgUfcUfuUfuUf | 125 | asAfsaAfaGfaCfuGfaucAfaAfuAfuGfususg | 221 |
| AD-63188 | AfscsAfuAfuUfuGfAfUfcAfgUfcUfuUfuUf | 126 | as(Aams)aAfaGfaCfuGfaucAfaAfuAfuGfususg | 222 |
| AD-64744 | ascsauauuugadTcagucdTuuuu | 127 | asAfsaAfaGfaCfuGfaucAfaAfuAfuGfususg | 223 |
| AD-64745 | AfscsAfuAfuUfuGfAfUfcAfgUfcUfuUfuUf | 128 | asAfsaaaGfacuGfaucAfaauaugususg | 224 |
| AD-64746 | AfscsAfuAfuUfuGfAfUfcAfgUfcUfuUfuUf | 129 | asdAsaaagacugaucdAadAuaugususg | 225 |
| AD-64747 | ascsauauuuGfaUfcagUfcuuUfuu | 130 | asAfsaaaGfacuGfaucAfaAfuaugususg | 226 |
| AD-64748 | ascsauauuugadTcagucdAuuuu | 131 | asdAsaaagacudGaucdAaauaugususg | 227 |
| AD-64749 | ascsauauuuGfaUfcagUfcuuUfuu | 132 | asAfsaAfaGfaCfuGfaucAfaAfuAfuGfususg | 228 |
| AD-64750 | ascsauauuugadTdCagucdTuuuu | 133 | asAfsaAfaGfaCfuGfaucAfaAfuAfuGfususg | 229 |
| AD-64751 | AfscsAfuAfuUfuGfAfUfcAfgUfcUfuUfuUf | 134 | asdAsaaadGacudGaucdAaauaugususg | 230 |
| AD-64752 | ascsauauuuGfaUfcagUfcuuuuu | 135 | asAfsaaaGfacuGfaucAfaAfuaugususg | 231 |
| AD-64753 | ascsauauuugadTcagucdAuuuu | 136 | asdAsaaadGacugaucdAaauaugususg | 232 |
| AD-64754 | ascsauauuuGfaUfcagUfcuuuuu | 137 | asAfsaAfaGfaCfuGfaucAfaAfuAfuGfususg | 233 |
| AD-64755 | ascsauauuugadTdCagucdCuuuu | 138 | asAfsaAfaGfaCfuGfaucAfaAfuAfuGfususg | 234 |
| AD-64756 | AfscsAfuAfuUfuGfAfUfcAfgUfcUfuUfuUf | 139 | asAfsaaaagacugaucAfaauaugususg | 235 |
| AD-64757 | AfscsAfuAfuUfuGfAfUfcAfgUfcUfuUfuUf | 140 | asAsaaagacudGaucdAaauaugususg | 236 |
| AD-64758 | ascsauauuuGfaUfcagUfcuuUfuu | 141 | asAfsaaaGfacUfGfaucAfaAfuaugususg | 237 |
| AD-64759 | ascsauauuugadTcagucdAuuuu | 142 | asdAsaaadGacudGaucdAaauaugususg | 238 |
| AD-64760 | ascsauauuuadTcagucuuuuu | 143 | asAfsaAfaGfaCfuGfaucAfaAfuAfuGfususg | 239 |
| AD-64761 | ascsauauuugadTcagucdGuuuu | 144 | asAfsaAfaGfaCfuGfaucAfaAfuAfuGfususg | 240 |
| AD-64762 | AfscsAfuAfuUfuGfAfUfcAfgUfcUfuUfuUf | 145 | asdAsaaagacugaucdAaauaugususg | 241 |
| AD-64763 | AfscsAfuAfuUfuGfAfUfcAfgUfcUfuUfuUf | 146 | asdAsaaagacudGaucAaauaugususg | 242 |
| AD-64764 | ascsauauuuGfaUfcagUfcuuuuu | 147 | asAfsaaaGfacUfGfaucAfaAfuaugususg | 243 |
| AD-64765 | ascsauauuugaUcaguc(Tgn)uuuu | 148 | asdAsaaagacudGaucdAaauaugususg | 244 |
| AD-64766 | ascsauauuugadTcagu(Cgn)uuuuu | 149 | asAfsaAfaGfaCfuGfaucAfaAfuAfuGfususg | 245 |
| AD-64767 | ascsauauuugadTcagucdCuuuu | 150 | asAfsaAfaGfaCfuGfaucAfaAfuAfuGfususg | 246 |
| AD-64768 | AfscsAfuAfuUfuGfAfUfcAfgUfcUfuUfuUf | 151 | asasaaagacudGaucdAaauaugususg | 247 |
| AD-64769 | AfscsAfuAfuUfuGfAfUfcAfgUfcUfuUfuUf | 152 | asAsaaagacudGaucAaauaugususg | 248 |
| AD-64770 | ascsauauuugadTcaguc(Tgn)uuuu | 153 | asdAsaaagacudGaucdAaauaugususg | 249 |
| AD-64771 | ascsauauuugaUcaguc(Tgn)uuuu | 154 | asdAsaaadGacugaucdAaauaugususg | 250 |
| AD-64772 | ascsauauuugadTcagucdAuuuu | 155 | asAfsaAfaGfaCfuGfaucAfaAfuAfuGfususg | 251 |
| AD-64773 | AfscsAfuAfuUfuGfAfUfcAfgUfcUfuUfuUf | 156 | asasaaadGacugaucdAaauaugususg | 252 |
| AD-64774 | AfscsAfuAfuUfuGfAfUfcAfgUfcUfuUfuUf | 157 | asAsaaadGacugaucAaauaugususg | 253 |
| AD-64775 | ascsauauuugadTcaguc(Tgn)uuuu | 158 | asdAsaaadGacugaucdAaauaugususg | 254 |
| AD-64776 | ascsauauuugaUcaguc(Tgn)uuuu | 159 | asdAsaaadGacudGaucdAaauaugususg | 255 |

TABLE 2B-continued

ANGPTL3 Modified Sequences

| Duplex Name | Sense Sequence 5' to 3' | SEQ ID NO | Antisense Sequence 5' to 3' | SEQ ID NO |
|---|---|---|---|---|
| AD-64777 | ascsauauuugadTcagucu(Tgn)uuu | 160 | asAfsaAfaGfaCfuGfaucAfaAfuAfuGfususg | 256 |
| AD-64778 | AfscsAfuAfuUfuGfAfUfcAfgUfcUfuUfuUf | 161 | asAfsaaaGfacuGfaucAfaAfuaugususg | 257 |
| AD-64779 | AfscsAfuAfuUfuGfAfUfcAfgUfcUfuUfuUf | 162 | asdAsaaagacudGaucdAaauaugususg | 258 |
| AD-64780 | AfscsAfuAfuUfuGfAfUfcAfgUfcUfuUfuUf | 163 | PasdAsaaagacudGaucdAaauaugususg | 259 |
| AD-64781 | ascsauauuugadTcaguc(Tgn)uuuu | 164 | asdAsaaadGacudGaucdAaauaugususg | 260 |
| AD-64782 | ascsauauuugaUcaguc(Tgn)uuuu | 165 | asAfsaAfaGfaCfuGfaucAfaAfuAfuGfususg | 261 |
| AD-64783 | AfscsAfuAfuUfuGfAfUfcAfgUfcUfuUfuUf | 166 | asAfsaaaGfacUfGfaucAfaAfuaugususg | 262 |
| AD-64784 | AfscsAfuAfuUfuGfAfUfcAfgUfcUfuUfuUf | 167 | asdAsaaadGacugaucdAaauaugususg | 263 |
| AD-64785 | AfscsAfuAfuUfuGfAfUfcAfgUfcUfuUfuUf | 168 | PasasaaagacudGaucdAaauaugususg | 264 |
| AD-64786 | ascsauauuugadTcaguc(Tgn)uuuu | 169 | PasdAsaaagacudGaucdAaauaugususg | 265 |

TABLE 3

AngPTL3 Single Dose Screen in Hep3B cells. Data are expressed as percent message remaining relative to AD-1955 non-targeting control.

| Duple Name | 10 nM AVG | 0.1 nM AVG | 10 nM STDEV | 0.1 nM STDEV |
|---|---|---|---|---|
| AD-57927 | 3.9 | 4.3 | 1.9 | 1.0 |
| AD-63131 | 14.3 | 15.6 | 7.7 | 6.0 |
| AD-63132 | 12.5 | 10.6 | 2.3 | 3.0 |
| AD-63133 | 8.6 | 7.5 | 1.4 | 1.9 |
| AD-63134 | 17.3 | 15.9 | 2.8 | 1.9 |
| AD-63136 | 2.7 | 4.3 | 0.9 | 1.4 |
| AD-63137 | 2.9 | 3.4 | 0.9 | 0.7 |
| AD-63138 | 13.6 | 18.8 | 3.9 | 3.9 |
| AD-63139 | 7.5 | 9.0 | 2.6 | 1.7 |
| AD-63140 | 13.0 | 15.0 | 8.6 | 6.7 |
| AD-63142 | 3.2 | 3.9 | 0.7 | 0.4 |
| AD-63143 | 5.3 | 4.6 | 2.3 | 2.2 |
| AD-63144 | 5.6 | 6.6 | 2.9 | 3.0 |
| AD-63145 | 7.3 | 6.6 | 1.8 | 0.9 |
| AD-63146 | 17.5 | 14.5 | 2.5 | 4.6 |
| AD-63148 | 2.9 | 3.1 | 1.4 | 2.2 |
| AD-63149 | 6.3 | 7.2 | 2.1 | 1.4 |
| AD-63150 | 4.8 | 6.5 | 1.9 | 2.5 |
| AD-63151 | 4.7 | 4.7 | 2.3 | 2.9 |
| AD-63152 | 10.3 | 12.2 | 2.0 | 1.5 |
| AD-63153 | 5.1 | 4.9 | 1.9 | 2.4 |
| AD-63154 | 9.4 | 7.9 | 3.7 | 3.0 |
| AD-63155 | 13.4 | 13.2 | 5.1 | 4.3 |
| AD-63156 | 3.3 | 4.4 | 1.1 | 1.4 |
| AD-63157 | 2.6 | 4.4 | 2.1 | 1.8 |
| AD-63158 | 16.7 | 23.9 | 8.7 | 7.2 |
| AD-63160 | 3.5 | 3.7 | 1.9 | 1.2 |
| AD-63161 | 11.7 | 12.6 | 5.7 | 1.2 |
| AD-63162 | 3.9 | 6.2 | 1.2 | 1.5 |
| AD-63163 | 3.7 | 3.6 | 2.5 | 1.7 |
| AD-63164 | 11.3 | 13.6 | 8.2 | 5.0 |
| AD-63165 | 12.5 | 13.3 | 3.7 | 5.2 |
| AD-63166 | 8.8 | 13.6 | 5.2 | 9.4 |
| AD-63167 | 3.3 | 2.8 | 1.2 | 0.9 |
| AD-63168 | 7.3 | 9.0 | 6.0 | 5.0 |
| AD-63169 | 10.8 | 12.1 | 8.7 | 7.2 |
| AD-63170 | 3.7 | 3.8 | 1.1 | 0.9 |
| AD-63171 | 12.5 | 16.4 | 6.9 | 2.6 |
| AD-63172 | 8.7 | 10.1 | 7.2 | 4.7 |
| AD-63173 | 3.0 | 3.6 | 1.3 | 2.5 |
| AD-63174 | 2.8 | 3.7 | 1.5 | 1.6 |

TABLE 3-continued

AngPTL3 Single Dose Screen in Hep3B cells. Data are expressed as percent message remaining relative to AD-1955 non-targeting control.

| Duple Name | 10 nM AVG | 0.1 nM AVG | 10 nM STDEV | 0.1 nM STDEV |
|---|---|---|---|---|
| AD-63175 | 5.2 | 3.4 | 2.8 | 2.6 |
| AD-63176 | 3.3 | 4.2 | 0.9 | 0.4 |
| AD-63177 | 5.3 | 7.3 | 2.3 | 0.6 |
| AD-63179 | 3.0 | 4.0 | 0.9 | 0.9 |
| AD-63180 | 66.8 | 92.2 | 22.2 | 13.5 |
| AD-63181 | 4.8 | 5.4 | 1.9 | 1.0 |
| AD-63182 | 14.7 | 23.1 | 4.7 | 6.4 |
| AD-63183 | 11.8 | 14.3 | 5.5 | 4.7 |
| AD-63185 | 7.9 | 8.8 | 0.7 | 2.8 |
| AD-63186 | 57.6 | 72.0 | 12.1 | 15.7 |
| AD-63187 | 9.8 | 14.1 | 4.8 | 2.8 |
| AD-63188 | 30.9 | 49.8 | 20.7 | 8.3 |
| AD-64744 | 16.6 | 57.4 | 1.4 | 9.8 |
| AD-64745 | 12.0 | 58.3 | 2.2 | 17.5 |
| AD-64746 | 67.3 | 99.4 | 6.1 | 14.5 |
| AD-64747 | 18.0 | 65.1 | 2.5 | 2.2 |
| AD-64748 | 69.0 | 87.2 | 5.2 | 5.6 |
| AD-64749 | 16.4 | 70.5 | 5.0 | 11.2 |
| AD-64750 | 12.3 | 44.3 | 4.6 | 7.0 |
| AD-64751 | 57.9 | 87.5 | 7.5 | 7.4 |
| AD-64752 | 18.7 | 54.1 | 4.0 | 16.1 |
| AD-64753 | 57.6 | 81.9 | 5.1 | 4.4 |
| AD-64754 | 21.2 | 72.3 | 2.4 | 6.7 |
| AD-64755 | 9.0 | 32.7 | 2.3 | 9.1 |
| AD-64756 | 17.2 | 53.7 | 3.9 | 7.9 |
| AD-64757 | 89.0 | 92.0 | 4.4 | 5.8 |
| AD-64758 | 23.5 | 66.1 | 10.9 | 4.9 |
| AD-64759 | 61.6 | 80.3 | 6.9 | 5.7 |
| AD-64760 | 8.7 | 50.0 | 3.6 | 5.7 |
| AD-64761 | 12.7 | 36.7 | 5.7 | 6.4 |
| AD-64762 | 107.7 | 98.0 | 9.1 | 10.9 |
| AD-64763 | 72.8 | 84.8 | 6.0 | 9.7 |
| AD-64764 | 21.7 | 57.5 | 7.8 | 6.3 |
| AD-64765 | 67.9 | 80.2 | 7.5 | 3.0 |
| AD-64766 | 11.3 | 38.8 | 5.4 | 11.3 |
| AD-64767 | 13.2 | 39.0 | 5.8 | 9.5 |
| AD-64768 | 74.3 | 102.3 | 6.5 | 9.2 |
| AD-64769 | 57.1 | 86.9 | 5.4 | 1.1 |
| AD-64770 | 68.5 | 78.2 | 3.2 | 9.0 |
| AD-64771 | 45.4 | 68.5 | 2.0 | 8.3 |
| AD-64772 | 11.8 | 50.0 | 2.7 | 1.7 |

TABLE 3-continued

AngPTL3 Single Dose Screen in Hep3B cells.
Data are expressed as percent message remaining
relative to AD-1955 non-targeting control.

| Duple Name | 10 nM AVG | 0.1 nM AVG | 10 nM STDEV | 0.1 nM STDEV |
| --- | --- | --- | --- | --- |
| AD-64773 | 53.8 | 98.1 | 1.3 | 8.6 |
| AD-64774 | 43.2 | 82.4 | 7.2 | 8.1 |
| AD-64775 | 42.9 | 78.7 | 1.4 | 13.8 |
| AD-64776 | 52.6 | 70.1 | 2.9 | 4.3 |
| AD-64777 | 19.8 | 65.8 | 3.7 | 6.8 |
| AD-64778 | 7.9 | 34.7 | 2.2 | 9.6 |
| AD-64779 | 66.9 | 86.3 | 7.3 | 7.9 |
| AD-64780 | 78.8 | 89.0 | 7.8 | 5.1 |
| AD-64781 | 54.6 | 82.1 | 12.9 | 11.2 |
| AD-64782 | 9.2 | 56.1 | 5.0 | 18.3 |
| AD-64783 | 8.0 | 35.7 | 1.4 | 8.5 |
| AD-64784 | 52.6 | 80.3 | 4.4 | 6.1 |
| AD-64785 | 92.4 | 93.9 | 9.8 | 4.3 |
| AD-64786 | 83.4 | 85.4 | 8.4 | 7.5 |

TABLE 4A

Additional Modified ANGPTL3 RNAi Agents.

| Duplex name | Modified Sense Sequence 5' to 3' | SEQ ID NO | Modified Antisense Sequence 5' to 3' | SEQ ID NO |
| --- | --- | --- | --- | --- |
| AD-62865 | UfsgsUfcAfcUfuGfAfAfcUfcAfaCfuCfaAfL96 | 266 | usUfsgAfgUfuGfaGfuucAfaGfuGfaCfasusa | 278 |
| AD-66916 | asascuaaCfuAfAfCfuuaauucaaaL96 | 267 | usUfsugaAfuUfAfaguuAfgUfuaguusgsc | 279 |
| AD-66917 | uscsacaaUfuAfAfGfcuccuucuuuL96 | 268 | asAfsagaAfgGfAfgcuuAfaUfugugasasc | 280 |
| AD-66918 | gsasgcaaCfuAfAfCfuaacuuaauuL96 | 269 | asAfsuuaAfgUfUfaguuaGfuUfgcucsusu | 281 |
| AD-66919 | ususauugUfuCfCfUfcuaguuauuuL96 | 270 | asAfsauaAfcUfAfgaggAfaCfaauaasasa | 282 |
| AD-66920 | asusuaagCfuCfCfUfucuuuuuauuL96 | 271 | asAfsuaaAfaAfGfaaggAfgCfuuaaususg | 283 |
| AD-66921 | usgsucacUfuGfAfAfcucaacucaaL96 | 272 | usUfsgagUfuGfAfguucAfaGfugacasusa | 284 |
| AD-66922 | gsasauauGfuCfAfCfuugaacucaaL96 | 273 | usUfsgagUfuCfAfagugAfcAfuauucsusu | 285 |
| AD-66923 | ascsauauUfuGfAfUfcagucuuuuuL96 | 274 | asAfsaaaGfaCfUfgaucAfaAfuaugususg | 286 |
| AD-66924 | csasacauAfuUfUfUfGfaucagucuuuL96 | 275 | asAfsagaCfuGfAfucaaAfuAfuguugsasg | 287 |
| AD-66925 | csusccauAfgUfGfAfagcaaucuaaL96 | 276 | usUfsagaUfuGfCfuucaCfuAfuggagsusa | 288 |
| AD-65695 | ascsauauUfuGfAfUfcagucuuuuuL96 | 277 | asAfsaaaGfacugaucAfaAfuaugususg | 289 |

TABLE 4B

Additional Modified ANGPTL3 RNAi Agents.

| Duplex name | Modified Sense Sequence 5' to 3' | SEQ ID NO | Modified Antisense Sequence 5' to 3' | SEQ ID NO |
|---|---|---|---|---|
| AD-62865 | UfsgsUfcAfcUfuGfAfAfcUfcAfaCfuCfaAf | 266 | usUfsgAfgUfuGfaGfuucAfaGfuGfaCfasusa | 278 |
| AD-66916 | asascuaaCfuAfAfCfuuaauucaaa | 267 | usUfsugaAfuUfAfaguuAfgUfuaguusgsc | 279 |
| AD-66917 | uscsacaaUfuAfAfGfcuccuucuuu | 268 | asAfsagaAfgGfAfgcuuAfaUfugugasasc | 280 |
| AD-66918 | gsasgcaaCfuAfAfCfuaacuuaauu | 269 | asAfsuuaAfgUfUfaguuaGfuUfgcucsusu | 281 |
| AD-66919 | ususauugUfuCfCfUfcuaguuauuu | 270 | asAfsauaAfcUfAfgaggAfaCfaauaasasa | 282 |
| AD-66920 | asusuaagCfuCfCfUfucuuuuuauu | 271 | asAfsuaaAfaAfGfaaggAfgCfuuaaususg | 283 |
| AD-66921 | usgsucacUfuGfAfAfcucaacucaa | 272 | usUfsgagUfuGfAfguucAfaGfugacasusa | 284 |
| AD-66922 | gsasauauGfuCfAfCfuugaacucaa | 273 | usUfsgagUfuCfAfagugAfcAfuauucsusu | 285 |
| AD-66923 | ascsauauUfuGfAfUfcagucuuuuu | 274 | asAfsaaaGfaCfUfgaucAfaAfuaugususg | 286 |
| AD-66924 | csasacauAfuUfUfGfaucagucuuu | 275 | asAfsagaCfuGfAfucaaAfuAfuguugsasg | 287 |
| AD-66925 | csusccauAfgUfGfAfagcaaucaa | 276 | usUfsagaUfuGfCfuucaCfuAfuggagsusa | 288 |
| AD-65695 | ascsauauUfuGfAfAfUfcagucuuuuu | 277 | asAfsaaaGfacugaucAfaAfuaugususg | 289 |

TABLE 5

Additional Unmodified ANGPTL3 RNAi Agents.

| Duplex name | Unmodified Sense Sequence 5' to 3' | SEQ ID NO | Unmodified Antisense Sequence 5' to 3' | SEQ ID NO | 5' Position of Antisense Strand in NM_014495.3 |
|---|---|---|---|---|---|
| AD-62865 | UGUCACUUGAACUCAACUCAA | 290 | UUGAGUUGAGUUCAAGUGACAUA | 302 | 425 |
| AD-66916 | AACUAACUAACUUAAUUCAAA | 291 | UUUGAAUUAAGUUAGUUAGUUGC | 303 | 509 |
| AD-66917 | UCACAAUUAAGCUCCUUCUUU | 292 | AAAGAAGGAGCUUAAUUGUGAAC | 304 | 83 |
| AD-66918 | GAGCAACUAACUAACUUAAUU | 293 | AAUUAAGUUAGUUAGUUGCUCUU | 305 | 505 |
| AD-66919 | UUAUUGUUCCUCUAGUUAUUU | 294 | AAAUAACUAGAGGAACAAUAAAA | 306 | 104 |
| AD-66920 | AUUAAGCUCCUUCUUUUUAUU | 295 | AAUAAAAAGAAGGAGCUUAAUUG | 307 | 88 |
| AD-66921 | UGUCACUUGAACUCAACUCAA | 296 | UUGAGUUGAGUUCAAGUGACAUA | 308 | 424 |
| AD-66922 | GAAUAUGUCACUUGAACUCAA | 297 | UUGAGUUCAAGUGACAUAUUCUU | 309 | 420 |
| AD-66923 | ACAUAUUUGAUCAGUCUUUUU | 298 | AAAAAGACUGAUCAAAUAUGUUG | 310 | 305 |
| AD-66924 | CAACAUAUUUGAUCAGUCUUU | 299 | AAAGACUGAUCAAAUAUGUUGAG | 311 | 303 |
| AD-66925 | CUCCAUAGUGAAGCAAUCAA | 300 | UUAGAUUGCUUCACUAUGGAGUA | 312 | 1041 |
| AD-65695 | ACAUAUUUGAUCAGUCUUUUU | 301 | AAAAAGACUGAUCAAAUAUGUUG | 313 | 305 |

Example 4. In Vivo ANGPTL3 Silencing in Wild-Type Mice

The in vivo efficacy and duration of a subset of the additional agents described above was assessed in wild-type (C57BL/6) mice. Six to eight week-old female mice were subcutaneously administered a single 3 mg/kg dose of the agents and the level of mouse ANGPTL3 was determined in the serum of the animals pre-dose, day 0, and on days 4, 10, 17, 27, 38, and 52 post-dose. Three mice per group were used for these assays. ANGPTL3 levels were assayed utilizing an ELISA assay, R&D Systems Mouse Angiopoietin-Like 3 Quantikine ELISA Kit (catalog number MANL30).

Figure 6B:
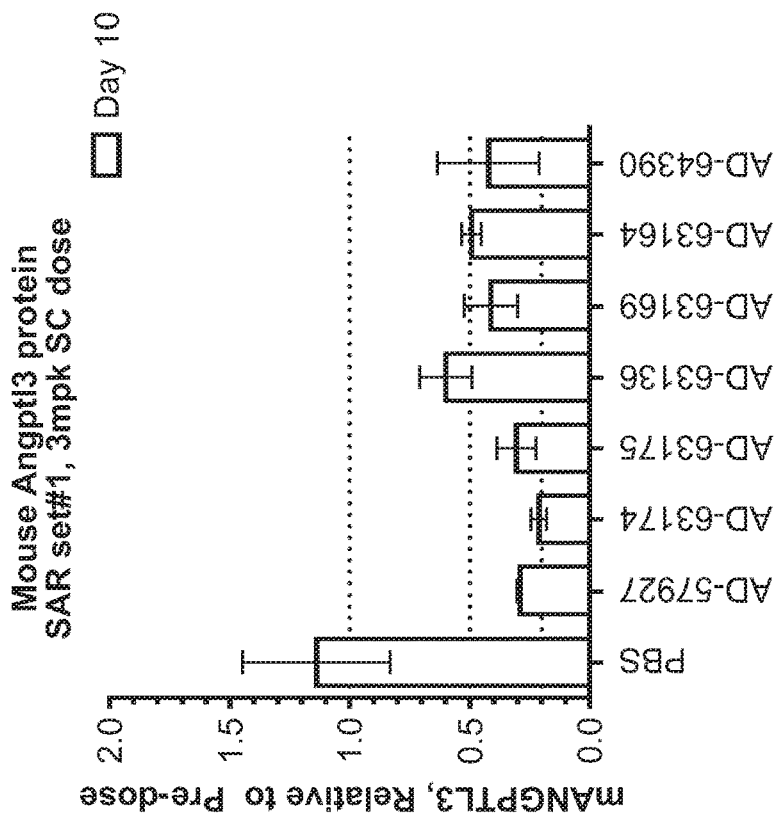
FIG. 6B is a graph showing the amount of mouse ANGPTL3 protein remaining in the serum of wild-type mice after a single 3 mg/kg subcutaneous dose of the indicated iRNA agents on day 10 post-dose. The amount of mouse ANGPTL3 protein presented is relative to the amount mouse ANGPTL3 protein present in a serum sample prior to administration.
Figure 6A:
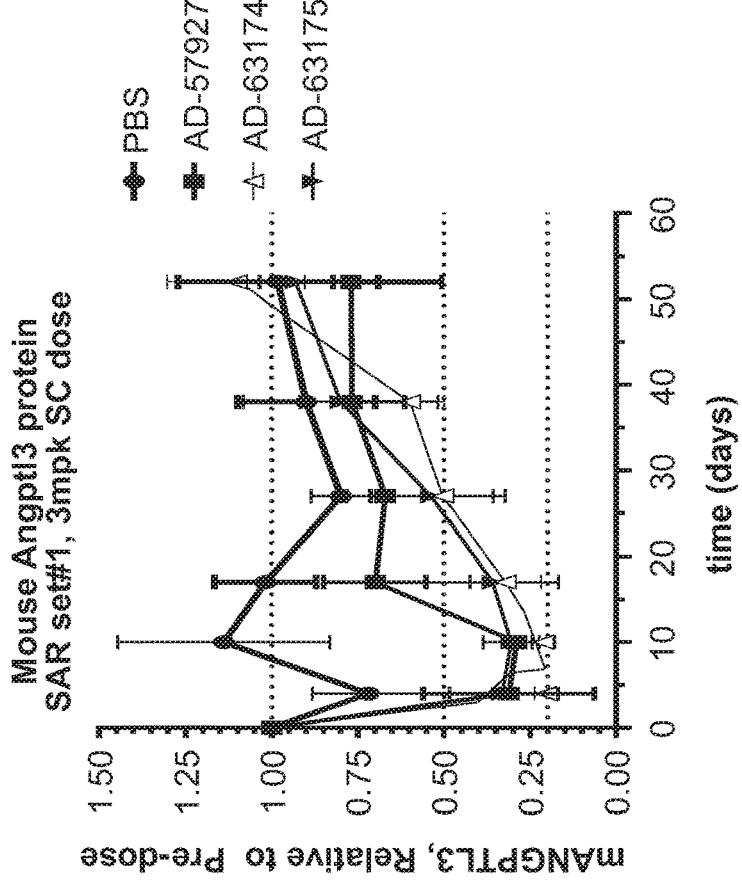
FIG. 6A is a graph showing the duration of response to the indicated iRNA agents represented by the amount of mouse ANGPTL3 protein remaining in the serum of wild-type mice after a single 3 mg/kg subcutaneous dose of the indicated iRNA agents over time. The amount of mouse ANGPTL3 protein presented is relative to the amount mouse ANGPTL3 protein present in a serum sample prior to administration.

The results of these assays are provided in FIGS. 6A and 6B. As demonstrated in FIG. 6A, all of the agents potently and durably inhibit ANGPTL3 expression and reach a nadir at about day 4 post-administration As demonstrated in FIG. 6B, at Day 10 post-dose, the level of ANGPTL3 is lowest in animals administered AD-63174 and AD-63175 as compared to the other agents assayed.

A second subset of the additional agents described above was also assessed in wild-type (C57BL/6) mice. Six to eight week-old female mice were subcutaneously administered either a single 1 mg/kg dose or a single 3 mg/kg dose of the agents and the level of mouse ANGPTL3 was determined in the serum of the animals pre-dose, day 0, and at days 5, 14, 21, 28, and 42 post-dose. (For the groups of animals administered AD-65695, due to the increased duration of response to this agent as compared to the response of the other agents tested, the level of mouse ANGPTL3 was also determined in the serum of the animals administered AD-65695 at day 55 post-dose). Three mice per group were used for these assays. ANGPTL3 levels were assayed utilizing an ELISA assay, as described above.

Figure 7B:
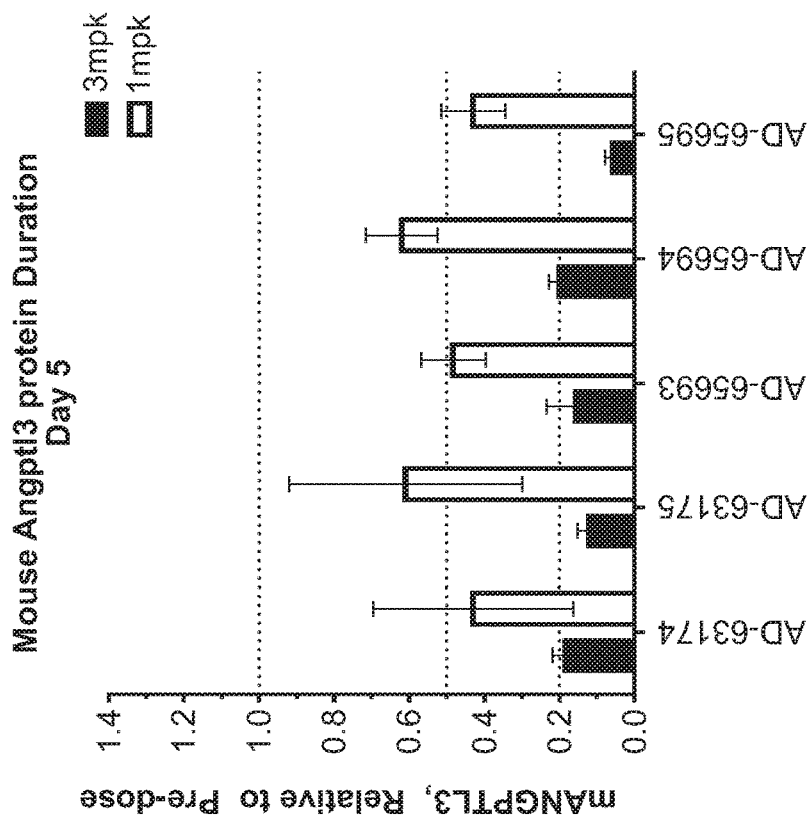
FIG. 7B is a graph showing the amount of mouse ANGPTL3 protein remaining in the serum of wild-type mice after a single 1 mg/kg or 3 mg/kg subcutaneous dose of the indicated iRNA agents on day 5 post-dose. The amount of mouse ANGPTL3 protein presented is relative to the amount mouse ANGPTL3 protein present in a serum sample prior to administration.
Figure 7A:
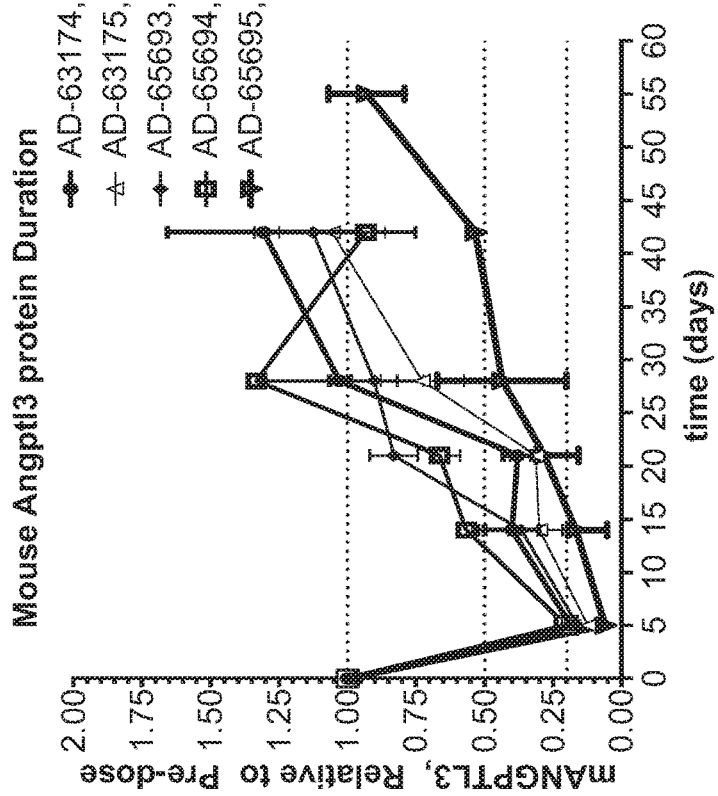
FIG. 7A is a graph showing the duration of response to the indicated iRNA agents represented by the amount of mouse ANGPTL3 protein remaining in the serum of wild-type mice after a single 3 mg/kg subcutaneous dose of the indicated iRNA agents over time. The amount of mouse ANGPTL3 protein presented is relative to the amount mouse ANGPTL3 protein present in a serum sample prior to administration.

The results of these assays are provided in FIGS. 7A and 7B and demonstrate that all of the agents potently and durably inhibit ANGPTL3 expression and reach a nadir at about day 5 post-administration (FIG. 7A) and that, relative to the other agents assayed, animals administered AD-65695 had the lowest ANGPTL3 levels at the 1 mg/kg and 3 mg/kg dose (FIG. 7B).

Example 5. In Vivo ANGPTL3 Silencing in Ob/Ob Mice

The in vivo efficacy and duration of a subset of the additional agents described above was assessed in ob/ob mice. Six to eight week-old female ob/ob mice were subcutaneously administered a single 3 mg/kg dose of the agents and the level of mouse ANGPTL3 was determined in the serum of the animals pre-dose, day 0, and at days 5, 13, 24, and 38 post-dose. Four mice per group were used for these assays. ANGPTL3 levels were assayed utilizing an ELISA assay, as described above.

Figure 8A:
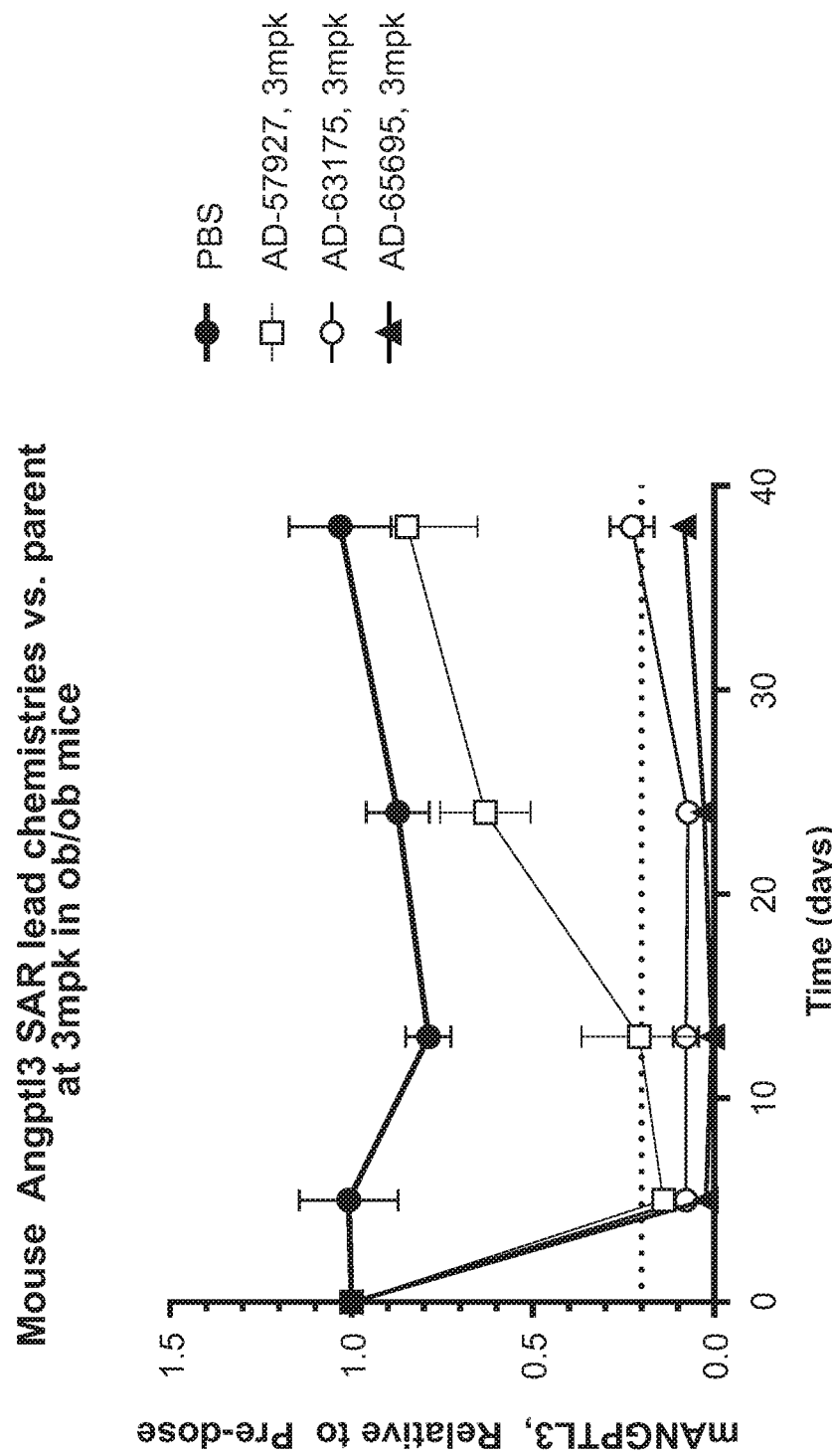
FIG. 8A is a graph showing the duration of response to the indicated iRNA agents represented by the amount of mouse ANGPTL3 protein remaining in the serum of ob/ob mice after a single 3 mg/kg subcutaneous dose of the indicated iRNA agents over time. The amount of mouse ANGPTL3 protein presented is relative to the amount mouse ANGPTL3 protein present in a serum sample prior to administration.
Figure 8B:
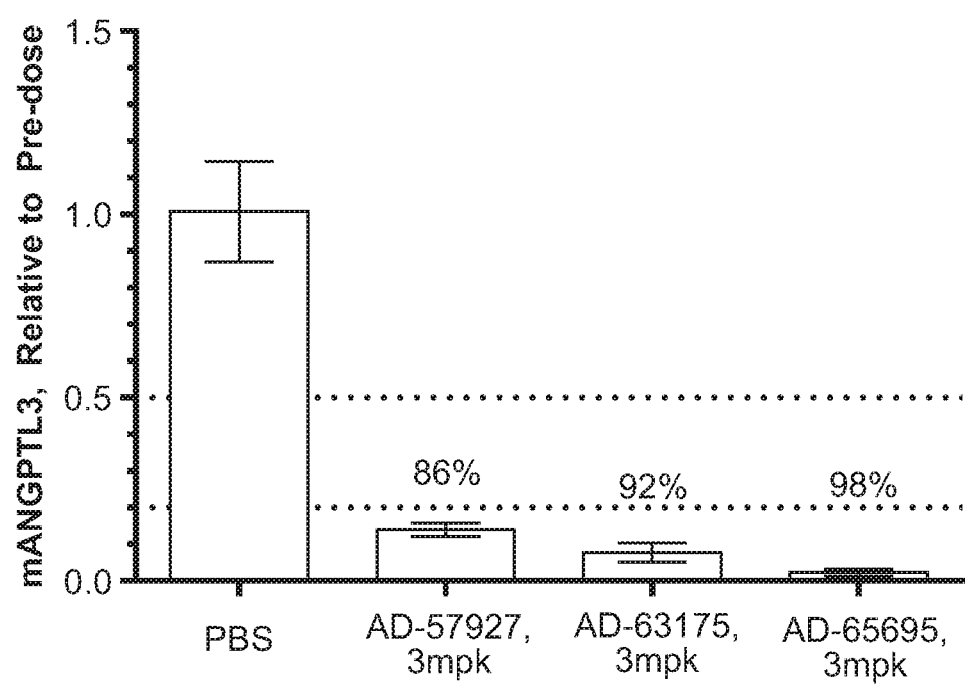
FIG. 8B is a graph showing the percent of silencing of mouse ANGPTL3 protein in the serum of ob/ob mice after a single 1 mg/kg or 3 mg/kg subcutaneous dose of the indicated iRNA agents on day 5 post-dose. The percent of silencing of mouse ANGPTL3 protein presented is relative to the level of mouse ANGPTL3 protein present in a serum sample prior to administration.

The results of these assays are provided in FIGS. 8A and 8B and demonstrate that all of the agents potently and durably inhibit ANGPTL3 expression and reach a nadir at about day 5 post-administration (FIG. 8A) and that, relative to the other agents assayed, animals administered AD-63175 or AD-65695 had the highest silencing of ANGPTL3 levels at a dose of 3 mg/kg (FIG. 8B).

The dose response of AD-65695 was assayed in ob/ob mice by subcutaneously administering a single dose of 0.3 mg/kg, 1 mg/kg, 3 mg/kg, or 9 mg/kg to the animals and the level of mouse ANGPTL3 was determined in the serum of the animals pre-dose and at days 5 and 13 post-dose. ANGPTL3 levels were assayed utilizing an ELISA assay, as described above, and the levels of serum triglycerides (TGs), low density lipoprotein cholesterol (LDLc), high density lipoprotein cholesterol (HDLc) and total cholesterol (TC) were also measured using an Olympus Analyzer.

Figure 9:
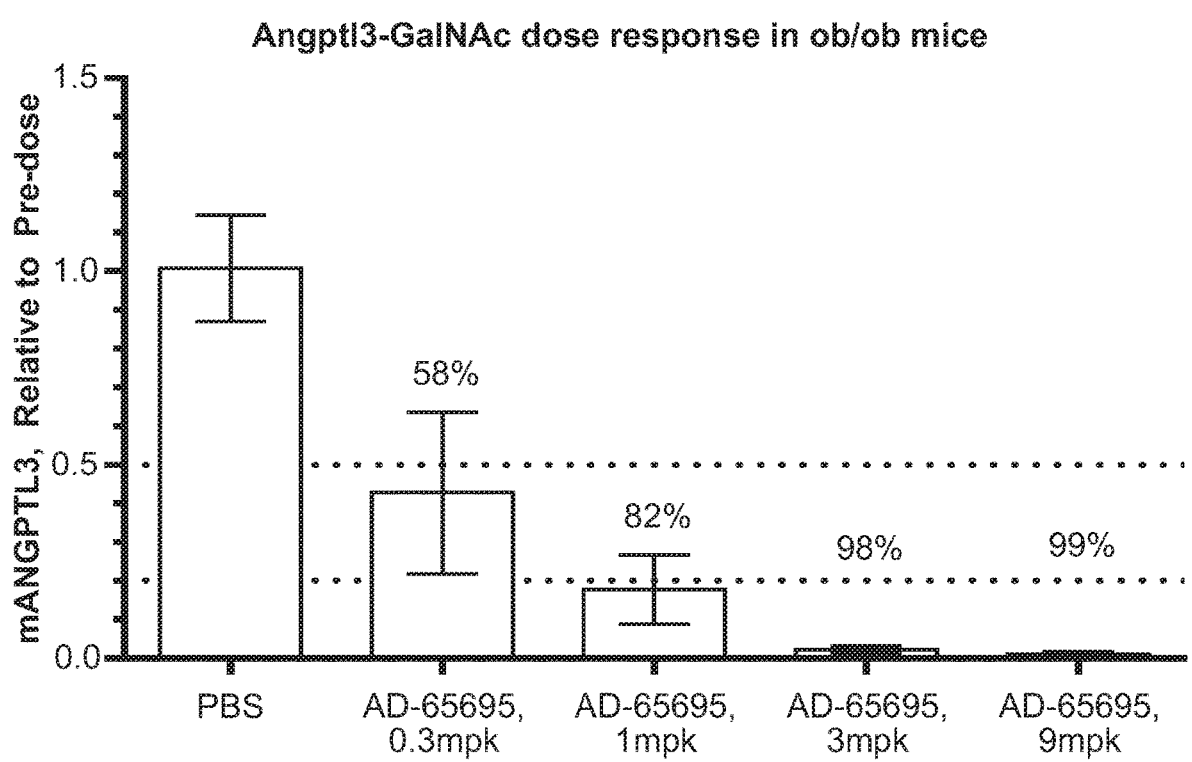
FIG. 9 is a graph showing the percent of silencing of mouse ANGPTL3 protein in the serum of ob/ob mice after a single 0.3 mg/kg, 1 mg/kg, 3 mg/kg, or 9 mg/kg subcutaneous dose of AD-65695 on day 5 post-dose. The percent of silencing of mouse ANGPTL3 protein is relative to the level of mouse ANGPTL3 protein present in a serum sample prior to administration.

FIG. 9 demonstrates that at day 5, there is a 58% silencing of ANGPTL3 protein in the serum of animals administered a 0.3 mg/kg dose of AD-65695, 82% silencing of ANGPTL3 protein in the serum of animals administered a 1 mg/kg dose of AD-65695, 98% silencing of ANGPTL3 protein in the serum of animals administered a 3 mg/kg dose of AD-65695, and 99% silencing of ANGPTL3 protein in the serum of animals administered a 9 mg/kg dose of AD-65695.

Figure 10A:
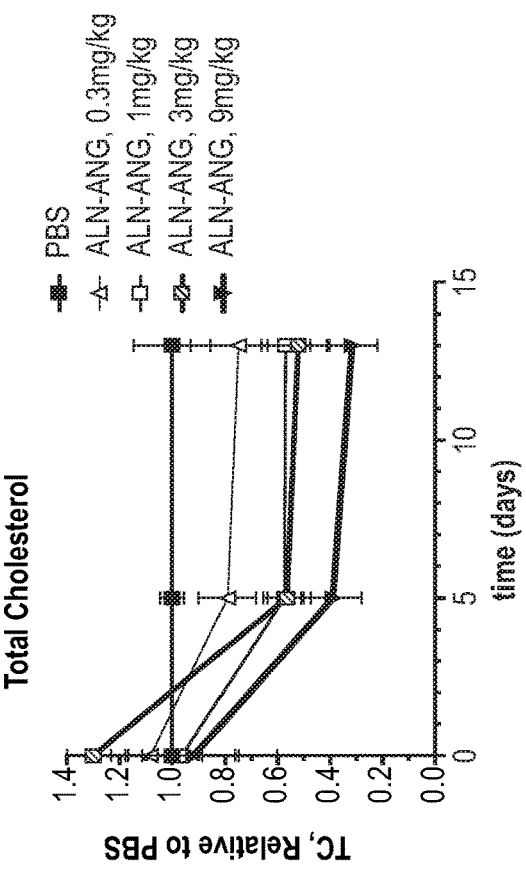
FIG. 10A is a graph showing the effects of a single 0.3 mg/kg, 1 mg/kg, 3 mg/kg, or 9 mg/kg subcutaneous dose of AD-65695 (ALN-ANG) on triglyceride (TG) levels in ob/ob mice. The amount of TG is presented as a ratio of the amount of TG in a serum sample from a mouse administered AD-65695 relative to the amount of TG in a serum sample from a mouse administered PBS.
Figure 10B:
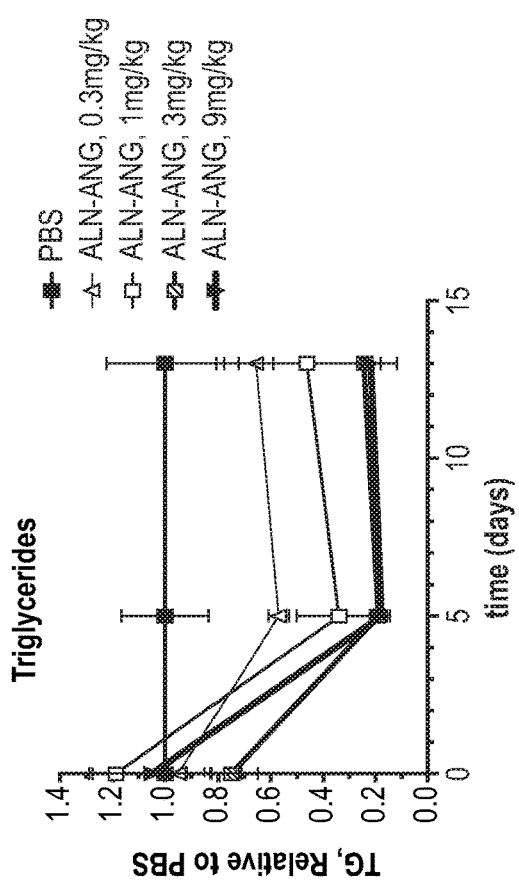
FIG. 10B is a graph showing the effects of a single 0.3 mg/kg, 1 mg/kg, 3 mg/kg, or 9 mg/kg subcutaneous dose of AD-65695 (ALN-ANG) on total cholesterol (TC) levels in ob/ob mice. The amount of TC is presented as a ratio of the amount of TC in a serum sample from a mouse administered AD-65695 relative to the amount of TC in a serum sample from a mouse administered PBS.
Figure 10C:
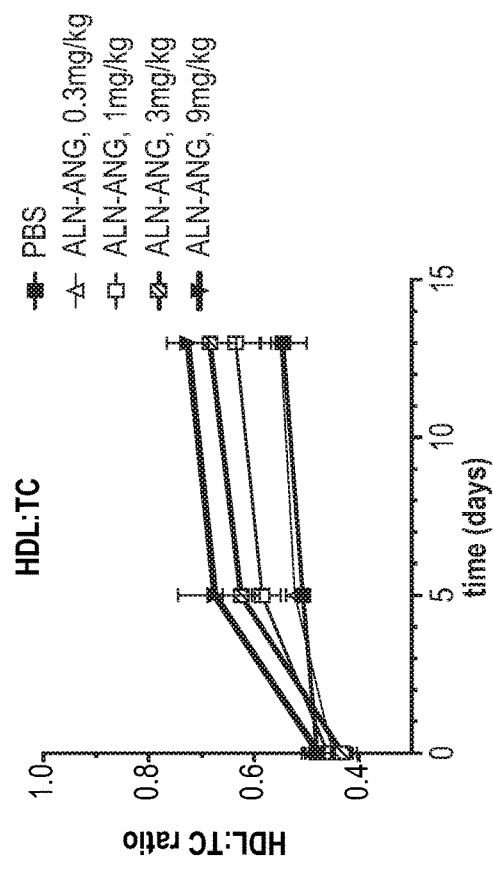
FIG. 10C is a graph showing the effects of a single 0.3 mg/kg, 1 mg/kg, 3 mg/kg, or 9 mg/kg subcutaneous dose of AD-65695 (ALN-ANG) on low density lipoprotein cholesterol (LDLc) levels in ob/ob mice. The amount of LDLc is presented as a ratio of the amount of LDLc in a serum sample from a mouse administered AD-65695 relative to the amount of LDLc in a serum sample from a mouse administered PBS.
Figure 10D:
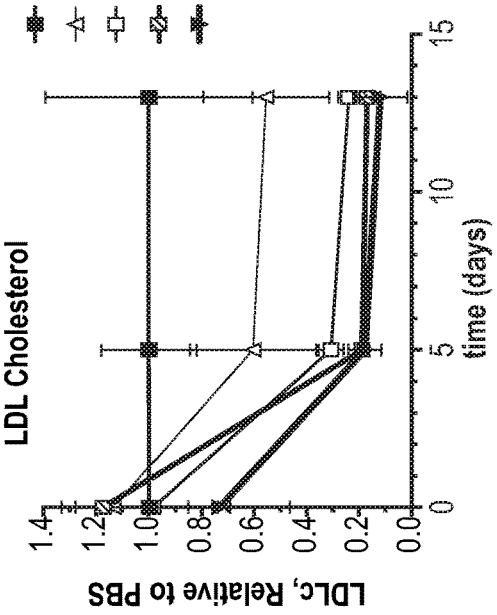
FIG. 10D is a graph showing the effects of a single 0.3 mg/kg, 1 mg/kg, 3 mg/kg, or 9 mg/kg subcutaneous dose of AD-65695 (ALN-ANG) on the ratio of high density lipoprotein cholesterol (HDL) levels to total cholesterol (TC) levels in ob/ob mice.

Shown in FIG. 10A are levels of TGs in ob/ob mice following administration of a PBS control or AD-65695; shown in FIG. 10B are levels of TC measured in ob/ob mice after administration of PBS control or AD-65695; shown in FIG. 10C are levels of LDLc in ob/ob mice following administration of a PBS control or AD-65695; and shown in FIG. 10D is the ratio of HDLc to TC in ob/ob mice following administration of a PBS control or AD-65695. The data demonstrates that administration of AD-65695 lowers TGs, LDLc, and TC in ob/ob mice, as compared to controls, at all doses assessed (an 80% reduction in serum LDLc and TGs was observed using a single 3 mg/kg does of AD_65695).

Example 6. In Vivo ANGPTL3 Silencing in AAV-TBG-ANGPTL3 Mice

Figure 11:
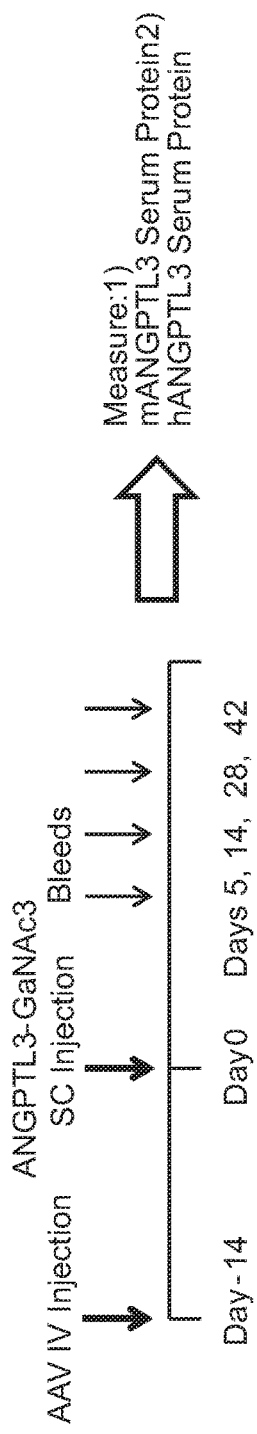
FIG. 11 depicts the dosing schedule and study design for determining the durability of the indicated iRNA agents in wild-type mice (C57BL/6) infected by intravenous administration of $1 \times 10^{11}$ viral particles of an adeno-associated virus 8 (AAV8) vector encoding the human ANGPTL3 gene (coding region) driven by the liver-specific thyroxine-binding globulin (TBG) promoter (AAV8-TBG-ANGPTL3).
Figure 12A:
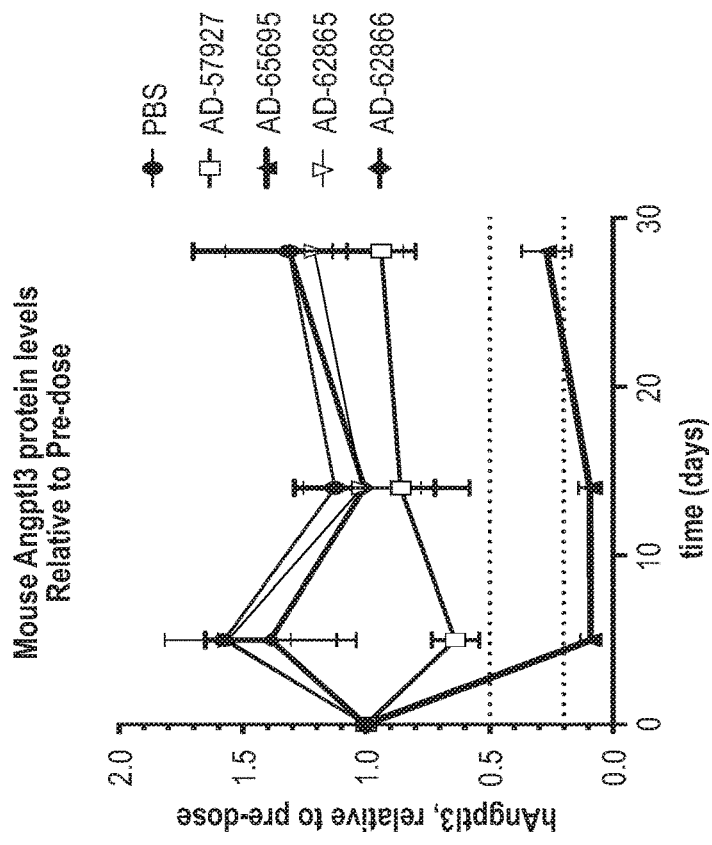
FIG. 12A is a graph showing the duration of response to the indicated iRNA agents represented by the amount of human ANGPTL3 protein remaining in the serum of AAV8-TBG-ANGPTL3 infected mice after a single 3 mg/kg subcutaneous dose of the indicated iRNA agents over time. The amount of human ANGPTL3 protein presented is relative to the amount of human ANGPTL3 protein present in a serum sample prior to administration (pre-dose).
Figure 12B:
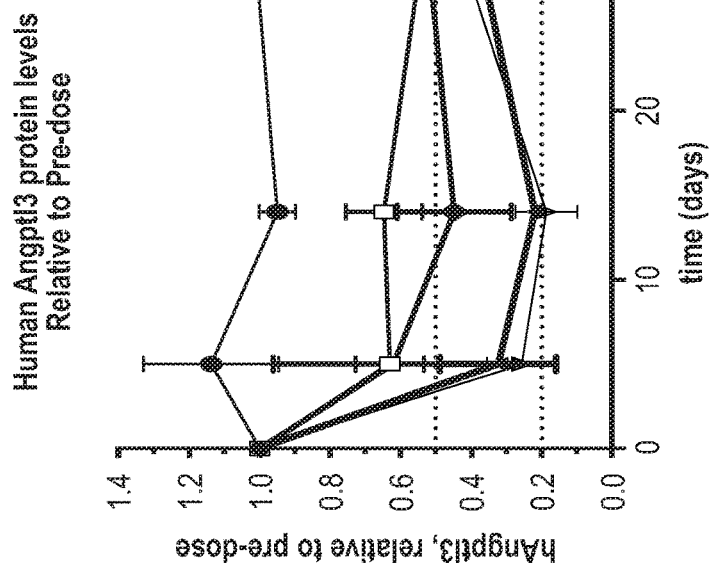
FIG. 12B is a graph showing the duration of response to the indicated iRNA agents represented by the amount of mouse ANGPTL3 protein remaining in the serum of AAV8-TBG-ANGPTL3 infected mice after a single 3 mg/kg subcutaneous dose of the indicated iRNA agents over time. The amount of mouse ANGPTL3 protein presented is relative to the amount of mouse ANGPTL3 protein present in a serum sample prior to administration (pre-dose).

To determine the durability of a single dose of a subset of the additional agents described above to reduce human ANGPTL3 protein levels, at pre-dose day −14 wild-type mice (C57BL/6) were infected by intravenous administration of 1×10$^{11}$ viral particles of an adeno-associated virus 8 (AAV8) vector encoding the human ANGPTL3 gene (coding region) driven by the liver-specific thyroxine-binding globulin (TBG) promoter (AAV8-TBG-ANGPTL3) in 200 At day 0, mice were subcutaneously administered a single 3 mg/kg of the agents and the level of ANGPTL3 was determined in the serum of the animals pre-dose and at days 5, 14, 28, and 42 post-dose (see FIG. 11). The level of mouse ANGPTL3 in the serum samples was determined using the ELISA assay described above, and the level of human ANGPTL3 in the serum samples was determined by ELISA assay which utilizes an antibody that detects human and Cynomologous ANGPTL3 but does not cross-react with mouse ANGPTL3 (R&D Systems Human Angiopoietin-Like 3 Quantikine ELISA Kit)]. Serum from naïve mice (mice that were not exposed to AAV) served as the negative control for these assays. Two of the agents administered, AD-57927 and AD-65695, cross-react with mouse, rat, Cynomologous, and human (m/r/cy/h) ANGPTL3 mRNA. The other two agents administered, AD-62865 and AD-62866, only cross-react with Cynomologous and human (cy/h) ANGPTL3 mRNA The levels of human ANGPTL3 protein following administration of the agents or a PBS control are shown in FIG. 12A and the levels of mouse ANGPTL3 following administration of the agents or a PBS control are shown in FIG. 12B and, as expected, there was no silencing of mouse ANGPTL3 following administration of the cy/h agents, AD-62865 and AD-62866. The results demonstrate that up to an 80% knock-down of human ANGPTL3 is achieved following administration of the agents with ~60% knock-down of ANGPTL3 sustained for at least 4 weeks. The data also demonstrate that there is >90% knock-down of mouse ANGPTL3 following administration of the cross-reactive m/r/cy/h agent, AD-65695, with ~75% knock-down of ANGPTL3 sustained for at least 4 weeks following a single 3 mg/kg dose of AD-65695. Furthermore, the data demonstrate that there was comparable efficacy and duration of ANGPTL3 knock-down following administration of the m/r/cy/h agent, AD-65695, and the cy/h agent, AD-62865.

Figure 13:
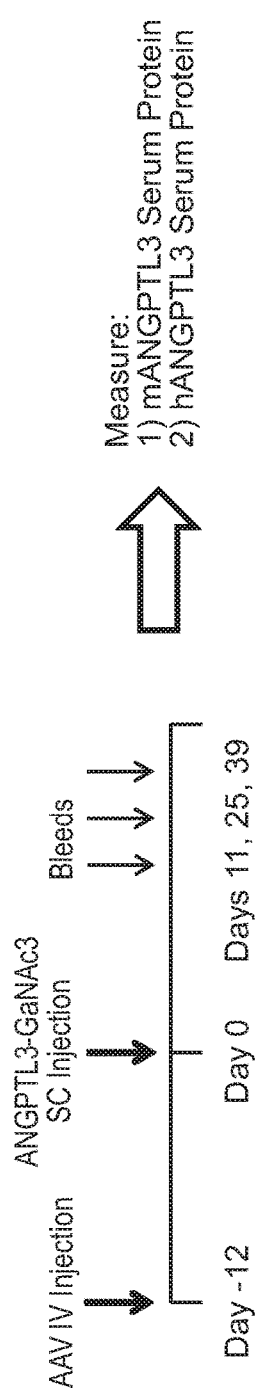
FIG. 13 depicts the dosing schedule and study design for titrating the dose and determining the durability of the indicated iRNA agents in AAV8-TBG-ANGPTL3 infected mice.

A single dose durability analysis was also performed with AD-65695, AD-62865 and AD-62866. As shown in FIG. 13, AAV8-TBG-ANGPTL3 infected mice were administered a single, 0.3 mg/kg, 1 mg/kg, or 3 mg/kg dose of AD-65695, or AAV8-TBG-ANGPTL3 infected mice were administered a single 1 mg/kg or 3 mg/kg dose of AD-62865, or AAV8-TBG-ANGPTL3 infected mice were administered a single 0.3 mg/kg dose of AD-62866. Serum was collected from the animals pre-dose and at days 11, 25, and 39 post-dose and the level of mouse and human ANGPTL3 was determined by ELISA assays as described above.

Figure 14A:
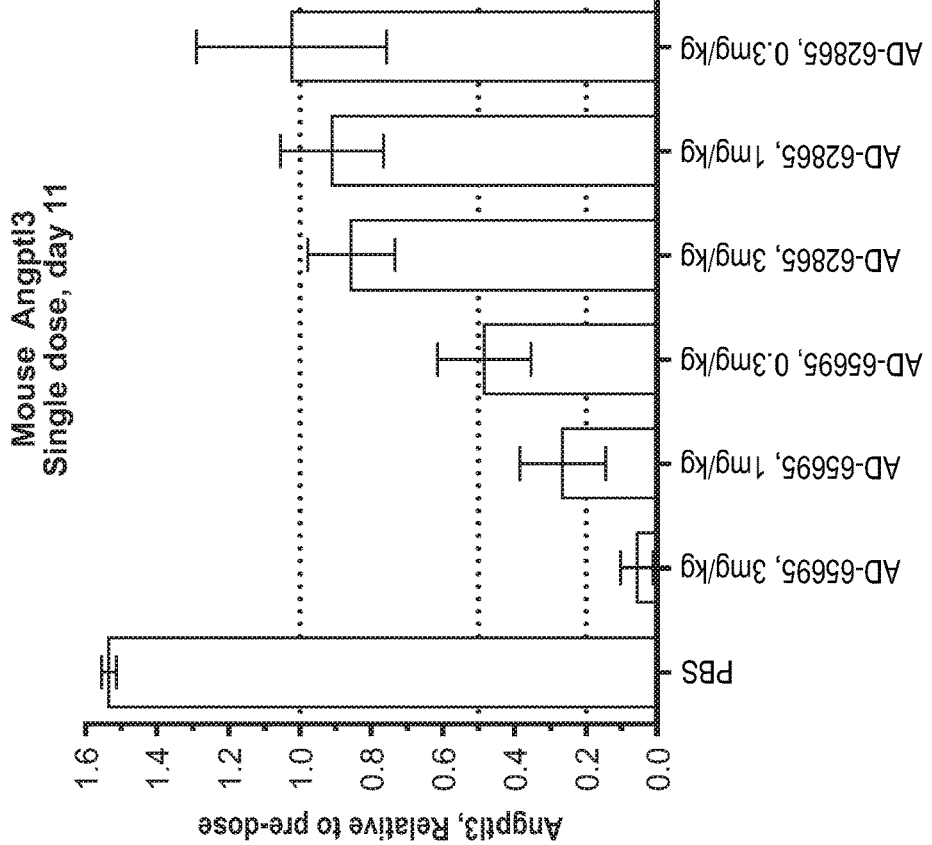
FIG. 14A is a graph showing the amount of human ANGPTL3 protein remaining in the serum of AAV8-TBG-ANGPTL3 infected mice after a single 3 mg/kg, 1 mg/kg, or 0.3 mg/kg subcutaneous dose of the indicated iRNA agents at day 11 post-dose. The amount of human ANGPTL3 protein presented is relative to the amount of human ANGPTL3 protein present in a serum sample prior to administration (pre-dose).
Figure 14B:
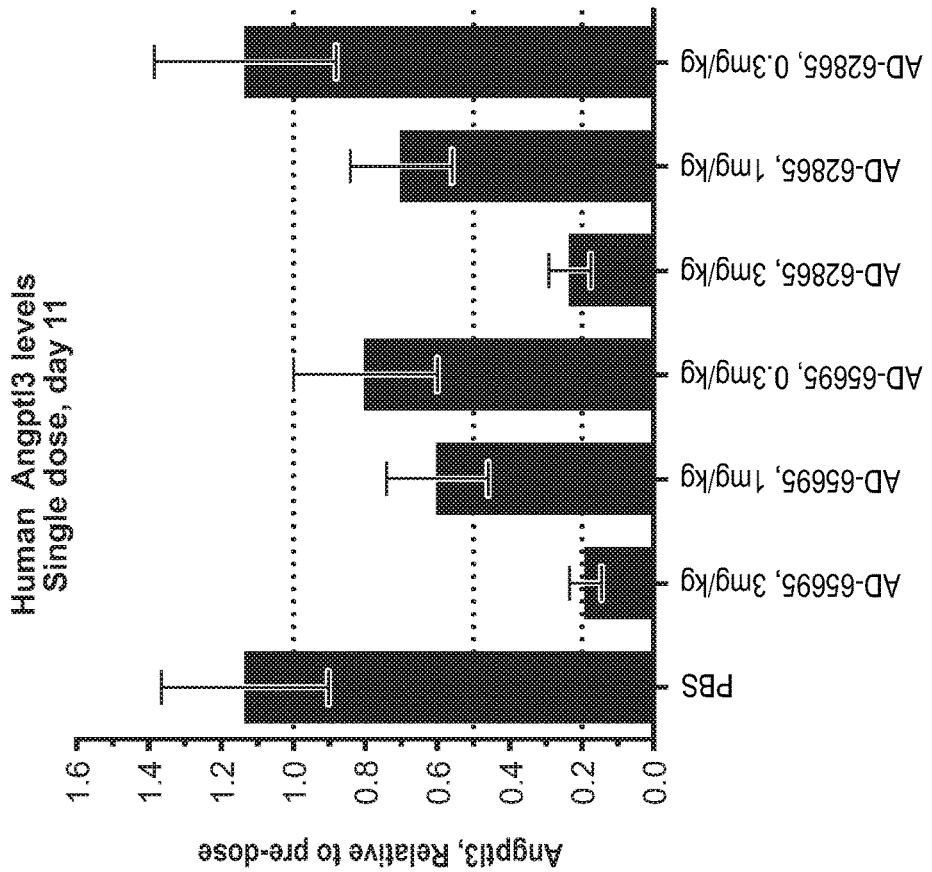
FIG. 14B is a graph showing the duration of response to the indicated iRNA agents represented by the amount of mouse ANGPTL3 protein remaining in the serum of AAV8-TBG-ANGPTL3 infected mice after a single 3 mg/kg, 1 mg/kg, or 0.3 mg/kg subcutaneous dose of the indicated iRNA agents at day 11 post-dose. The amount of mouse ANGPTL3 protein presented is relative to the amount of mouse ANGPTL3 protein present in a serum sample prior to administration (pre-dose).
Figure 15A:
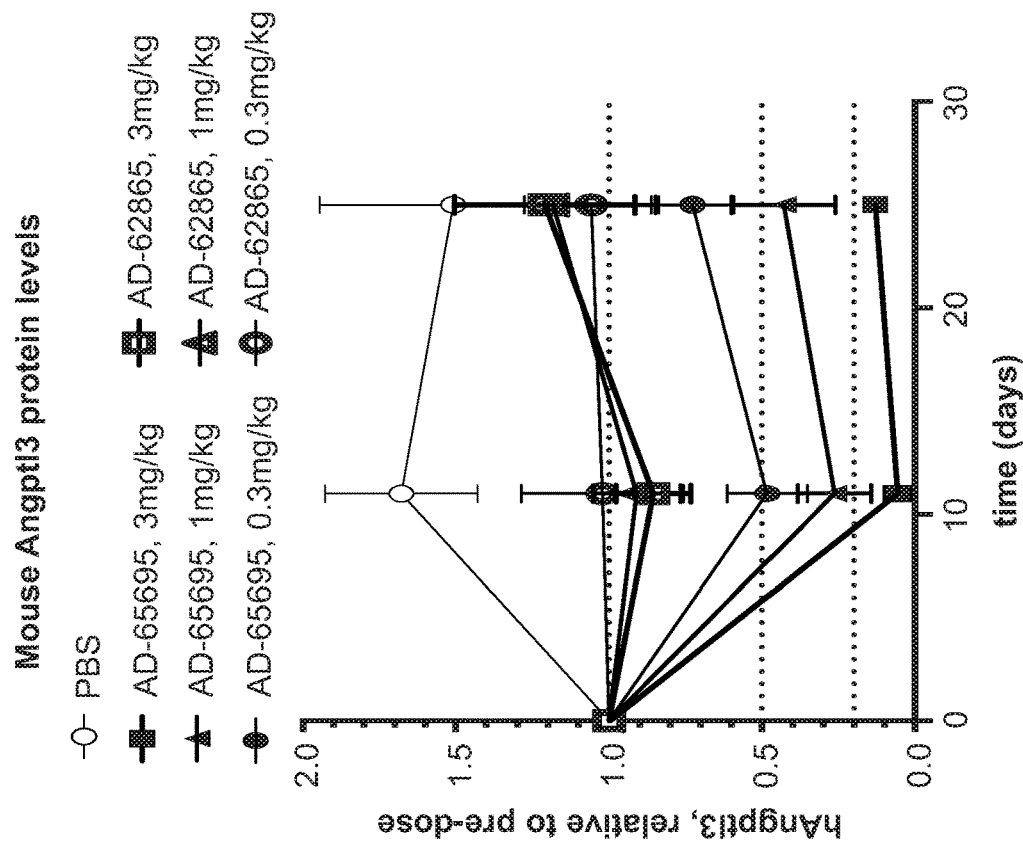
FIG. 15A is a graph showing the duration of response to the indicated iRNA agents represented by the amount of human ANGPTL3 protein remaining in the serum of AAV8-TBG-ANGPTL3 infected mice after a single 3 mg/kg, 1 mg/kg, or 0.3 mg/kg subcutaneous dose of the indicated iRNA agents over time. The amount of human ANGPTL3 protein presented is relative to the amount of human ANGPTL3 protein present in a serum sample prior to administration (pre-dose).
Figure 15B:
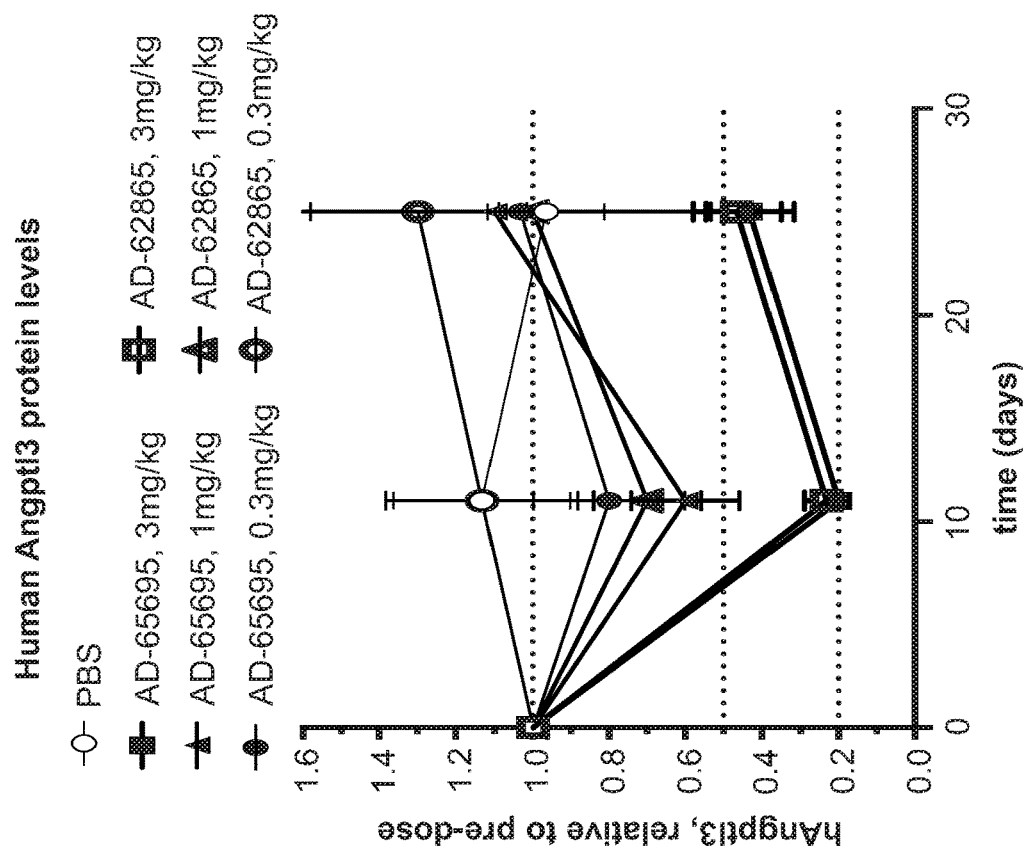
FIG. 15B is a graph showing the duration of response to the indicated iRNA agents represented by the amount of mouse ANGPTL3 protein remaining in the serum of AAV8-TBG-ANGPTL3 infected mice after a single 3 mg/kg, 1 mg/kg, or 0.3 mg/kg subcutaneous dose of the indicated iRNA agents over time. The amount of mouse ANGPTL3 protein presented is relative to the amount of mouse ANGPTL3 protein present in a serum sample prior to administration (pre-dose).

The data from these analyses are presented in FIGS. 14A, 14B, 15A, and 15B. FIGS. 14A and 14B provide the levels of human and mouse ANGPTL3, respectively, following administration of the agents at day 11 post-dose. FIGS. 15A and 15B provide the levels of human and mouse ANGPTL3, respectively, following administration of a single, 0.3 mg/kg, 1 mg/kg, or 3 mg/kg dose of AD-65695 pre-dose and at days 11, 25, and 39. The data demonstrate that AD-65695 (m/r/cy/h agent) has an effective dose in 80% of the animals ($ED_{80}$) of 3 mg/kg and an $ED_{40}$ of 1 mg/kg for human ANGPTL3. The data also demonstrate that AD-65695 has an $ED_{90}$ of 3 mg/kg, an $ED_{70}$ of 1 mg/kg, and an $ED_{50}$ of 0.3 mg/kg for mouse ANGPTL3. In addition, the data demonstrate that AD-62865 (cy/h agent) has an $ED_{80}$ of 3 mg/kg for human ANGPTL3.

Figure 16:
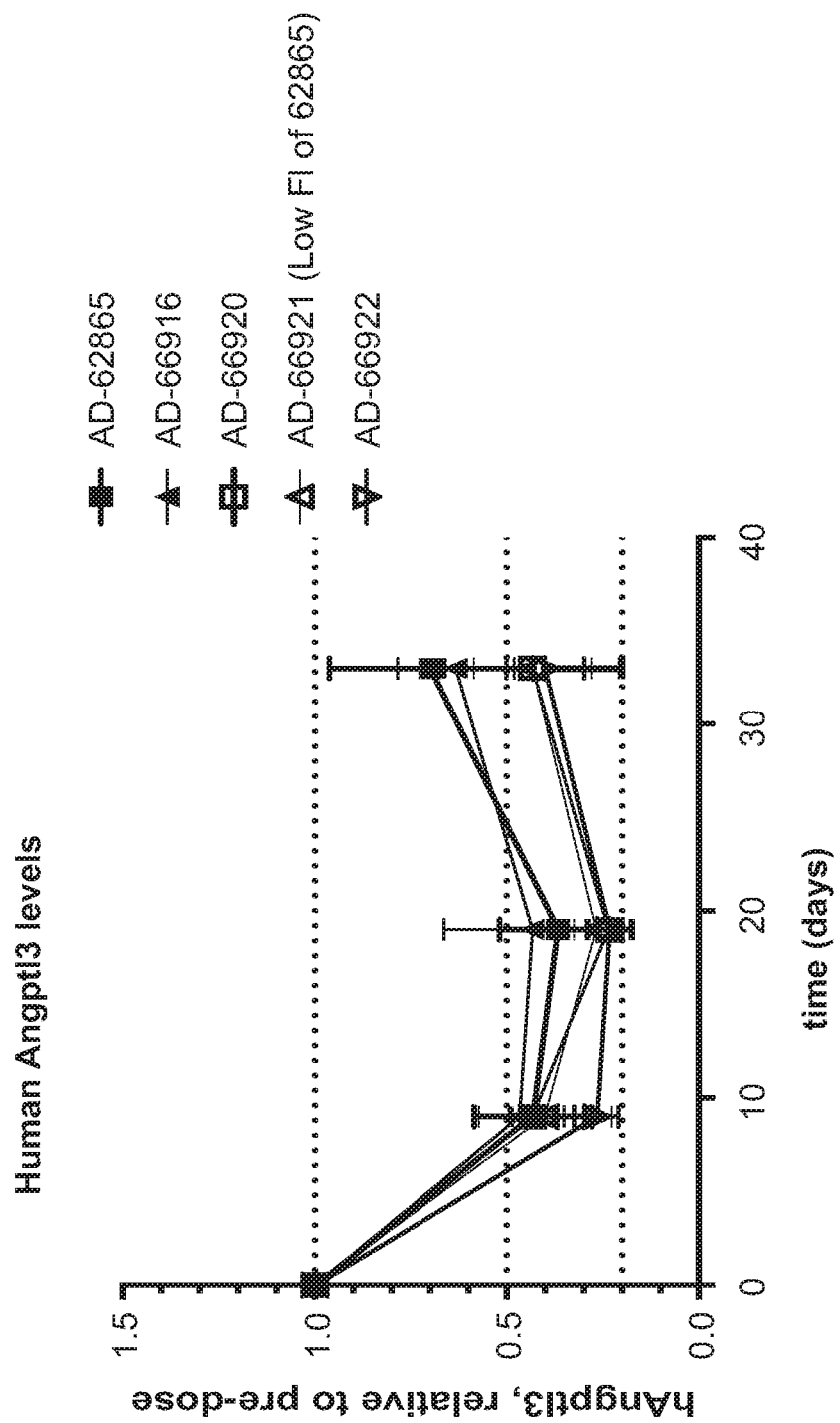
FIG. 16 is a graph showing the duration of response to the indicated iRNA agents represented by the amount of human ANGPTL3 protein remaining in the serum of AAV8-TBG-ANGPTL3 infected mice after a single 1 mg/kg subcutaneous dose of the indicated iRNA agents over time. The amount of human ANGPTL3 protein presented is relative to the amount of human ANGPTL3 protein present in a serum sample prior to administration (pre-dose).

The efficacy of additional agents having fewer 2'-fluoro modified nucleotides as compared to the parent sequence from which they were derived (described in Tables 4A and 4B above) was assayed in AAV8-TBG-ANGPTL3 infected mice by administration of a single 1 mg/kg dose of the agents. Serum was collected from the animals pre-dose and at day 9 post-dose and the level of mouse and human ANGPTL3 was determined by ELISA assays as described above. The results of these assays are provided in Table 6, below, and FIG. 16 which demonstrate that three of the agents having fewer 2'-fluoro modified nucleotides as compared to the parent sequence, AD-66920, AD-66921, and AD-66922, have improved duration of human ANGPTL3 knock-down over the cy/h specific agent, AD-62865.

TABLE 6

In Vivo ANGPTL3 Silencing in AAV-TBG-ANGPTL3 Mice

| Group | n# | Duplex Name | Dose (mg/kg) | Human Angptl3 Mean | SD | Mouse Angptl3 Mean | SD | Mouse cross reactivity | 5' Target Position of Antisense Strand in NM_ 014495.3 |
|---|---|---|---|---|---|---|---|---|---|
| 1 | 2 | PBS | | 0.8 | 0.3 | 1.4 | 0.08 | | |
| 2 | 3 | AD-62865 | 1 | 0.44 | 0.14 | 1.0 | 0.16 | | |
| 3 | 3 | AD-66916 | 1 | 0.44 | 0.11 | 1.3 | 0.25 | | 482 |
| 4 | 3 | AD-66917 | 1 | 0.58 | 0.22 | 1.2 | 0.17 | | 56 |
| 5 | 3 | AD-66918 | 1 | 1.39 | 0.68 | 0.9 | 0.42 | | 478 |
| 6 | 3 | AD-66919 | 1 | 0.88 | 0.25 | 1.1 | 0.16 | | 77 |
| 7 | 3 | AD-66920 | 1 | 0.41 | 0.05 | 1.0 | 0.14 | | 61 |
| 8 | 3 | AD-66921 | 1 | 0.39 | 0.14 | 1.1 | 0.40 | | 398 |
| 9 | 3 | AD-66922 | 1 | 0.27 | 0.08 | 1.2 | 0.38 | | 393 |
| 10 | 3 | AD-66923 | 1 | 0.67 | 0.21 | 0.3 | 0.07 | yes | 278 |
| 11 | 3 | AD-66924 | 1 | 0.62 | 0.20 | 0.5 | 0.07 | yes | 276 |
| 12 | 3 | AD-66925 | 1 | 0.70 | 0.22 | 0.9 | 0.11 | | 1014 |
| | 3 | AD-65695 | 1 | 0.60 | 0.14 | 0.3 | 0.08 | yes | 278 |

TABLE 7A

Additional Modified ANGPTL3 RNAi Agents.

| DuplexName | Modified Sense Sequence 5' to 3' | SEQ ID NO | Modified Antisense Sequence 5' to 3' | SEQ ID NO |
|---|---|---|---|---|
| AD-67021 | gsasauadTgudGacuugaa(Cgn)ucaaL96 | 314 | usdTsgaguucaagdTgdAcauauucsusu | 335 |
| AD-67022 | gsasauadTgudGacuugaa(Cgn)ucaaL96 | 315 | us(Ufms)gaguucaagdTgdAcauauucsusu | 336 |
| AD-67173 | gsasauauGfuCfAfCfuugaacucaaL96 | 316 | usdTsgaguucaagdTgdAcauauucsusu | 337 |
| AD-67174 | gsasauadTgudGacuugaa(Cgn)ucaaL96 | 317 | usUfsgagUfuCfAfagugAfcAfuauucsusu | 338 |
| AD-66922 | gsasauauGfuCfAfCfuugaacucaaL96 | 318 | usUfsgagUfuCfAfagugAfcAfuauucsusu | 339 |
| AD-67008 | asusuaadGcudGcuucuuu(Tgn)uauuL96 | 319 | asdAsuaaaaagaadGgdAgcuuaasusg | 340 |
| AD-67007 | asusuaadGcudGcuucuuu(Tgn)uauuL96 | 320 | asAfsuaaAfaagaaggAfgCfuuaasusg | 341 |
| AD-67006 | asusuaagCfuCfCfUfucuuuuuauuL96 | 321 | asdAsuaaaaagaadGgdAgcuuaasusg | 342 |
| AD-66920 | asusuaagCfuCfCfUfucuuuuuauuL96 | 322 | asAfsuaaAfaAfGfaaggAfgCfuuaasusg | 343 |
| AD-67028 | ascsauadTuudCaucaguc(Tgn)uuuuL96 | 323 | asdAsaaagacugadTcdAaauaugususg | 344 |
| AD-67013 | usgsucadCuudCaacucaa(Cgn)ucaaL96 | 324 | usdTsgaguugagudTcdAagugacasusa | 345 |
| AD-67014 | usgsucadCuudCaacucaa(Cgn)ucaaL96 | 325 | us(Ufms)gaguugagudTcdAagugacasusa | 346 |
| AD-66921 | usgsucacUfuGfAfAfcucaacucaaL96 | 326 | usUfsgagUfuGfAfguucAfaGfugacasusa | 347 |
| AD-66974 | asascuaacuuacuuaau(Tgn)caaaL96 | 327 | usdTsugaauuaagdTudAguuaguusgsc | 348 |

TABLE 7A-continued

Additional Modified ANGPTL3 RNAi Agents.

| DuplexName | Modified Sense Sequence 5' to 3' | SEQ ID NO | Modified Antisense Sequence 5' to 3' | SEQ ID NO |
|---|---|---|---|---|
| AD-66973 | asascudAacuuacuuaau(Tgn)caaaL96 | 328 | usdTsugaauuaagdTudAguuaguusgsc | 349 |
| AD-66916 | asascuaaCfuAfAfCfuuaauucaaaL96 | 329 | usUfsugaAfuUfAfaguuAfgUfuaguusgsc | 350 |
| AD-66925 | csusccauAfgUfGfAfagcaaucuaaL96 | 330 | usUfsagaUfuGfCfuucaCfuAfuggagsusa | 351 |
| AD-67042 | csusccadTagdAgaagcaa(Tgn)cuaaL96 | 331 | usdTsagauugcuudCadCuauggagsusa | 352 |
| AD-66923 | ascsauauUfuGfAfUfcagucuuuuuL96 | 332 | asAfsaaaGfaCfUfgaucAfaAfuaugususg | 353 |
| AD-67026 | ascsauauUfuGfAfUfcagucuuuuuL96 | 333 | asdAsaaagacugadTcdAaauaugususg | 354 |
| AD-67027 | ascsauadTuudCaucaguc(Tgn)uuuuL96 | 334 | asAfsaaaGfacugaucAfaAfuaugususg | 355 |

TABLE 7B

Additional Modified ANGPTL3 RNAi Agents.

| DuplexName | Modified Sense Sequence 5' to 3' | SEQ ID NO | Modified Antisense Sequence 5' to 3' | SEQ ID NO |
|---|---|---|---|---|
| AD-67021 | gsasauadTgudGacuugaa(Cgn)ucaa | 314 | usdTsgaguucaagdTgdAcauauucsusu | 335 |
| AD-67022 | gsasauadTgudGacuugaa(Cgn)ucaa | 315 | us(Ufms)gaguucaagdTgdAcauauucsusu | 336 |
| AD-67173 | gsasauauGfuCfAfCfuugaacucaa | 316 | usdTsgaguucaagdTgdAcauauucsusu | 337 |
| AD-67174 | gsasauadTgudGacuugaa(Cgn)ucaa | 317 | usUfsgagUfuCfAfagugAfcAfuauucsusu | 338 |
| AD-66922 | gsasauauGfuCfAfCfuugaacucaa | 318 | usUfsgagUfuCfAfagugAfcAfuauucsusu | 339 |
| AD-67008 | asuuaadGcudGcuucuuu(Tgn)uauu | 319 | asdAsuaaaaagaadGgdAgcuuaausgsg | 340 |
| AD-67007 | asuuaadGcudGcuucuuu(Tgn)uauu | 320 | asAfsuaaAfaagaaggAfgCfuuaausgsg | 341 |
| AD-67006 | asuuaagCfuCfCfUfucuuuuuauu | 321 | asdAsuaaaaagaadGgdAgcuuaaususg | 342 |
| AD-66920 | asuuaagCfuCfCfUfucuuuuuauu | 322 | asAfsuaaAfaAfGfaaggAfgCfuuaaususg | 343 |
| AD-67028 | ascsauadTuudCaucaguc(Tgn)uuuu | 323 | asdAsaaagacugadTcdAaauaugususg | 344 |
| AD-67013 | usgsucadCuudCaacucaa(Cgn)ucaa | 324 | usdTsgaguugagudTcdAagugacasusa | 345 |
| AD-67014 | usgsucadCuudCaacucaa(Cgn)ucaa | 325 | us(Ufms)gaguugagudTcdAagugacasusa | 346 |
| AD-66921 | usgsucacUfuGfAfAfcucaacucaa | 326 | usUfsgagUfuGfAfguucAfaGfugacasusa | 347 |
| AD-66974 | asascuaacuuacuuaau(Tgn)caaa | 327 | usUfsugaauuaagdTudAguuaguusgsc | 348 |
| AD-66973 | asascudAacuuacuuaau(Tgn)caaa | 328 | usdTsugaauuaagdTudAguuaguusgsc | 349 |
| AD-66916 | asascuaaCfuAfAfCfuuaauucaaa | 329 | usUfsugaAfuUfAfaguuAfgUfuaguusgsc | 350 |
| AD-66925 | csusccauAfgUfGfAfagcaaucuaa | 330 | usUfsagaUfuGfCfuucaCfuAfuggagsusa | 351 |
| AD-67042 | csusccadTagdAgaagcaa(Tgn)cuaa | 331 | usdTsagauugcuudCadCuauggagsusa | 352 |
| AD-66923 | ascsauauUfuGfAfUfcagucuuuuu | 332 | asAfsaaaGfaCfUfgaucAfaAfuaugususg | 353 |
| AD-67026 | ascsauauUfuGfAfUfcagucuuuuu | 333 | asdAsaaagacugadTcdAaauaugususg | 354 |
| AD-67027 | ascsauadTuudCaucaguc(Tgn)uuuu | 334 | asAfsaaaGfacugaucAfaAfuaugususg | 355 |

TABLE 7C

Additional Unmodified ANGPTL3 RNAi Agents.

| DuplexName | Unmodified Sense Sequence 5' to 3' | SEQ ID NO | Unmodified Antisense Sequence 5' to 3' | SEQ ID NO |
|---|---|---|---|---|
| AD-67021 | GAAUAUGUGACUUGAACUCAA | 356 | UUGAGUUCAAGUGACAUAUUCUU | 377 |
| AD-67022 | GAAUAUGUGACUUGAACUCAA | 357 | UUGAGUUCAAGUGACAUAUUCUU | 378 |
| AD-67173 | GAAUAUGUCACUUGAACUCAA | 358 | UUGAGUUCAAGUGACAUAUUCUU | 379 |
| AD-67174 | GAAUAUGUGACUUGAACUCAA | 359 | UUGAGUUCAAGUGACAUAUUCUU | 380 |
| AD-66922 | GAAUAUGUCACUUGAACUCAA | 360 | UUGAGUUCAAGUGACAUAUUCUU | 381 |
| AD-67008 | AUUAAGCUGCUUCUUUUAUU | 361 | AAUAAAAAGAAGGAGCUUAAUUG | 382 |
| AD-67007 | AUUAAGCUGCUUCUUUUAUU | 362 | AAUAAAAAGAAGGAGCUUAAUUG | 383 |
| AD-67006 | AUUAAGCUCCUUCUUUUAUU | 363 | AAUAAAAAGAAGGAGCUUAAUUG | 384 |
| AD-66920 | AUUAAGCUCCUUCUUUUAUU | 364 | AAUAAAAAGAAGGAGCUUAAUUG | 385 |
| AD-67028 | ACAUAUUCAUCAGUCUUUUU | 365 | AAAAAGACUGAUCAAAUAUGUUG | 386 |
| AD-67013 | UGUCACUUCAACUCAACUCAA | 366 | UUGAGUUGAGUUCAAGUGACAUA | 387 |
| AD-67014 | UGUCACUUCAACUCAACUCAA | 367 | UUGAGUUGAGUUCAAGUGACAUA | 388 |
| AD-66921 | UGUCACUUGAACUCAACUCAA | 368 | UUGAGUUGAGUUCAAGUGACAUA | 389 |
| AD-66974 | AACUAACUUACUUAAUCAAA | 369 | UUUGAAUUAAGUUAGUUAGUUGC | 390 |
| AD-66973 | AACUAACUUACUUAAUCAAA | 370 | UUUGAAUUAAGUUAGUUAGUUGC | 391 |
| AD-66916 | AACUAACUAACUUAAUUCAAA | 371 | UUUGAAUUAAGUUAGUUAGUUGC | 392 |
| AD-66925 | CUCCAUAGUGAAGCAAUCUAA | 372 | UUAGAUUGCUUCACUAUGGAGUA | 393 |
| AD-67042 | CUCCAUAGAGAAGCAAUCUAA | 373 | UUAGAUUGCUUCACUAUGGAGUA | 394 |
| AD-66923 | ACAUAUUUGAUCAGUCUUUUU | 374 | AAAAAGACUGAUCAAAUAUGUUG | 395 |
| AD-67026 | ACAUAUUUGAUCAGUCUUUUU | 375 | AAAAAGACUGAUCAAAUAUGUUG | 396 |
| AD-67027 | ACAUAUUCAUCAGUCUUUUU | 376 | AAAAAGACUGAUCAAAUAUGUUG | 397 |

Example 7. In Vivo ANGPTL3 Silencing in AAV-TBG-ANGPTL3 Mice

A second subset of the additional agents listed in Tables 7A, 7B, and 7C were assayed in AAV8-TBG-ANGPTL3 infected mice. The modified nucleotide sequences of the sense and antisense strands of these sequences are provided in Tables 8A and 8B. Briefly, and as described above, at pre-dose day −14, wild-type mice (C57BL/6) were infected by intravenous administration of 1×10¹¹ viral particles. At day 0, mice were administered a single 1 mg/kg or 3 mg/kg dose of the agents. Serum was collected from the animals pre-dose and at days 14 and 28 post-dose and the level of mouse and human ANGPTL3 was determined by ELISA assays as described above.

Figure 17B:
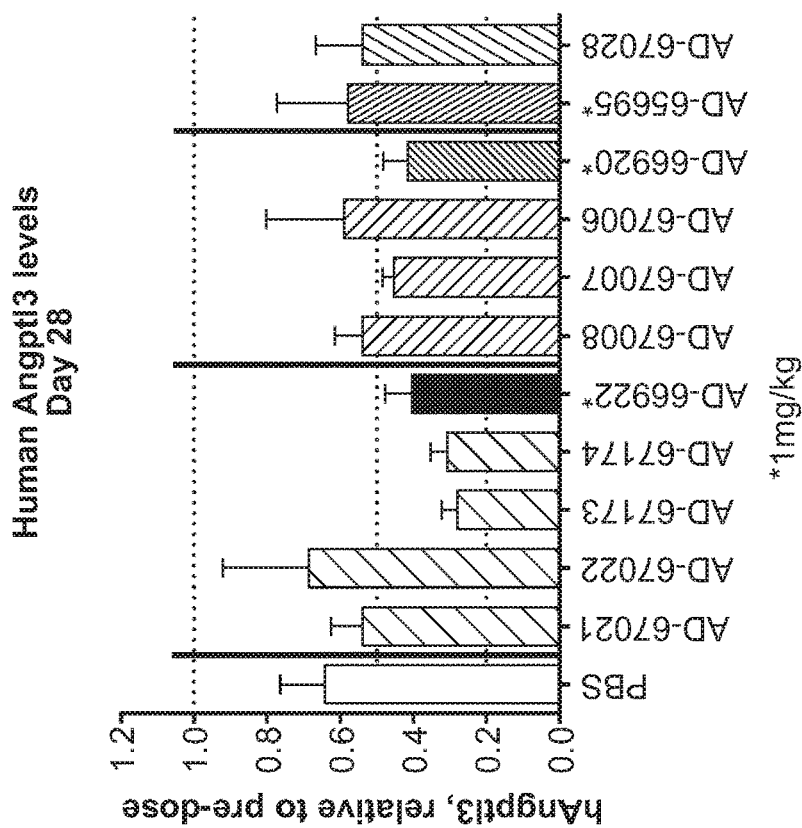
FIG. 17B is a graph depicting the amount of human ANGPTL3 protein remaining in the serum of AAV8-TBG-ANGPTL3 infected mice after a single 1 mg/kg or 3 mg/kg subcutaneous dose of the indicated iRNA agents at day 28 post-dose. The amount of human ANGPTL3 protein presented is relative to the amount of human ANGPTL3 protein present in a serum sample prior to administration (pre-dose).
Figure 17A:
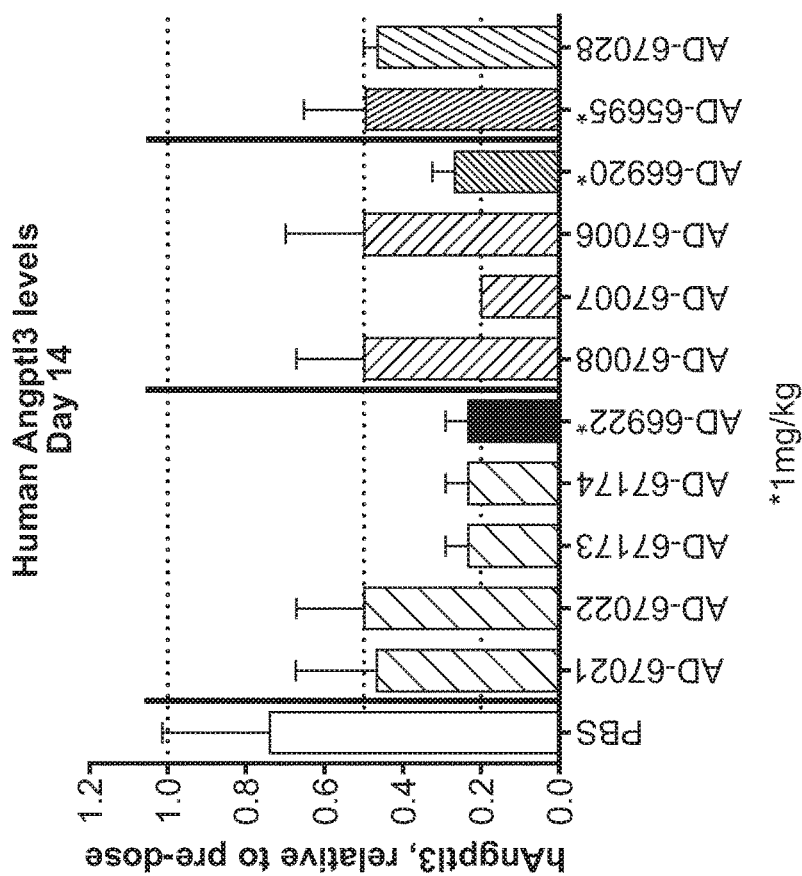
FIG. 17A is a graph depicting the amount of human ANGPTL3 protein remaining in the serum of AAV8-TBG-ANGPTL3 infected mice after a single 1 mg/kg or 3 mg/kg subcutaneous dose of the indicated iRNA agents at day 14 post-dose. The amount of human ANGPTL3 protein presented is relative to the amount of human ANGPTL3 protein present in a serum sample prior to administration (pre-dose).

The results of these assays are provided in Table 9, below, and FIGS. 17A and 17B. The results demonstrate that agents AD-67173, AD-67174, AD-66922, AD-67007, and AD-66920 have improved duration of human ANGPTL3 knock-down.

TABLE 8A

| Duplex ID | Sense Sequence 5' to 3' | SEQ ID NO | Antisense Sequence 5' to 3' | SEQ ID NO |
|---|---|---|---|---|
| AD-67021 | gsasauadTgudGacuugaa(Cgn)ucaaL96 | 398 | usdTsgaguucaagdTgdAcauauucsusu | 408 |
| AD-67022 | gsasauadTgudGacuugaa(Cgn)ucaaL96 | 399 | us(Ufms)gaguucaagdTgdAcauauucsusu | 409 |
| AD-67173 | gsasauauGfuCfAfCfuugaacucaaL96 | 400 | usdTsgaguucaagdTgdAcauauucsusu | 410 |
| AD-67174 | gsasauadTgudGacuugaa(Cgn)ucaaL96 | 401 | usUfsgagUfuCfAfagugAfcAfuauucsusu | 411 |
| AD-66922 | gsasauauGfuCfAfCfuugaacucaaL96 | 402 | usUfsgagUfuCfAfagugAfcAfuauucsusu | 412 |

TABLE 8A-continued

| Duplex ID | Sense Sequence 5' to 3' | SEQ ID NO | Antisense Sequence 5' to 3' | SEQ ID NO |
|---|---|---|---|---|
| AD-67008 | asusuaadGcudGcuucuuu(Tgn)uauuL96 | 403 | asdAsuaaaaagaadGgdAgcuuaaususg | 413 |
| AD-67007 | asusuaadGcudGcuucuuu(Tgn)uauuL96 | 404 | asAfsuaaAfaagaaggAfgCfuuaaususg | 414 |
| AD-67006 | asusuaagCfuCfCfUfucuuuuuauuL96 | 405 | asdAsuaaaaagaadGgdAgcuuaaususg | 415 |
| AD-66920 | asusuaagCfuCfCfUfucuuuuuauuL96 | 406 | asAfsuaaAfaAfGfaaggAfgCfuuaaususg | 416 |
| AD-67028 | ascsauadTuudCaucaguc(Tgn)uuuuL96 | 407 | asdAsaaagacugadTcdAaauaugususg | 417 |

TABLE 8B

| Duplex ID | Sense Sequence 5' to 3' | SEQ ID NO | Antisense Sequence 5' to 3' | SEQ ID NO |
|---|---|---|---|---|
| AD-67021 | gsasauadTgudGacuugaa(Cgn)ucaa | 398 | usdTsgaguucaagdTgdAcauauucsusu | 408 |
| AD-67022 | gsasauadTgudGacuugaa(Cgn)ucaa | 399 | us(Ufms)gaguucaagdTgdAcauauucsusu | 409 |
| AD-67173 | gsasauauGfuCfAfCfuugaacucaa | 400 | usdTsgaguucaagdTgdAcauauucsusu | 410 |
| AD-67174 | gsasauadTgudGacuugaa(Cgn)ucaa | 401 | usUfsgagUfuCfAfagugAfcAfuauucsusu | 411 |
| AD-66922 | gsasauauGfuCfAfCfuugaacucaa | 402 | usUfsgagUfuCfAfagugAfcAfuauucsusu | 412 |
| AD-67008 | asusuaadGcudGcuucuuu(Tgn)uauu | 403 | asdAsuaaaaagaadGgdAgcuuaaususg | 413 |
| AD-67007 | asusuaadGcudGcuucuuu(Tgn)uauu | 404 | asAfsuaaAfaagaaggAfgCfuuaaususg | 414 |
| AD-67006 | asusuaagCfuCfCfUfucuuuuuauu | 405 | asdAsuaaaaagaadGgdAgcuuaaususg | 415 |
| AD-66920 | asusuaagCfuCfCfUfucuuuuuauu | 406 | asAfsuaaAfaAfGfaaggAfgCfuuaaususg | 416 |
| AD-67028 | ascsauadTuudCaucaguc(Tgn)uuuu | 407 | asdAsaaagacugadTcdAaauaugususg | 417 |

TABLE 9

| Duplex | Dose (mg/kg) | Day 14, Relative to Pre-dose Human Angptl3 | |
|---|---|---|---|
| | | Mean | SD |
| PBS | 0 | 0.74 | 0.27 |
| AD-67021 | 3 | 0.48 | 0.22 |
| AD-67022 | 3 | 0.52 | 0.17 |
| AD-67173 | 3 | 0.25 | 0.03 |
| AD-67174 | 3 | 0.22 | 0.05 |
| AD-66922 | 1 | 0.26 | 0.06 |
| AD-67008 | 3 | 0.50 | 0.18 |
| AD-67007 | 3 | 0.21 | 0.02 |
| AD-67006 | 3 | 0.50 | 0.18 |
| AD-66920 | 1 | 0.25 | 0.05 |
| AD-65695 | 1 | 0.49 | 0.15 |
| AD-67028 | 3 | 0.47 | 0.04 |

In another experiment, a further subset of the additional agents listed in Tables 7A, 7B, and 7C were assayed in AAV8-TBG-ANGPTL3 infected mice. The modified nucleotide sequences of the sense and antisense strands of these sequences are provided in Tables 10A and 10B. Briefly, and as described above, at pre-dose day −14, wild-type mice (C57BL/6) were infected by intravenous administration of $1\times10^{11}$ viral particles. At day 0, mice were administered a single 1 mg/kg or 3 mg/kg dose of the agents. Serum was collected from the animals pre-dose and at days 14 and 28 post-dose and the level of mouse and human ANGPTL3 was determined by ELISA assays as described above.

The results of these assays at day 14 post-dose are provided in Table 11, below, and FIG. 18A, and the results of these assays at day 28 post-dose are provided in Table 12, below and FIG. 18B. The results demonstrate that agents AD-66921, AD-66916, and AD-67042 have improved duration of human ANGPTL3 knock-down.

TABLE 10A

| Duplex ID | Sense Sequene 5' to 3' | SEQ ID NO | Antisense Sequence 5' to 3' | SEQ ID NO |
|---|---|---|---|---|
| AD-67013 | usgsucadCuudCaacucaa(Cgn)ucaaL96 | 418 | usdTsgaguugagudTcdAagugacasusa | 430 |
| AD-67014 | usgsucadCuudCaacucaa(Cgn)ucaaL96 | 419 | us(Ufms)gaguugagudTcdAagugacasusa | 431 |

TABLE 10A-continued

| Duplex ID | Sense Sequene 5' to 3' | SEQ ID NO | Antisense Sequence 5' to 3' | SEQ ID NO |
|---|---|---|---|---|
| AD-66921 | usgsucacUfuGfAfAfcucaacucaaL96 | 420 | usUfsgagUfuGfAfguucAfaGfugacasusa | 432 |
| AD-66974 | asascuaacuuacuuaau(Tgn)caaaL96 | 421 | usdTsugaauuaagdTudAguuaguusgsc | 433 |
| AD-66973 | asascudAacuuacuuaau(Tgn)caaaL96 | 422 | usdTsugaauuaagdTudAguuaguusgsc | 434 |
| AD-66916 | asascuaaCfuAfAfCfuuaauucaaaL96 | 423 | usUfsugaAfuUfAfaguuAfgUfuaguusgsc | 435 |
| AD-66925 | csusccauAfgUfGfAfagcaaucuaaL96 | 424 | usUfsagaUfuGfCfuucaCfuAfuggagsusa | 436 |
| AD-67042 | csusccadTagdAgaagcaa(Tgn)cuaaL96 | 425 | usdTsagauugcuudCadCuauggagsusa | 437 |
| AD-66923 | ascsauauUfuGfAfUfcagucuuuuuL96 | 426 | asAfsaaaGfaCfUfgaucAfaAfuaugususg | 438 |
| AD-67026 | ascsauauUfuGfAfUfcagucuuuuuL96 | 427 | asdAsaaagacugadTcdAaauaugususg | 439 |
| AD-67027 | ascsauadTuudCaucaguc(Tgn)uuuuL96 | 428 | asAfsaaaGfacugaucAfaAfuaugususg | 440 |
| AD-67028 | ascsauadTuudCaucaguc(Tgn)uuuuL96 | 429 | asdAsaaagacugadTcdAaauaugususg | 441 |

TABLE 10B

| Duplex ID | Sense Sequene 5' to 3' | SEQ ID NO | Antisense Sequence 5' to 3' | SEQ ID NO |
|---|---|---|---|---|
| AD-67013 | usgsucadCuudCaacucaa(Cgn)ucaa | 418 | usdTsgaguugagudTcdAagugacasusa | 430 |
| AD-67014 | usgsucadCuudCaacucaa(Cgn)ucaa | 419 | us(Ufms)gaguugagudTcdAagugacasusa | 431 |
| AD-66921 | usgsucacUfuGfAfAfcucaacucaa | 420 | usUfsgagUfuGfAfguucAfaGfugacasusa | 432 |
| AD-66974 | asascuaacuuacuuaau(Tgn)caaa | 421 | usdTsugaauuaagdTudAguuaguusgsc | 433 |
| AD-66973 | asascudAacuuacuuaau(Tgn)caaa | 422 | usdTsugaauuaagdTudAguuaguusgsc | 434 |
| AD-66916 | asascuaaCfuAfAfCfuuaauucaaa | 423 | usUfsugaAfuUfAfaguuAfgUfuaguusgsc | 435 |
| AD-66925 | csusccauAfgUfGfAfagcaaucuaa | 424 | usUfsagaUfuGfCfuucaCfuAfuggagsusa | 436 |
| AD-67042 | csusccadTagdAgaagcaa(Tgn)cuaa | 425 | usdTsagauugcuudCadCuauggagsusa | 437 |
| AD-66923 | ascsauauUfuGfAfUfcagucuuuuu | 426 | asAfsaaaGfaCfUfgaucAfaAfuaugususg | 438 |
| AD-67026 | ascsauauUfuGfAfUfcagucuuuuu | 427 | asdAsaaagacugadTcdAaauaugususg | 439 |
| AD-67027 | ascsauadTuudCaucaguc(Tgn)uuuu | 428 | asAfsaaaGfacugaucAfaAfuaugususg | 440 |
| AD-67028 | ascsauadTuudCaucaguc(Tgn)uuuu | 429 | asdAsaaagacugadTcdAaauaugususg | 441 |

TABLE 11

| siRNA | Dose (mg/kg) | Day 14, Relative to PBS Human Angptl3 Mean | SD |
|---|---|---|---|
| PBS | 0 | 1.00 | 0.12 |
| AD-67013 | 3 | 0.86 | 0.06 |
| AD-67014 | 3 | 0.67 | 0.15 |
| AD-66921 | 1 | 0.44 | 0.18 |
| AD-66974 | 3 | 0.75 | 0.03 |
| AD-66973 | 3 | 0.76 | 0.05 |
| AD-66916 | 1 | 0.41 | 0.05 |
| AD-66925 | 1 | 0.65 | 0.13 |
| AD-67042 | 3 | | |
| AD-65695 | 1 | 0.59 | 0.19 |
| AD-66923 | 1 | 0.64 | 0.25 |
| AD-67026 | 3 | 0.56 | 0.03 |
| AD-67027 | 3 | 0.66 | 0.23 |
| AD-67028 | 3 | 0.65 | 0.21 |

TABLE 12

| siRNA | Dose (mg/kg) | Day 28, Relative to PBS Human Angptl3 | |
|---|---|---|---|
| | | Mean | SD |
| PBS | 0 | 1.00 | 0.12 |
| AD-67013 | 3 | 1.50 | 1.28 |
| AD-67014 | 3 | 0.90 | 0.23 |
| AD-66921 | 1 | 0.44 | 0.11 |
| AD-66974 | 3 | 0.96 | 0.10 |
| AD-66973 | 3 | 1.00 | 0.34 |
| AD-66916 | 1 | 0.57 | 0.06 |
| AD-66925 | 1 | 1.01 | 0.28 |
| AD-67042 | 3 | | |
| AD-65695 | 1 | 0.85 | 0.17 |
| AD-66923 | 1 | 0.85 | 0.25 |
| AD-67026 | 3 | 0.64 | 0.06 |
| AD-67027 | 3 | 0.58 | 0.11 |
| AD-67028 | 3 | 1.32 | 1.01 |

Example 8. In Vivo ANGPTL3 Silencing in Non-Human Primates

Male cynomolgus monkeys (n=3/group) were subcutaneously administered a single 1 mg/kg dose of AD-65695 or AD-66920, or a single 3 mg/kg dose of AD-66920 on day 1. Fasted serum was collected on days 4, 8, 11, 15, and 22 post-dose and the protein level of Angplt3 and the serum lipid levels were measured.

Figure 19A:
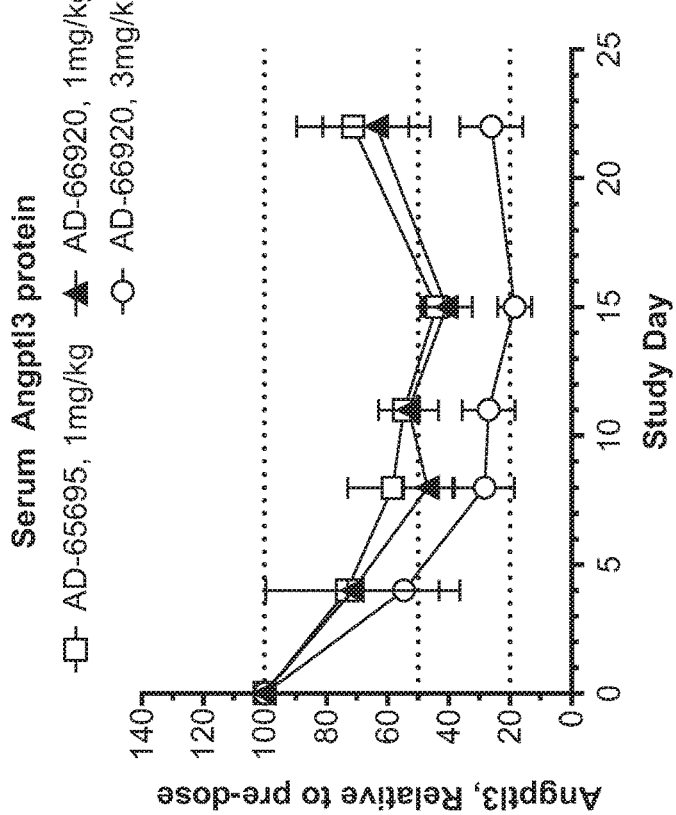
FIG. 19A is a graph showing the duration of response to the indicated iRNA agents represented by the amount of Cynomolgus ANGPTL3 protein remaining in the serum of lean Cynomolgus monkeys administered a single 1 mg/kg or 3 mg/kg dose of the indicated iRNA agents over time. The amount of Cynomolgus ANGPTL3 protein presented is relative to the amount of human ANGPTL3 protein present in a serum sample prior to administration (pre-dose).
Figure 19B:
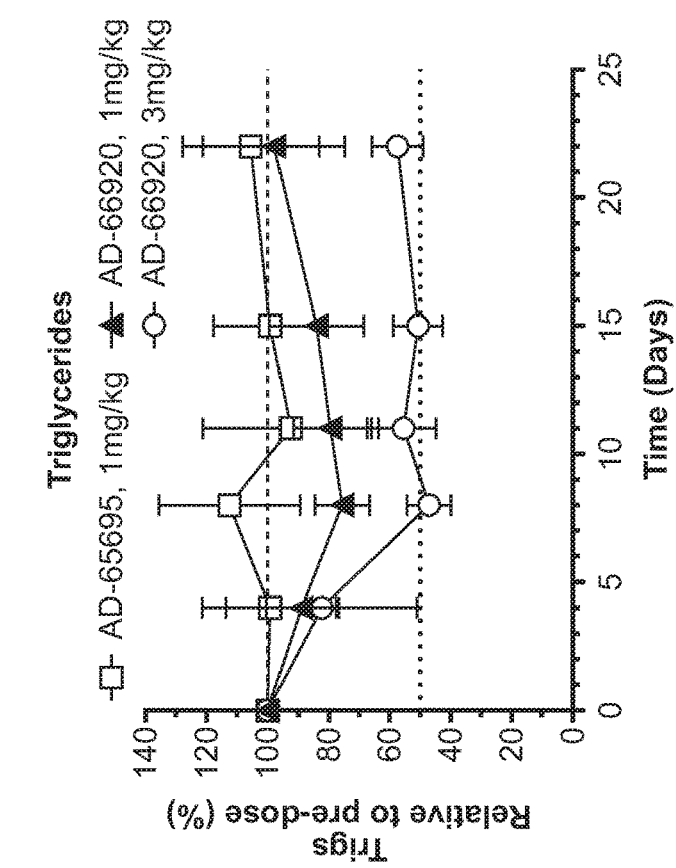
FIG. 19B is a graph showing the percent of triglycerides remaining in the serum of Cynomolgus monkeys administered a single 1 mg/kg or 3 mg/kg dose of the indicated iRNA agents over time. The amount of triglycerides presented is relative to the amount of Cynomolgus triglycerides present in a serum sample prior to administration (pre-dose).

The results of these assays are provided in FIGS. 19A and 19B and demonstrate that there is up to an 80% knockdown of serum ANGPTL3 protein following a single 3 mg/kg dose of AD-66920 (h/cy) and about a 50% lowering of the level of serum triglycerides. A single 1 mg/kg dose of AD-66920 had a modest effect on the level of serum triglycerides. Surprisingly, although administration of a single 1 mg/kg dose of AD-65695 lowered ANGPTL3 protein levels to a similar level as a single 1 mg/kg dose of AD-66920, a single 1 mg/kg dose of AD-65695 was about three times less potent than a single 1 mg/kg dose of AD-66920 in the AAV8-TBG-ANGPTL3 mouse model and had no effect on serum triglycerides.

Example 9. In Vivo ANGPTL3 Silencing in AAV-TBG-ANGPTL3 Mice

The in vivo efficacy of an additional set of agents targeting ANGPTL3 was assayed in AAV8-TBG-ANGPTL3 infected mice. The modified nucleotide sequences of the sense and antisense strands of these sequences are provided in Tables 13A and 13B. Briefly, and as described above, at pre-dose day −21 wild-type mice (C57BL/6; n=3) were infected by intravenous administration of 1×10[11] viral particles. At day 0, mice were administered a single 1 mg/kg dose of the agents. Serum was collected from the animals pre-dose and at day 28 post-dose and the level of human ANGPTL3 was determined by ELISA assays as described above.

Figure 20:
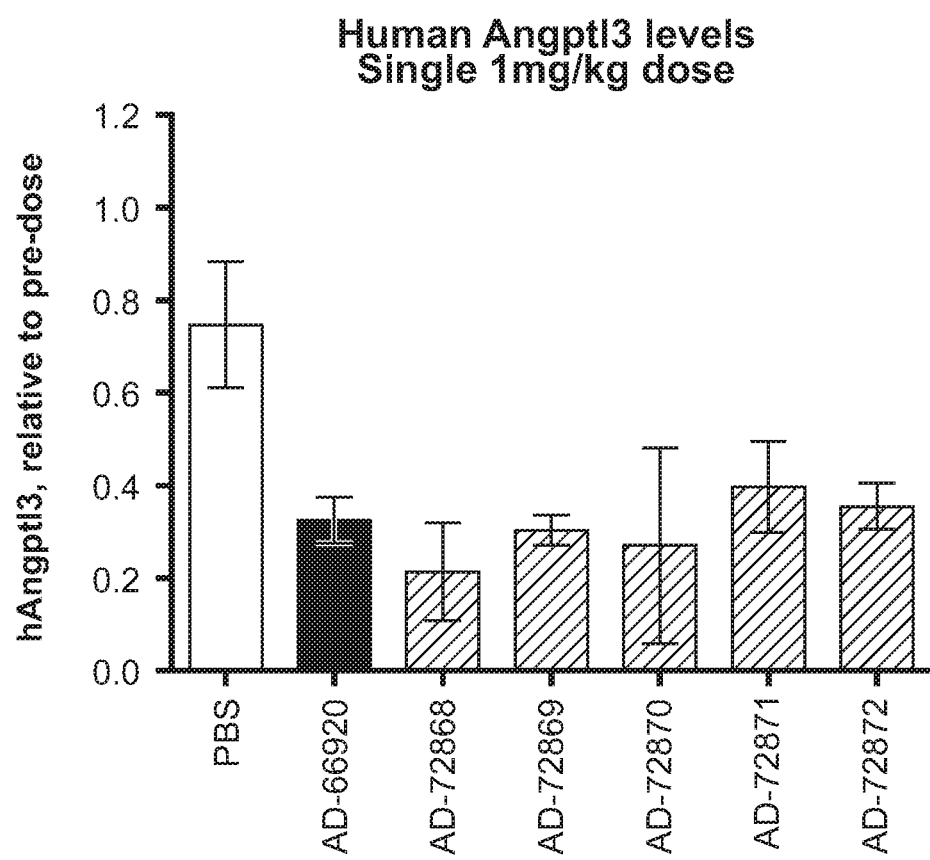
FIG. 20 is a graph depicting the amount of human ANGPTL3 protein remaining in the serum of AAV8-TBG-ANGPTL3 infected mice after a single 1 mg/kg subcutaneous dose of the indicated iRNA agents at day 28 post-dose. The amount of human ANGPTL3 protein presented is relative to the amount of human ANGPTL3 protein present in a serum sample prior to administration (pre-dose).

The results of these assays are provided in FIG. 20 and demonstrate that these agents effectively knockdown human ANGPTL3 protein levels.

A further set of the agents targeting ANGPTL3 listed in Tables 13A and 13B was assayed for in vivo efficacy in AAV8-TBG-ANGPTL3 infected mice. As described above, at pre-dose day −21 wild-type mice (C57BL/6; n=3) were infected by intravenous administration of 1×10[11] viral particles. At day 0, mice were administered a single 1 mg/kg dose of the agents. Serum was collected from the animals pre-dose and at day 28 post-dose and the level of human and mouse ANGPTL3 was determined by ELISA assays as described above.

Figure 21A:
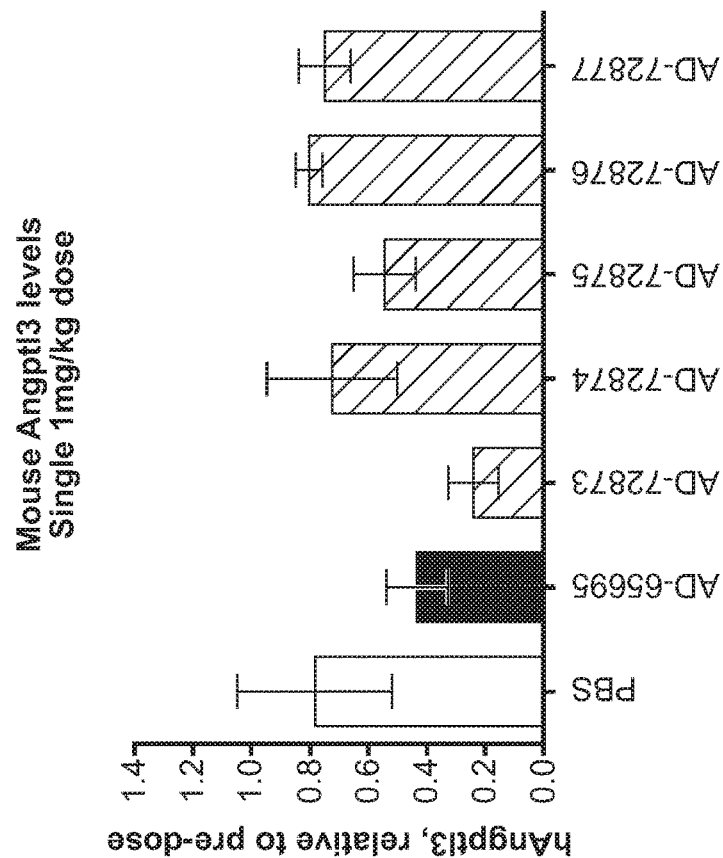
FIG. 21A is a graph depicting the amount of human ANGPTL3 protein remaining in the serum of AAV8-TBG-ANGPTL3 infected mice after a single 1 mg/kg subcutaneous dose of the indicated iRNA agents at day 28 post-dose. The amount of human ANGPTL3 protein presented is relative to the amount of human ANGPTL3 protein present in a serum sample prior to administration (pre-dose).
Figure 21B:
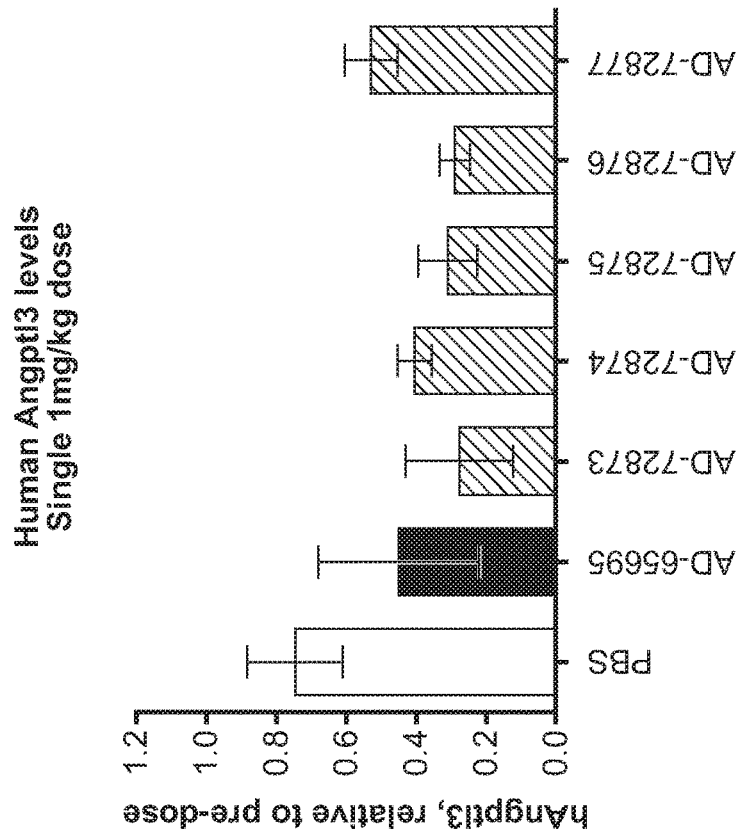
FIG. 21B is a graph depicting the amount of mouse ANGPTL3 protein remaining in the serum of AAV8-TBG-ANGPTL3 infected mice after a single 1 mg/kg subcutaneous dose of the indicated iRNA agents at day 28 post-dose. The amount of human ANGPTL3 protein presented is relative to the amount of human ANGPTL3 protein present in a serum sample prior to administration (pre-dose).

The results of these assays are provided in FIGS. 21A and 21B and demonstrate that these agents effectively knockdown mouse and human ANGPTL3 protein levels.

Example 10. In Vitro ANGPTL3 Silencing in AAV-TBG-ANGPTL3 Mice

Further iRNA agents targeting the ANGPTL3 gene were synthesized as described above. A detailed list of the additional unmodified ANGPTL3 sense and antisense strand sequences is shown in Table 14 and a detailed list of the modified sense and antisense strand sequences of these additional agents is shown in Tables 13A, 13B, 15A and 15B.

These additional agents were evaluated in in vitro assays in Hep3b and primary Cynomolgus monkey hepatocytes by single dose transfections of the agents at 10 nM and 0.1 nM final duplex concentration. (See Table 16).

Hep3b cells were cultured and transfected as described above. Free uptake silencing in primary cynomolgus hepatocytes was assessed following incubation with ANGPTL3 agents for 24 hours. The method was similar to that described above, with the exception that 5 μL complete growth medium was substituted for the 5 μL containing Lipofectamine RNAiMax and Optimem. The results of these assays (provided in Table 16) illustrate that many of the duplexes potently inhibited ANGPTL3 mRNA expression.

TABLE 13A

Additional Modified ANGPTL3 RNAi Agents.

| Duplex Name | Sense Sequence 5' to 3' | SEQ ID NO | Antisense Sequence 5' to 3' | SEQ ID NO |
|---|---|---|---|---|
| AD-66920 | asusuaagCfuCfCfUfucuuuuuauuL96 | 442 | asAfsuaaAfaAfGfaaggAfgCfuuaaususg | 454 |
| AD-72868 | asusuaagCfuCfCfUfucuuuuuauaL96 | 443 | VP(Tams)AfsuaaAfaAfGfaaggAfgCfuuaaususg | 455 |
| AD-72869 | asusuaagcuCfcUfucuuuuuauuL96 | 444 | asAfsuaaaaagaaGfgAfgcuuaaususg | 456 |
| AD-72870 | asusuaagcCfcUfucuuuuuauuL96 | 445 | asAfsuaaaaagaadGgAfgcuuaaususg | 457 |
| AD-72871 | asusuaagcuCfcUfucuuu(Tgn)uauuL96 | 446 | asAfsuaaaaagaaGfgAfgcuuaaususg | 458 |
| AD-72872 | asusuaagcuCfcUfucuauauauuL96 | 447 | asAfsuaaaaagaaGfgAfgcuuaaususg | 459 |
| AD-65695 | ascsauauUfuGfAfUfcagucuuuuuL96 | 448 | asAfsaaaGfacugaucAfaAfuauguususg | 460 |

TABLE 13A-continued

Additional Modified ANGPTL3 RNAi Agents.

| Duplex Name | Sense Sequence 5' to 3' | SEQ ID NO | Antisense Sequence 5' to 3' | SEQ ID NO |
|---|---|---|---|---|
| AD-72873 | ascsauauUfuGfAfUfcagucuuuuaL96 | 449 | VP(Tams)AfsaaaGfacugaucAfaAfuaugususg | 461 |
| AD-72874 | ascsauauuuGfaUfcagucuuuuuL96 | 450 | asAfsaaagacugaUfcAfaauaugususg | 462 |
| AD-72875 | ascsauauuuGfaUfcagucuuuuuL96 | 451 | asAfsaaagacugadTcAfaauaugususg | 463 |
| AD-72876 | ascsauauuuGfaUfcaguc(Tgn)uuuuL96 | 452 | asAfsaaagacugaUfcAfaauaugususg | 464 |
| AD-72877 | ascsauauuuGfaUfcagacauuuuL96 | 453 | asAfsaaagacugaUfcAfaauaugususg | 465 |

TABLE 13B

Additional Modified ANGPTL3 RNAi Agents.

| Duplex Name | Sense Sequence 5' to 3' | SEQ ID NO | Antisense Sequence 5' to 3' | SEQ ID NO |
|---|---|---|---|---|
| AD-66920 | asusuaagCfuCfCfUfucuuuuuauu | 442 | asAfsuaaAfaAfGfaaggAfgCfuuaaaususg | 454 |
| AD-72868 | asusuaagCfuCfCfUfucuuuuuaua | 443 | VP(Tams)AfsuaaAfaAfGfaaggAfgCfuuaaaususg | 455 |
| AD-72869 | asusuaagcuCfcUfucuuuuuauu | 444 | asAfsuaaaaagaaGfgAfgcuuaaususg | 456 |
| AD-72870 | asusuaagcuCfcUfucuuuuuauu | 445 | asAfsuaaaaagaadGgAfgcuuaaususg | 457 |
| AD-72871 | asusuaagcuCfcUfucuuu(Tgn)uauu | 446 | asAfsuaaaaagaaGfgAfgcuuaaususg | 458 |
| AD-72872 | asusuaagcuCfcUfucuauauauu | 447 | asAfsuaaaaagaaGfgAfgcuuaaususg | 459 |
| AD-65695 | ascsauauUfuGfAfUfcagucuuuuu | 448 | asAfsaaaGfacugaucAfaAfuaugususg | 460 |
| AD-72873 | ascsauauUfuGfAfUfcagucuuuua | 449 | VP(Tams)AfsaaaGfacugaucAfaAfuaugususg | 461 |
| AD-72874 | ascsauauuuGfaUfcagucuuuuu | 450 | asAfsaaagacugaUfcAfaauaugususg | 462 |
| AD-72875 | ascsauauuuGfaUfcagucuuuuu | 451 | asAfsaaagacugadTcAfaauaugususg | 463 |
| AD-72876 | ascsauauuuGfaUfcaguc(Tgn)uuuu | 452 | asAfsaaagacugaUfcAfaauaugususg | 464 |
| AD-72877 | ascsauauuuGfaUfcagacauuuu | 453 | asAfsaaagacugaUfcAfaauaugususg | 465 |

TABLE 14

Additional Unmodified ANGPTL3 RNAi Agents.

| Duplex Name | Sense Sequence 5' to 3' | SEQ ID NO | Antisense Sequence 5' to 3' | SEQ ID NO | Antisense target position in NM_014495.3 |
|---|---|---|---|---|---|
| AD-66916 | AACUAACUAACUUAAUUCAAA | 466 | UUUGAAUUAAGUUAGUUAGUUGC | 507 | 480-502 |
| AD-66922 | GAAUAUGUCACUUGAACUCAA | 467 | UUGAGUUCAAGUGACAUAUUCUU | 508 | 391-413 |
| AD-74755 | AAACUCUAAACUUGACUAAAU | 468 | AUUUAGUCAAGUUUAGAGUUUUA | 509 | 1853-1874 |
| AD-74756 | AACUAACUUAAUUCAAAAUCA | 469 | UGAUUUUGAAUUAAGUUAGUUAG | 510 | 515-536 |
| AD-74757 | CCAGAAGUAACUUCACUUAAA | 470 | UUUAAGUGAAGUUACUUCUGGGU | 511 | 555-576 |
| AD-74758 | GAACUCAACUCAAAACUUGAA | 471 | UUCAAGUUUUGAGUUGAGUUCAA | 512 | 435-456 |
| AD-74759 | CAACUCAAAACUUGAAAGCCU | 472 | AGGCUUUCAAGUUUUGAGUUGAG | 513 | 440-461 |
| AD-74760 | UUCCACGUUGCUUGAAAUUGA | 473 | UCAAUUUCAAGCAACGUGGAACU | 514 | 46-67 |
| AD-74761 | GUUGCUUGAAAUUGAAAAUCA | 474 | UGAUUUUCAAUUUCAAGCAACGU | 515 | 52-73 |

TABLE 14-continued

Additional Unmodified ANGPTL3 RNAi Agents.

| Duplex Name | Sense Sequence 5' to 3' | SEQ ID NO | Antisense Sequence 5' to 3' | SEQ ID NO | Antisense target position in NM_014495.3 |
|---|---|---|---|---|---|
| AD-74762 | GAUCACAAAACUUCAAUGAAA | 475 | UUUCAUUGAAGUUUUGUGAUCCA | 516 | 952-973 |
| AD-74763 | UCAAGAUUUGCUAUGUUAGAA | 476 | UUCUAACAUAGCAAAUCUUGAUU | 517 | 183-204_C21A |
| AD-74764 | CAAAAUCAAGAUUUGCUAUGU | 477 | ACAUAGCAAAUCUUGAUUUUGGC | 518 | 178-199 |
| AD-74765 | GAACUACUCCCUUUCUUCAGU | 478 | ACUGAAGAAAGGGAGUAGUUCUU | 519 | 751-772 |
| AD-74766 | AGAAAUUUCUCUAUCUUCCAA | 479 | UUGGAAGAUAGAGAAAUUUCUGU | 520 | 716-737 |
| AD-74767 | UGAACUGAGGCAAAUUUAAAA | 480 | UUUUAAAUUUGCCUCAGUUCAUU | 521 | 1461-1482 |
| AD-74768 | CAUCCAACAGAUUCAGAAAGA | 481 | UCUUUCUGAAUCUGUUGGAUGGA | 522 | 1434-1455_C21A |
| AD-74769 | AAAAUCAAGAUUUGCUAUGUU | 482 | AACAUAGCAAAUCUUGAUUUUGG | 523 | 179-200 |
| AD-74770 | AGAGCAAAAUCUAAGCCAGAA | 483 | UUCUGGCUUAGAUUUUGCUCUUG | 524 | 1341-1362_G21A |
| AD-74771 | AUCAUAUGAGCUAAUAUCACA | 484 | UGUGAUAUUAGCUCAUAUGAUGC | 525 | 1798-1819 |
| AD-74772 | AAUAAACCUCGUAACAAGUUA | 485 | UAACUUGUUACGAGGUUUAUUUC | 526 | 2339-2360 |
| AD-74773 | CAACAGCAUAGUCAAAUAAAA | 486 | UUUUAUUUGACUAUGCUGUUGGU | 527 | 651-672 |
| AD-74774 | AAAACAACCUAAAUGGUAAAU | 487 | AUUUACCAUUUAGGUUGUUUUCU | 528 | 1309-1330 |
| AD-74775 | CACUUAAAACUUUUGUAGAAA | 488 | UUUCUACAAAAGUUUUAAGUGAA | 529 | 568-589 |
| AD-74776 | AUUAAAAUAAGUUCGCUGUCU | 489 | AGACAGCGAACUUAUUUUAAUAC | 530 | 2070-2091 |
| AD-74777 | CAAAACUUCAAUGAAACGUGA | 490 | UCACGUUUCAUUGAAGUUUUGUG | 531 | 957-978_G21A |
| AD-74778 | AGAUGGAUCACAAAACUUCAA | 491 | UUGAAGUUUUGUGAUCCAUCUAU | 532 | 947-968 |
| AD-74779 | CACUUAAUACUAUGAAAACAA | 492 | UUGUUUUCAUAGUAUUAAGUGUU | 533 | 2194-2215 |
| AD-74780 | ACUAAGUCACAUUGACUUUAA | 493 | UUAAAGUCAAUGUGACUUAGUAG | 534 | 2111-2132 |
| AD-74781 | UAUUAAAUAACUUUUCUAAAU | 494 | AUUUAGAAAAGUUAUUUAAUAAG | 535 | 1746-1767 |
| AD-74782 | ACACUUAAUACUAUGAAACA | 495 | UGUUUUCAUAGUAUUAAGUGUUA | 536 | 2193-2214 |
| AD-74783 | UUUAUGAAACCUAAUGAAGCA | 496 | UGCUUCAUUAGGUUUCAUAAAUA | 537 | 2035-2056 |
| AD-74784 | CAAACAUUAUAUUGAAUAUUA | 497 | UAAUAUUCAAUAUAAUGUUUGUU | 538 | 1103-1124_C21A |
| AD-74785 | AAACCAGUGAAAUCAAAGAAA | 498 | UUUCUUUGAUUUCACUGGUUUGC | 539 | 343-364_G21A |
| AD-74786 | GAGUUAAAGUUUAUAUUUCCA | 499 | UGGAAAUAUAAACUUUAACUCGA | 540 | 2271-2292_C21A |
| AD-74787 | CCAAUAUAAACAAUUAAACCA | 500 | UGGUUUAAUUGUUUAUAUUGGUC | 541 | 632-653 |
| AD-74788 | GUGGAGAAAACAACCUAAAUA | 501 | UAUUUAGGUUGUUUUCUCCACAC | 542 | 1303-1324_G21A |
| AD-74789 | AACUCAACUCAAAACUUGAAA | 502 | UUUCAAGUUUUGAGUUGAGUUCA | 543 | 436-457 |
| AD-74790 | AAUGUUCACAAUUAAGCUCCU | 503 | AGGAGCUUAAUUGUGAACAUUUU | 544 | 80-101 |
| AD-74791 | GCAGAAUUAAAUACUGUAUUA | 504 | UAAUACAGUAUUUAAUUCUGCUU | 545 | 2053-2074 |
| AD-74792 | UGAAUGAAAUAAGAAAUGUAA | 505 | UUACAUUUCUUAUUUCAUUCAAC | 546 | 772-793 |
| AD-74793 | UACAUAUAAACUACAAGUCAA | 506 | UUGACUUGUAGUUUAUAUGUAGU | 547 | 386-407 |

TABLE 15A

Additional Modified ANGPTL3 RNAi Agents.

| Duplex Name | Sense Sequence 5' to 3' | SEQ ID NO: | Antisense Sequence 5' to 3' | SEQ ID NO: |
|---|---|---|---|---|
| AD-66916 | asascuaaCfuAfAfCfuuaaauucaaaL96 | 548 | usUfsugaAfuUfAfaguuAfgUfuaguusgsc | 589 |
| AD-66922 | gsasauauGfuCfAfCfuugaacucaaL96 | 549 | usUfsgagUfuCfAfagugAfcAfuauucsusu | 590 |
| AD-74755 | asasacucUfaAfAfCfuugacuaaauL96 | 550 | asUfsuuaGfuCfAfaguuUfaGfaguuusasa | 591 |
| AD-74756 | asascuaaCfuUfAfAfuucaaaaucaL96 | 551 | usGfsauuUfuGfAfauuaAfgUfuaguusasg | 592 |
| AD-74757 | cscsagaaGfuAfAfCfuucacuaaaL96 | 552 | usUfsuaaGfuGfAfaguuAfcUfucuggsgsu | 593 |
| AD-74758 | gsasacucAfaCfUfCfaaaacuugaaL96 | 553 | usUfscaaGfuUfUfugagUfuGfaguucsasa | 594 |
| AD-74759 | csasacucAfaAfAfCfuugaaagccuL96 | 554 | asGfsgcuUfuCfAfaguuUfuGfaguugsasg | 595 |
| AD-74760 | ususccacGfuUfGfCfuugaaauugaL96 | 555 | usCfsaauUfuCfAfagcaAfcGfuggaascsu | 596 |
| AD-74761 | gsusugcuUfgAfAfAfuugaaaaucaL96 | 556 | usGfsauuUfuCfAfauuuCfaAfgcaacsgsu | 597 |
| AD-74762 | gsasucacAfaAfAfCfuucaaugaaaL96 | 557 | usUfsucaUfuGfAfaguuUfuGfugaucscsa | 598 |
| AD-74763 | uscsaagaUfuUfGfCfuauguuagaaL96 | 558 | usUfscuaAfcAfUfagcaAfaUfcuugasusu | 599 |
| AD-74764 | csasaaauCfaAfGfAfuuugcuauguL96 | 559 | asCfsauaGfcAfAfaucuUfgAfuuuugsgsc | 600 |
| AD-74765 | gsasacuaCfuCfCfCfuuuucuucaguL96 | 560 | asCfsugaAfgAfAfagggAfgUfaguucsusu | 601 |
| AD-74766 | asgsaaauUfuCfUfCfuaucuuccaaL96 | 561 | usUfsggaAfgAfUfagagAfaAfuuucusgsu | 602 |
| AD-74767 | usgsaacuGfaGfGfCfaaauuuaaaL96 | 562 | usUfsuuaAfaUfUfugccUfcAfguucasusu | 603 |
| AD-74768 | csasuccaAfcAfGfAfuucagaaagaL96 | 563 | usCfsuuuCfuGfAfaucuGfuUfggaugsgsa | 604 |
| AD-74769 | asasaaucAfaGfAfUfuugcuauguuL96 | 564 | asAfscauAfgCfAfaaucUfgAfauuuusgsg | 605 |
| AD-74770 | asgsagcaAfaAfUfCfuaagccagaaL96 | 565 | usUfscugGfcUfUfagauUfuUfgcucususg | 606 |
| AD-74771 | asuscauaUfgAfGfCfuaauaucacaL96 | 566 | usGfsugaUfaUfUfagcUfaUfaugausgsc | 607 |
| AD-74772 | asasuaaaCfcUfCfGfuaacaaguuaL96 | 567 | usAfsacuUfgUfUfacgaGfgUfuuuauususc | 608 |
| AD-74773 | csasacagCfaUfAfGfucaaauaaaaL96 | 568 | usUfsuuaUfuUfGfacuaUfgCfuguugsgsu | 609 |
| AD-74774 | asasaacaAfcCfUfAfaauggaaauL96 | 569 | asUfsuuaCfcAfUfuuagGfuUfguuuuscsu | 610 |
| AD-74775 | csascuuaAfaAfCfUfuuuuguagaaL96 | 570 | usUfsucuAfcAfAfaaguUfuUfaagugsasa | 611 |
| AD-74776 | asusuaaaAfuAfAfGfuucgcugucuL96 | 571 | asGfsacaGfcGfAfacuuAfuUfuuaausasc | 612 |
| AD-74777 | csasaaacUfuCfAfAfugaaacgugaL96 | 572 | usCfsacgUfuUfCfauugAfaGfuuuugsusg | 613 |
| AD-74778 | asgsauggAfuCfAfCfaaaacuucaaL96 | 573 | usUfsgaaGfuUfUfugugAfuCfcaucusasu | 614 |
| AD-74779 | csascuuaAfuAfCfUfaugaaaacaaL96 | 574 | usUfsguuUfuCfAfuaguAfuUfaagusgsu | 615 |
| AD-74780 | ascsuaagUfcAfCfAfuugacuuuaL96 | 575 | usUfsaaaGfuCfAfauguGfaCfuuagusasg | 616 |
| AD-74781 | usasuuaaAfuAfAfCfuuuucuaaauL96 | 576 | asUfsuuaGfaAfAfaguuAfuUfuaauasasg | 617 |
| AD-74782 | ascsacuuAfaUfAfCfuaugaaaacaL96 | 577 | usGfsuuuUfcAfUfaguaUfuAfagugususa | 618 |
| AD-74783 | ususuaugAfaAfCfCfuaaugaagcaL96 | 578 | usGfscuuCfaUfUfagguUfuCfauaaasusa | 619 |
| AD-74784 | csasaacaUfuAfUfAfuugaauauuaL96 | 579 | usAfsauaUfuCfAfauauAfaUfguuugsusu | 620 |
| AD-74785 | asasaccaGfuGfAfAfaucaaagaaaL96 | 580 | usUfsucuUfuGfAfuuucAfcUfgguuusgsc | 621 |
| AD-74786 | gsasguuaAfaGfUfUfuauauuuccaL96 | 581 | usGfsgaaAfuAfUfaaacUfuUfaacucsgsa | 622 |
| AD-74787 | cscsaauaUfaAfAfCfaauuaaaccaL96 | 582 | usGfsguuUfaAfUfuguuUfaUfauuggsusc | 623 |
| AD-74788 | gsusggagAfaAfAfCfaaccuaaauaL96 | 583 | usAfsuuuAfgGfUfuguuUfuCfuccacsasc | 624 |
| AD-74789 | asascucaAfcUfCfAfaaaacuugaaL96 | 584 | usUfsucaAfgUfUfuugaGfuUfgaguuscsa | 625 |

TABLE 15A-continued

Additional Modified ANGPTL3 RNAi Agents.

| | | | | |
|---|---|---|---|---|
| AD-74790 | asasuguuCfaCfAfAfuuaagcuccuL96 | 585 | asGfsgagCfuUfAfauugUfgAfacauususu | 626 |
| AD-74791 | gscsagaaUfuAfAfAfuacuguauuaL96 | 586 | usAfsauaCfaGfUfauuuAfaUfucugcsusu | 627 |
| AD-74792 | usgsaaugAfaAfUfAfagaaauguaaL96 | 587 | usUfsacaUfuUfCfuuauUfuCfauucasasc | 628 |
| AD-74793 | usascauaUfaAfAfCfuacaagucaaL96 | 588 | usUfsgacUfuGfUfaguuUfaUfauguasgsu | 629 |

| Duplex Name | mRNA Target Sequence in NM_014495.3 | SEQ ID NO: |
|---|---|---|
| AD-66916 | GCAACUAACUAACUUAAUUCAAA | 630 |
| AD-66922 | AAGAAUAUGUCACUUGAACUCAA | 631 |
| AD-74755 | UAAAACUCUAAACUUGACUAAAU | 632 |
| AD-74756 | CUAACUAACUUAAUUCAAAAUCA | 633 |
| AD-74757 | ACCCAGAAGUAACUUCACUUAAA | 634 |
| AD-74758 | UUGAACUCAACUCAAAACUUGAA | 635 |
| AD-74759 | CUCAACUCAAAACUUGAAAGCCU | 636 |
| AD-74760 | AGUUCCACGUUGCUUGAAAUUGA | 637 |
| AD-74761 | ACGUUGCUUGAAAUUGAAAAUCA | 638 |
| AD-74762 | UGGAUCACAAAACUUCAAUGAAA | 639 |
| AD-74763 | AAUCAAGAUUUGCUAUGUUAGAC | 640 |
| AD-74764 | GCCAAAAUCAAGAUUUGCUAUGU | 641 |
| AD-74765 | AAGAACUACUCCCUUUCUUCAGU | 642 |
| AD-74766 | ACAGAAAUUUCUCUAUCUUCCAA | 643 |
| AD-74767 | AAUGAACUGAGGCAAAUUUAAAA | 644 |
| AD-74768 | UCCAUCCAACAGAUUCAGAAAGC | 645 |
| AD-74769 | CCAAAAUCAAGAUUUGCUAUGUU | 646 |
| AD-74770 | CAAGAGCAAAAUCUAAGCCAGAG | 647 |
| AD-74771 | GCAUCAUAUGAGCUAAUAUCACA | 648 |
| AD-74772 | GAAAUAAACCUCGUAACAAGUUA | 649 |
| AD-74773 | ACCAACAGCAUAGUCAAAUAAAA | 650 |
| AD-74774 | AGAAAACAACCUAAAUGGUAAAU | 651 |
| AD-74775 | UUCACUUAAAACUUUUGUAGAAA | 652 |
| AD-74776 | GUAUUAAAAUAAGUUCGCUGUCU | 653 |
| AD-74777 | CACAAAACUUCAAUGAAACGUGG | 654 |
| AD-74778 | AUAGAUGGAUCACAAAACUUCAA | 655 |
| AD-74779 | AACACUUAAUACUAUGAAAACAA | 656 |
| AD-74780 | CUACUAAGUCACAUUGACUUUAA | 657 |
| AD-74781 | CUUAUUAAAUAACUUUUCUAAAU | 658 |
| AD-74782 | UAACACUUAAUACUAUGAAAACA | 659 |
| AD-74783 | UAUUUAUGAAACCUAAUGAAGCA | 660 |
| AD-74784 | AACAAACAUUAUAUUGAAUAUUC | 661 |
| AD-74785 | GCAAACCAGUGAAAUCAAAGAAG | 662 |
| AD-74786 | UCGAGUUAAAGUUUAUAUUUCCC | 663 |

TABLE 15A-continued

Additional Modified ANGPTL3 RNAi Agents.

| | | |
|---|---|---|
| AD-74787 | GACCAAUAUAAACAAUUAAACCA | 664 |
| AD-74788 | GUGUGGAGAAAACAACCUAAAUG | 665 |
| AD-74789 | UGAACUCAACUCAAAACUUGAAA | 666 |
| AD-74790 | AAAAUGUUCACAAUUAAGCUCCU | 667 |
| AD-74791 | AAGCAGAAUUAAAUACUGUAUUA | 668 |
| AD-74792 | GUUGAAUGAAAUAAGAAAUGUAA | 669 |
| AD-74793 | ACUACAUAUAAACUACAAGUCAA | 670 |

TABLE 15B

Additional Modified ANGPTL3 RNAi Agents.

| Duplex Name | Sense Sequence 5' to 3' | SEQ ID NO: | Antisense Sequence 5' to 3' | SEQ ID NO: |
|---|---|---|---|---|
| AD-66916 | asascuaaCfuAfAfCfuuaauucaaa | 548 | usUfsugaAfuUfAfaguuAfgUfuaguusgsc | 589 |
| AD-66922 | gsasauauGfuCfAfCfuugaacucaa | 549 | usUfsgagUfuCfAfagugAfcAfuauucsusu | 590 |
| AD-74755 | asasacucUfaAfAfCfuugacuaaau | 550 | asUfsuuaGfuCfAfaguuUfaGfaguuususa | 591 |
| AD-74756 | asascuaaCfuUfAfAfuucaaaauca | 551 | usGfsauuUfuGfAfauuaAfgUfuaguusasg | 592 |
| AD-74757 | cscsagaaGfuAfAfCfuucacuuaaa | 552 | usUfsuaaGfuGfAfaguuAfcUfucuggsgsu | 593 |
| AD-74758 | gsasacucAfaCfUfCfaaaacuugaa | 553 | usUfscaaGfuUfUfugagUfuGfaguucsasa | 594 |
| AD-74759 | csasacucAfaAfAfCfuugaaagccu | 554 | asGfsgcuUfuCfAfaguuUfuGfaguugsasg | 595 |
| AD-74760 | ususccacGfuUfGfCfuugaaauuga | 555 | usCfsaauUfuCfAfagcaAfcGfuggaascsu | 596 |
| AD-74761 | gsusugcuUfgAfAfAfuugaaaauca | 556 | usGfsauuUfuCfAfauuuCfaAfgcaacsgsu | 597 |
| AD-74762 | gsasucacAfaAfAfCfuucaaugaaa | 557 | usUfsucaUfuGfAfaguuUfuGfugaucscsa | 598 |
| AD-74763 | uscsaagaUfuUfGfCfuauguuagaa | 558 | usUfscuaAfcAfUfagcaAfaUfcuugasusu | 599 |
| AD-74764 | csasaaauCfaAfGfAfuuugcuaugu | 559 | asCfsauaGfcAfAfaucuUfgAfuuuugsgsc | 600 |
| AD-74765 | gsasacuaCfuCfCfCfuuucuucagu | 560 | asCfsugaAfgAfAfagggAfgUfaguucsusu | 601 |
| AD-74766 | asgsaaauUfuCfUfCfuaucuuccaa | 561 | usUfsggaAfgAfUfagagAfaAfuuucsgsu | 602 |
| AD-74767 | usgsaacuGfaGfGfCfaaauuuaaaa | 562 | usUfsuuaAfaUfUfugccUfcAfguucasusu | 603 |
| AD-74768 | csasuccaAfcAfGfAfuucagaaaga | 563 | usCfsuuuCfuGfAfaucuGfuUfggaugsgsa | 604 |
| AD-74769 | asasaaucAfaGfAfUfuugcuauguu | 564 | asAfscauAfgCfAfaaucUfgAfuuuusgsg | 605 |
| AD-74770 | asgsagcaAfaAfUfCfuaagccagaa | 565 | usUfscugGfcUfUfagauUfuUfgcucsususg | 606 |
| AD-74771 | asuscauaUfgAfGfCfuaauaucaca | 566 | usGfsugaUfaUfUfagcuCfaUfaugausgsc | 607 |
| AD-74772 | asasauaaaCfcUfCfGfuaacaaguua | 567 | usAfsacuUfgUfUfacgaGfgUfuuauususc | 608 |
| AD-74773 | csasacagCfaUfAfGfucaaauaaaa | 568 | usUfsuuaUfuUfGfacuaUfgCfuguugsgsu | 609 |
| AD-74774 | asasaacaAfcCfUfAfaaugguaaau | 569 | asUfsuuaCfcAfUfuuagGfuUfguuusucsu | 610 |
| AD-74775 | csascuuaAfaAfCfUfuuuguagaaa | 570 | usUfsucuAfcAfAfaaguUfuUfaagugsasa | 611 |
| AD-74776 | asusuaaaAfuAfAfGfuucgcugucu | 571 | asGfsacaGfcGfAfacuuAfuUfuuaausasc | 612 |
| AD-74777 | csasaaacUfuCfAfAfugaaacguga | 572 | usCfsacgUfuUfCfauugAfaGfuuuugsusg | 613 |
| AD-74778 | asgsauggAfuCfAfCfaaaacuucaa | 573 | usUfsgaaGfuUfUfugugAfuCfcaucsasa | 614 |
| AD-74779 | csascuuaAfuAfCfUfaugaaaacaa | 574 | usUfsguuUfuCfAfuaguAfuUfaagugsusu | 615 |

TABLE 15B-continued

Additional Modified ANGPTL3 RNAi Agents.

| Duplex Name | Sense | SEQ ID | Antisense | SEQ ID |
|---|---|---|---|---|
| AD-74780 | ascsuaagUfcAfCfAfuugacuuuaa | 575 | usUfsaaaGfuCfAfauguGfaCfuuagusasg | 616 |
| AD-74781 | usasuuaaAfuAfAfCfuuuucuaaau | 576 | asUfsuuaGfaAfAfaguuAfuUfuaauasasg | 617 |
| AD-74782 | ascsacuuAfaUfAfCfuaugaaaaca | 577 | usGfsuuuUfcAfUfaguaUfuAfagugususa | 618 |
| AD-74783 | ususuaugAfaAfCfCfuaaugaagca | 578 | usGfscuuCfaUfUfagguUfuCfauaaasusa | 619 |
| AD-74784 | csasaacaUfuAfUfAfuugaauauua | 579 | usAfsauaUfuCfAfauauAfaUfguuugsusu | 620 |
| AD-74785 | asasaccaGfuGfAfAfaucaaagaaa | 580 | usUfsucuUfuGfAfuuucAfcUfgguuusgsc | 621 |
| AD-74786 | gsasguuaAfaGfUfUfuauauuucca | 581 | usGfsgaaAfuAfUfaaacUfuUfaacucsgsa | 622 |
| AD-74787 | cscsaauaUfaAfAfCfaauuaaacca | 582 | usGfsguuUfaAfUfuguuUfaUfauuggsusc | 623 |
| AD-74788 | gsusggagAfaAfAfCfaaccuaaaua | 583 | usAfsuuuAfgGfUfuguuUfuCfuccacsasc | 624 |
| AD-74789 | asascucaAfcUfCfAfaaacuugaaa | 584 | usUfsucaAfgUfUfuugaGfuUfgaguuscsa | 625 |
| AD-74790 | asasuguuCfaCfAfAfuuaagcuccu | 585 | asGfsgagCfuUfAfauugUfgAfacauususu | 626 |
| AD-74791 | gscsagaaUfuAfAfAfuacuguauua | 586 | usAfsauaCfaGfUfauuuAfaUfucugcsusu | 627 |
| AD-74792 | usgsaaugAfaAfUfAfagaaauguaa | 587 | usUfsacaUfuUfCfuuauUfuCfauucasasc | 628 |
| AD-74793 | usascauaUfaAfAfCfuacaagucaa | 588 | usUfsgacUfuGfUfaguuUfaUfauguasgsu | 629 |

| Duplex Name | mRNA Target Sequence in NM_014495.3 | SEQ ID NO: |
|---|---|---|
| AD-66916 | GCAACUAACUAACUUAAUUCAAA | 630 |
| AD-66922 | AAGAAUAUGUCACUUGAACUCAA | 631 |
| AD-74755 | UAAACUCUAAACUUGACUAAAU | 632 |
| AD-74756 | CUAACUAACUUAAUUCAAAAUCA | 633 |
| AD-74757 | ACCCAGAAGUAACUUCACUUAAA | 634 |
| AD-74758 | UUGAACUCAACUCAAAACUUGAA | 635 |
| AD-74759 | CUCAACUCAAAACUUGAAAGCCU | 636 |
| AD-74760 | AGUUCCACGUUGCUUGAAAUUGA | 637 |
| AD-74761 | ACGUUGCUUGAAAUUGAAAAUCA | 638 |
| AD-74762 | UGGAUCACAAAACUUCAAUGAAA | 639 |
| AD-74763 | AAUCAAGAUUUGCUAUGUUAGAC | 640 |
| AD-74764 | GCCAAAAUCAAGAUUUGCUAUGU | 641 |
| AD-74765 | AAGAACUACUCCCUUUCUUCAGU | 642 |
| AD-74766 | ACAGAAAUUUCUCUAUCUUCCAA | 643 |
| AD-74767 | AAUGAACUGAGGCAAAUUUAAAA | 644 |
| AD-74768 | UCCAUCCAACAGAUUCAGAAAGC | 645 |
| AD-74769 | CCAAAAUCAAGAUUUGCUAUGUU | 646 |
| AD-74770 | CAAGAGCAAAAUCUAAGCCAGAG | 647 |
| AD-74771 | GCAUCAUAUGAGCUAAUAUCACA | 648 |
| AD-74772 | GAAAUAAACCUCGUAACAAGUUA | 649 |
| AD-74773 | ACCAACAGCAUAGUCAAAUAAAA | 650 |
| AD-74774 | AGAAACAACCUAAAUGGUAAAU | 651 |
| AD-74775 | UUCACUUAAAACUUUUGUAGAAA | 652 |
| AD-74776 | GUAUUAAAAUAAGUUCGCUGUCU | 653 |

TABLE 15B-continued

Additional Modified ANGPTL3 RNAi Agents.

| | | |
|---|---|---|
| AD-74777 | CACAAAACUUCAAUGAAACGUGG | 654 |
| AD-74778 | AUAGAUGGAUCACAAAACUUCAA | 655 |
| AD-74779 | AACACUUAAUACUAUGAAAACAA | 656 |
| AD-74780 | CUACUAAGUCACAUUGACUUUAA | 657 |
| AD-74781 | CUUAUUAAAUAACUUUUCUAAAU | 658 |
| AD-74782 | UAACACUUAAUACUAUGAAAACA | 659 |
| AD-74783 | UAUUUAUGAAACCUAAUGAAGCA | 660 |
| AD-74784 | AACAAACAUUAUAUUGAAUAUUC | 661 |
| AD-74785 | GCAAACCAGUGAAAUCAAAGAAG | 662 |
| AD-74786 | UCGAGUUAAAGUUUAUAUUUCCC | 663 |
| AD-74787 | GACCAAUAUAAACAAUUAAACCA | 664 |
| AD-74788 | GUGUGGAGAAAACAACCUAAAUG | 665 |
| AD-74789 | UGAACUCAACUCAAAACUUGAAA | 666 |
| AD-74790 | AAAAUGUUCACAAUUAAGCUCCU | 667 |
| AD-74791 | AAGCAGAAUUAAAUACUGUAUUA | 668 |
| AD-74792 | GUUGAAUGAAAUAAGAAAUGUAA | 669 |
| AD-74793 | ACUACAUAUAAACUACAAGUCAA | 670 |

TABLE 16

AngPTL3 Single Dose Screen in Hep3B cells and Primary Cynomolgus Monkey Hepatocytes. Data are expressed as percent message remaining relative to AD-1955 non-targeting control.

| | Hep3b | | | | Cynomolgus Monkey Hepatocytes | | | |
|---|---|---|---|---|---|---|---|---|
| DuplexID | 10 nM_ AVG | 10 nM_ STDEV | 0.1 nM_ AVG | 0.1 nM_ STDEV | 10 nM_ AVG | 10 nM_ STDEV | 0.1 nM_ AVG | 0.1 nM_ STDEV |
| AD-66916 | 5.2 | 2.1 | 17.9 | 4.1 | 5.2 | 0.4 | 40.5 | 5.4 |
| AD-66922 | 12.5 | 2.1 | 41.5 | 17.0 | 4.6 | 0.6 | 43.5 | 8.2 |
| AD-74755 | 18.2 | 5.9 | 44.3 | 3.5 | 68.7 | 7.8 | 79.2 | 11.5 |
| AD-74756 | 10.4 | 4.1 | 56.9 | 12.5 | 9.9 | 2.4 | 50.7 | 7.4 |
| AD-74757 | 10.7 | 6.5 | 38.3 | 12.4 | 5.6 | 0.8 | 34.5 | 4.0 |
| AD-74758 | 19.3 | 3.1 | 120.4 | 19.5 | 24.1 | 6.9 | 78.4 | 17.7 |
| AD-74759 | 20.4 | 3.9 | 132.1 | 34.5 | 26.7 | 4.0 | 80.4 | 8.3 |
| AD-74760 | 21.6 | 4.7 | 140.1 | 16.8 | 12.8 | 1.5 | 72.5 | 6.4 |
| AD-74761 | 19.9 | 2.4 | 107.8 | 30.0 | 12.6 | 1.1 | 71.9 | 12.3 |
| AD-74762 | 11.0 | 5.0 | 55.0 | 11.0 | 6.4 | 1.2 | 78.5 | 17.1 |
| AD-74763 | 13.5 | 4.1 | 67.5 | 13.6 | 21.2 | 5.2 | 76.8 | 13.4 |
| AD-74764 | 10.4 | 3.0 | 70.7 | 21.4 | 15.8 | 1.4 | 63.1 | 4.8 |
| AD-74765 | 16.5 | 3.6 | 83.1 | 16.4 | 22.0 | 2.5 | 82.2 | 10.4 |
| AD-74766 | 11.3 | 6.2 | 56.0 | 25.3 | 7.8 | 0.4 | 51.3 | 2.1 |
| AD-74767 | 8.6 | 3.2 | 70.9 | 19.7 | 14.8 | 5.8 | 61.5 | 4.7 |
| AD-74768 | 28.8 | 10.1 | 120.3 | 24.3 | 37.6 | 5.3 | 81.1 | 9.6 |
| AD-74769 | 14.5 | 5.5 | 65.4 | 28.5 | 10.3 | 1.6 | 63.5 | 8.9 |
| AD-74770 | 42.4 | 13.0 | 95.0 | 23.6 | 59.8 | 8.1 | 104.6 | 14.8 |
| AD-74771 | 30.0 | 12.2 | 79.7 | 15.3 | 73.7 | 10.0 | 87.6 | 17.1 |
| AD-74772 | 22.9 | 3.8 | 60.4 | 10.9 | 80.9 | 9.1 | 83.8 | 8.0 |
| AD-74773 | 11.2 | 3.3 | 47.4 | 14.1 | 9.7 | 1.8 | 56.3 | 1.8 |
| AD-74774 | 57.3 | 4.8 | 99.3 | 8.1 | 65.0 | 4.2 | 81.3 | 9.3 |
| AD-74775 | 13.8 | 3.6 | 83.1 | 21.8 | 54.2 | 4.0 | 92.0 | 5.5 |
| AD-74776 | 50.6 | 11.5 | 114.3 | 39.7 | 80.2 | 11.0 | 97.3 | 9.4 |
| AD-74777 | 14.8 | 3.8 | 76.7 | 27.0 | 39.4 | 12.1 | 92.1 | 4.2 |
| AD-74778 | 22.0 | 13.0 | 62.8 | 24.6 | 15.6 | 3.0 | 70.4 | 7.4 |
| AD-74779 | 45.5 | 9.0 | 64.7 | 4.7 | 82.8 | 15.1 | 87.0 | 9.0 |
| AD-74780 | 38.3 | 13.9 | 81.0 | 22.9 | 77.4 | 7.4 | 82.0 | 4.3 |
| AD-74781 | 44.5 | 10.1 | 78.5 | 15.9 | 79.5 | 3.3 | 88.7 | 7.9 |

TABLE 16-continued

AngPTL3 Single Dose Screen in Hep3B cells and Primary
Cynomolgus Monkey Hepatocytes. Data are expressed as percent message
remaining relative to AD-1955 non-targeting control.

| | Hep3b | | | | Cynomolgus Monkey Hepatocytes | | | |
| --- | --- | --- | --- | --- | --- | --- | --- | --- |
| DuplexID | 10 nM_ AVG | 10 nM_ STDEV | 0.1 nM_ AVG | 0.1 nM_ STDEV | 10 nM_ AVG | 10 nM_ STDEV | 0.1 nM_ AVG | 0.1 nM_ STDEV |
| AD-74782 | 59.1 | 18.5 | 137.3 | 65.4 | 79.1 | 3.6 | 88.5 | 4.3 |
| AD-74783 | 115.4 | 42.4 | 109.6 | 32.6 | 91.8 | 5.6 | 95.3 | 9.2 |
| AD-74784 | 11.5 | 4.6 | 47.8 | 18.3 | 8.6 | 2.8 | 56.7 | 10.7 |
| AD-74785 | 15.0 | 13.9 | 43.9 | 7.4 | 12.1 | 2.6 | 72.4 | 14.0 |
| AD-74786 | 32.1 | 10.3 | 61.0 | 14.6 | 85.5 | 7.2 | 93.3 | 22.2 |
| AD-74787 | 60.9 | 12.4 | 86.4 | 26.2 | 88.1 | 11.9 | 96.6 | 21.4 |
| AD-74788 | 17.8 | 7.7 | 69.9 | 23.8 | 19.3 | 1.2 | 79.2 | 15.3 |
| AD-74789 | 30.6 | 3.6 | 64.0 | 6.9 | 24.6 | 1.3 | 76.0 | 9.5 |
| AD-74790 | 15.4 | 3.5 | 56.9 | 10.5 | 9.2 | 0.6 | 58.7 | 12.4 |
| AD-74791 | 30.7 | 6.3 | 49.3 | 6.9 | 81.3 | 8.3 | 87.3 | 3.8 |
| AD-74792 | 10.5 | 2.4 | 30.1 | 6.4 | 10.5 | 1.2 | 54.7 | 7.3 |
| AD-74793 | 12.1 | 4.9 | 30.9 | 16.2 | 13.2 | 2.1 | 83.2 | 12.7 |

We claim:

1. A double-stranded ribonucleic acid (dsRNA) agent for inhibiting expression of angiopoietin-like 3 (ANGPTL3), wherein the dsRNA comprises a sense strand and an antisense strand forming a double stranded region, wherein the antisense strand comprises at least 15 contiguous nucleotides differing by no more than 3 nucleotides from the nucleotide sequence 5'-UUGAGUUGAGUUCAAGUGA-CAUA 3' (SEQ ID NO: 308), wherein substantially all of the nucleotides of the sense strand and substantially all of the nucleotides of the antisense strand comprise a modification selected from the group consisting of a 2'-O-methyl modification and a 2'-fluoro modification, and wherein the sense strand comprises no more that four 2'-fluoro modified nucleotides, and the antisense strand comprises no more than six 2'-fluoro modified nucleotides.

2. The dsRNA agent of claim 1, wherein all of the nucleotides of the sense strand are modified nucleotides; or wherein all of the nucleotides of the antisense strand are modified nucleotides.

3. The dsRNA agent of claim 1, further comprising at least one phosphorothioate internucleotide linkage.

4. The dsRNA agent of claim 1, wherein each strand is no more than 30 nucleotides in length.

5. The dsRNA agent of claim 1, wherein at least one strand comprises a 3' overhang of at least 1 nucleotide.

6. The dsRNA agent of claim 1, further comprising a ligand.

7. The dsRNA agent of claim 6, wherein the ligand is conjugated to the 3' end of the sense strand of the dsRNA agent.

8. The dsRNA agent of claim 7, wherein the ligand is an N-acetylgalactosamine (GalNAc) derivative.

9. The dsRNA agent of claim 8, wherein the ligand is

10. The dsRNA agent of claim 1, wherein the double-stranded region is 15-30 nucleotide pairs in length.

11. The dsRNA agent of claim 1, wherein each strand is 15-30 nucleotides in length.

12. The dsRNA agent of claim 1, wherein each of the sense strand and the antisense strand independently are 21 to 23 nucleotides in length.

13. The dsRNA agent of claim 1, wherein the sense strand has a total of 21 nucleotides and the antisense strand has a total of 23 nucleotides.

14. The dsRNA agent of claim 1, wherein the antisense strand comprises the nucleotide sequence 5'-UUGAGUUGAGUUCAAGUGACAUA 3' (SEQ ID NO: 308).

15. The dsRNA agent of claim 1, wherein the antisense strand consists of the nucleotide sequence 5'-UUGAGUUGAGUUCAAGUGACAUA-3' (SEQ ID NO: 308).

16. The dsRNA agent of claim 1, wherein the sense strand comprises the nucleotide sequence 5'-UGUCACUUGAA-CUCAACUCAA-3' (SEQ ID NO:296) and the antisense strand comprises the nucleotide sequence 5'-UUGAGUUGAGUUCAAGUGACAUA-3' (SEQ ID NO:308).

17. The dsRNA agent of claim 16, wherein the sense strand comprises the nucleotide sequence 5'-usgsucacUfuG-fAfAfcucaacucaa-3' (SEQ ID NO:272) and the antisense strand comprises the nucleotide sequence 5'-usUfsgagUfuG-fAfguucAfaGfugacasusa-3' (SEQ ID NO:284), wherein a, g, c and u are 2'-O-methyl (2'-OMe) A, G, C, and U; Af, Gf, Cf, and Uf are 2'-fluoro A, G, C and U; and s is a phosphorothioate linkage.

18. The dsRNA agent of claim 17, further comprising a ligand.

19. The dsRNA of claim 18, wherein the ligand is one or more GalNAc derivatives attached through a monovalent, a bivalent, or a trivalent branched linker.

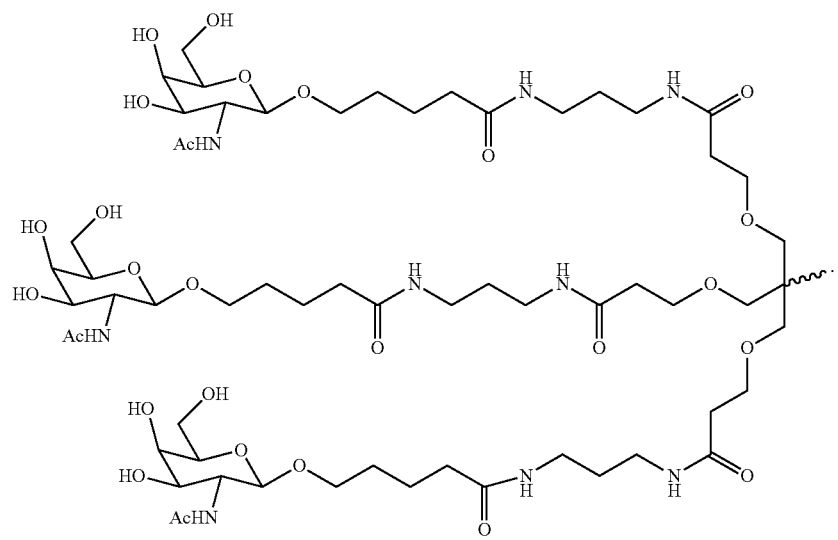 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

20. The dsRNA agent of claim 19, wherein the ligand is

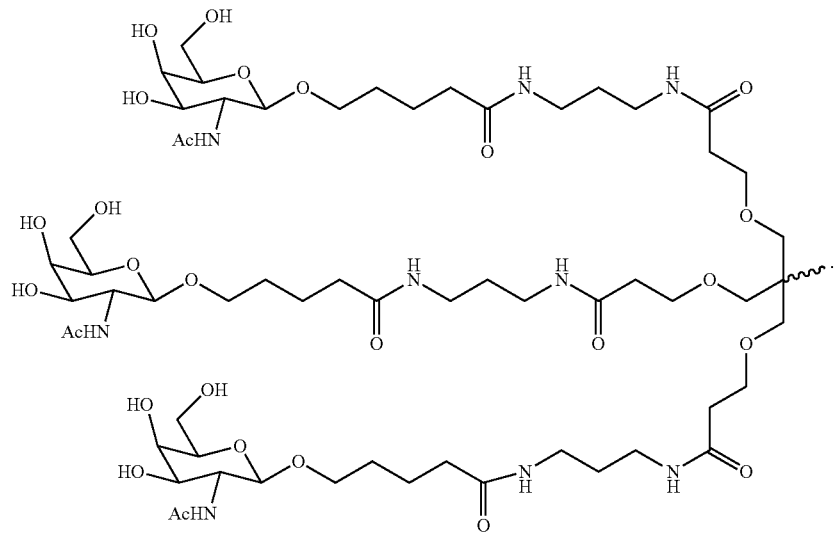

21. The dsRNA agent of claim 18, wherein the ligand is attached to the 3' end of the sense strand.

22. The dsRNA agent of claim 1, wherein at least one strand comprises a 3' overhang of at least 2 nucleotides.

23. The dsRNA agent of claim 1, wherein the double-stranded region is 17-23 nucleotide pairs in length.

24. The dsRNA agent of claim 1, wherein the double-stranded region is 17-25 nucleotide pairs in length.

25. The dsRNA agent of claim 1, wherein the double-stranded region is 23-27 nucleotide pairs in length.

26. The dsRNA agent of claim 1, wherein the double-stranded region is 19-21 nucleotide pairs in length.

27. The dsRNA agent of claim 1, wherein the double-stranded region is 21-23 nucleotide pairs in length.

28. The dsRNA agent of claim 1, wherein each strand is 19-30 nucleotides in length.

29. The dsRNA agent of claim 9 or 20, wherein the dsRNA agent is conjugated to the ligand as shown in the following schematic

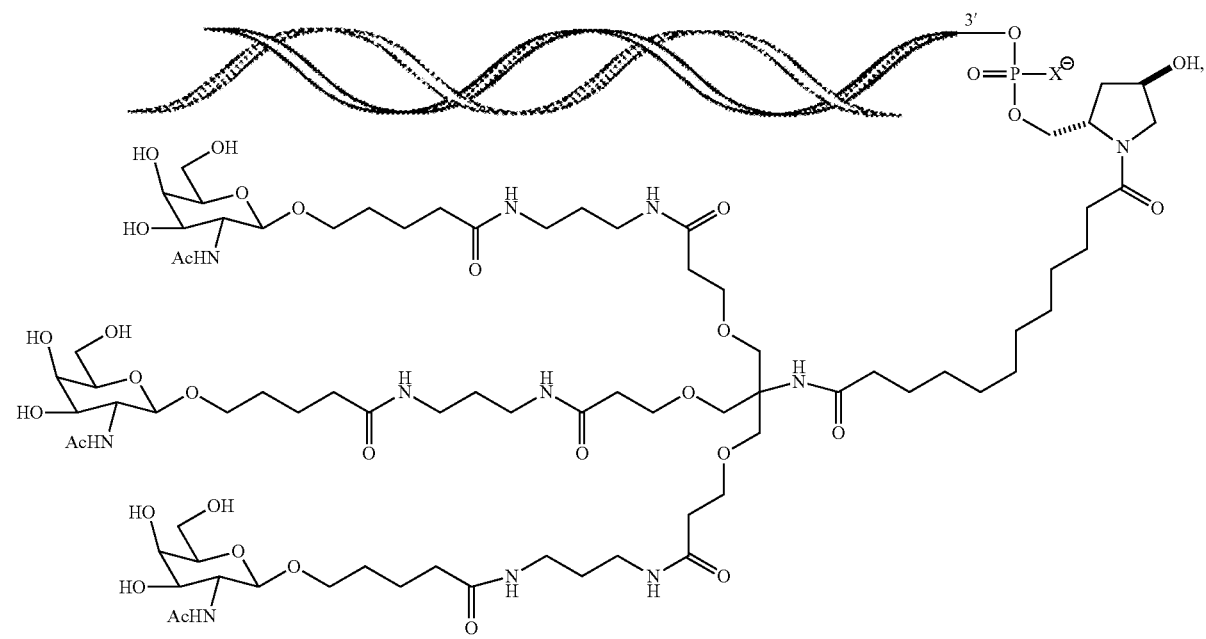

wherein X is O or S.

30. The dsRNA agent of claim 29, wherein the X is O.

31. The dsRNA agent of claim 1, wherein the antisense strand comprises the nucleotide sequence 5'-UTGAGUUGAGUTCAAGUGACAUA-3' (SEQ ID NO: 387).

32. The dsRNA agent of claim 1, wherein the antisense strand consists of the nucleotide sequence 5'-UTGAGUUGAGUTCAAGUGACAUA-3' (SEQ ID NO: 387).

33. The dsRNA agent of claim 1, wherein the sense strand comprises the nucleotide sequence 5'-UGUCACUUCAACUCAACUCAA-3' (SEQ ID NO:366) and the antisense strand comprises the nucleotide sequence 5'-UTGAGUUGAGUTCAAGUGACAUA-3' (SEQ ID NO:387).

34. The dsRNA agent of claim 33, wherein the sense strand comprises the nucleotide sequence 5'-usgsucadCuudCaacucaa(Cgn)ucaa-3' (SEQ ID NO:324) and the antisense strand comprises the nucleotide sequence 5'-usdTsgaguugagudTcdAagugacasusa-3' (SEQ ID NO:345), wherein a, g, c and u are 2'-O-methyl (2'-OMe) A, G, C, and U; Af, Gf, Cf, and Uf are 2'-fluoro A, G, C and U; dT is deoxythymidine; dA is deoxyadenosine; (Cgn) is Cytidineglycol nucleic acid (GNA); and s is a phosphorothioate linkage.

35. The dsRNA agent of claim 34, further comprising a ligand.

36. A pharmaceutical composition for inhibiting expression of an ANGPTL3 gene comprising the dsRNA agent of claim 35.

37. A double stranded ribonucleic acid (dsRNA) agent for inhibiting expression of angiopoietin-like 3 (ANGPTL3), wherein the dsRNA comprises a sense strand and an antisense strand forming a double stranded region, wherein the sense strand consists of the nucleotide sequence 5'-usgsucacUfuGfAfAfcucaacucaaL96-3' (SEQ ID NO:272) and the antisense strand consists of the nucleotide sequence 5'-usUfsgagUfuGfAfguucAfaGfugacasusa-3' (SEQ ID NO:284), wherein a, g, c and u are 2'-O-methyl (2'-OMe) A, G, C, and U; Af, Gf, Cf, and Uf are 2'-fluoro A, G, C and U; s is a phosphorothioate linkage; and L96 is N-[tris(GalNAc-alkyl)-amidodecanoyl)]-4-hydroxyprolinol.

38. A pharmaceutical composition for inhibiting expression of an ANGPTL3 gene comprising the dsRNA agent of claim 37.

39. An isolated cell containing the dsRNA agent of claim 1 or 17.

40. A pharmaceutical composition for inhibiting expression of an ANGPTL3 gene comprising the dsRNA agent of claim 1 or 17.

41. A method of inhibiting ANGPTL3 expression in a cell, the method comprising:
(a) contacting the cell with the dsRNA agent of any one of claims 1, 17, and 37; and
(b) maintaining the cell produced in step (a) for a time sufficient to obtain degradation of the mRNA transcript of an ANGPTL3 gene, thereby inhibiting expression of the ANGPTL3 gene in the cell.

42. The method of claim 41, wherein said cell is within a subject.

43. The method of claim 42, wherein the subject is a human.

44. The method of claim 43, wherein the human subject suffers from a disorder of lipid metabolism.

45. The method of claim 44, wherein the disorder of lipid metabolism is hyperlipidemia or hypertriglyceridemia.

46. A method of treating a subject having a disorder that would benefit from a reduction in ANGPTL3 expression, comprising administering to the subject a therapeutically effective amount of the dsRNA agent of any one of claims 1, 17, and 37, thereby treating said subject.

* * * * *